United States Patent
Nimmerjahn et al.

(10) Patent No.: US 10,738,282 B2
(45) Date of Patent: Aug. 11, 2020

(54) USE OF PHOSPHOLIPID SCRAMBLASE INHIBITORS FOR MODULATING INFLAMMATORY IMMUNE RESPONSES

(71) Applicant: Salk Institute for Biological Studies, La Jolla, CA (US)

(72) Inventors: Axel Nimmerjahn, San Diego, CA (US); Charles L. Clark, Santee, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 198 days.

(21) Appl. No.: 15/849,069

(22) Filed: Dec. 20, 2017

(65) Prior Publication Data
US 2018/0171305 A1 Jun. 21, 2018

Related U.S. Application Data

(60) Provisional application No. 62/436,591, filed on Dec. 20, 2016.

(51) Int. Cl.
*C12N 7/00* (2006.01)
*A61K 31/713* (2006.01)
*A61K 38/46* (2006.01)
*A61P 29/00* (2006.01)
*A61P 37/06* (2006.01)
*C12N 15/113* (2010.01)
*C12N 15/86* (2006.01)
*A61K 48/00* (2006.01)

(52) U.S. Cl.
CPC .............. *C12N 7/00* (2013.01); *A61K 31/713* (2013.01); *A61K 38/46* (2013.01); *A61P 29/00* (2018.01); *A61P 37/06* (2018.01); *C12N 15/1137* (2013.01); *C12N 15/86* (2013.01); *C12Y 306/00* (2013.01); *A61K 48/0008* (2013.01); *C12N 2310/11* (2013.01); *C12N 2310/122* (2013.01); *C12N 2310/14* (2013.01); *C12N 2310/531* (2013.01); *C12N 2320/31* (2013.01); *C12N 2710/10041* (2013.01); *C12N 2710/10043* (2013.01); *C12N 2710/10071* (2013.01); *C12N 2710/10343* (2013.01); *C12N 2710/16641* (2013.01); *C12N 2710/16643* (2013.01); *C12N 2710/16671* (2013.01)

(58) Field of Classification Search
None
See application file for complete search history.

(56) References Cited

U.S. PATENT DOCUMENTS

| 8,691,229 B2 * | 4/2014 | Chan .................. A61K 39/395 424/138.1 |
| 2013/0231267 A1 | 9/2013 | O'Shea |

OTHER PUBLICATIONS

Huszthy, et al. (2009) "Remission of Invasive, Cancer Stem-Like Glioblastoma Xenografts Using Lentiviral Vector-Mediated Suicide Gene Therapy", PLoS One, 4(7): e6314, 13 pages long.*
Tufail, et al. (2017) "Phsophatidylserine Exposure Controls Viral Innate Immune Responses by Microglia", Neuron, 93(3): 574-86.e8.*
Rao, et al. (2009) "siRNA vs. shRNA: similarities and differences", Advanced Drug Delivery Reviews, 61(9): 746-59. (Year: 2009).*
Nimmerjahn, "Modulating Plasma Membrane Phosphatidylserine Exchange Controls Innate Immune Responses," Abstract of poster presented at the 2015 NIH Common Fund High-Risk, High-Reward Research Program Symposium, Bethesda, Maryland, Dec. 7, 2015.

* cited by examiner

*Primary Examiner* — Robert M Kelly
(74) *Attorney, Agent, or Firm* — Klarquist Sparkman, LLP

(57) ABSTRACT

The finding that phosphatidylserine (PtdSer) exposure on the outer leaflet of virally transduced cells triggers their engulfment by resident immune cells is described. It is demonstrated that inhibition of phospholipid scramblase 1 (PLSCR1) activity prevents PtdSer externalization and enables prolonged protection of vector-transduced cells from phagocytosis. Methods of inhibiting a virus vector-induced inflammatory response in tissue, methods of prolonging virus vector encoded transgene expression, and methods of modulating an inflammatory response in tissue of a subject, by administering an inhibitor of PLSCR1 are described.

24 Claims, 50 Drawing Sheets
(50 of 50 Drawing Sheet(s) Filed in Color)
Specification includes a Sequence Listing.

FIG. 3A
FIG. 3B
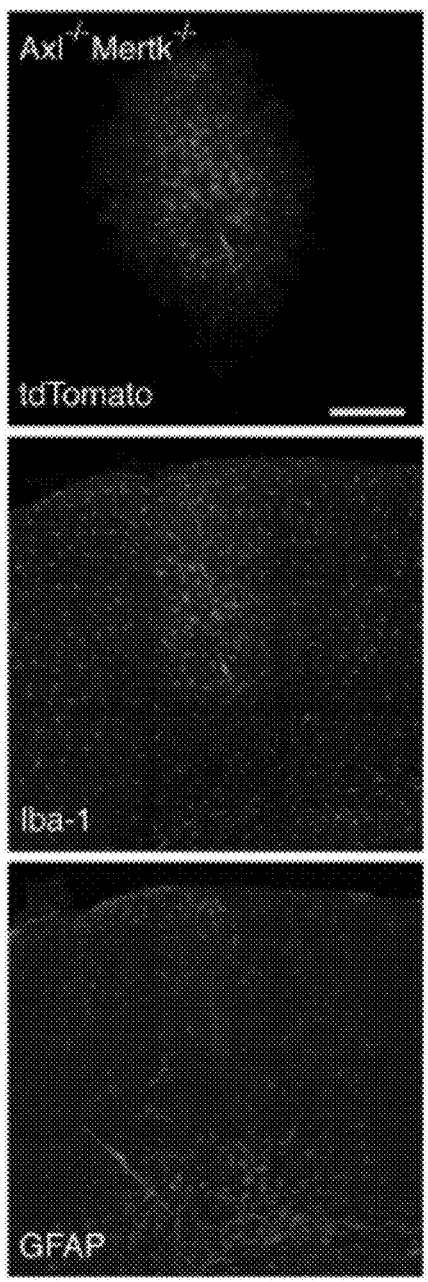
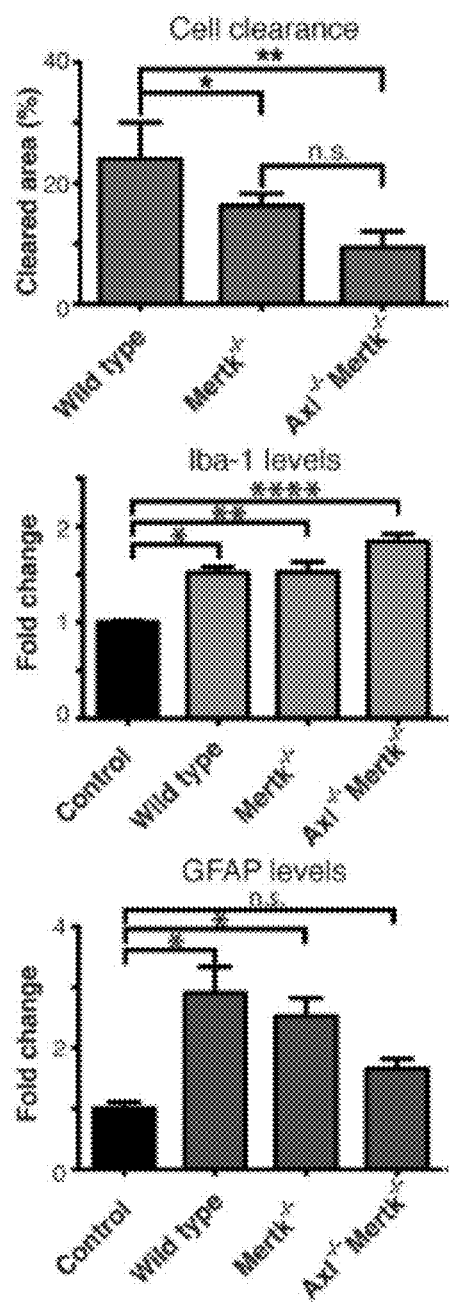

FIG. 8A
FIG. 8B
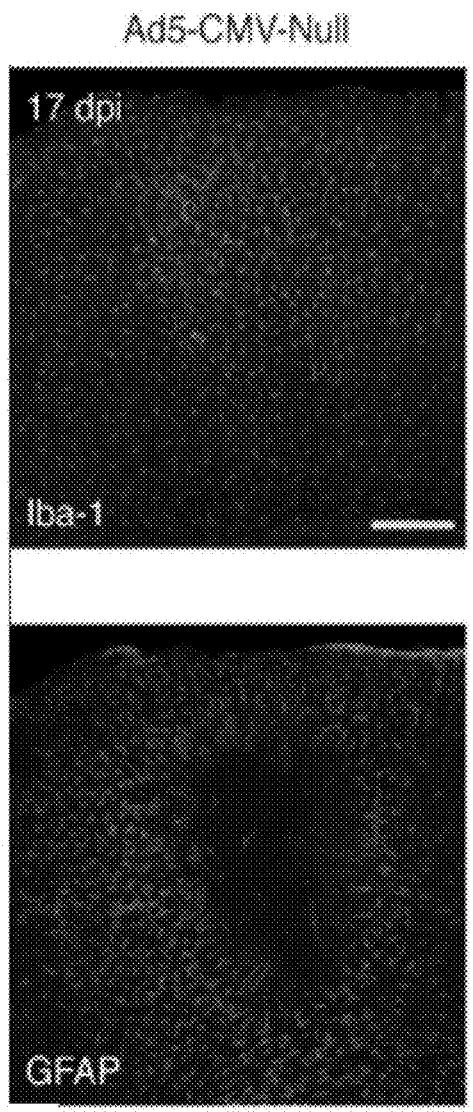
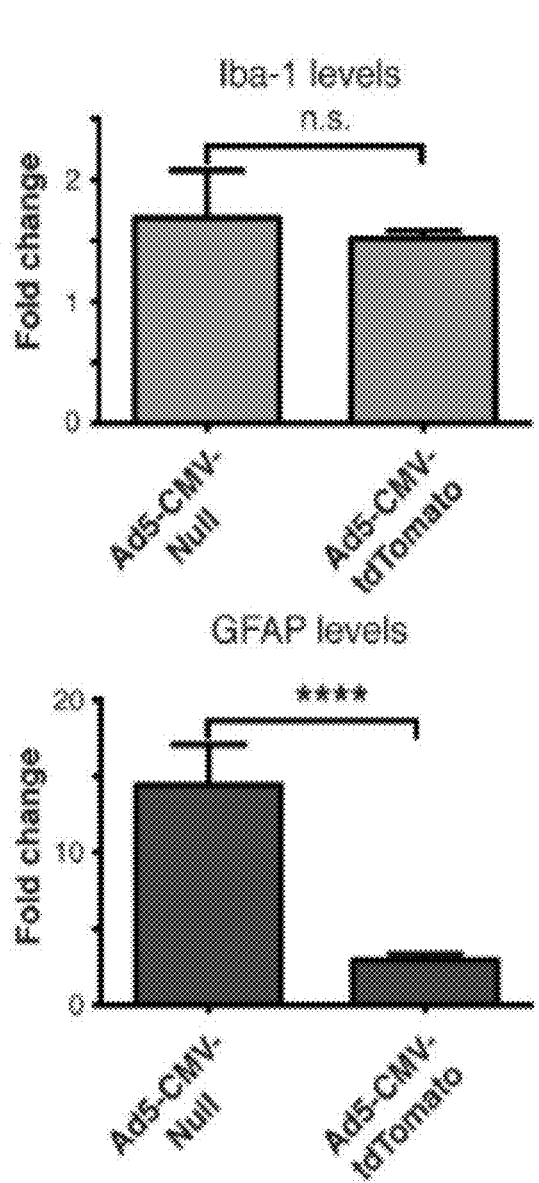

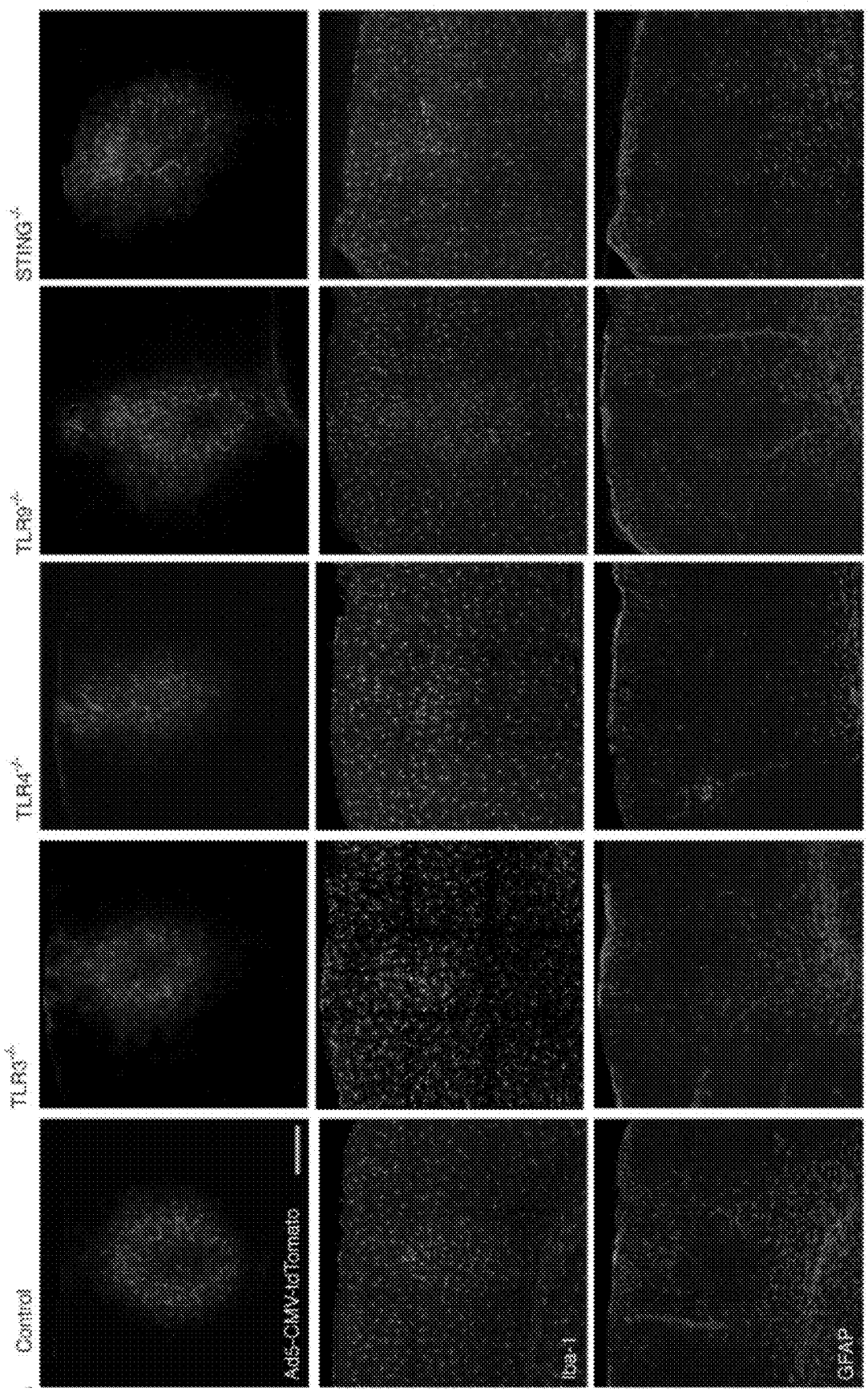

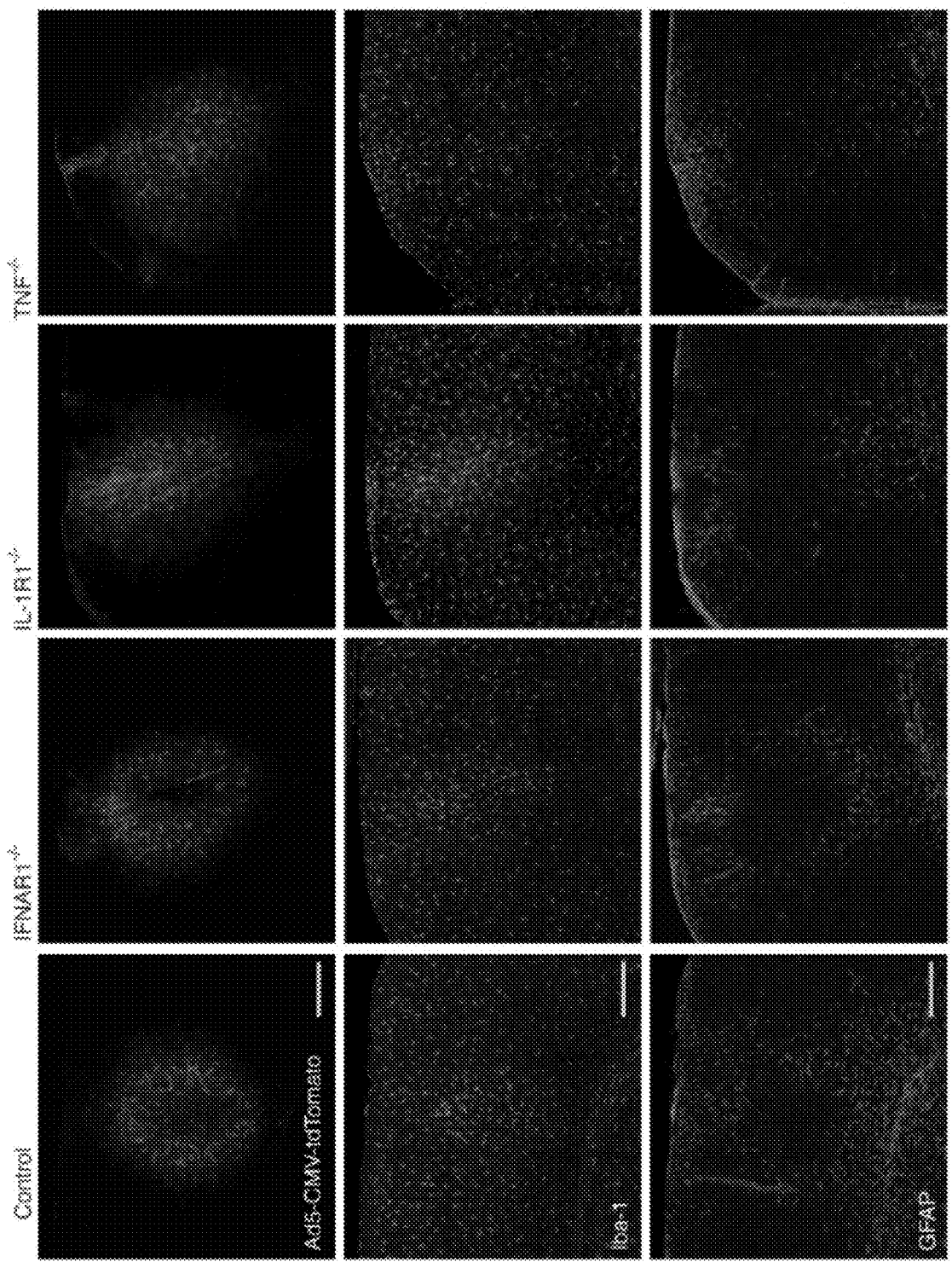

FIG. 15A
FIG. 15B
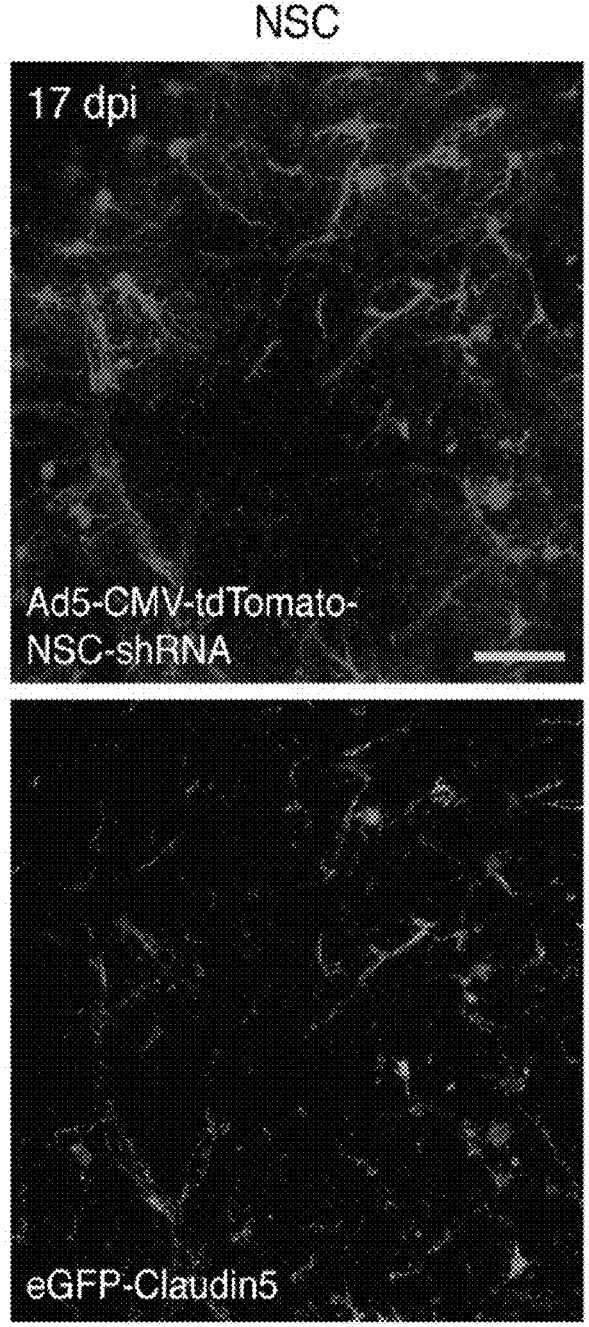
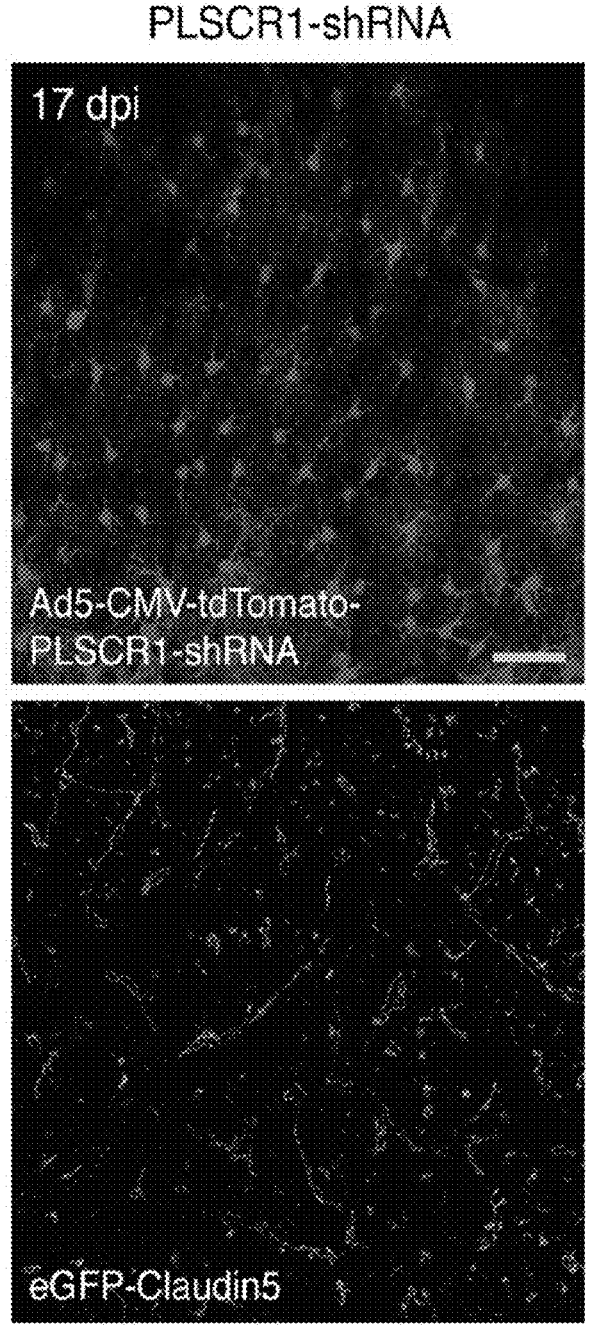

FIG. 16A
FIG. 16B
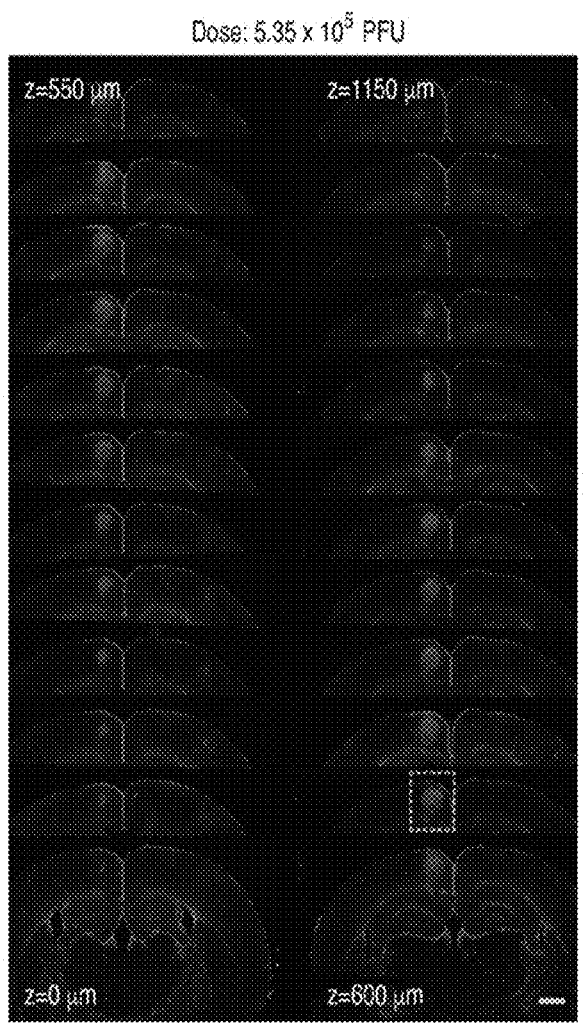
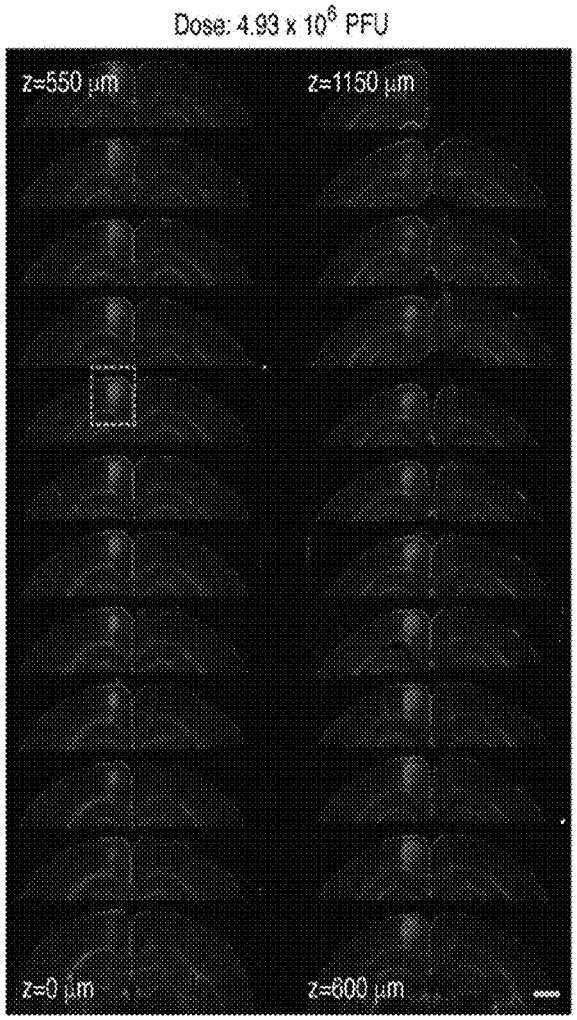

SEQUENCE LISTING

<160> NUMBER OF SEQ ID NOS: 23

<210> SEQ ID NO 1
<211> LENGTH: 38541
<212> TYPE: DNA
<213> ORGANISM: Artificial Sequence
<220> FEATURE:
<223> OTHER INFORMATION: Synthetic adenovirus vector (CMV-tdTomato-NSC-shRNA)

<400> SEQUENCE: 1

```
gttccactga gcgtcagacc ccttaataag atgatcttct tgagatcgtt ttggtctgcg      60
cgtaatctct tgctctgaaa acgaaaaaac cgccttgcag ggcggttttt cgaaggttct     120
ctgagctacc aactctttga accgaggtaa ctggcttgga ggagcgcagt caccaaaact     180
tgtcctttca gtttagcctt aaccggcgca tgacttcaag actaactcct ctaaatcaat     240
taccagtggc tgctgccagt ggtgcttttg catgtctttc cggttggac tcaagacgat      300 agttaccgga taaggcgcag cggtcggact gaacgggggg ttcgtgcata cagtccagct     360
tggagcgaac tgcctacccg gaactgagtg tcaggcgtgg aatgagacaa acgcggccat     420
aacagcggaa tgacaccggt aaaccgaaag gcaggaacag gagagcgcac gagggagccg     480
ccaggggaaa cgcctggtat ctttatagtc ctgtcgggtt tcgccaccac tgatttgagc     540
gtcagatttc gtgatgcttg tcagggggggc ggagcctatg gaaaaacggc tttgccgcgg     600
ccctctcact tccctgttaa gtatcttcct ggcatcttcc aggaaatctc cgccccgttc     660
gtaagccatt tccgctcgcc gcagtcgaac gaccgagcgt agcgagtcag tgagcgagga     720
agcggaatat atcctgtatc acatattctg ctgacgcacc ggtgcagcct ttttttctcct     780 gccacatgaa gcacttcact gacaccctca tcagtgccaa catagtaagc cagtatacac     840
tccgctagcg ctgaggtctg cctcgtgaag aaggtgttgc tgactcatac caggcctgaa     900
tcgccccatc atccagccag aaagtgaggg agccacggtt gatgagagct ttgttgtagg     960
tggaccagtt ggtgattttg aacttttgct ttgccacgga acggtctgcg ttgtcggaa     1020 gatgcgtgat ctgatccttc aactcagcaa aagttcgatt tattcaacaa agccacgttg    1080
tgtctcaaaa tctctgatgt tacattgcac aagataaaaa tatatcatca tgaacaataa    1140
aactgtctgc ttacataaac agtaatacaa ggggtgttga tactctcagt acaatctgct    1200
ctgatgccgc atagttaagc cagtatctgc tccctgcttg tgtgttggag gtcgctgagt    1260
agtgcgcgag caaaatttaa gctacaacaa ggcaaggctt gaccgacaat tgcatgaaga    1320
atctgcttag ggttaggcgt tttgcgctgc ttcgcgatgt acgggccaga tatacgcgta    1380
```

-continued

```
tctgagggga ctagggtgtg tttaggcgaa aagcggggct tcggttgtac gcggttagga      1440
gtcccctcag gatatagtag tttcgctttt gcatagggag ggggaaatgt agtcttatgc      1500
aatactcttg tagtcttgca acatggtaac gatgagttag caacatgcct tacaaggaga      1560
gaaaaagcac cgtgcatgcc gattggtgga agtaaggtgg tacgatcgtg ccttattagg      1620
aaggcaacag acgggtctga catggattgg acgaaccact gaattccgca ttgcagagat      1680
attgtattta agtgcctagc tcgatacaat aaacgccatt tgaccattca ccacattggt      1740
gtgcacctcc aagctgggta cggatccggc cttgccggcc tcgagcggcc gctagcgccg      1800
ccactatggg atcaagatcg ccaaaaaaga agagaaaggt gccgaagaag catgcagcac      1860
caccaaaaaa aaaacgaaaa gtagaagacc cacgatttat gtacccatac gatgttcctg      1920
actatgcggg tatgaaaaac atcaaaaaaa accaggtaat gaacctgggt ccgaactcta      1980
aactgctgaa agaatacaaa tcccagctga tcgaactgaa catcgaacag ttcgaagcag      2040
gtatcggtct gatcctgggt gatgcttaca tccgttctcg tgatgaaggt aaaacctact      2100
gtatgcagtt cgagtggaaa aacaaagcat acatggacca cgtatgtctg ctgtacgatc      2160
agtgggtact gtccccgccg cacaaaaaag aacgtgttaa ccacctgggt aacctggtaa      2220
tcacctgggg cgcccagact ttcaaacacc aagcttccaa caaactggct aacctgttca      2280
tcgttaacaa caaaaaaacc atcccgaaca acctggttga aaactacctg accccgatgt      2340
ctctggcata ctggttcatg gatgatggtg gtaaatggga ttacaacaaa aactctacca      2400
acaaatcgat cgtactgaac acccagtctt tcactttcga agaagtagaa tacctggtta      2460
agggtctgcg taacaaattc caactgaact gttacgtaaa aatcaacaaa aacaaaccga      2520
tcatctacat cgattctatg tcttacctga tcttctacaa cctgatcaaa ccgtacctga      2580
tcccgcagat gatgtacaaa ctgccgaaca ctatctcctc cgaaactttc ctgaaataag      2640
gtaccgatcc agacatgata agatacattg atgagtttgg acaaaccaca actagaatgc      2700
agtgaaaaaa atgctttatt tgtgaaattt gtgatgctat tgctttattt gtaaccatta      2760
taagctgcaa taaacaagtt aacaacaaca attgcattca ttttatgttt caggttcagg      2820
gggaggtgtg ggaggttttt taaagcaagt aaaacctcta caaatgtggt atggctgatt      2880
atgatcatcg taaacttggt ctgacagtta ccaatgctta atcagtgagg cacctatctc      2940
agcgatctgt ctatttcgtt catccatagt tgcctgactc cccgtcgtgt agataactac      3000
gatacgggag ggcttaccat ctggccccag tgctgcaatg ataccgcgag acccacgctc      3060
accggctcca gatttatcag caataaacca gccagccgga agggccgagc gcagaagtgg      3120
tcctgcaact ttatccgcct ccatccagtc tattaattgt tgccgggaag ctagagtaag      3180
tagttcgcca gttaatagtt tgcgcaacgt tgttgccatt gctacaggca tcgtggtgtc      3240
acgctcgtcg tttggtatgg cttcattcag ctccggttcc caacgatcaa ggcgagttac      3300
atgatccccc atgttgtgca aaaaagcggt tagctccttc ggtcctccga tcgttgtcag      3360
aagtaagttg gccgcagtgt tatcactcat ggttatggca gcactgcata attctcttac      3420
tgtcatgcca tccgtaagat gcttttctgt gactggtgag tactcaacca agtcattctg      3480
agaatagtgt atgcggcgac cgagttgctc ttgcccggcg tcaatacggg ataataccgc      3540
gccacatagc agaactttaa aagtgctcat cattggaaaa cgttcttcgg ggcgaaaact      3600
ctcaaggatc ttaccgctgt tgagatccag ttcgatgtaa cccactcgtg cacccaactg      3660
atcttcagca tcttttactt tcaccagcgt ttctgggtgt gcaaaaacag gaaggcaaaa      3720
tgccgcaaaa aagggaataa gggcgacacg gaaatgttga atactcatac tcttcctttt      3780
```

```
tcaatattat tgaagcattt atcagggtta ttgtctcatg agcggataca tatttgaatg    3840
tatttagaaa aataaacaaa tagggggttcc gcgcacattt ccccgaaaag tgccacctga    3900
cgtctaagaa accattatta tcatgacatt aacctataaa aataggcgta tcacgaggcc    3960
ctttcgtctc gcgcgtttcg gtgatgacgg tgaaaacctc tgacacatgc agctcccgga    4020
gacggtcaca gcttgtctgt aagcggatgc cgggagcaga caagcccgtc agggcgcgtc    4080
agcgggtgtt ggcgggtgtc ggggctggct taactatgcg gcatcagagc agattgtact    4140
gagagtgcac catatgcggt gtgaaatacc gcacagatgc gtaaggagaa ataccgcat    4200 caggcgccat tcgccattca ggctgcgcaa ctgttgggaa gggcgatcgg tgcgggcctc    4260
ttcgctatta cgccagctgg cgaaaggggg atgtgctgca aggcgattaa gttgggtaac    4320
gccagggttt tcccagtcac gacgttgtaa aacgacggcc agtgaattac caactttgta    4380
caaaaaagca gattaccctg ttatccctac atcatcaata atataccttt ttttggattg    4440
aagccaatat gataatgagg gggtggagtt tgtgacgtgg cgcggggcgt gggaacgggg    4500
cgggtgacgt agtagtgtgg cggaagtgtg atgttgcaag tgtggcggaa cacatgtaag    4560
cgacggatgt ggcaaaagtg acgttttttgg tgtgcgccgg tgtacacagg aagtgacaat    4620
tttcgcgcgg ttttaggcgg atgttgtagt aaatttgggc gtaaccgagt aagatttggc    4680
cattttcgcg gaaaactga ataagaggaa gtgaaatctg aataattttg tgttactcat    4740
agcgcgtaat atttgtctag ggccgcgggg actttgaccg tttacgtgga gactcgccca    4800
ggtgtttttc tcaggtgttt tccgcgttcc gggtcaaagt tggcgttta ttattaatta    4860 agtttaaacg gcgcgcctaa tagtaatcaa ttacggggtc attagttcat agcccatata    4920
tggagttccg cgttacataa cttacggtaa atggcccgcc tggctgaccg cccaacgacc    4980
cccgcccatt gacgtcaata atgacgtatg ttcccatagt aacgccaata gggactttcc    5040
attgacgtca atgggtggag tatttacggt aaactgccca cttggcagta catcaagtgt    5100
atcatatgcc aagtacgccc cctattgacg tcaatgacgg taaatggccc gcctggcatt    5160
atgcccagta catgacctta tgggactttc ctacttggca gtacatctac gtattagtca    5220
tcgctattac catggtgatg cggttttggc agtacatcaa tgggcgtgga tagcggtttg    5280
actcacgggg atttccaagt ctccacccca ttgacgtcaa tgggagtttg ttttggcacc    5340
aaaatcaacg ggactttcca aaatgtcgta acaactccgc cccattgacg caaatgggcg    5400
gtaggcgtgt acggtgggag gtctatataa gcagagctgg tttagtgaac cgtcagatgg    5460
taccggcccc gggagacggc ggcggtggcg gcgcgggcag agcaaggacg cggcggatcc    5520
cactcgcaca gcagcgcact cggtgccccg cgcagggtcg gtaccgaatt gccaccatgg    5580
tgagcaaggg cgaggaggtc atcaaagagt tcatgcgctt caaggtgcgc atggagggct    5640
ccatgaacgg ccacgagttc gagatcgagg gcgagggcga gggccgcccc tacgagggca    5700
cccagaccgc caagctgaag gtgaccaagg gcggcccctt gcccttcgcc tgggacatcc    5760
tgtcccccca gttcatgtac ggctccaagg cgtacgtgaa gcaccccgcc gacatccccg    5820
attacaagaa gctgtccttc cccgagggct tcaagtggga gcgcgtgatg aacttcgagg    5880
acggcggtct ggtgaccgtg acccaggact cctccctgca ggacggcacg ctgatctaca    5940
aggtgaagat gcgcggcacc aacttccccc ccgacggccc cgtaatgcag aagaagacca    6000
tgggctggga ggcctccacc gagcgcctgt accccgcga cggcgtgctg aagggcgaga    6060
tccaccaggc cctgaagctg aaggacggcg gccactacct ggtggagttc aagaccatct    6120
```

```
acatggccaa gaagcccgtg caactgcccg gctactacta cgtggacacc aagctggaca    6180
tcacctccca caacgaggac tacaccatcg tggaacagta cgagcgctcc gagggccgcc    6240
accacctgtt cctggggcat ggcaccggca gcaccggcag cggcagctcc ggcaccgcct    6300
cctccgagga caacaacatg gccgtcatca aagagttcat gcgcttcaag gtgcgcatgg    6360
agggctccat gaacggccac gagttcgaga tcgagggcga gggcgagggc cgcccctacg    6420
agggcaccca gaccgccaag ctgaaggtga ccaaggcgg cccctgccc ttcgcctggg    6480
acatcctgtc cccccagttc atgtacggct ccaaggcgta cgtgaagcac cccgccgaca    6540
tccccgatta caagaagctg tccttccccg agggcttcaa gtgggagcgc gtgatgaact    6600
tcgaggacgg cggtctggtg accgtgaccc aggactcctc cctgcaggac ggcacgctga    6660
tctacaaggt gaagatgcgc ggcaccaact ccccccccga cggccccgta atgcagaaga    6720
agaccatggg ctgggaggcc tccaccgagc gcctgtaccc ccgcgacggc gtgctgaagg    6780
gcgagatcca ccaggccctg aagctgaagg acggcggccg ctacctggtg gagttcaaga    6840
ccatctacat ggccaagaag cccgtgcaac tgcccggcta ctactacgtg gacaccaagc    6900
tggacatcac ctcccacaac gaggactaca ccatcgtgga acagtacgag cgctccgagg    6960
gccgccacca cctgttcctg tacggcatgg acgagctgta caagtaaaat tcatactcga    7020
gatacatatg ataagatctg tttgaatgag gcttcagtac tttacagaat cgttgcctgc    7080
acatcttgga aacacttgct gggattactt cttcaggtta acccaacaga aggctcgaga    7140
aggtatattg ctgttgacag tgagcgatct cgcttgggcg agagtaagta gtgaagccac    7200
agatgtactt actctcgccc aagcgagagt gcctactgcc tcggaattca gggggctact    7260
ttaggagcaa ttatcttgtt tactaaaact gaataccttg ctatctcttt gatacatttt    7320
tacaaagctg aattaaaatg gtataaatta aatcactaga tctatagata tcataaccgg    7380
tatagcggcc gcaagaggta agggtttaag ggatggtcgg ttggtggggt attaatgttt    7440
aattacctgg agcacctgcc tgaaatcact ttttttcagg ttggaatcga taatcaacct    7500
ctggattaca aaatttgtga aagattgact ggtattctta actatgttgc tccttttacg    7560
ctatgtggat acgctgcttt aatgcctttg tatcatgcta ttgcttcccg tatggctttc    7620
attttctcct ccttgtataa atcctggttg ctgtctcttt atgaggagtt gtggcccgtt    7680
gtcaggcaac gtggcgtggt gtgcactgtg tttgctgacg caacccccac tggttggggc    7740
attgccacca cctgtcagct cctttccggg actttcgctt tccccctccc tattgccacg    7800
gcggaactca tcgccgcctg ccttgcccgc tgctggacag ggctcggct gttgggcact    7860
gacaattccg tggtgttgtc ggggaagctg acgtcctttc catggctgct cgcctgtgtt    7920
gccacctgga ttctgcgcgg gacgtccttc tgctacgtcc cttcggccct caatccagcg    7980
gaccttcctt cccgcggcct gctgccggct ctgcggcctc ttccgcgtct cgccttcgc    8040
cctcagacga tcggatctc cctttgggcc gcctcccgc ctgctgcagg gcgcatcgt    8100
ggatgggagt ccgtgtgtgc ctggagatta ccctggacac ctctgctttt ttttttttac    8160
tttagcggtt gcctcctagg cctgactcct tcccatgttg aactggaggc agccacgtta    8220
ggtgtcaatg tcctggcatc agtatgaaca gtcagtagtc ccaggcagg gccacacttc    8280
tcccatcttc tgcttccacc ccagcttgtg attgctagcc tcccagagct caattgctgt    8340
gccttctagt tgccagccat ctgttgtttg ccctccccc gtgccttcct tgaccctgga    8400
aggtgccact cccactgtcc tttcctaata aaatgaggaa attgcatcgc attgtctgag    8460
taggtgtcat tctattctgg ggggtggggt ggggcaggac agcaagggg aggattggga    8520
```

```
agacaatagc aggcatgctg gggatgcggt gggctctatg gacgcgtcgg ccgctgcagc    8580
tcgagtctag agctgacggc gcgcctgaaa tgtgtgggcg tggcttaagg gtgggaaaga    8640
atatataagg tgggggtctt atgtagtttt gtatctgttt tgcagcagcc gccgccgcca    8700
tgagcaccaa ctcgtttgat ggaagcattg tgagctcata tttgacaacg cgcatgcccc    8760
catgggccgg ggtgcgtcag aatgtgatgg gctccagcat tgatggtcgc cccgtcctgc    8820
ccgcaaactc tactaccttg acctacgaga ccgtgtctgg aacgccgttg gagactgcag    8880
cctccgccgc cgcttcagcc gctgcagcca cccgcccgcgg gattgtgact gactttgctt    8940
tcctgagccc gcttgcaagc agtgcagctt cccgttcatc cgcccgcgat gacaagttga    9000
cggctctttt ggcacaattg gattctttga cccgggaact taatgtcgtt tctcagcagc    9060
tgttggatct gcgccagcag gtttctgccc tgaaggcttc ctcccctccc aatgcgtttt    9120
aaaacataaa taaaaaacca gactctgttt ggatttggat caagcataag tgtcttgctg    9180
tctttattta gggttttgc gcgcgcggta ggcccgggac cagcggtctc ggtcgttgag    9240
ggtcctgtgt attttttcca ggacgtggta aaggtgactc tggatgttca gatacatggg    9300
cataagcccg tctctggggt ggaggtagca ccactgcaga gcttcatgct gcggggtggt    9360
gttgtagatg atccagtcgt agcaggagcg ctgggcgtgg tgcctaaaaa tgtcttcag    9420 tagcaagctg attgccaggg gcaggcccctt ggtgtaagtg tttacaaagc ggttaagctg    9480
ggatgggtgc atacgtgggg atatgagatg catcttggac tgtattttta ggttggctat    9540
gttcccagcc atatccctcc ggggattcat gttgtgcaga accaccagca cagtgtatcc    9600
ggtgcacttg ggaaatttgt catgtagctt agaaggaaat gcgtggaaga acttggagac    9660
gcccttgtga cctccaagat tttccatgca ttcgtccata atgatggcaa tgggcccacg    9720
ggcggcggcc tgggcgaaga tatttctggg atcactaacg tcatagttgt gttccaggat    9780
gagatcgtca taggccattt ttacaaagcg cgggcggagg gtgccagact gcggtataat    9840
ggttccatcc ggcccagggg cgtagttacc ctcacagatt tgcatttccc acgctttgag    9900
ttcagatggg gggatcatgt ctacctgcgg ggcgatgaag aaaacggttt ccggggtagg    9960
ggagatcagc tgggaagaaa gcaggttcct gagcagctgc gacttaccgc agccggtggg   10020
cccgtaaatc acacctatta ccgggtgcaa ctggtagtta agagagctgc agctgccgtc   10080
atccctgagc agggggggcca cttcgttaag catgtccctg actcgcatgt tttccctgac   10140
caaatccgcc agaaggcgct cgccgcccag cgatagcagt tcttgcaagg aagcaaagtt   10200
tttcaacggt ttgagaccgt ccgccgtagg catgcttttg agcgtttgac caagcagttc   10260
caggcggtcc cacagctcgg tcacctgctc tacggcatct cgatccagca tatctcctcg   10320
tttcgcgggt tgggcggct ttcgctgtac ggcagtagtc ggtgctcgtc cagacgggcc   10380
agggtcatgt ctttccacgg gcgcagggtc ctcgtcagcg tagtctgggt cacggtgaag   10440
gggtgcgctc cgggctgcgc gctggccagg gtgcgcttga gctggtcct gctggtgctg   10500 aagcgctgcc ggtcttcgcc ctgcgcgtcg gccaggtagc atttgaccat ggtgtcatag   10560
tccagcccct ccgcggcgtg gcccttggcg cgcagcttgc ccttggagga ggcgccgcac   10620
gaggggcagt gcagactttt gagggcgtag agcttgggcg cgagaaatac cgattccggg   10680
gagtaggcat ccgcgccgca ggccccgcag acggtctcgc attccacgag ccaggtgagc   10740 tctgccgtt cggggtcaaa aaccaggttt ccccatgct ttttgatgcg tttcttacct   10800 ctggttttcca tgagccggtg tccacgctcg gtgacgaaaa ggctgtccgt gtccccgtat   10860
```

```
acagacttga gaggcctgtc ctcgagcggt gttccgcggt cctcctcgta tagaaactcg   10920
gaccactctg agacaaaggc tcgcgtccag gccagcacga aggaggctaa gtgggagggg   10980
tagcggtcgt tgtccactag ggggtccact cgctccaggg tgtgaagaca catgtcgccc   11040
tcttcggcat caaggaaggt gattggtttg taggtgtagg ccacgtgacc gggtgttcct   11100
gaaggggggc tataaaaggg ggtgggggcg cgttcgtcct cactctcttc cgcatcgctg   11160
tctgcgaggg ccagctgttg gggtgagtac tccctctgaa aagcgggcat gacttctgcg   11220
ctaagattgt cagtttccaa aaacgaggag gatttgatat tcacctggcc cgcggtgatg   11280
cctttgaggg tggccgcatc catctggtca gaaaagacaa tctttttgtt gtcaagcttg   11340
gtggcaaacg acccgtagag ggcgttggac agcaacttgg cgatggagcg cagggtttgg   11400
tttttgtcgc gatcggcgcg ctccttggcc gcgatgttta gctgcacgta ttcgcgcgca   11460
acgcaccgcc attcgggaaa gacggtggtg cgctcgtcgg gcaccaggtg cacgcgccaa   11520
ccgcggttgt gcagggtgac aaggtcaacg ctggtggcta cctctccgcg taggcgctcg   11580
ttggtccagc agaggcggcc gcccttgcgc gagcagaatg gcggtagggg gtctagctgc   11640
gtctcgtccg gggggtctgc gtccacggta aagaccccgg gcagcaggcg cgcgtcgaag   11700
tagtctatct tgcatccttg caagtctagc gcctgctgcc atgcgcgggc ggcaagcgcg   11760
cgctcgtatg ggttgagtgg gggaccccat ggcatggggt gggtgagcgc ggaggcgtac   11820
atgccgcaaa tgtcgtaaac gtagaggggc tctctgagta ttccaagata tgtagggtag   11880
catcttccac cgcggatgct ggcgcgcacg taatcgtata gttcgtgcga gggagcgagg   11940
aggtcgggac cgaggttgct acgggcgggc tgctctgctc ggaagactat ctgcctgaag   12000
atggcatgtg agttggatga tatggttgga cgctggaaga cgttgaagct ggcgtctgtg   12060
agacctaccg cgtcacgcac gaaggaggcg taggagtcgc gcagcttgtt gaccagctcg   12120
gcggtgacct gcacgtctag ggcgcagtag tccagggttt ccttgatgat gtcatactta   12180
tcctgtccct tttttttcca cagctcgcgg ttgaggacaa actcttcgcg gtctttccag   12240
tactcttgga tcggaaaccc gtcggcctcc gaacggtaag agcctagcat gtagaactgg   12300
ttgacggcct ggtaggcgca gcatcccttt tctacgggta gcgcgtatgc ctgcgcggcc   12360
ttccggagcg aggtgtgggt gagcgcaaag gtgtccctga ccatgacttt gaggtactgg   12420
tatttgaagt cagtgtcgtc gcatccgccc tgctcccaga gcaaaaagtc cgtgcgcttt   12480
ttggaacgcg gatttggcag ggcgaaggtg acatcgttga agagtatctt tcccgcgcga   12540
ggcataaagt tgcgtgtgat gcggaagggt cccggcacct cggaacggtt gttaattacc   12600
tgggcggcga gcacgatctc gtcaaagccg ttgatgttgt ggcccacaat gtaaagttcc   12660
aagaagcgcg ggatgccctt gatggaaggc aattttttaa gttcctcgta ggtgagctct   12720
tcaggggagc tgagcccgtg ctctgaaagg gcccagtctg caagatgagg gttggaagcg   12780
acgaatgagc tccacaggtc acgggccatt agcatttgca ggtggtcgcg aaaggtccta   12840
aactggcgac ctatggccat ttttctgggg gtgatgcagt agaaggtaag cgggtcttgt   12900
tcccagcggt cccatccaag gttcgcggct aggtctcgcg cggcagtcac tagaggctca   12960
tctccgccga acttcatgac cagcatgaag ggcacgagct gcttcccaaa gccccccatc   13020
caagtatagg tctctacatc gtaggtgaca aagagacgct cggtgcgagg atgcgagccg   13080
atcgggaaga actggatctc ccgccaccaa ttggaggagt ggctattgat gtggtgaaag   13140
tagaagtccc tgcgacgggc cgaacactcg tgctggcttt tgtaaaaacg tgcgcagtac   13200
tggcagcggt gcacgggctg tacatcctgc acgaggttga cctgacgacc gcgcacaagg   13260
```

```
aagcagagtg ggaatttgag cccctcgcct ggcgggtttg gctggtggtc ttctacttcg   13320
gctgcttgtc cttgaccgtc tggctgctcg aggggagtta cggtggatcg gaccaccacg   13380
ccgcgcgagc ccaaagtcca gatgtccgcg cgcggcggtc ggagcttgat gacaacatcg   13440
cgcagatggg agctgtccat ggtctggagc tcccgcggcg tcaggtcagg cgggagctcc   13500
tgcaggttta cctcgcatag acgggtcagg gcgcgggcta gatccaggtg atacctaatt   13560
tccaggggct ggttggtggc ggcgtcgatg gcttgcaaga ggccgcatcc ccgcggcgcg   13620
actacggtac cgcgcggcgg gcggtgggcc gcggggtgt ccttggatga tgcatctaaa    13680
agcggtgacg cgggcgagcc cccggaggta ggggggggctc cggacccgcc gggagagggg   13740
gcaggggcac gtcggcgccg cgcgcgggca ggagctggtg ctgcgcgcgt aggttgctgg    13800
cgaacgcgac gacgcggcgg ttgatctcct gaatctggcg cctctgcgtg aagacgacgg   13860
gcccggtgag cttgagcctg aaagagagtt cgacagaatc aatttcggtg tcgttgacgg   13920
cggcctggcg caaaatctcc tgcacgtctc ctgagttgtc ttgataggcg atctcggcca    13980
tgaactgctc gatctcttcc tcctggagat ctccgcgtcc ggctcgctcc acggtggcgg   14040
cgaggtcgtt ggaaatgcgg gccatgagct gcgagaaggc gttgaggcct ccctcgttcc    14100
agacgcggct gtagaccacg ccccccttcgg catcgcgggc gcgcatgacc acctgcgcga   14160
gattgagctc cacgtgccgg gcgaagacgg cgtagtttcg caggcgctga aagaggtagt   14220
tgagggtggt ggcggtgtgt tctgccacga agaagtacat aacccagcgt cgcaacgtgg   14280
attcgttgat atcccccaag gcctcaaggc gctccatggc ctcgtagaag tccacggcga   14340
agttgaaaaa ctgggagttg cgcgccgaca cggttaactc ctcctccaga agacggatga    14400
gctcggcgac agtgtcgcgc acctcgcgct caaaggctac aggggcctct tcttcttctt   14460
caatctcctc ttccataagg gcctcccctt cttcttcttc tggcggcggt gggggagggg   14520
ggacacggcg gcgacgacgg cgcaccggga ggcggtcgac aaagcgctcg atcatctccc    14580
cgcggcgacg gcgcatggtc tcggtgacgg cgcggccgtt ctcgcggggg cgcagttgga   14640
agacgccgcc cgtcatgtcc cggttatggg ttggcggggg gctgccatgc ggcagggata    14700
cggcgctaac gatgcatctc aacaattgtt gtgtaggtac tccgccgccg agggacctga   14760
gcgagtccgc atcgaccgga tcggaaaacc tctcgagaaa ggcgtctaac cagtcacagt   14820
cgcaaggtag gctgagcacc gtggcgggcg gcagcgggcg gcggtcgggg ttgtttctgg   14880
cggaggtgct gctgatgatg taattaaagt aggcggtctt gagacggcgg atggtcgaca   14940
gaagcaccat gtccttgggt ccggcctgct gaatgcgcag gcggtcggcc atgccccagg   15000
cttcgttttg acatcggcgc aggtctttgt agtagtcttg catgagcctt tctaccggca   15060
cttcttcttc tccttcctct tgtcctgcat ctccttgcatc tatcgctgcg gcggcggcgg   15120
agtttggccg taggtggcgc cctcttcctc ccatgcgtgt gaccccgaag cccctcatcg    15180
gctgaagcag ggctaggtcg cgcacaacgc gctcggctaa tatggcctgc tgcacctgcg   15240
tgagggtaga ctggaagtca tccatgtcca caaagcggtg gtatgcgccc gtgttgatgg   15300
tgtaagtgca gttggccata acggaccagt taacggtctg gtgacccggc tgcgagagct   15360
cggtgtacct gagacgcgag taagccctcg agtcaaatac gtagtcgttg caagtccgca   15420
ccaggtactg gtatcccacc aaaaagtgcg gcggcggctg gcggtagagg ggccagcgta   15480
gggtggccgg ggctccgggg gcgagatctt ccaacataag gcgatgatat ccgtagatgt   15540
acctggacat ccaggtgatg ccggcggcgg tggtggaggc gcgcggaaag tcgcggacgc   15600
```

```
ggttccagat gttgcgcagc ggcaaaaagt gctccatggt cgggacgctc tggccggtca   15660
ggcgcgcgca atcgttgacg ctctagaccg tgcaaaagga gagcctgtaa gcgggcactc   15720
ttccgtggtc tggtggataa attcgcaagg gtatcatggc ggacgaccgg ggttcgagcc   15780
ccgtatccgg ccgtccgccg tgatccatgc ggttaccgcc cgcgtgtcga acccaggtgt   15840
gcgacgtcag acaacggggg agtgctcctt ttggcttcct tccaggcgcg gcggctgctg   15900
cgctagcttt tttggccact ggccgcgcgc agcgtaagcg gttaggctgg aaagcgaaag   15960
cattaagtgg ctcgctccct gtagccggag ggttattttc caagggttga gtcgcgggac   16020
ccccggttcg agtctcggac cggcggact gcggcgaacg ggggtttgcc tccccgtcat   16080
gcaagacccc gcttgcaaat tcctccggaa acagggacga gccccttttt tgcttttccc   16140
agatgcatcc ggtgctgcgg cagatgcgcc ccctcctca gcagcggcaa gagcaagagc   16200
agcggcagac atgcagggca ccctcccctc ctcctaccgc gtcaggaggg gcgacatccg   16260
cggttgacgc ggcagcagat ggtgattacg aaccccgcg gcgccgggcc cggcactacc   16320
tggacttgga ggagggcgag ggcctggcgc ggctaggagc ccctctcct gagcggtacc   16380 caagggtgca gctgaagcgt gatacgcgtg aggcgtacgt gccgcggcag aacctgtttc   16440
gcgaccgcga gggagaggag cccgaggaga tgcgggatcg aaagttccac gcagggcgcg   16500
agctgcggca tggcctgaat cgcgagcggt tgctgcgcga ggaggacttt gagcccgacg   16560
cgcgaaccgg gattagtccc gcgcgcgcac acgtggcggc cgccgacctg gtaaccgcat   16620
acgagcagac ggtgaaccag gagattaact ttcaaaaaag ctttaacaac cacgtgcgta   16680
cgcttgtggc gcgcgaggag gtggctatag gactgatgca tctgtgggac tttgtaagcg   16740
cgctggagca aaacccaaat agcaagccgc tcatggcgca gctgttcctt atagtgcagc   16800
acagcaggga caacgaggca ttcagggatg cgctgctaaa catagtagag cccgagggcc   16860
gctggctgct cgatttgata aacatcctgc agagcatagt ggtgcaggag cgcagcttga   16920
gcctggctga caaggtggcc gccatcaact attccatgct tagcctgggc aagttttacg   16980
cccgcaagat ataccatacc ccttacgttc ccatagacaa ggaggtaaag atcgaggggt   17040
tctacatgcg catggcgctg aaggtgctta ccttgagcga cgacctgggc gtttatcgca   17100
acgagcgcat ccacaaggcc gtgagcgtga ccggcggcg cgagctcagc gaccgcgagc   17160
tgatgcacag cctgcaaagg gccctggctg cacgggcag cggcgataga gaggccgagt   17220
cctactttga cgcgggcgct gacctgcgct gggccccaag ccgacgcgcc ctggaggcag   17280
ctggggccgg acctgggctg gcggtggcac ccgcgcgcgc tggcaacgtc ggcggcgtgg   17340
aggaatatga cgaggacgat gagtacgagc cagaggacgg cgagtactaa gcggtgatgt   17400
ttctgatcag atgatgcaag acgcaacgga cccggcggtg cgggcggcgc tgcagagcca   17460
gccgtccggc cttaactcca cggacgactg gcgccaggtc atggaccgca tcatgtcgct   17520
gactgcgcgc aatcctgacg cgttccggca gcagccgcag gccaaccggc tctccgcaat   17580
tctggaagcg gtggtcccgg cgcgcgcaaa ccccacgcac gagaaggtgc tggcgatcgt   17640
aaacgcgctg gccgaaaaca gggccatccg gcccgacgag gccggcctgg tctacgacgc   17700
gctgcttcag cgcgtggctc gttacaacag cggcaacgtg cagaccaacc tggaccggct   17760
ggtgggggat gtgcgcgagg ccgtggcgca gcgtgagcgc gcgcagcagc agggcaacct   17820
gggctccatg gttgcactaa acgccttcct gagtacacag cccgccaacg tgccgcgggg   17880
acaggaggac tacaccaact ttgtgagcgc actgcgcgcta atggtgactg agacaccgca   17940
aagtgaggtg taccagtctg ggccagacta ttttttccag accagtagac aaggcctgca   18000
```

```
gaccgtaaac ctgagccagg ctttcaaaaa cttgcagggg ctgtgggggg tgcgggctcc    18060
cacaggcgac cgcgcgaccg tgtctagctt gctgacgccc aactcgcgcc tgttgctgct    18120
gctaatagcg cccttcacgg acagtggcag cgtgtcccgg gacacatacc taggtcactt    18180
gctgacactg taccgcgagg ccataggtca ggcgcatgtg gacgagcata ctttccagga    18240
gattacaagt gtcagccgcg cgctggggca ggaggacacg ggcagcctgg aggcaaccct    18300
aaactacctg ctgaccaacc ggcggcagaa gatcccctcg ttgcacagtt taaacagcga    18360
ggaggagcgc attttgcgct acgtgcagca gagcgtgagc cttaacctga tgcgcgacgg    18420
ggtaacgccc agcgtggcgc tggacatgac cgcgcgcaac atggaaccgg gcatgtatgc    18480
ctcaaaccgg ccgttttatca accgcctaat ggactacttg catcgcgcgg ccgccgtgaa    18540
ccccgagtat ttcaccaatg ccatcttgaa cccgcactgg ctaccgcccc tggtttccta    18600
caccggggga ttcgaggtgc ccgagggtaa cgatggattc ctctgggacg acatagacga    18660
cagcgtgttt tccccgcaac cgcagaccct gctagagttg caacagcgcg agcaggcaga    18720
ggcggcgctg cgaaaggaaa gcttccgcag gccaagcagc ttgtccgatc taggcgctgc    18780
ggccccgcgg tcagatgcta gtagcccatt tccaagcttg ataggggtctc ttaccagcac    18840 tcgcaccacc cgcccgcgcc tgctgggcga ggaggagtac ctaaacaact cgctgctgca    18900
gccgcagcgc gaaaaaaacc tgcctccggc atttcccaac aacgggatag agagcctagt    18960
ggacaagatg agtagatgga agacgtacgc gcaggagcac agggacgtgc caggcccgcg    19020
cccgcccacc cgtcgtcaaa ggcacgaccg tcagcggggt ctggtgtggg aggacgatga    19080
ctcggcagac gacagcagcg tcctggatttt gggagggagt ggcaacccgt ttgcgcacct    19140
tcgccccagg ctggggagaa tgttttaaaa aaaaaaagc atgatgcaaa ataaaaaact    19200
caccaaggcc atggcaccga cgttggtttt tcttgtattc cccttagtat gcggcgcgcg    19260
gcgatgtatg aggaaggtcc tcctccctcc tacgagagtg tggtgagcgc ggcgccagtg    19320
gcggcggcgc tgggttctcc cttcgatgct cccctggacc cgccgtttgt gcctccgcgg    19380
tacctgcggc ctaccggggg gagaaacagc atccgttact ctgagttggc acccctattc    19440
gacaccaccc gtgtgtacct ggtggacaac aagtcaacgg atgtggcatc cctgaactac    19500
cagaacgacc acagcaactt tctgaccacg gtcattcaaa acaatgacta cagcccgggg    19560
gaggcaagca cacagaccat caatcttgac gaccggtcgc actggggcgg cgacctgaaa    19620
accatcctgc ataccaacat gccaaatgtg aacgagttca tgtttaccaa taagtttaag    19680
gcgcgggtga tggtgtcgcg cttgcctact aaggacaatc aggtggagct gaaatacgag    19740
tgggtggagt tcacgctgcc cgagggcaac tactccgaga ccatgaccat agaccttatg    19800
aacaacgcga tcgtggagca ctacttgaaa gtgggcagac agaacggggt tctggaaagc    19860
gacatcgggg taaagtttga cacccgcaac ttcagactgg ggtttgaccc cgtcactggt    19920
cttgtcatgc ctgggtata tacaaacgaa gccttccatc cagacatcat tttgctgcca    19980
ggatgcgggg tggacttcac ccacagccgc ctgagcaact tgttgggcat ccgcaagcgg    20040
caacccttcc aggagggctt taggatcacc tacgatgatc tggagggtgg taacattccc    20100
gcactgttgg atgtggacgc ctaccaggcg agccttgaaa atgacaccga acagggcggg    20160
ggtggcgcag gcggcagcaa cagcagtggc agcggcgcgg aagagaactc caacgcggca    20220
gccgcggcaa tgcagccggt ggaggacatg aacgatcatg ccattcgcgg cgacaccttt    20280
gccacacggg ctgaggagaa gcgcgctgag gccgaagcag cggccgaagc tgccgccccc    20340
```

```
gctgcgcaac ccgaggtcga gaagcctcag aagaaaccgg tgatcaaacc cctgacagag    20400
gacagcaaga aacgcagtta caacctaata agcaatgaca gcaccttcac ccagtaccgc    20460
agctggtacc ttgcatacaa ctacggcgac cctcagaccg gaatccgctc atggaccctg    20520
ctttgcactc ctgacgtaac ctgcggctcg gagcaggtct actggtcgtt gccagacatg    20580
atgcaagacc ccgtgacctt ccgctccacg cgccagatca gcaactttcc ggtggtgggc    20640
gccgagctgt tgcccgtgca ctccaagagc ttctacaacg accaggccgt ctactcccaa    20700
ctcatccgcc agtttacctc tctgacccac gtgttcaatc gctttcccga gaaccagatt    20760
ttggcgcgcc cgccagcccc caccatcacc accgtcagtg aaaacgttcc tgctctcaca    20820
gatcacggga cgctaccgct gcgcaacagc atcggaggag tccagcgagt gaccattact    20880
gacgccagac gccgcacctg cccctacgtt tacaaggccc tgggcatagt ctcgccgcgc    20940
gtcctatcga gccgcacttt tgagcaagc atgtccatcc ttatatcgcc cagcaataac    21000
acaggctggg gcctgcgctt cccaagcaag atgtttggcg gggccaagaa gcgctccgac    21060
caacacccag tgcgcgtgcg cgggcactac cgcgcgccct ggggcgcgca caaacgcggc    21120
cgcactgggc gcaccaccgt cgatgacgcc atcgacgcgg tggtggagga ggcgcgcaac    21180
tacacgccca cgccgccacc agtgtccaca gtggacgcgg ccattcagac cgtggtgcgc    21240
ggagcccggc gctatgctaa aatgaagaga cggcggaggc gcgtagcacg tcgccaccgc    21300
cgccgacccg gcactgccgc ccaacgcgcg gcggcggccc tgcttaaccg cgcacgtcgc    21360
accggccgac gggcggccat gcgggccgct cgaaggctgg ccgcgggtat tgtcactgtg    21420 cccccccaggt ccaggcgacg agcggccgcc gcagcagccg cggccattag tgctatgact    21480
cagggtcgca ggggcaacgt gtattgggtg cgcgactcgg ttagcggcct gcgcgtgccc    21540
gtgcgcaccc gcccccgcg caactagatt gcaagaaaaa actacttaga ctcgtactgt    21600
tgtatgtatc cagcggcggc ggcgcgcaac gaagctatgt ccaagcgcaa aatcaaagaa    21660
gagatgctcc aggtcatcgc gccggagatc tatggccccc cgaagaagga agagcaggat    21720
tacaagcccc gaaagctaaa gcgggtcaaa aagaaaaaga agatgatga tgatgaactt    21780 gacgacgagg tggaactgct gcacgctacc gcgcccaggc gacgggtaca gtggaaaggt    21840
cgacgcgtaa aacgtgtttt gcgacccggc accaccgtag tctttacgcc cggtgagcgc    21900
tccacccgca cctacaagcg cgtgtatgat gaggtgtacg gcgacgagga cctgcttgag    21960
caggccaacg agcgcctcgg ggagtttgcc tacggaaagc ggcataagga catgctggcg    22020
ttgccgctgg acgagggcaa cccaacacct agcctaaagc ccgtaacact gcagcaggtg    22080
ctgcccgcgc ttgcaccgtc cgaagaaaag cgcggcctaa agcgcgagtc tggtgacttg    22140
gcacccaccg tgcagctgat ggtacccaag cgccagcgac tggaagatgt cttggaaaaa    22200
atgaccgtgg aacctgggct ggagcccgag gtccgcgtgc ggccaatcaa gcaggtggcg    22260
ccgggactgg gcgtgcagac cgtggacgtt cagatacccca ctaccagtag caccagtatt    22320
gccaccgcca cagagggcat ggagacacaa acgtccccgg ttgcctcagc ggtggcggat    22380
gccgcggtgc aggcggtcgc tgcggccgcg tccaagacct ctacggaggt gcaaacggac    22440
ccgtggatgt ttcgcgtttc agcccccgg cgcccgcgcg ttcgaggaa gtacggcgcc    22500 gccagcgcgc tactgcccga atatgcccta catccttcca ttgcgcctac ccccggctat    22560
cgtggctaca cctaccgccc cagaagacga gcaactaccc gacgcgaac caccactgga    22620 acccgccgcc gccgtcgccg tcgccagccc gtgctggccc cgatttccgt gcgcagggtg    22680
gctcgcgaag gaggcaggac cctggtgctg ccaacagcgc gctaccaccc cagcatcgtt    22740
```

```
taaaagccgg tctttgtggt tcttgcagat atggccctca cctgccgcct ccgtttcccg    22800
gtgccgggat tccgaggaag aatgcaccgt aggaggggca tggccggcca cggcctgacg    22860
ggcggcatgc gtcgtgcgca ccaccggcgg cggcgcgcgt cgcaccgtcg catgcgcggc    22920
ggtatcctgc ccctccttat tccactgatc gccgcggcga ttggcgccgt gcccggaatt    22980
gcatccgtgg ccttgcaggc gcagagacac tgattaaaaa caagttgcat gtggaaaaat    23040
caaaataaaa agtctggact ctcacgctcg cttggtcctg taactatttt gtagaatgga    23100
agacatcaac tttgcgtctc tggccccgcg acacggctcg cgcccgttca tgggaaactg    23160
gcaagatatc ggcaccagca atatgagcgg tggcgccttc agctggggct cgctgtggag    23220
cggcattaaa aatttcggtt ccaccgttaa gaactatggc agcaaggcct ggaacagcag    23280
cacaggccag atgctgaggg ataagttgaa agagcaaaat ttccaacaaa aggtggtaga    23340
tggcctggcc tctggcatta gcggggtggt ggacctggcc aaccaggcag tgcaaaataa    23400
gattaacagt aagcttgatc cccgccctcc cgtagaggag cctccaccgg ccgtggagac    23460
agtgtctcca gaggggcgtg gcgaaaagcg tccgcgcccc gacagggaag aaactctggt    23520
gacgcaaata gacgagcctc cctcgtacga ggaggcacta aagcaaggcc tgcccaccac    23580
ccgtcccatc gcgcccatgg ctaccggagt gctgggccag cacacacccg taacgctgga    23640
cctgcctccc ccgccgaca cccagcagaa acctgtgctg ccaggcccga ccgccgttgt    23700
tgtaacccgt cctagccgcg cgtccctgcg ccgcgccgcc agcggtccgc gatcgttgcg    23760
gcccgtagcc agtggcaact ggcaaagcac actgaacagc atcgtgggtc tgggggtgca    23820
atccctgaag cgccgacgat gcttctgaat agctaacgtg tcgtatgtgt gtcatgtatg    23880
cgtccatgtc gccgccagag gagctgctga gccgccgcgc gcccgctttc caagatggct    23940 acccttcga tgatgccgca gtggtcttac atgcacatct cgggccagga cgcctcggag    24000
tacctgagcc ccgggctggt gcagtttgcc cgcgccaccg agacgtactt cagcctgaat    24060
aacaagttta gaaaccccac ggtggcgcct acgcacgacg tgaccacaga ccggtcccag    24120
cgtttgacgc tgcggttcat ccctgtggac cgtgaggata ctgcgtactc gtacaaggcg    24180
cggttcaccc tagctgtggg tgataaccgt gtgctggaca tggcttccac gtactttgac    24240
atccgcggcg tgctggacag gggccctact tttaagccct actctggcac tgcctacaac    24300
gccctggctc ccaagggtgc cccaaatcct tgcgaatggg atgaagctgc tactgctctt    24360
gaaataaacc tagaagaaga ggacgatgac aacgaagacg aagtagacga gcaagctgag    24420
cagcaaaaaa ctcacgtatt tgggcaggcg ccttattctg gtataaatat tacaaaggag    24480
ggtattcaaa taggtgtcga aggtcaaaca cctaaatatg ccgataaaac atttcaacct    24540
gaacctcaaa taggagaatc tcagtggtac gaaactgaaa ttaatcatgc agctgggaga    24600
gtccttaaaa agactacccc aatgaaacca tgttacggtt catatgcaaa acccacaaat    24660
gaaaatggag gcaaggcat tcttgtaaag caacaaaatg gaaagctaga agtcaagtg    24720 gaaatgcaat ttttctcaac tactgaggcg accgcaggca atggtgataa cttgactcct    24780
aaagtggtat tgtacagtga agatgtagat atagaaaccc cagacactca tatttcttac    24840
atgcccacta ttaaggaagg taactcacga gaactaatgg ccaacaatc tatgcccaac    24900 aggcctaatt acattgcttt tagggacaat tttattggtc taatgtatta caacagcacg    24960
ggtaatatgg gtgttctggc gggccaagca tcgcagttga atgctgttgt agatttgcaa    25020
gacagaaaca cagagctttc ataccagctt ttgcttgatt ccattggtga tagaaccagg    25080
```

```
tacttttcta tgtggaatca ggctgttgac agctatgatc cagatgttag aattattgaa    25140
aatcatggaa ctgaagatga acttccaaat tactgctttc cactgggagg tgtgattaat    25200
acagagactc ttaccaaggt aaaacctaaa acaggtcagg aaaatggatg ggaaaaagat    25260
gctacagaat tttcagataa aaatgaaata agagttggaa ataattttgc catggaaatc    25320
aatctaaatg ccaacctgtg gagaaatttc ctgtactcca acatagcgct gtatttgccc    25380
gacaagctaa agtacagtcc ttccaacgta aaaattttctg ataacccaaa cacctacgac    25440
tacatgaaca agcgagtggt ggctcccggg ttagtggact gctacattaa ccttggagca    25500
cgctggtccc ttgactatat ggacaacgtc aacccattta accaccaccg caatgctggc    25560
ctgcgctacc gctcaatgtt gctgggcaat ggtcgctatg tgcccttcca catccaggtg    25620
cctcagaagt tctttgccat taaaaacctc cttctcctgc cgggctcata cacctacgag    25680
tggaacttca ggaaggatgt taacatggtt ctgcagagct ccctaggaaa tgacctaagg    25740
gttgacggag ccagcattaa gtttgatagc atttgccttt acgccacctt cttccccatg    25800
gcccacaaca ccgcctccac gcttgaggcc atgcttagaa acgacaccaa cgaccagtcc    25860
tttaacgact atctctccgc cgccaacatg ctctacccta tacccgccaa cgctaccaac    25920
gtgcccatat ccatcccctc ccgcaactgg gcggctttcc gcggctgggc cttcacgcgc    25980
cttaagacta aggaaacccc atcactgggc tcgggctacg acccttatta cacctactct    26040
ggctctatac cctacctaga tggaaccttt tacctcaacc acacctttaa gaaggtggcc    26100
attacctttg actcttctgt cagctggcct ggcaatgacc gcctgcttac ccccaacgag    26160
tttgaaatta agcgctcagt tgacggggag ggttacaacg ttgcccagtg taacatgacc    26220
aaagactggt tcctggtaca aatgctagct aactacaaca ttggctacca gggcttctat    26280
atcccagaga gctacaagga ccgcatgtac tccttcttta gaaacttcca gcccatgagc    26340
cgtcaggtgg tggatgatac taaatacaag gactaccaac aggtgggcat cctacaccaa    26400
cacaacaact ctggatttgt tggctacctt gccccccaca tgcgcgaagg acaggcctac    26460
cctgctaact tcccctatcc gcttataggc aagaccgcag ttgacagcat tacccagaaa    26520
aagtttcttt gcgatcgcac cctttggcgc atcccattct ccagtaactt tatgtccatg    26580
ggcgcactca cagacctggg ccaaaacctt ctctacgcca actccgccca cgcgctagac    26640
atgacttttg aggtggatcc catggacgag cccacccttc tttatgtttt gtttgaagtc    26700
tttgacgtgg tccgtgtgca ccggccgcac cgcggcgtca tcgaaaccgt gtacctgcgc    26760
acgcccttct cggccggcaa cgccacaaca taaagaagca agcaacatca acaacagctg    26820
ccgccatggg ctccagtgag caggaactga agccattgt caaagatctt ggttgtgggc    26880
catatttttt gggcacctat gacaagcgct ttccaggctt tgtttctcca cacaagctcg    26940
cctgcgccat agtcaatacg gccggtcgcg agactggggg cgtacactgg atggcctttg    27000
cctggaaccc gcactcaaaa acatgctacc tctttgagcc ctttggcttt tctgaccagc    27060
gactcaagca ggtttaccag tttgagtacg agtcactcct gcgccgtagc gccattgctt    27120
cttcccccga ccgctgtata acgctggaaa agtccaccca aagcgtacag gggcccaact    27180
cggccgcctg tggactattc tgctgcatgt ttctccacgc cttgtgccaac tggccccaaa    27240 ctcccatgga tcacaacccc accatgaacc ttattaccgg ggtacccaac tccatgctca    27300
acagtcccca ggtacagccc accctgcgtc gcaaccagga acagctctac agcttcctgg    27360
agcgccactc gccctacttc cgcagccaca gtgcgcagat taggagcgcc acttcttttt    27420
gtcacttgaa aaacatgtaa aaataatgta ctagagacac tttcaataaa ggcaaatgct    27480
```

```
tttatttgta cactctcggg tgattattta cccccaccct tgccgtctgc gccgtttaaa   27540
aatcaaaggg gttctgccgc gcatcgctat gcgccactgg cagggacacg ttgcgatact   27600
ggtgtttagt gctccactta aactcaggca caaccatccg cggcagctcg gtgaagtttt   27660
cactccacag gctgcgcacc atcaccaacg cgtttagcag gtcgggcgcc gatatcttga   27720
agtcgcagtt ggggcctccg ccctgcgcgc gcgagttgcg atacacaggg ttgcagcact   27780
ggaacactat cagcgccggg tggtgcacgc tggccagcac gctcttgtcg gagatcagat   27840
ccgcgtccag gtcctccgcg ttgctcaggg cgaacggagt caactttggt agctgccttc   27900 ccaaaaggg cgcgtgccca ggctttgagt tgcactcgca ccgtagtggc atcaaaaggt   27960
gaccgtgccc ggtctgggcg ttaggataca gcgcctgcat aaaagccttg atctgcttaa   28020
aagccacctg agcctttgcg ccttcagaga agaacatgcc gcaagacttg ccggaaaact   28080
gattggccgg acaggccgcg tcgtgcacgc agcaccttgc gtcggtgttg gagatctgca   28140
ccacatttcg gccccaccgg ttcttcacga tcttggcctt gctagactgc tccttcagcg   28200
cgcgctgccc gttttcgctc gtcacatcca tttcaatcac gtgctcctta tttatcataa   28260
tgcttccgtg tagacactta agctcgcctt cgatctcagc gcagcggtgc agccacaacg   28320
cgcagcccgt gggctcgtga tgcttgtagg tcacctctgc aaacgactgc aggtacgcct   28380
gcaggaatcg ccccatcatc gtcacaaagg tcttgttgct ggtgaaggtc agctgcaacc   28440
cgcggtgctc ctcgttcagc caggtcttgc atacggccgc cagagcttcc acttggtcag   28500
gcagtagttt gaagttcgcc tttagatcgt tatccacgtg gtacttgtcc atcagcgcgc   28560
gcgcagcctc catgcccttc tcccacgcag acacgatcgg cacactcagc gggttcatca   28620
ccgtaatttc actttccgct tcgctgggct cttcctcttc ctcttgcgtc cgcataccac   28680
gcgccactgg gtcgtcttca ttcagccgcc gcactgtgcg cttacctcct ttgccatgct   28740
tgattagcac cggtgggttg ctgaaaccca ccatttgtag cgccacatct tctctttctt   28800
cctcgctgtc cacgattacc tctggtgatg gcgggcgctc gggcttggga aagggcgct   28860 tcttttcttt cttgggcgca atggccaaat ccgccgccga ggtcgatggc gcgggctgg   28920 gtgtgcgcgg caccagcgcg tcttgtgatg agtcttcctc gtcctcggac tcgatacgcc   28980
gcctcatccg cttttttggg ggcgcccggg gaggcggcgg cgacggggac ggggacgaca   29040
cgtcctccat ggttggggga cgtcgcgccg caccgcgtcc gcgctcgggg gtggtttcgc   29100
gctgctcctc ttcccgactg gccatttcct tctcctatag gcagaaaaag atcatggagt   29160
cagtcgagaa gaaggacagc ctaaccgccc cctctgagtt cgccaccacc gcctccaccg   29220
atgccgccaa cgcgcctacc accttccccg tcgaggcacc cccgcttgag gaggaggaag   29280
tgattatcga gcaggaccca ggttttgtaa gcgaagacga cgaggaccgc tcagtaccaa   29340
cagaggataa aaagcaagac caggacaacg cagaggcaaa cgaggaacaa gtcgggcggg   29400
gggacgaaag gcatggcgac tacctagatg tgggagacga cgtgctgttg aagcatctgc   29460
agcgccagtg cgccattatc tgcgacgcgt tgcaagagcg cagcgatgtg cccctcgcca   29520
tagcggatgt cagccttgcc tacgaacgcc acctattctc accgcgcgta ccccccaaac   29580
gccaagaaaa cggcacatgc gagcccaacc cgcgcctcaa cttctacccc gtatttgccg   29640
tgccagaggt gcttgccacc tatcacatct ttttccaaaa ctgcaagata cccctatcct   29700
gccgtgccaa ccgcagccga gcggacaagc agctggcctt gcggcagggc gctgtcatac   29760
ctgatatcgc ctcgctcaac gaagtgccaa aaatctttga gggtcttgga cgcgacgaga   29820
```

| | |
|---|---|
| agcgcgcggc aaacgctctg caacaggaaa acagcgaaaa tgaaagtcac tctggagtgt | 29880 |
| tggtggaact cgagggtgac aacgcgcgcc tagccgtact aaaacgcagc atcgaggtca | 29940 |
| cccactttgc ctacccggca cttaacctac cccccaaggt catgagcaca gtcatgagtg | 30000 |
| agctgatcgt gcgccgtgcg cagccctgg agagggatgc aaatttgcaa gaacaaacag | 30060 |
| aggagggcct acccgcagtt ggcgacgagc agctagcgcg ctggcttcaa acgcgcgagc | 30120 |
| ctgccgactt ggaggagcga cgcaaactaa tgatggccgc agtgctcgtt accgtggagc | 30180 |
| ttgagtgcat gcagcggttc tttgctgacc cggagatgca gcgcaagcta gaggaaacat | 30240 |
| tgcactacac ctttcgacag ggctacgtac gccaggcctg caagatctcc aacgtggagc | 30300 |
| tctgcaacct ggtctcctac cttggaattt tgcacgaaaa ccgccttggg caaaacgtgc | 30360 |
| ttcattccac gctcaagggc gaggcgcgcc gcgactacgt ccgcgactgc gtttacttat | 30420 |
| ttctatgcta cacctggcag acggccatgg gcgtttggca gcagtgcttg gaggagtgca | 30480 |
| acctcaagga gctgcagaaa ctgctaaagc aaaacttgaa ggacctatgg acggccttca | 30540 |
| acgagcgctc cgtggccgcg cacctggcgg acatcatttt ccccgaacgc ctgcttaaaa | 30600 |
| ccctgcaaca gggtctgcca gacttcacca gtcaaagcat gttgcagaac tttaggaact | 30660 |
| ttatcctaga gcgctcagga atcttgcccg ccacctgctg tgcacttcct agcgactttg | 30720 |
| tgcccattaa gtaccgcgaa tgccctccgc cgctttgggg ccactgctac cttctgcagc | 30780 |
| tagccaacta ccttgcctac cactctgaca taatggaaga cgtgagcggt gacggtctac | 30840 |
| tggagtgtca ctgtcgctgc aacctatgca ccccgcaccg ctccctggtt tgcaattcgc | 30900 |
| agctgcttaa cgaaagtcaa attatcggta cctttgagct gcagggtccc tcgcctgacg | 30960 |
| aaaagtccgc ggctccgggg ttgaaactca ctccggggct gtggacgtcg gcttaccttc | 31020 |
| gcaaatttgt acctgaggac taccacgccc acgagattag gttctacgaa gaccaatccc | 31080 |
| gcccgccaaa tgcggagctt accgcctgcg tcattaccca gggccacatt cttggccaat | 31140 |
| tgcaagccat caacaaagcc cgccaagagt ttctgctacg aaagggacgg ggggtttact | 31200 |
| tggacccca gtccggcgag gagctcaacc caatcccccc gccgcgcag ccctatcagc | 31260 |
| agcagccgcg ggcccttgct tcccaggatg gcacccaaaa agaagctgca gctgccgccg | 31320 |
| ccacccacgg acgaggagga atactgggac agtcaggcag aggaggtttt ggacgaggag | 31380 |
| gaggaggaca tgatggaaga ctgggagagc ctagacgagg aagcttccga ggtcgaagag | 31440 |
| gtgtcagacg aaacaccgtc accctcggtc gcattcccct cgccggcgcc ccagaaatcg | 31500 |
| gcaaccggtt ccagcatggc tacaacctcc gctcctcagg cgccgccggc actgcccgtt | 31560 |
| cgccgaccca accgtagatg ggacaccact ggaaccaggg ccggtaagtc caagcagccg | 31620 |
| ccgccgttag cccaagagca acaacagcgc caaggctacc gctcatggcg cgggcacaag | 31680 |
| aacgccatag ttgcttgctt gcaagactgt ggggcaaca tctccttcgc ccgccgcttt | 31740 |
| cttctctacc atcacggcgt ggccttcccc cgtaacatcc tgcattacta ccgtcatctc | 31800 |
| tacagcccat actgcaccgg cggcagcggc agcggcagca acagcagcgg ccacacagaa | 31860 |
| gcaaaggcga ccggatagca agactctgac aaagcccaag aaatccacag cggcggcagc | 31920 |
| agcaggagga ggagcgctgc gtctggcgcc caacgaaccc gtatcgaccc gcgagcttag | 31980 |
| aaacaggatt tttcccactc tgtatgctat atttcaacag agcaggggcc aagaacaaga | 32040 |
| gctgaaaata aaaaacaggt ctctgcgatc cctcacccgc agctgcctgt atcacaaaag | 32100 |
| cgaagatcag cttcggcgca cgctggaaga cgcggaggct ctcttcagta aatactgcgc | 32160 |
| gctgactctt aaggactagt ttcgcgccct ttctcaaatt taagcgcgaa aactacgtca | 32220 |

```
tctccagcgg ccacacccgg cgccagcacc tgtcgtcagc gccatttatg agcaaggaaa   32280
ttcccacgcc ctacatgtgg agttaccagc cacaaatggg acttgcggct ggagctgccc   32340
aagactactc aacccgaata aactacatga gcgcgggacc ccacatgata tcccgggtca   32400
acggaatacg cgcccaccga aaccgaattc tcctggaaca ggcggctatt accaccacac   32460
ctcgtaataa ccttaatccc cgtagttggc ccgctgccct ggtgtaccag gaaagtcccg   32520
ctcccaccac tgtggtactt cccagagacg cccaggccga agttcagatg actaactcag   32580
gggcgcagct tgcgggcggc tttcgtcaca gggtgcggtc gcccgggcag ggtataactc   32640
acctgacaat cagagggcga ggtattcagc tcaacgacga gtcggtgagc tcctcgcttg   32700
gtctccgtcc ggacgggaca tttcagatcg gcggcgccgg ccgctcttca ttcacgcctc   32760
gtcaggcaat cctaactctg cagacctcgt cctctgagcc gcgtctggag ggcattggaa   32820
ctctgcaatt tattgaggag tttgtgccat cggtctactt taaccccttc tcgggacctc   32880
ccggccacta tccggatcaa tttattccta actttgacgc ggtaaaggac tcggcggacg   32940
gctacgactg aatgttaagt ggagaggcag agcaactgcg cctgaaacac ctggtccact   33000
gtcgccgcca caagtgcttt gcccgcgact ccggtgagtt ttgctacttt gaattgcccg   33060
aggatcatat cgagggcccg gcgcacggcg tccggcttac cgcccaggga gagcttgccc   33120
gtagcctgat tcgggagttt acccagcgcc ccctgctagt tgagcgggac aggggaccct   33180
gtgttctcac tgtgatttgc aactgtccta accctggatt acaatttaaa tgcggtctca   33240
aagatcttat tccctttaac taataaaaaa aaataataaa gcatcactta cttaaaatca   33300
gttagcaaat ttctgtccag tttattcagc agcacctcct tgccctcctc ccagctctgg   33360
tattgcagct cctcctggc tgcaaacttt ctccacaatc taatggaat gtcagtttcc    33420 tcctgttcct gtccatccgc acccactatc ttcatgttgt tgcagatgaa gcgcgcaaga   33480
ccgtctgaag ataccttcaa ccccgtgtat ccatatgaca cggaaaccgg tcctccaact   33540
gtgccttttc ttactcctcc ctttgtatcc cccaatgggt ttcaagagag tccccctggg   33600
gtactctctt tgcgcctatc cgaacctcta gttacctcca atggcatgct tgcgctcaaa   33660
atgggcaacg gcctctctct ggacgaggcc ggcaaccta cctcccaaaa tgtaaccact    33720
gtgagcccac ctctcaaaaa aaccaagtca aacataaacc tggaaatatc tgcacccctc   33780
acagttacct cagaagccct aactgtggct gccgccgcac ctctaatggt cgcgggcaac   33840
acactcacca tgcaatcaca ggccccgcta accgtgcacg actccaaact tagcattgcc   33900
acccaaggac ccctcacagt gtcagaagga agctagcccc tgcaaacatc aggccccctc   33960
accaccaccg atagcagtac ccttactatc actgcctcac cccctctaac tactgccact   34020
ggtagcttgg gcattgactt gaaagagccc atttatacac aaaatggaaa actaggacta   34080
aagtacgggg ctcctttgca tgtaacagac gacctaaaca ctttgaccgt agcaactggt   34140
ccaggtgtga ctattaataa tacttccttg caaactaaag ttactggagc cttgggtttt   34200
gattcacaag gcaatatgca acttaatgta gcaggaggac taaggattga ttctcaaaac   34260
agacgcctta tacttgatgt tagttatccg tttgatgctc aaaaccaact aaatctaaga   34320
ctaggacagg ccctcttttt tataaactca gcccacaact tggatattaa ctacaacaaa   34380
ggcctttact tgtttacagc ttcaaacaat tccaaaaagc ttgaggttaa cctaagcact   34440
gccaaggggt tgatgtttga cgctacagcc atagccatta atgcaggaga tgggcttgaa   34500
tttggttcac ctaatgcacc aaacacaaat cccctcaaaa caaaaattgg ccatggccta   34560
```

```
gaatttgatt caaacaaggc tatggttcct aaactaggaa ctggccttag ttttgacagc    34620
acaggtgcca ttacagtagg aaacaaaaat aatgataagc taactttgtg gaccacacca    34680
gctccatctc ctaactgtag actaaatgca gagaaagatg ctaaactcac tttggtctta    34740
acaaaatgtg gcagtcaaat acttgctaca gtttcagttt tggctgttaa aggcagtttg    34800
gctccaatat ctggaacagt tcaaagtgct catcttatta taagatttga cgaaaatgga    34860
gtgctactaa acaattcctt cctggaccca gaatattgga actttagaaa tggagatctt    34920
actgaaggca cagcctatac aaacgctgtt ggatttatgc ctaacctatc agcttatcca    34980
aaatctcacg gtaaaactgc caaaagtaac attgtcagtc aagtttactt aaacggagac    35040
aaaactaaac ctgtaacact aaccattaca ctaaacggta cacaggaaac aggagacaca    35100
actccaagtg catactctat gtcattttca tgggactggt ctggccacaa ctacattaat    35160
gaaatatttg ccacatcctc ttacactttt tcatacattg cccaagaata aagaatcgtt    35220
tgtgttatgt ttcaacgtgt ttattttttca attgcagaaa atttcaagtc attttttcatt    35280 cagtagtata gccccaccac cacatagctt atacagatca ccgtacctta atcaaactca    35340
cagaacccta gtattcaacc tgccacctcc ctcccaacac acagagtaca cagtcctttc    35400
tccccggctg gccttaaaaa gcatcatatc atgggtaaca gacatattct taggtgttat    35460
attccacacg gtttcctgtc gagccaaacg ctcatcagtg atattaataa actccccggg    35520
cagctcactt aagttcatgt cgctgtccag ctgctgagcc acaggctgct gtccaacttg    35580
cggttgctta acgggcggcg aaggagaagt ccacgcctac atgggggtag agtcataatc    35640
gtgcatcagg atagggcggt ggtgctgcag cagcgcgcga ataaactgct gccgccgccg    35700
ctccgtcctg caggaataca acatggcagt ggtctcctca gcgatgattc gcaccgcccg    35760
cagcataagg cgccttgtcc tccgggcaca gcagcgcacc ctgatctcac ttaaatcagc    35820
acagtaactg cagcacagca ccacaatatt gttcaaaatc ccacagtgca aggcgctgta    35880
tccaaagctc atggcgggga ccacagaacc cacgtggcca tcataccaca agcgcaggta    35940
gattaagtgg cgacccctca taaacacgct ggacataaac attacctctt ttggcatgtt    36000
gtaattcacc acctcccggt accatataaa cctctgatta acatggcgc catccaccac    36060 catcctaaac cagctggcca aaacctgccc gccggctata cactgcaggg aaccgggact    36120
ggaacaatga cagtggagag cccaggactc gtaaccatgg atcatcatgc tcgtcatgat    36180
atcaatgttg gcacaacaca ggcacacgtg catacacttc ctcaggatta caagctcctc    36240
ccgcgttaga accatatccc agggaacaac ccattcctga atcagcgtaa atcccacact    36300
gcagggaaga cctcgcacgt aactcacgtt gtgcattgtc aaagtgttac attcgggcag    36360
cagcggatga tcctccagta tggtagcgcg ggtttctgtc tcaaaaggag gtagacgatc    36420
cctactgtac ggagtgcgcc gagacaaccg agatcgtgtt ggtcgtagtg tcatgccaaa    36480
tggaacgccg gacgtagtca tatttcctga agcaaaacca ggtgcgggcg tgacaaacag    36540
atctgcgtct ccggtctcgc cgcttagatc gctctgtgta gtagttgtag tatatccact    36600
ctctcaaagc atccaggcgc cccctggctt cgggttctat gtaaactcct tcatgcgccg    36660
ctgccctgat aacatccacc accgcagaat aagccacacc cagccaacct acacattcgt    36720
tctgcgagtc acacacggga ggagcgggaa gagctggaag aaccatgttt ttttttttat    36780
tccaaaagat tatccaaaac ctcaaaatga agatctatta agtgaacgcg ctcccctccg    36840
gtggcgtggt caaactctac agccaaagaa cagataatgg catttgtaag atgttgcaca    36900
atggcttcca aaaggcaaac ggccctcacg tccaagtgga cgtaaaggct aaacccttca    36960
```

```
gggtgaatct cctctataaa cattccagca ccttcaacca tgcccaaata attctcatct   37020
cgccaccttc tcaatatatc tctaagcaaa tcccgaatat taagtccggc cattgtaaaa   37080
atctgctcca gagcgccctc caccttcagc ctcaagcagc gaatcatgat tgcaaaaatt   37140
caggttcctc acagacctgt ataagattca aaagcgaaac attaacaaaa ataccgcgat   37200
cccgtaggtc ccttcgcagg gccagctgaa cataatcgtg caggtctgca cggaccagcg   37260
cggccacttc cccgccagga accatgacaa agaacccac actgattatg acacgcatac    37320
tcggagctat gctaaccagc gtagccccga tgtaagcttg ttgcatgggc ggcgatataa   37380
aatgcaaggt gctgctcaaa aaatcaggca agcctcgcg caaaaaagaa agcacatcgt    37440
agtcatgctc atgcagataa aggcaggtaa gctccggaac caccacagaa aaagacacca   37500 ttttctctc aaacatgtct gcgggtttct gcataaacac aaaataaaat aacaaaaaaa    37560
catttaaaca ttagaagcct gtcttacaac aggaaaaaca acccttataa gcataagacg   37620
gactacggcc atgccggcgt gaccgtaaaa aaactggtca ccgtgattaa aaagcaccac   37680
cgacagctcc tcggtcatgt ccggagtcat aatgtaagac tcggtaaaca catcaggttg   37740
attcacatcg gtcagtgcta aaaagcgacc gaaatagccc gggggaatac ataccccgcag   37800 gcgtagagac aacattacag cccccatagg aggtataaca aaattaatag gagagaaaaa   37860
cacataaaca cctgaaaaac cctcctgcct aggcaaaata gcaccctccc gctccagaac   37920
aacatacagc gcttccacag cggcagccat aacagtcagc cttaccagta aaaagaaaa    37980 cctattaaaa aaacaccact cgacacggca ccagctcaat cagtcacagt gtaaaaaagg   38040
gccaagtgca gagcgagtat atataggact aaaaaatgac gtaacggtta aagtccacaa   38100
aaaacaccca gaaaaccgca cgcgaaccta cgcccagaaa cgaaagccaa aaaacccaca   38160
acttcctcaa atcgtcactt ccgttttccc acgttacgtc acttcccatt ttaagaaaac   38220
tacaattccc aacacataca agttactccg ccctaaaacc tacgtcaccc gccccgttcc   38280
cacgccccgc gccacgtcac aaactccacc ccctcattat catattggct tcaatccaaa   38340
ataaggtata ttattgatga tgtagggata acagggtaat aaaatccgggg atcctctaga   38400 gtcgacctgc aggcatgcaa gcttggcgta atcatggtca tagctgtttc ctgtgtgaaa   38460
ttgttatccg ctcacaattc cacacaacat acgagccgga agcataaagt gtaaagcctg   38520
gggtgcctaa tgagtgagct a                                            38541
```

<210> SEQ ID NO 2
<211> LENGTH: 38541
<212> TYPE: DNA
<213> ORGANISM: Artificial Sequence
<220> FEATURE:
<223> OTHER INFORMATION: Synthetic adenovirus virus vector (CMV-
      tdTomato-PLSCR1-shRNA)

<400> SEQUENCE: 2

```
gttccactga gcgtcagacc ccttaataag atgatcttct tgagatcgtt ttggtctgcg      60
cgtaatctct tgctctgaaa acgaaaaaac cgccttgcag ggcggttttt cgaaggttct     120
ctgagctacc aactctttga accgaggtaa ctggcttgga ggagcgcagt caccaaaact     180
tgtcctttca gtttagcctt aaccggcgca tgacttcaag actaactcct ctaaatcaat     240
taccagtggc tgctgccagt ggtgcttttg catgtctttc cggttggac tcaagacgat      300 agttaccgga taaggcgcag cggtcggact gaacgggggg ttcgtgcata cagtccagct    360
tggagcgaac tgcctacccg gaactgagtg tcaggcgtgg aatgagacaa acgcggccat     420
```

```
aacagcggaa tgacaccggt aaaccgaaag gcaggaacag gagagcgcac gagggagccg      480 ccagggaaa cgcctggtat ctttatagtc ctgtcgggtt tcgccaccac tgatttgagc       540
gtcagatttc gtgatgcttg tcagggggc ggagcctatg gaaaaacggc tttgccgcgg       600
ccctctcact tccctgttaa gtatcttcct ggcatcttcc aggaaatctc cgccccgttc      660
gtaagccatt tccgctcgcc gcagtcgaac gaccgagcgt agcgagtcag tgagcgagga      720
agcggaatat atcctgtatc acatattctg ctgacgcacc ggtgcagcct tttttctcct      780
gccacatgaa gcacttcact gacaccctca tcagtgccaa catagtaagc cagtatacac      840
tccgctagcg ctgaggtctg cctcgtgaag aaggtgttgc tgactcatac caggcctgaa      900 tcgcccatc atccagccag aaagtgaggg agccacggtt gatgagagct ttgttgtagg       960
tggaccagtt ggtgattttg aacttttgct ttgccacgga acggtctgcg ttgtcgggaa     1020
gatgcgtgat ctgatccttc aactcagcaa aagttcgatt tattcaacaa agccacgttg     1080
tgtctcaaaa tctctgatgt tacattgcac aagataaaaa tatatcatca tgaacaataa     1140
aactgtctgc ttacataaac agtaatacaa ggggtgttga tactctcagt acaatctgct     1200
ctgatgccgc atagttaagc cagtatctgc tccctgcttg tgtgttggag gtcgctgagt     1260
agtgcgcgag caaaatttaa gctacaacaa ggcaaggctt gaccgacaat gcatgaaga      1320 atctgcttag ggttaggcgt tttgcgctgc ttcgcgatgt acgggccaga tatacgcgta     1380
tctgagggga ctagggtgtg tttaggcgaa aagcggggct tcggttgtac gcggttagga     1440 gtccctcag gatatagtag tttcgctttt gcatagggag ggggaaatgt agtcttatgc      1500
aatactcttg tagtcttgca acatggtaac gatgagttag caacatgcct tacaaggaga     1560
gaaaaagcac cgtgcatgcc gattggtgga agtaaggtgg tacgatcgtg ccttattagg     1620
aaggcaacag acgggtctga catggattgg acgaaccact gaattccgca ttgcagagat     1680
attgtattta agtgcctagc tcgatacaat aaacgccatt tgaccattca ccacattggt     1740
gtgcacctcc aagctgggta cggatccggc cttgccggcc tcgagcggcc gctagcgccg     1800
ccactatggg atcaagatcg ccaaaaaaga agagaaaggt gccgaagaag catgcagcac     1860
caccaaaaaa aaaacgaaaa gtagaagacc cacgatttat gtacccatac gatgttcctg     1920
actatgcggg tatgaaaaac atcaaaaaaa accaggtaat gaacctgggt ccgaactcta     1980
aactgctgaa agaatacaaa tcccagctga tcgaactgaa catcgaacag ttcgaagcag     2040
gtatcggtct gatcctgggt gatgcttaca tccgttctcg tgatgaaggt aaaacctact     2100
gtatgcagtt cgagtggaaa aacaaagcat acatggacca cgtatgtctg ctgtacgatc     2160
agtgggtact gtccccgccg cacaaaaaag aacgtgttaa ccacctgggt aacctggtaa     2220
tcacctgggg cgcccagact ttcaaacacc aagctttcaa caaactggct aacctgttca     2280
tcgttaacaa caaaaaaacc atcccgaaca acctggttga aaactacctg accccgatgt     2340
ctctggcata ctggttcatg gatgatggtg gtaaatggga ttacaacaaa aactctacca     2400
acaaatcgat cgtactgaac acccagtctt tcactttcga agaagtagaa tacctggtta     2460
agggtctgcg taacaaattc caactgaact gttacgtaaa aatcaacaaa acaaaccga     2520 tcatctacat cgattctatg tcttacctga tcttctacaa cctgatcaaa ccgtacctga     2580
tcccgcagat gatgtacaaa ctgccgaaca ctatctcctc cgaaactttc ctgaaataag     2640
gtaccgatcc agacatgata agatacattg atgagtttgg acaaaccaca actagaatgc     2700
agtgaaaaaa atgctttatt tgtgaaattt gtgatgctat tgctttattt gtaaccatta     2760
```

```
taagctgcaa taaacaagtt aacaacaaca attgcattca ttttatgttt caggttcagg    2820
gggaggtgtg ggaggttttt taaagcaagt aaaacctcta caaatgtggt atggctgatt    2880
atgatcatcg taaacttggt ctgacagtta ccaatgctta atcagtgagg cacctatctc    2940
agcgatctgt ctatttcgtt catccatagt tgcctgactc cccgtcgtgt agataactac    3000
gatacgggag ggcttaccat ctggccccag tgctgcaatg ataccgcgag acccacgctc    3060
accggctcca gatttatcag caataaacca gccagccgga agggccgagc gcagaagtgg    3120
tcctgcaact ttatccgcct ccatccagtc tattaattgt tgccgggaag ctagagtaag    3180
tagttcgcca gttaatagtt tgcgcaacgt tgttgccatt gctacaggca tcgtggtgtc    3240
acgctcgtcg tttggtatgg cttcattcag ctccggttcc caacgatcaa ggcgagttac    3300
atgatccccc atgttgtgca aaaagcggt tagctccttc ggtcctccga tcgttgtcag    3360
aagtaagttg gccgcagtgt tatcactcat ggttatggca gcactgcata attctcttac    3420
tgtcatgcca tccgtaagat gcttttctgt gactggtgag tactcaacca agtcattctg    3480
agaatagtgt atgcggcgac cgagttgctc ttgcccggcg tcaatacggg ataataccgc    3540
gccacatagc agaactttaa aagtgctcat cattggaaaa cgttcttcgg ggcgaaaact    3600
ctcaaggatc ttaccgctgt tgagatccag ttcgatgtaa cccactcgtg cacccaactg    3660
atcttcagca tcttttactt tcaccagcgt ttctgggtga gcaaaaacag gaaggcaaaa    3720
tgccgcaaaa aagggaataa gggcgacacg gaaatgttga atactcatac tcttcctttt    3780
tcaatattat tgaagcattt atcagggtta ttgtctcatg agcggataca tatttgaatg    3840
tatttagaaa aataaacaaa tagggggttcc gcgcacattt ccccgaaaag tgccacctga    3900
cgtctaagaa accattatta tcatgacatt aacctataaa aataggcgta tcacgaggcc    3960
ctttcgtctc gcgcgtttcg gtgatgacgg tgaaaacctc tgacacatgc agctcccgga    4020
gacggtcaca gcttgtctgt aagcggatgc cgggagcaga caagcccgtc agggcgcgtc    4080
agcgggtgtt ggcgggtgtc ggggctggct taactatgcg gcatcagagc agattgtact    4140
gagagtgcac catatgcggt gtgaaatacc gcacagatgc gtaaggagaa ataccgcat    4200 caggcgccat tcgccattca ggctgcgcaa ctgttgggaa gggcgatcgg tgcgggcctc    4260
ttcgctatta cgccagctgg cgaaaggggg atgtgctgca aggcgattaa gttgggtaac    4320
gccagggttt tcccagtcac gacgttgtaa aacgacggcc agtgaattac caactttgta    4380
caaaaaagca gattaccctg ttatccctac atcatcaata atataccttta ttttggattg    4440 aagccaatat gataatgagg gggtggagtt tgtgacgtgg cgcggggcgt gggaacgggg    4500
cgggtgacgt agtagtgtgg cggaagtgtg atgttgcaag tgtggcggaa cacatgtaag    4560
cgacggatgg gcaaaagtg acgttttttgg tgtgcgccgg tgtacacagg aagtgacaat    4620
tttcgcgcgg tttaggcgg atgttgtagt aaatttgggc gtaaccgagt aagatttggc    4680
cattttcgcg ggaaaactga ataagaggaa gtgaaatctg aataattttg tgttactcat    4740
agcgcgtaat atttgtctag ggccgcgggg actttgaccg tttacgtgga gactcgccca    4800 ggtgttttttc tcaggtgttt tccgcgttcc gggtcaaagt tggcgtttta ttattaatta    4860
agtttaaacg gcgcgcctaa tagtaatcaa ttacggggtc attagttcat agcccatata    4920
tggagttccg cgttacataa cttacggtaa atggcccgcc tggctgaccg cccaacgacc    4980
cccgcccatt gacgtcaata atgacgtatg ttcccatagt aacgccaata gggactttcc    5040
attgacgtca atgggtggag tatttacggt aaactgccca cttggcagta catcaagtgt    5100
atcatatgcc aagtacgccc cctattgacg tcaatgacgg taaatggccc gcctggcatt    5160
```

```
atgcccagta catgaccttt tgggactttc ctacttggca gtacatctac gtattagtca    5220
tcgctattac catggtgatg cggttttggc agtacatcaa tgggcgtgga tagcggtttg    5280
actcacgggg atttccaagt ctccacccca ttgacgtcaa tgggagtttg ttttggcacc    5340
aaaatcaacg ggactttcca aaatgtcgta acaactccgc cccattgacg caaatgggcg    5400
gtaggcgtgt acggtgggag gtctatataa gcagagctgg tttagtgaac cgtcagatgg    5460
taccggcccc gggagacggc ggcggtggcg gcgcgggcag agcaaggacg cggcggatcc    5520
cactcgcaca gcagcgcact cggtgccccg cgcagggtcg gtaccgaatt gccaccatgg    5580
tgagcaaggg cgaggaggtc atcaaagagt tcatgcgctt caaggtgcgc atggagggct    5640
ccatgaacgg ccacgagttc gagatcgagg gcgagggcga gggccgcccc tacgagggca    5700
cccagaccgc caagctgaag gtgaccaagg gcggcccccct gcccttcgcc tgggacatcc    5760
tgtcccccca gttcatgtac ggctccaagg cgtacgtgaa gcaccccgcc gacatccccg    5820
attacaagaa gctgtccttc cccgagggct caagtgggga gcgcgtgatg aacttcgagg    5880
acggcggtct ggtgaccgtg acccaggact cctccctgca ggacggcacg ctgatctaca    5940
aggtgaagat gcgcggcacc aacttccccc ccgacgcccc cgtaatgcag aagaagacca    6000
tgggctggga ggcctccacc gagcgcctgt accccgcga cggcgtgctg aagggcgaga    6060
tccaccaggc cctgaagctg aaggacgcg gccactacct ggtggagttc aagaccatct    6120
acatggccaa gaagcccgtg caactgcccg gctactacta cgtggacacc aagctggaca    6180
tcacctccca caacgaggac tacaccatcg tggaacagta cgagcgctcc gagggccgcc    6240
accacctgtt cctggggcat ggcaccggca gcaccggcag cggcagctcc ggcaccgcct    6300
cctccgagga caacaacatg gccgtcatca aagagttcat gcgcttcaag gtgcgcatgg    6360
agggctccat gaacggccac gagttcgaga tcgagggcga gggcgagggc cgcccctacg    6420
agggcaccca gaccgccaag ctgaaggtga ccaaggggcgg ccccctgccc ttcgcctggg    6480
acatcctgtc cccccagttc atgtacggct ccaaggcgta cgtgaagcac cccgccgaca    6540
tccccgatta caagaagctg tccttccccg agggcttcaa gtgggagcgc gtgatgaact    6600
tcgaggacgg cggtctggtg accgtgaccc aggactcctc cctgcaggac ggcacgctga    6660
tctacaaggt gaagatgcgc ggcaccaact tccccccga cggccccgta atgcagaaga    6720
agaccatggg ctgggaggcc tccaccgagc gcctgtaccc ccgcgacggc gtgctgaagg    6780
gcgagatcca ccagccctg aagctgaagg acggcggccg ctacctggtg gagttcaaga    6840
ccatctacat ggccaagaag cccgtgcaac tgcccggcta ctacgtg gacaccaagc    6900 tggacatcac ctcccacaac gaggactaca ccatcgtgga acagtacgag cgctccgagg    6960
gccgccacca cctgttcctg tacggcatgg acgagctgta caagtaaaat tcatactcga    7020
gatacatatg ataagatctg tttgaatgag gcttcagtac tttacagaat cgttgcctgc    7080
acatcttgga acacttgct gggattactt cttcaggtta acccaacaga aggctcgaga    7140
aggtatattg ctgttgacag tgagcggctg gaatacttag ctcagatcta gtgaagccac    7200
agatgtagat ctgagctaag tattccagct gcctactgcc tcggaattca aggggctact    7260
ttaggagcaa ttatcttgtt tactaaaact gaataccttg ctatctcttt gatacatttt    7320
tacaaagctg aattaaaatg gtataaatta atcactaga tctatagata tcataaccgg    7380
tatagcggcc gcaagaggta agggtttaag ggatggtcgg ttggtggggt attaatgttt    7440
aattacctgg agcacctgcc tgaaatcact ttttttcagg ttggaatcga taatcaacct    7500
```

```
ctggattaca aaatttgtga aagattgact ggtattctta actatgttgc tccttttacg    7560
ctatgtggat acgctgcttt aatgcctttg tatcatgcta ttgcttcccg tatggctttc    7620
attttctcct ccttgtataa atcctggttg ctgtctcttt atgaggagtt gtggcccgtt    7680
gtcaggcaac gtggcgtggt gtgcactgtg tttgctgacg caaccccac tggttggggc     7740
attgccacca cctgtcagct cctttccggg actttcgctt tcccctccc tattgccacg     7800
gcggaactca tcgccgcctg ccttgccgc tgctggacag gggctcggct gttgggcact     7860
gacaattccg tggtgttgtc ggggaagctg acgtcctttc catggctgct cgcctgtgtt    7920
gccacctgga ttctgcgcgg gacgtccttc tgctacgtcc cttcggccct caatccagcg    7980
gaccttcctt cccgcggcct gctgccggct ctgcggcctc ttccgcgtct tcgccttcgc    8040
cctcagacga gtcggatctc cctttgggcc gcctccccgc ctgctgcagg gcgccatcgt    8100
ggatgggagt ccgtgtgtgc ctggagatta ccctggacac ctctgctttt tttttttttac   8160
tttagcggtt gcctcctagg cctgactcct tcccatgttg aactggaggc agccacgtta    8220
ggtgtcaatg tcctggcatc agtatgaaca gtcagtagtc ccagggcagg gccacacttc    8280
tcccatcttc tgcttccacc ccagcttgtg attgctagcc tcccagagct caattgctgt    8340
gccttctagt tgccagccat ctgttgtttg ccccctccccc gtgccttcct tgaccctgga    8400
aggtgccact cccactgtcc tttcctaata aatgaggaa attgcatcgc attgtctgag     8460
taggtgtcat tctattctgg ggggtggggt ggggcaggac agcaaggggg aggattggga    8520
agacaatagc aggcatgctg gggatgcggt gggctctatg gacgcgtcgg ccgctgcagc    8580
tcgagtctag agctgacggc gcgcctgaaa tgtgtgggcg tggcttaagg gtgggaagaa    8640
atatataagg tgggggtctt atgtagtttt gtatctgttt tgcagcagcc gccgccgcca    8700
tgagcaccaa ctcgtttgat ggaagcattg tgagctcata tttgacaacg cgcatgcccc    8760
catgggccgg ggtgcgtcag aatgtgatgg gctccagcat tgatggtcgc cccgtcctgc    8820
ccgcaaactc tactaccttg acctacgaga ccgtgtctgg aacgccgttg gagactgcag    8880
cctccgccgc cgcttcagcc gctgcagcca ccgcccgcgg gattgtgact gactttgctt    8940
tcctgagccc gcttgcaagc agtgcagctt cccgttcatc cgcccgcgat gacaagttga    9000
cggctctttt ggcacaattg gattctttga cccgggaact taatgtcgtt tctcagcagc    9060
tgttggatct gcgccagcag gtttctgccc tgaaggcttc ctcccctccc aatgcggttt    9120
aaaacataaa taaaaaacca gactctgttt ggatttggat caagcataag tgtcttgctg    9180
tctttattta ggggttttgc gcgcgcggta ggcccgggac cagcggtctc ggtcgttgag    9240
ggtcctgtgt atttttttcca ggacgtggta aaggtgactc tggatgttca gatacatggg   9300
cataagcccg tctctggggt ggaggtagca ccactgcaga gcttcatgct gcggggtggt    9360
gttgtagatg atccagtcgt agcaggagcg ctgggcgtgg tgcctaaaaa tgtctttcag    9420
tagcaagctg attgccaggg gcaggcccct ggtgtaagtg tttacaaagc ggttaagctg    9480
ggatgggtgc atacgtgggg atatgagatg catcttggac tgtatttta ggttggctat     9540
gttcccagcc atatccctcc ggggattcat gttgtgcaga accaccagca cagtgtatcc    9600
ggtgcacttg ggaaatttgt catgtagctt agaaggaaat gcgtggaaga acttggagac    9660
gcccttgtga cctccaagat tttccatgca ttcgtccata atgatggcaa tgggcccacg    9720
ggcggcggcc tgggcgaaga tatttctggg atcactaacg tcatagttgt gttccaggat    9780
gagatcgtca taggccattt ttacaaagcg cgggcggagg gtgccagact gcggtataat    9840
ggttccatcc ggcccagggg cgtagttacc ctcacagatt tgcatttccc acgctttgag    9900
```

```
ttcagatggg gggatcatgt ctacctgcgg ggcgatgaag aaaacggttt ccggggtagg   9960
ggagatcagc tgggaagaaa gcaggttcct gagcagctgc gacttaccgc agccggtggg  10020
cccgtaaatc acacctatta ccgggtgcaa ctggtagtta agagagctgc agctgccgtc  10080
atccctgagc aggggggcca cttcgttaag catgtccctg actcgcatgt tttccctgac  10140
caaatccgcc agaaggcgct cgccgcccag cgatagcagt tcttgcaagg aagcaaagtt  10200
tttcaacggt ttgagaccgt ccgccgtagg catgcttttg agcgtttgac caagcagttc  10260
caggcggtcc cacagctcgg tcacctgctc tacggcatct cgatccagca tatctcctcg  10320
tttcgcgggt tggggcggct ttcgctgtac ggcagtagtc ggtgctcgtc cagacgggcc  10380
agggtcatgt ctttccacgg gcgcagggtc ctcgtcagcg tagtctgggt cacggtgaag  10440
gggtgcgctc cgggctgcgc gctggccagg gtgcgcttga ggctggtcct gctggtgctg  10500
aagcgctgcc ggtcttcgcc ctgcgcgtcg gccaggtagc atttgaccat ggtgtcatag  10560
tccagcccct ccgcggcgtg gcccttggcg cgcagcttgc ccttggagga ggcgccgcac  10620
gaggggcagt gcagactttt gagggcgtag agcttgggcg cgagaaatac cgattccggg  10680
gagtaggcat ccgcgccgca ggccccgcag acggtctcgc attccacgag ccaggtgagc  10740
tctggccgtt cggggtcaaa accaggtttt cccccatgct ttttgatgcg tttcttacct  10800
ctggtttcca tgagccggtg tccacgctcg gtgacgaaaa ggctgtccgt gtccccgtat  10860
acagacttga gaggcctgtc ctcgagcggt gttccgcggt cctcctcgta tagaaactcg  10920
gaccactctg agacaaaggc tcgcgtccag gccagcacga aggaggctaa gtgggagggg  10980
tagcggtcgt tgtccactag ggggtccact cgctccaggg tgtgaagaca catgtcgccc  11040
tcttcggcat caaggaaggt gattggtttg taggtgtagg ccacgtgacc gggtgttcct  11100
gaagggggc tataaaaggg ggtgggggcg cgttcgtcct cactctcttc cgcatcgctg  11160
tctgcgaggg ccagctgttg gggtgagtac tccctctgaa aagcgggcat gacttctgcg  11220
ctaagattgt cagtttccaa aaacgaggag gatttgatat tcacctggcc cgcggtgatg  11280
cctttgaggg tggccgcatc catctggtca gaaaagacaa tcttttttgtt gtcaagcttg  11340
gtggcaaacg acccgtagag ggcgttggac agcaacttgg cgatggagcg cagggtttgg  11400
tttttgtcgc gatcggcgcg ctccttggcc gcgatgttta gctgcacgta ttcgcgcgca  11460
acgcaccgcc attcgggaaa gacggtggtg cgctcgtcgg gcaccaggtg cacgcgccaa  11520
ccgcggttgt gcagggtgac aaggtcaacg ctggtggcta cctctccgcg taggcgctcg  11580
ttggtccagc agaggcggcc gcccttgcgc gagcagaatg gcggtagggg gtctagctgc  11640
gtctcgtccg ggggggtctgc gtccacggta agacccccgg gcagcaggcg cgcgtcgaag  11700
tagtctatct tgcatccttg caagtctagc gcctgctgcc atgcgcgggc ggcaagcgcg  11760
cgctcgtatg ggttgagtgg gggaccccat ggcatggggt gggtgagcgc ggaggcgtac  11820
atgccgcaaa tgtcgtaaac gtagagggc tctctgagta ttccaagata tgtagggtag  11880
catcttccac cgcggatgct ggcgcgcacg taatcgtata gttcgtgcga gggagcgagg  11940
aggtcgggac cgaggttgct acgggcgggc tgctctgctc ggaagactat ctgcctgaag  12000
atggcatgtg agttggatga tatggttgga cgctggaaga cgttgaagct ggcgtctgtg  12060
agacctaccg cgtcacgcac gaaggaggcg taggagtcgc gcagcttgtt gaccagctcg  12120
gcggtgacct gcacgtctag ggcgcagtag tccagggttt ccttgatgat gtcatactta  12180
tcctgtccct ttttttttcca cagctcgcgg ttgaggacaa actcttcgcg gtctttccag  12240
```

```
tactcttgga tcggaaaccc gtcggcctcc gaacggtaag agcctagcat gtagaactgg    12300
ttgacggcct ggtaggcgca gcatcccttt tctacgggta gcgcgtatgc ctgcgcggcc    12360
ttccggagcg aggtgtgggt gagcgcaaag gtgtccctga ccatgacttt gaggtactgg    12420
tatttgaagt cagtgtcgtc gcatccgccc tgctcccaga gcaaaaagtc cgtgcgcttt    12480
ttggaacgcg gatttggcag ggcgaaggtg acatcgttga agagtatctt tcccgcgcga    12540
ggcataaagt tgcgtgtgat gcggaagggt cccggcacct cggaacggtt gttaattacc    12600
tgggcggcga gcacgatctc gtcaaagccg ttgatgttgt ggcccacaat gtaaagttcc    12660
aagaagcgcg ggatgccctt gatggaaggc aattttttaa gttcctcgta ggtgagctct    12720 tcagggagc tgagcccgtg ctctgaaagg gcccagtctg caagatgagg gttggaagcg    12780
acgaatgagc tccacaggtc acgggccatt agcatttgca ggtggtcgcg aaaggtccta    12840
aactggcgac ctatggccat tttttctggg gtgatgcagt agaaggtaag cgggtcttgt    12900
tcccagcggt cccatccaag gttcgcggct aggtctcgcg cggcagtcac tagaggctca    12960
tctccgccga acttcatgac cagcatgaag ggcacgagct gcttcccaaa ggcccccatc    13020
caagtatagg tctctacatc gtaggtgaca aagagacgct cggtgcgagg atgcgagccg    13080
atcgggaaga actggatctc ccgccaccaa ttggaggagt ggctattgat gtggtgaaag    13140
tagaagtccc tgcgacgggc cgaacactcg tgctggcttt tgtaaaaacg tgcgcagtac    13200
tggcagcggt gcacgggctg tacatcctgc acgaggttga cctgacgacc cgcacaaggg    13260
aagcagagtg ggaatttgag cccctcgcct ggcgggtttg gctggtggtc ttctacttcg    13320
gctgcttgtc cttgaccgtc tggctgctcg aggggagtta cggtggatcg gaccaccacg    13380
ccgcgcgagc ccaaagtcca gatgtccgcg cgcggcggtc ggagcttgat gacaacatcg    13440
cgcagatggg agctgtccat ggtctggagc tcccgcggcg tcaggtcagg cgggagctcc    13500
tgcaggttta cctcgcatag acgggtcagg gcgcgggcta gatccaggtg atacctaatt    13560
tccaggggct ggttggtggc ggcgtcgatg gcttgcaaga ggccgcatcc ccgcggcgcg    13620
actacggtac cgcgcggcgg gcggtgggcc gcggggtgt ccttggatga tgcatctaaa    13680
agcggtgacg cgggcgagcc cccggaggta gggggggctc cggacccgcc gggagagggg    13740
gcaggggcac gtcggcgccg cgcgcgggca ggagctggtg ctgcgcgcgt aggttgctgg    13800
cgaacgcgac gacgcggcgg ttgatctcct gaatctggcg cctctgcgtg aagacgacgg    13860
gcccggtgag cttgagcctg aaagagagtt cgacagaatc aatttcggtg tcgttgacgg    13920
cggcctggcg caaaatctcc tgcacgtctc ctgagttgtc ttgataggcg atctcggcca    13980
tgaactgctc gatctcttcc tcctggagat ctccgcgtcc ggctcgctcc acggtggcgg    14040
cgaggtcgtt ggaaatgcgg gccatgagct gcgagaaggc gttgaggcct ccctcgttcc    14100
agacgcggct gtagaccacg cccccttcgg catcgcgggc gcgcatgacc acctgcgcga    14160
gattgagctc cacgtgccgg gcgaagacgg cgtagtttcg caggcgctga aagaggtagt    14220
tgagggtggt ggcggtgtgt tctgccacga agaagtacat aacccagcgt cgcaacgtgg    14280
attcgttgat atcccccaag gcctcaaggc gctccatggc ctcgtagaag tccacggcga    14340
agttgaaaaa ctgggagttg cgcgccgaca cggttaactc ctcctccaga agacggatga    14400
gctcggcgac agtgtcgcgc acctcgcgct caaaggctac aggggcctct tcttcttctt    14460
caatctcctc ttccataagg gcctcccctt cttcttcttc tggcggcggt ggggagggg    14520 ggacacggcg gcgacgacgg cgcaccggga ggcggtcgac aaagcgctcg atcatctccc    14580
cgcggcgacg gcgcatggtc tcggtgacgg cgcggccgtt ctcgcggggg gcagttgga    14640
```

```
agacgccgcc cgtcatgtcc cggttatggg ttggcggggg gctgccatgc ggcagggata   14700
cggcgctaac gatgcatctc aacaattgtt gtgtaggtac tccgccgccg agggacctga   14760
gcgagtccgc atcgaccgga tcggaaaacc tctcgagaaa ggcgtctaac cagtcacagt   14820
cgcaaggtag gctgagcacc gtggcgggcg gcagcgggcg gcggtcgggg ttgtttctgg   14880
cggaggtgct gctgatgatg taattaaagt aggcggtctt gagacggcgg atggtcgaca   14940
gaagcaccat gtccttgggt ccggcctgct gaatgcgcag gcggtcggcc atgccccagg   15000
cttcgttttg acatcggcgc aggtctttgt agtagtcttg catgagcctt tctaccggca   15060
cttcttcttc tccttcctct tgtcctgcat ctcttgcatc tatcgctgcg gcggcggcgg   15120
agtttggccg taggtggcgc cctcttcctc ccatgcgtgt gaccccgaag cccctcatcg   15180
gctgaagcag ggctaggtcg gcgacaacgc gctcggctaa tatggcctgc tgcacctgcg   15240
tgagggtaga ctggaagtca tccatgtcca caaagcggtg gtatgcgccc gtgttgatgg   15300
tgtaagtgca gttggccata acggaccagt taacggtctg gtgacccggc tgcgagagct   15360
cggtgtacct gagacgcgag taagccctcg agtcaaatac gtagtcgttg caagtccgca   15420
ccaggtactg gtatcccacc aaaaagtgcg gcggcggctg gcggtagagg ggccagcgta   15480
gggtggccgg ggctccgggg gcgagatctt ccaacataag gcgatgatat ccgtagatgt   15540
acctggacat ccaggtgatg ccggcggcgg tggtggaggc gcgcggaaag tcgcggacgc   15600
ggttccagat gttgcgcagc ggcaaaaagt gctccatggt cgggacgctc tggccggtca   15660
ggcgcgcgca atcgttgacg ctctagaccg tgcaaaagga gagcctgtaa gcgggcactc   15720
ttccgtggtc tggtggataa attcgcaagg gtatcatggc ggacgaccgg ggttcgagcc   15780
ccgtatccgg ccgtccgccg tgatccatgc ggttaccgcc cgcgtgtcga acccaggtgt   15840
gcgacgtcag acaacggggg agtgctcctt ttggcttcct tccaggcgcg gcggctgctg   15900
cgctagcttt tttggccact ggccgcgcgc agcgtaagcg gttaggctgg aaagcgaaag   15960
cattaagtgg ctcgctccct gtagccggag ggttattttc caagggttga gtcgcgggac   16020
ccccggttcg agtctcggac cggccggact gcggcgaacg ggggtttgcc tccccgtcat   16080
gcaagacccc gcttgcaaat tcctccggaa acagggacga gccccttttt tgcttttccc   16140
agatgcatcc ggtgctgcgg cagatgcgcc cccctcctca gcagcggcaa gagcaagagc   16200
agcggcagac atgcagggca ccctcccctc ctcctaccgc gtcaggaggg gcgacatccg   16260
cggttgacgc ggcagcagat ggtgattacg aaccccgcg gcgccgggcc cggcactacc   16320
tggacttgga ggagggcgag ggcctggcgc ggctaggagc ccctctcct gagcggtacc   16380 caagggtgca gctgaagcgt gatacgcgtg aggcgtacgt gccgcggcag aacctgtttc   16440
gcgaccgcga gggagaggag cccgaggaga tgcgggatcg aaagttccac gcagggcgcg   16500
agctgcggca tggcctgaat cgcgagcggt tgctgcgcga ggaggacttt gagcccgacg   16560
cgcgaaccgg gattagtccc gcgcgcgcac acgtggcggc cgccgacctg gtaaccgcat   16620
acgagcagac ggtgaaccag gagattaact ttcaaaaaag ctttaacaac cacgtgcgta   16680
cgcttgtggc gcgcgaggag gtggctatag gactgatgca tctgtgggac tttgtaagcg   16740
cgctggagca aaacccaaat agcaagccgc tcatggcgca gctgttcctt atagtgcagc   16800
acagcaggga caacgaggca ttcagggatg cgctgctaaa catagtagag cccgagggcc   16860
gctggctgct cgatttgata aacatcctgc agagcatagt ggtgcaggag cgcagcttga   16920
gcctggctga caaggtggcc gccatcaact attccatgct tagcctgggc aagttttacg   16980
```

```
cccgcaagat ataccatacc ccttacgttc ccatagacaa ggaggtaaag atcgagggt    17040 tctacatgcg catggcgctg aaggtgctta ccttgagcga cgacctgggc gtttatcgca   17100
acgagcgcat ccacaaggcc gtgagcgtga gccggcggcg cgagctcagc gaccgcgagc   17160
tgatgcacag cctgcaaagg gccctggctg cacgggcag cggcgataga gaggccgagt    17220
cctactttga cgcgggcgct gacctgcgct gggccccaag ccgacgcgcc ctggaggcag   17280
ctggggccgg acctgggctg gcggtggcac ccgcgcgcgc tggcaacgtc ggcggcgtgg   17340
aggaatatga cgaggacgat gagtacgagc cagaggacgg cgagtactaa gcggtgatgt   17400
ttctgatcag atgatgcaag acgcaacgga cccggcggtg cgggcggcgc tgcagagcca   17460
gccgtccggc cttaactcca cggacgactg gcgccaggtc atggaccgca tcatgtcgct   17520
gactgcgcgc aatcctgacg cgttccggca gcagccgcag gccaaccggc tctccgcaat   17580
tctggaagcg gtggtcccgg cgcgcgcaaa ccccacgcac gagaaggtgc tggcgatcgt   17640
aaacgcgctg gccgaaaaca gggccatccg gcccgacgag gccggcctgg tctacgacgc   17700
gctgcttcag cgcgtggctc gttacaacag cggcaacgtg cagaccaacc tggaccggct   17760
ggtgggggat gtgcgcgagg ccgtggcgca gcgtgagcgc gcgcagcagc agggcaacct   17820
gggctccatg gttgcactaa acgccttcct gagtacacag cccgccaacg tgccgcgggg   17880
acaggaggac tacaccaact ttgtgagcgc actgcggcta atggtgactg agacaccgca   17940
aagtgaggtg taccagtctg gccagacta ttttttccag accagtagac aaggcctgca   18000
gaccgtaaac ctgagccagg ctttcaaaaa cttgcagggg ctgtgggggg tgcgggctcc   18060
cacaggcgac cgcgcgaccg tgtctagctt gctgacgccc aactcgcgcc tgttgctgct   18120
gctaatagcg cccttcacgg acagtggcag cgtgtcccgg acacatacc taggtcactt    18180 gctgacactg taccgcgagg ccataggtca ggcgcatgtg gacgagcata ctttccagga   18240
gattacaagt gtcagccgcg cgctggggca ggaggacacg ggcagcctgg aggcaaccct   18300
aaactacctg ctgaccaacc ggcggcagaa gatccctcg ttgcacagtt taaacagcga    18360
ggaggagcgc attttgcgct acgtgcagca gagcgtgagc cttaacctga tgcgcgacgg   18420
ggtaacgccc agcgtggcgc tggacatgac cgcgcgcaac atggaaccgg gcatgtatgc   18480
ctcaaaccgg ccgtttatca accgcctaat ggactacttg catcgcgcgg ccgccgtgaa   18540
ccccgagtat ttcaccaatg ccatcttgaa cccgcactgg ctaccgcccc ctggtttcta   18600 caccgggggga ttcgaggtgc ccgagggtaa cgatggattc ctctgggacg acatagacga   18660
cagcgtgttt tccccgcaac cgcagaccct gctagagttg caacagcgcg agcaggcaga   18720
ggcggcgctg cgaaaggaaa gcttccgcag gccaagcagc ttgtccgatc taggcgctgc   18780
ggccccgcgg tcagatgcta gtagcccatt tccaagcttg atagggtctc ttaccagcac   18840
tcgcaccacc cgcccgcgcc tgctgggcga ggaggagtac ctaaacaact cgctgctgca   18900
gccgcagcgc gaaaaaaacc tgcctccggc atttcccaac aacgggatag agagcctagt   18960
ggacaagatg agtagatgga agacgtacgc gcaggagcac agggacgtgc caggcccgcg   19020
cccgcccacc cgtcgtcaaa ggcacgaccg tcagcggggt ctggtgtggg aggacgatga   19080
ctcggcagac gacagcagcg tcctggattt ggagggagt ggcaacccgt ttgcgcacct    19140
tcgccccagg ctggggagaa tgttttaaaa aaaaaaagc atgatgcaaa ataaaaaact    19200
caccaaggcc atggcaccga gcgttggttt tcttgtattc cccttagtat gcggcgcgcg   19260
gcgatgtatg aggaaggtcc tcctcccctcc tacgagagtc tggtgagcgc ggcgccagtg   19320
gcggcggcgc tgggttctcc cttcgatgct cccctggacc cgccgtttgt gcctccgcgg   19380
```

```
tacctgcggc ctaccggggg gagaaacagc atccgttact ctgagttggc acccctattc    19440
gacaccaccc gtgtgtacct ggtggacaac aagtcaacgg atgtggcatc cctgaactac    19500
cagaacgacc acagcaactt tctgaccacg gtcattcaaa acaatgacta cagcccgggg    19560
gaggcaagca cacagaccat caatcttgac gaccggtcgc actggggcgg cgacctgaaa    19620
accatcctgc ataccaacat gccaaatgtg aacgagttca tgtttaccaa taagtttaag    19680
gcgcgggtga tggtgtcgcg cttgcctact aaggacaatc aggtggagct gaaatacgag    19740
tgggtggagt tcacgctgcc cgagggcaac tactccgaga ccatgaccat agaccttatg    19800
aacaacgcga tcgtggagca ctacttgaaa gtgggcagac agaacggggt tctggaaagc    19860
gacatcgggg taaagtttga cacccgcaac ttcagactgg ggtttgaccc cgtcactggt    19920
cttgtcatgc ctggggtata tacaaacgaa gccttccatc cagacatcat tttgctgcca    19980
ggatgcgggg tggacttcac ccacagccgc ctgagcaact tgttgggcat ccgcaagcgg    20040
caacccttcc aggagggctt taggatcacc tacgatgatc tggagggtgg taacattccc    20100
gcactgttgg atgtggacgc ctaccaggcg agcttgaaag atgacaccga acagggcggg    20160
ggtggcgcag gcggcagcaa cagcagtggc agcggcgcgg aagagaactc caacgcggca    20220
gccgcggcaa tgcagccggt ggaggacatg aacgatcatg ccattcgcgg cgacaccttt    20280
gccacacggg ctgaggagaa gcgcgctgag gccgaagcag cggccgaagc tgccgccccc    20340
gctgcgcaac ccgaggtcga aagcctcag aagaaaccgg tgatcaaacc cctgacagag    20400
gacagcaaga aacgcagtta caacctaata agcaatgaca gcaccttcac ccagtaccgc    20460
agctggtacc ttgcatacaa ctacggcgac cctcagaccg gaatccgctc atggaccctg    20520
ctttgcactc ctgacgtaac ctgcggctcg gagcaggtct actggtcgtt gccagacatg    20580
atgcaagacc ccgtgacctt ccgctccacg cgccagatca gcaactttcc ggtggtgggc    20640
gccgagctgt tgcccgtgca ctccaagagc ttctacaacg accaggccgt ctactcccaa    20700
ctcatccgcc agtttacctc tctgacccac gtgttcaatc gctttcccga gaaccagatt    20760
ttggcgcgcc cgccagcccc caccatcacc accgtcagtg aaaacgttcc tgctctcaca    20820
gatcacggga cgctaccgct gcgcaacagc atcggaggag tccagcgagt gaccattact    20880
gacgccagac gccgcacctg cccctacgtt tacaaggccc tgggcatagt ctcgccgcgc    20940
gtcctatcga gccgcacttt ttgagcaagc atgtccatcc ttatatcgcc cagcaataac    21000
acaggctggg gcctgcgctt cccaagcaag atgtttggcg gggccaagaa gcgctccgac    21060
caacacccag tgcgcgtgcg cgggcactac cgcgcgccct ggggcgcgca caaacgcggc    21120
cgcactgggc gcaccaccgt cgatgacgcc atcgacgcgg tggtggagga ggcgcgcaac    21180
tacacgcccc gccgccacc agtgtccaca gtggacgcgg ccattcagac cgtggtgcgc    21240
ggagcccggc gctatgctaa aatgaagaga cggcggaggc gcgtagcacg tcgccaccgc    21300
cgccgacccg gcactgccgc ccaacgcgcg cggcggcccc tgcttaaccg cgcacgtcgc    21360
accggccgac gggcggccat gcgggccgct cgaaggctgg ccgcgggtat tgtcactgtg    21420
cccccccagt ccaggcgacg agcggccgcc gcagcagccg cggccattag tgctatgact    21480
cagggtcgca ggggcaacgt gtattgggtg cgcgactcgg ttagcggcct gcgcgtgccc    21540
gtgcgcaccc gcccccgcg caactagatt gcaagaaaaa actacttaga ctcgtactgt    21600
tgtatgtatc cagcggcggc ggcgcgcaac gaagctatgt ccaagcgcaa aatcaaagaa    21660
gagatgctcc aggtcatcgc gccggagatc tatggccccc cgaagaagga agagcaggat    21720
```

```
tacaagcccc gaaagctaaa gcgggtcaaa aagaaaaaga aagatgatga tgatgaactt   21780
gacgacgagg tggaactgct gcacgctacc gcgcccaggc gacgggtaca gtggaaaggt   21840
cgacgcgtaa aacgtgtttt gcgacccggc accaccgtag tctttacgcc cggtgagcgc   21900
tccacccgca cctacaagcg cgtgtatgat gaggtgtacg gcgacgagga cctgcttgag   21960
caggccaacg agcgcctcgg ggagtttgcc tacggaaagc ggcataagga catgctggcg   22020
ttgccgctgg acgagggcaa cccaacacct agcctaaagc ccgtaacact gcagcaggtg   22080
ctgcccgcgc ttgcaccgtc cgaagaaaag cgcggcctaa agcgcgagtc tggtgacttg   22140
gcacccaccg tgcagctgat ggtacccaag cgccagcgac tggaagatgt cttggaaaaa   22200
atgaccgtgg aacctgggct ggagcccgag gtccgcgtgc ggccaatcaa gcaggtggcg   22260
ccgggactgg gcgtgcagac cgtggacgtt cagatacccc ctaccagtag caccagtatt   22320
gccaccgcca cagagggcat ggagacacaa acgtccccgg ttgcctcagc ggtggcggat   22380
gccgcggtgc aggcggtcgc tgcggccgcg tccaagacct ctacggaggt gcaaacggac   22440
ccgtggatgt ttcgcgtttc agccccccgg cgcccgcgcg gttcgaggaa gtacggcgcc   22500
gccagcgcgc tactgcccga atatgcccta catccttcca ttgcgcctac ccccggctat   22560
cgtggctaca cctaccgccc cagaagacga gcaactaccc gacgccgaac caccactgga   22620
acccgccgcc gccgtcgccg tcgccagccc gtgctggccc cgatttccgt gcgcagggtg   22680
gctcgcgaag gaggcaggac cctggtgctg ccaacagcgc gctaccaccc cagcatcgtt   22740
taaaagccgg tctttgtggt tcttgcagat atggccctca cctgccgcct ccgtttcccg   22800
gtgccgggat tccgaggaag aatgcaccgt aggaggggca tggccggcca cggcctgacg   22860
ggcggcatgc gtcgtgcgca ccaccggcgg cggcgcgcgt cgcaccgtcg catgcgcggc   22920
ggtatcctgc ccctccttat tccactgatc gccgcggcga ttggcgccgt gcccggaatt   22980
gcatccgtgg ccttgcaggc gcagagacac tgattaaaaa caagttgcat gtggaaaaat   23040
caaaataaaa agtctggact ctcacgctcg cttggtcctg taactatttt gtagaatgga   23100
agacatcaac tttgcgtctc tggccccgcg acacggctcg cgcccgttca tgggaaactg   23160
gcaagatatc ggcaccagca atatgagcgg tggcgccttc agctgggggct cgctgtggag   23220
cggcattaaa aatttcggtt ccaccgttaa gaactatggc agcaaggcct ggaacagcag   23280
cacaggccag atgctgaggg ataagttgaa agagcaaaat ttccaacaaa aggtggtaga   23340
tggcctggcc tctggcatta gcggggtggt ggacctggcc aaccaggcag tgcaaaataa   23400
gattaacagt aagcttgatc cccgcccctcc cgtagaggag cctccaccgg ccgtggagac   23460
agtgtctcca gaggggcgtg gcgaaaagcg tccgcgcccc gacagggaag aaactctggt   23520
gacgcaaata gacgagcctc cctcgtacga ggaggcacta aagcaaggcc tgcccaccac   23580
ccgtcccatc gcgcccatgg ctaccggagt gctgggccag cacacacccg taacgctgga   23640
cctgcctccc cccgccgaca cccagcagaa acctgtgctg ccaggcccga ccgccgttgt   23700
tgtaacccgt cctagccgcg cgtccctgcg ccgcccgcc agcggtccgc gatcgttgcg   23760
gcccgtagcc agtggcaact ggcaaagcac actgaacagc atcgtgggtc tggggggtgca   23820
atccctgaag cgccgacgat gcttctgaat agctaacgtg tcgtatgtgt gtcatgtatg   23880
cgtccatgtc gccgccagag gagctgctga ccgccgcgc gcccgctttc caagatggct   23940
accccttcga tgatgccgca gtggtcttac atgcacatct cgggccagga cgcctcggag   24000
tacctgagcc ccgggctggt gcagtttgcc cgcgccaccg agacgtactt cagcctgaat   24060
aacaagtttta gaaaccccac ggtggcgcct acgcacgacg tgaccacaga ccggtcccag   24120
```

```
cgtttgacgc tgcggttcat ccctgtggac cgtgaggata ctgcgtactc gtacaaggcg    24180
cggttcaccc tagctgtggg tgataaccgt gtgctggaca tggcttccac gtactttgac    24240
atccgcggcg tgctggacag gggccctact tttaagccct actctggcac tgcctacaac    24300
gccctggctc ccaagggtgc cccaaatcct tgcgaatggg atgaagctgc tactgctctt    24360
gaaataaacc tagaagaaga ggacgatgac aacgaagacg aagtagacga gcaagctgag    24420
cagcaaaaaa ctcacgtatt tgggcaggcg ccttattctg gtataaatat tacaaaggag    24480
ggtattcaaa taggtgtcga aggtcaaaca cctaaatatg ccgataaaac atttcaacct    24540
gaacctcaaa taggagaatc tcagtggtac gaaactgaaa ttaatcatgc agctgggaga    24600
gtccttaaaa agactacccc aatgaaacca tgttacggtt catatgcaaa acccacaaat    24660
gaaaatggag gcaaggcat tcttgtaaag caacaaaatg gaaagctaga agtcaagtg    24720 gaaatgcaat ttttctcaac tactgaggcg accgcaggca atggtgataa cttgactcct    24780
aaagtggtat tgtacagtga agatgtagat atagaaaccc cagacactca tatttcttac    24840
atgcccacta ttaaggaagg taactcacga gaactaatgg ccaacaatc tatgcccaac    24900 aggcctaatt acattgcttt tagggacaat tttattggtc taatgtatta caacagcacg    24960
ggtaatatgg gtgttctggc gggccaagca tcgcagttga atgctgttgt agatttgcaa    25020
gacagaaaca cagagctttc ataccagctt ttgcttgatt ccattggtga tagaaccagg    25080
tacttttcta tgtggaatca ggctgttgac agctatgatc cagatgttag aattattgaa    25140
aatcatggaa ctgaagatga acttccaaat tactgctttc cactgggagg tgtgattaat    25200
acagagactc ttaccaaggt aaaacctaaa acaggtcagg aaaatggatg ggaaaaagat    25260
gctacagaat tttcagataa aaatgaaata agagttggaa ataattttgc catggaaatc    25320
aatctaaatg ccaacctgtg gagaaatttc ctgtactcca acatagcgct gtatttgccc    25380
gacaagctaa agtacagtcc ttccaacgta aaaatttctg ataacccaaa cacctacgac    25440
tacatgaaca agcgagtggt ggctcccggg ttagtggact gctacattaa ccttggagca    25500
cgctggtccc ttgactatat ggacaacgtc aacccattta accaccaccg caatgctggc    25560
ctgcgctacc gctcaatgtt gctgggcaat ggtcgctatg tgcccttcca catccaggtg    25620
cctcagaagt tctttgccat taaaaacctc cttctcctgc cgggctcata cacctacgag    25680
tggaacttca ggaaggatgt taacatggtt ctgcagagct ccctaggaaa tgacctaagg    25740
gttgacggag ccagcattaa gtttgatagc atttgccttt acgccacctt cttccccatg    25800
gcccacaaca ccgcctccac gcttgaggcc atgcttagaa acgacaccaa cgaccagtcc    25860
tttaacgact atctctccgc cgccaacatg ctctacccta tacccgccaa cgctaccaac    25920
gtgcccatat ccatcccctc ccgcaactgg gcggctttcc gcggctgggc cttcacgcgc    25980
cttaagacta aggaaacccc atcactgggc tcgggctacg acccttatta cacctactct    26040
ggctctatac cctacctaga tggaaccttt acctcaacc acaccttaa gaaggtggcc    26100 attaccttg actcttctgt cagctggcct ggcaatgacc gcctgcttac ccccaacgag    26160
tttgaaatta gcgctcagt tgacggggag ggttacaacg ttgcccagtg taacatgacc    26220
aaagactggt tcctggtaca aatgctagct aactacaaca ttggctacca gggcttctat    26280
atcccagaga gctacaagga ccgcatgtac tccttcttta gaaacttcca gcccatgagc    26340
cgtcaggtgg tggatgatac taaatacaag gactaccaac aggtgggcat cctacaccaa    26400
cacaacaact ctggatttgt tggctacctt gcccccacca tgcgcgaagg acaggcctac    26460
```

```
cctgctaact tcccctatcc gcttataggc aagaccgcag ttgacagcat tacccagaaa   26520
aagtttcttt gcgatcgcac cctttggcgc atcccattct ccagtaactt tatgtccatg   26580
ggcgcactca cagacctggg ccaaaacctt ctctacgcca actccgccca cgcgctagac   26640
atgacttttg aggtggatcc catggacgag cccaccttc tttatgtttt gtttgaagtc    26700
tttgacgtgg tccgtgtgca ccggccgcac cgcggcgtca tcgaaaccgt gtacctgcgc   26760
acgcccttct cggccggcaa cgccacaaca taaagaagca agcaacatca acaacagctg   26820
ccgccatggg ctccagtgag caggaactga aagccattgt caaagatctt ggttgtgggc   26880 catattttt gggcacctat gacaagcgct ttccaggctt tgtttctcca cacaagctcg     26940
cctgcgccat agtcaatacg gccggtcgcg agactggggg cgtacactgg atggcctttg   27000
cctggaaccc gcactcaaaa acatgctacc tctttgagcc ctttggcttt tctgaccagc   27060
gactcaagca ggtttaccag tttgagtacg agtcactcct gcgccgtagc gccattgctt   27120 cttccccga ccgctgtata acgctggaaa agtccaccca aagcgtacag ggcccaact     27180 cggccgcctg tggactattc tgctgcatgt ttctccacgc ctttgccaac tggccccaaa   27240
ctcccatgga tcacaacccc accatgaacc ttattaccgg ggtacccaac tccatgctca   27300
acagtcccca ggtacagccc accctgcgtc gcaaccagga acagtctctac agcttcctgg  27360 agcgccactc gccctacttc cgcagccaca gtgcgcagat taggagcgcc acttcttttt   27420
gtcacttgaa aaacatgtaa aaataatgta ctagagacac tttcaataaa ggcaaatgct   27480
tttatttgta cactctcggg tgattattta ccccacccct tgccgtctgc gccgtttaaa   27540
aatcaaaggg gttctgccgc gcatcgctat gcgccactgg cagggacacg ttgcgatact   27600
ggtgtttagt gctccactta aactcaggca caaccatccg cggcagctcg gtgaagtttt   27660
cactccacag gctgcgcacc atcaccaacg cgtttagcag gtcgggcgcc gatatcttga   27720
agtcgcagtt ggggcctccg ccctgcgcgc gcgagttgcg atacacaggg ttgcagcact   27780
ggaacactat cagcgccggg tggtgcacgc tggccagcac gctcttgtcg gagatcagat   27840
ccgcgtccag gtcctccgcg ttgctcaggg cgaacggagt caactttggt agctgccttc   27900 ccaaaaggg cgcgtgccca ggcttttgagt tgcactcgca ccgtagtggc atcaaaaggt    27960
gaccgtgccc ggtctgggcg ttaggataca gcgcctgcat aaaagccttg atctgcttaa   28020
aagccacctg agcctttgcg ccttcagaga agaacatgcc gcaagacttg ccggaaaact   28080
gattggccgg acaggccgcg tcgtgcacgc agcaccttgc gtcggtgttg gagatctgca   28140
ccacatttcg gccccaccgg ttcttcacga tcttggcctt gctagactgc tccttcagcg   28200
cgcgctgccc gttttcgctc gtcacatcca tttcaatcac gtgctcctta tttatcataa   28260
tgcttccgtg tagacactta agctcgcctt cgatctcagc gcagcggtgc agccacaacg   28320
cgcagcccgt gggctcgtga tgcttgtagg tcacctctgc aaacgactgc aggtacgcct   28380
gcaggaatcg ccccatcatc gtcacaaagg tcttgttgct ggtgaaggtc agctgcaacc   28440
cgcggtgctc ctcgttcagc caggtcttgc atacggccgc cagagcttcc acttggtcag   28500
gcagtagttt gaagttcgcc tttagatcgt tatccacgtg gtacttgtcc atcagcgcgc   28560
gcgcagcctc catgcccttc tcccacgcag acacgatcgg cacactcagc gggttcatca   28620
ccgtaatttc actttccgct tcgctgggct cttcctcttc ctcttgcgtc cgcataccac   28680
gcgccactgg gtcgtcttca ttcagccgcc gcactgtgcg cttacctcct ttgccatgct   28740
tgattagcac cggtggggttg ctgaaaccca ccatttgtag cgccacatct tctctttctt   28800
cctcgctgtc cacgattacc tctggtgatg gcgggcgctc gggcttggga gaaggcgct     28860
```

```
tcttttcctt cttgggcgca atggccaaat ccgccgccga ggtcgatggc cgcgggctgg   28920
gtgtgcgcgg caccagcgcg tcttgtgatg agtcttcctc gtcctcggac tcgatacgcc   28980
gcctcatccg cttttttggg ggcgcccggg gaggcggcgg cgacggggac ggggacgaca   29040
cgtcctccat ggttggggga cgtcgcgccg caccgcgtcc gcgctcgggg gtggtttcgc   29100
gctgctcctc ttcccgactg gccatttcct tctcctatag gcagaaaaag atcatggagt   29160
cagtcgagaa gaaggacagc ctaaccgccc cctctgagtt cgccaccacc gcctccaccg   29220
atgccgccaa cgcgcctacc accttccccg tcgaggcacc cccgcttgag gaggaggaag   29280
tgattatcga gcaggaccca ggttttgtaa gcgaagacga cgaggaccgc tcagtaccaa   29340
cagaggataa aaagcaagac caggacaacg cagaggcaaa cgaggaacaa gtcgggcggg   29400
gggacgaaag gcatggcgac tacctagatg tgggagacga cgtgctgttg aagcatctgc   29460
agcgccagtg cgccattatc tgcgacgcgt tgcaagagcg cagcgatgtg cccctcgcca   29520
tagcggatgt cagccttgcc tacgaacgcc acctattctc accgcgcgta ccccccaaac   29580
gccaagaaaa cggcacatgc gagcccaacc cgcgcctcaa cttctacccc gtatttgccg   29640
tgccagaggt gcttgccacc tatcacatct ttttccaaaa ctgcaagata cccctatcct   29700
gccgtgccaa ccgcagccga gcggacaagc agctggcctt gcggcagggc gctgtcatac   29760
ctgatatcgc ctcgctcaac gaagtgccaa aaatctttga gggtcttgga cgcgacgaga   29820
agcgcgcggc aaacgctctg caacaggaaa acagcgaaaa tgaaagtcac tctggagtgt   29880
tggtggaact cgagggtgac aacgcgcgcc tagccgtact aaaacgcagc atcgaggtca   29940
cccactttgc ctacccggca cttaacctac cccccaaggt catgagcaca gtcatgagtg   30000
agctgatcgt gcgccgtgcg cagccccctgg agagggatgc aaatttgcaa gaacaaacag   30060
aggagggcct accgcagtt ggcgacgagc agctagcgcg ctggcttcaa acgcgcgagc   30120
ctgccgactt ggaggagcga cgcaaactaa tgatggccgc agtgctcgtt accgtggagc   30180
ttgagtgcat gcagcggttc tttgctgacc cggagatgca gcgcaagcta gaggaaacat   30240
tgcactacac cttcgacag ggctacgtac gccaggcctg caagatctcc aacgtggagc   30300
tctgcaacct ggtctcctac cttggaattt tgcacgaaaa ccgccttggg caaaacgtgc   30360
ttcattccac gctcaagggc gaggcgcgcc gcgactacgt ccgcgactgc gtttacttat   30420
ttctatgcta cacctggcag acggccatgg gcgtttggca gcagtgcttg gaggagtgca   30480
acctcaagga gctgcagaaa ctgctaaagc aaaacttgaa ggacctatgg acggccttca   30540
acgagcgctc cgtggccgcg cacctggcgg acatcatttt ccccgaacgc ctgcttaaaa   30600
ccctgcaaca gggtctgcca gacttcacca gtcaaagcat gttgcagaac tttaggaact   30660
ttatcctaga gcgctcagga atcttgcccg ccacctgctg tgcacttcct agcgactttg   30720
tgcccattaa gtaccgcgaa tgccctccgc cgctttgggg ccactgctac cttctgcagc   30780
tagccaacta ccttgcctac cactctgaca taatggaaga cgtgagcggt gacggtctac   30840
tggagtgtca ctgtcgctgc aacctatgca cccccgcacc ctccctggtt tgcaattcgc   30900
agctgcttaa cgaaagtcaa attatcggta cctttgagct gcagggtccc tcgcctgacg   30960
aaaagtccgc ggctccgggg ttgaaactca ctccggggct gtggacgtcg gcttaccttc   31020
gcaaatttgt acctgaggac taccacgccc acgagattag gttctacgaa gaccaatccc   31080
gcccgccaaa tgcggagctt accgcctgcg tcattaccca gggccacatt cttgccaat    31140 tgcaagccat caacaaagcc cgccaagagt ttctgctacg aaagggacgg ggggtttact   31200
```

```
tggaccccca gtccggcgag gagctcaacc caatcccccc gccgccgcag ccctatcagc   31260
agcagccgcg ggcccttgct tcccaggatg gcacccaaaa agaagctgca gctgccgccg   31320
ccacccacgg acgaggagga atactgggac agtcaggcag aggaggtttt ggacgaggag   31380
gaggaggaca tgatggaaga ctgggagagc ctagacgagg aagcttccga ggtcgaagag   31440
gtgtcagacg aaacaccgtc accctcggtc gcattcccct cgccggcgcc ccagaaatcg   31500
gcaaccggtt ccagcatggc tacaacctcc gctcctcagg cgccgccggc actgcccgtt   31560
cgccgaccca accgtagatg ggacaccact ggaaccaggg ccggtaagtc caagcagccg   31620
ccgccgttag cccaagagca acaacagcgc caaggctacc gctcatggcg cgggcacaag   31680
aacgccatag ttgcttgctt gcaagactgt gggggcaaca tctccttcgc ccgccgcttt   31740
cttctctacc atcacggcgt ggccttcccc cgtaacatcc tgcattacta ccgtcatctc   31800
tacagcccat actgcaccgg cggcagcggc agcggcagca acagcagcgg ccacacagaa   31860
gcaaaggcga ccggatagca agactctgac aaagcccaag aaatccacag cggcggcagc   31920
agcaggagga ggagcgctgc gtctggcgcc caacgaaccc gtatcgaccc gcgagcttag   31980
aaacaggatt tttcccactc tgtatgctat atttcaacag agcaggggcc aagaacaaga   32040
gctgaaaata aaaaacaggt ctctgcgatc cctcacccgc agctgcctgt atcacaaaag   32100
cgaagatcag cttcggcgca cgctggaaga cgcggaggct ctcttcagta aatactgcgc   32160
gctgactctt aaggactagt ttcgcgccct ttctcaaatt taagcgcgaa aactacgtca   32220
tctccagcgg ccacacccgg cgccagcacc tgtcgtcagc gccatttatg agcaaggaaa   32280
ttcccacgcc ctacatgtgg agttaccagc cacaaatggg acttgcggct ggagctgccc   32340
aagactactc aacccgaata aactacatga gcgcgggacc ccacatgata tcccgggtca   32400
acggaatacg cgcccaccga aaccgaattc tcctggaaca ggcggctatt accaccacac   32460
ctcgtaataa ccttaatccc cgtagttggc ccgctgccct ggtgtaccag gaaagtcccg   32520
ctcccaccac tgtggtactt cccagagacg cccaggccga agttcagatg actaactcag   32580
gggcgcagct tgcgggcggc tttcgtcaca gggtgcggtc gcccgggcag ggtataactc   32640
acctgacaat cagagggcga ggtattcagc tcaacgacga gtcggtgagc tcctcgcttg   32700
gtctccgtcc ggacgggaca tttcagatcg gcggcgccgg ccgctcttca ttcacgcctc   32760
gtcaggcaat cctaactctg cagacctcgt cctctgagcc gcgctctgga ggcattggaa   32820
ctctgcaatt tattgaggag tttgtgccat cggtctactt taaccccttc tcgggacctc   32880
ccggccacta tccggatcaa tttattccta actttgacgc ggtaaaggac tcggcggacg   32940
gctacgactg aatgttaagt ggagaggcag agcaactgcg cctgaaacac ctggtccact   33000
gtcgccgcca caagtgcttt gcccgcgact ccggtgagtt ttgctacttt gaattgcccg   33060
aggatcatat cgagggcccg gcgcacggcg tccggcttac cgcccaggga gagcttgccc   33120
gtagcctgat tcgggagttt acccagcgcc ccctgctagt tgagcgggac aggggaccct   33180
gtgttctcac tgtgatttgc aactgtccta accctggatt acaatttaaa tgcggtctca   33240
aagatcttat tccctttaac taataaaaaa aaataataaa gcatcactta cttaaaatca   33300
gttagcaaat ttctgtccag tttattcagc agcacctcct tgccctcctc ccagctctgg   33360
tattgcagct tcctcctggc tgcaaacttt ctccacaatc taaatggaat gtcagtttcc   33420
tcctgttcct gtccatccgc acccactatc ttcatgttgt tgcagatgaa gcgcgcaaga   33480
ccgtctgaag ataccttcaa ccccgtgtat ccatatgaca cggaaaccgg tcctccaact   33540
gtgccttttc ttactcctcc ctttgtatcc cccaatgggt ttcaagagag tccccctggg   33600
```

```
gtactctctt tgcgcctatc cgaacctcta gttacctcca atggcatgct tgcgctcaaa    33660
atgggcaacg gcctctctct ggacgaggcc ggcaaccttc cctcccaaaa tgtaaccact    33720
gtgagcccac ctctcaaaaa aaccaagtca aacataaacc tggaaatatc tgcacccctc    33780
acagttacct cagaagccct aactgtggct gccgccgcac ctctaatggt cgcgggcaac    33840
acactcacca tgcaatcaca ggcccgcta accgtgcacg actccaaact tagcattgcc    33900
acccaaggac ccctcacagt gtcagaagga agctagccc tgcaaacatc aggcccctc    33960 accaccaccg atagcagtac ccttactatc actgcctcac cccctctaac tactgccact    34020
ggtagcttgg gcattgactt gaaagagccc atttatacac aaaatggaaa actaggacta    34080
aagtacgggg ctcctttgca tgtaacagac gacctaaaca ctttgaccgt agcaactggt    34140
ccaggtgtga ctattaataa tacttccttg caaactaaag ttactggagc cttgggtttt    34200
gattcacaag gcaatatgca acttaatgta gcaggaggac taaggattga ttctcaaaac    34260
agacgcctta tacttgatgt tagttatccg tttgatgctc aaaaccaact aaatctaaga    34320
ctaggacagg gccctctttt tataaactca gcccacaact tggatattaa ctacaacaaa    34380
ggcctttact tgtttacagc ttcaaacaat tccaaaaagc ttgaggttaa cctaagcact    34440 gccaagggt tgatgtttga cgctacagcc atagccatta atgcaggaga tgggcttgaa    34500
tttggttcac ctaatgcacc aaacacaaat cccctcaaaa caaaaattgg ccatggccta    34560
gaatttgatt caaacaaggc tatggttcct aaactaggaa ctggccttag ttttgacagc    34620
acaggtgcca ttacagtagg aaacaaaaat aatgataagc taactttgtg gaccacacca    34680
gctccatctc ctaactgtag actaaatgca gagaaagatg ctaaactcac tttggtctta    34740
acaaaatgtg gcagtcaaat acttgctaca gtttcagttt tggctgttaa aggcagtttg    34800
gctccaatat ctggaacagt tcaaagtgct catcttatta taagatttga cgaaaatgga    34860
gtgctactaa acaattcctt cctggaccca gaatattgga actttagaaa tggagatctt    34920
actgaaggca cagcctatac aaacgctgtt ggatttatgc ctaacctatc agcttatcca    34980
aaatctcacg gtaaaactgc caaaagtaac attgtcagtc aagtttactt aaacggagac    35040
aaaactaaac ctgtaacact aaccattaca ctaaacggta cacaggaaac aggagacaca    35100
actccaagtg catactctat gtcattttca tgggactggt ctggccacaa ctacattaat    35160
gaaatatttg ccacatcctc ttacactttt tcatacattg cccaagaata aagaatcgtt    35220
tgtgttatgt ttcaacgtgt ttatttttca attgcagaaa atttcaagtc attttttcatt    35280 cagtagtata gccccaccac cacatagctt atacagatca ccgtaccta atcaaactca    35340 cagaacccta gtattcaacc tgccacctcc ctcccaacac acagagtaca cagtcctttc    35400
tccccggctg gccttaaaaa gcatcatatc atgggtaaca gacatattct taggtgttat    35460
attccacacg gtttcctgtc gagccaaacg ctcatcagtg atattaataa actccccggg    35520
cagctcactt aagttcatgt cgctgtccag ctgctgagcc acaggctgct gtccaacttg    35580
cggttgctta acgggcggcg aaggagaagt ccacgcctac atgggggtag agtcataatc    35640
gtgcatcagg atagggcggt ggtgctgcag cagcgcgcga ataaactgct gccgccgccg    35700
ctccgtcctg caggaataca acatggcagt ggtctcctca gcgatgattc gcaccgcccg    35760
cagcataagg cgccttgtcc tccgggcaca gcagcgcacc ctgatctcac ttaaatcagc    35820
acagtaactg cagcacagca ccacaatatt gttcaaaatc ccacagtgca aggcgctgta    35880
tccaaagctc atggcgggga ccacagaacc cacgtggcca tcataccaca agcgcaggta    35940
```

```
gattaagtgg cgacccctca taaacacgct ggacataaac attacctctt ttggcatgtt   36000
gtaattcacc acctcccggt accatataaa cctctgatta acatggcgc catccaccac   36060 catcctaaac cagctggcca aaacctgccc gccggctata cactgcaggg aaccgggact   36120
ggaacaatga cagtggagag cccaggactc gtaaccatgg atcatcatgc tcgtcatgat   36180
atcaatgttg gcacaacaca ggcacacgtg catacacttc ctcaggatta caagctcctc   36240
ccgcgttaga accatatccc agggaacaac ccattcctga atcagcgtaa atcccacact   36300
gcagggaaga cctcgcacgt aactcacgtt gtgcattgtc aaagtgttac attcgggcag   36360
cagcggatga tcctccagta tggtagcgcg ggtttctgtc tcaaaaggag gtagacgatc   36420
cctactgtac ggagtgcgcc gagacaaccg agatcgtgtt ggtcgtagtg tcatgccaaa   36480
tggaacgccg gacgtagtca tatttcctga agcaaaacca ggtgcgggcg tgacaaacag   36540
atctgcgtct ccggtctcgc cgcttagatc gctctgtgta gtagttgtag tatatccact   36600
ctctcaaagc atccaggcgc ccctggctt cgggttctat gtaaactcct tcatgcgccg   36660
ctgccctgat aacatccacc accgcagaat aagccacacc cagccaacct acacattcgt   36720
tctgcgagtc acacacggga ggagcgggaa gagctggaag aaccatgttt ttttttttat   36780
tccaaaagat tatccaaaac ctcaaaatga agatctatta agtgaacgcg ctcccctccg   36840
gtggcgtggt caaactctac agccaaagaa cagataatgg catttgtaag atgttgcaca   36900
atggcttcca aaaggcaaac ggccctcacg tccaagtgga cgtaaaggct aaaccttca    36960 gggtgaatct cctctataaa cattccagca ccttcaacca tgcccaaata attctcatct   37020
cgccaccttc tcaatatatc tctaagcaaa tcccgaatat taagtccggc cattgtaaaa   37080
atctgctcca gagcgccctc caccttcagc ctcaagcagc gaatcatgat tgcaaaaatt   37140
caggttcctc acagacctgt ataagattca aaagcggaac attaacaaaa ataccgcgat   37200
cccgtaggtc ccttcgcagg gccagctgaa cataatcgtg caggtctgca cggaccagcg   37260
cggccacttc cccgccagga accatgacaa agaacccac actgattatg acacgcatac   37320
tcggagctat gctaaccagc gtagccccga tgtaagcttg ttgcatgggc ggcgatataa   37380
aatgcaaggt gctgctcaaa aaatcaggca aagcctcgcg caaaaaagaa agcacatcgt   37440
agtcatgctc atgcagataa aggcaggtaa gctccggaac caccacagaa aaagacacca   37500
tttttctctc aaacatgtct gcgggtttct gcataaacac aaaataaaat aacaaaaaaa   37560
catttaaaca ttagaagcct gtcttacaac aggaaaaaca acccttataa gcataagacg   37620
gactacggcc atgccggcgt gaccgtaaaa aaactggtca ccgtgattaa aaagcaccac   37680
cgacagctcc tcggtcatgt ccggagtcat aatgtaagac tcggtaaaca catcaggttg   37740
attcacatcg gtcagtgcta aaagcgacc gaaatagccc gggggaatac atacccgcag   37800
gcgtagagac aacattacag cccccatagg aggtataaca aaattaatag gagagaaaaa   37860
cacataaaca cctgaaaaac cctcctgcct aggcaaaata gcaccctccc gctccagaac   37920
aacatacagc gcttccacag cggcagccat aacagtcagc cttaccagta aaaagaaaa    37980 cctattaaaa aaacaccact cgacacggca ccagctcaat cagtcacagt gtaaaaaagg   38040
gccaagtgca gagcgagtat atataggact aaaaaatgac gtaacggtta aagtccacaa   38100
aaaacaccca gaaaaccgca cgcgaaccta cgcccagaaa cgaaagccaa aaaacccaca   38160
acttcctcaa atcgtcactt ccgttttccc acgttacgtc acttcccatt ttaagaaaac   38220
tacaattccc aacacataca agttactccg ccctaaaacc tacgtcaccc gccccgttcc   38280
cacgccccgc gccacgtcac aaactccacc ccctcattat catattggct tcaatccaaa   38340
```

```
ataaggtata ttattgatga tgtagggata acagggtaat aaatccgggg atcctctaga    38400
gtcgacctgc aggcatgcaa gcttggcgta atcatggtca tagctgtttc ctgtgtgaaa    38460
ttgttatccg ctcacaattc cacacaacat acgagccgga agcataaagt gtaaagcctg    38520
gggtgcctaa tgagtgagct a                                              38541

<210> SEQ ID NO 3
<211> LENGTH: 39429
<212> TYPE: DNA
<213> ORGANISM: Artificial Sequence
<220> FEATURE:
<223> OTHER INFORMATION: Synthetic adenovirus vector (CMV-PLSCR1D284A-
      P2A-tdTomato)

<400> SEQUENCE: 3
gttccactga gcgtcagacc ccttaataag atgatcttct tgagatcgtt ttggtctgcg      60
cgtaatctct tgctctgaaa acgaaaaaac cgccttgcag ggcggttttt cgaaggttct     120
ctgagctacc aactctttga accgaggtaa ctggcttgga gagcgcagt caccaaaact     180 tgtcctttca gtttagcctt aaccggcgca tgacttcaag actaactcct ctaaatcaat     240
taccagtggc tgctgccagt ggtgcttttg catgtctttc cgggttggac tcaagacgat     300
agttaccgga taaggcgcag cggtcggact gaacggggggg ttcgtgcata cagtccagct     360
tggagcgaac tgcctacccg gaactgagtg tcaggcgtgg aatgagacaa acgcggccat     420
aacagcggaa tgacaccggt aaaccgaaag gcaggaacag gagagcgcac gagggagccg     480
ccaggggaaa cgcctggtat ctttatagtc ctgtcgggtt cgccaccac tgatttgagc     540 gtcagatttc gtgatgcttg tcagggggc ggagcctatg gaaaaacggc tttgccgcgg     600
ccctctcact tccctgttaa gtatcttcct ggcatcttcc aggaaatctc cgccccgttc     660
gtaagccatt tccgctcgcc gcagtcgaac gaccgagcgt agcgagtcag tgagcgagga     720
agcggaatat atcctgtatc acatattctg ctgacgcacc ggtgcagcct ttttctcct     780 gccacatgaa gcacttcact gacaccctca tcagtgccaa catagtaagc cagtatacac     840
tccgctagcg ctgaggtctg cctcgtgaag aaggtgttgc tgactcatac caggcctgaa     900
tcgccccatc atccagccag aaagtgaggg agccacggtt gatgagagct ttgttgtagg     960
tggaccagtt ggtgattttg aacttttgct ttgccacgga acgtctgcg ttgtcgggaa    1020 gatgcgtgat ctgatccttc aactcagcaa aagttcgatt tattcaacaa agccacgttg    1080
tgtctcaaaa tctctgatgt tacattgcac aagataaaaa tatatcatca tgaacaataa    1140
aactgtctgc ttacataaac agtaatacaa ggggtgttga tactctcagt acaatctgct    1200
ctgatgccgc atagttaagc cagtatctgc tccctgcttg tgtgttggag gtcgctgagt    1260
agtgcgcgag caaaatttaa gctacaacaa ggcaaggctt gaccgacaat gcatgaaga    1320 atctgcttag ggttaggcgt tttgcgctgc ttcgcgatgt acgggccaga tatacgcgta    1380
tctgagggga ctagggtgtg tttaggcgaa agcgggggct tcggttgtac gcggttagga    1440
gtcccctcag gatatagtag tttcgctttt gcatagggag ggggaaatgt agtcttatgc    1500
aatactcttg tagtcttgca acatggtaac gatgagttag caacatgcct tacaaggaga    1560
gaaaaagcac cgtgcatgcc gattggtgga agtaaggtgg tacgatcgtg ccttattagg    1620
aaggcaacag acgggtctga catggattgg acgaaccact gaattccgca ttgcagagat    1680
attgtattta agtgcctagc tcgatacaat aaacgccatt tgaccattca ccacattggt    1740
gtgcacctcc aagctgggta cggatccggc cttgccggcc tcgagcggcc gctagcgccg    1800
```

```
ccactatggg atcaagatcg ccaaaaaaga agagaaaggt gccgaagaag catgcagcac   1860
caccaaaaaa aaaacgaaaa gtagaagacc cacgatttat gtacccatac gatgttcctg   1920
actatgcggg tatgaaaaac atcaaaaaaa accaggtaat gaacctgggt ccgaactcta   1980
aactgctgaa agaatacaaa tcccagctga tcgaactgaa catcgaacag ttcgaagcag   2040
gtatcggtct gatcctgggt gatgcttaca tccgttctcg tgatgaaggt aaaacctact   2100
gtatgcagtt cgagtggaaa aacaaagcat acatggacca cgtatgtctg ctgtacgatc   2160
agtgggtact gtccccgccg cacaaaaaag aacgtgttaa ccacctgggt aacctggtaa   2220
tcacctgggg cgcccagact ttcaaacacc aagctttcaa caaactggct aacctgttca   2280
tcgttaacaa caaaaaaacc atcccgaaca acctggttga aaactacctg ccccgatgt    2340 ctctggcata ctggttcatg gatgatggtg gtaaatggga ttacaacaaa aactctacca   2400
acaaatcgat cgtactgaac acccagtctt tcactttcga agaagtagaa tacctggtta   2460
agggtctgcg taacaaattc caactgaact gttacgtaaa aatcaacaaa aacaaaccga   2520
tcatctacat cgattctatg tcttacctga tcttctacaa cctgatcaaa ccgtacctga   2580
tcccgcagat gatgtacaaa ctgccgaaca ctatctcctc cgaaactttc ctgaaataag   2640
gtaccgatcc agacatgata agatacattg atgagtttgg acaaaccaca actagaatgc   2700
agtgaaaaaa atgctttatt tgtgaaattt gtgatgctat tgcttttattt gtaaccatta   2760 taagctgcaa taaacaagtt aacaacaaca attgcattca ttttatgttt caggttcagg   2820
gggaggtgtg ggaggttttt taaagcaagt aaaacctcta caaatgtggt atggctgatt   2880
atgatcatcg taaacttggt ctgacagtta ccaatgctta atcagtgagg cacctatctc   2940
agcgatctgt ctatttcgtt catccatagt tgcctgactc cccgtcgtgt agataactac   3000
gatacgggag ggcttaccat ctggccccag tgctgcaatg ataccgcgag acccacgctc   3060
accggctcca gatttatcag caataaacca gccagccgga agggccgagc gcagaagtgg   3120
tcctgcaact ttatccgcct ccatccagtc tattaattgt tgccgggaag ctagagtaag   3180
tagttcgcca gttaatagtt tgcgcaacgt tgttgccatt gctacaggca tcgtggtgtc   3240
acgctcgtcg tttggtatgg cttcattcag ctccggttcc caacgatcaa ggcgagttac   3300
atgatccccc atgttgtgca aaaaagcggt tagctccttc ggtcctccga tcgttgtcag   3360
aagtaagttg gccgcagtgt tatcactcat ggttatggca gcactgcata attctcttac   3420
tgtcatgcca tccgtaagat gcttttctgt gactggtgag tactcaacca agtcattctg   3480
agaatagtgt atgcggcgac cgagttgctc ttgcccggcg tcaatacggg ataataccgc   3540
gccacatagc agaactttaa aagtgctcat cattggaaaa cgttcttcgg ggcgaaaact   3600
ctcaaggatc ttaccgctgt tgagatccag ttcgatgtaa cccactcgtg cacccaactg   3660
atcttcagca tcttttactt tcaccagcgt ttctgggtga gcaaaaacag gaaggcaaaa   3720
tgccgcaaaa aagggaataa gggcgacacg gaaatgttga atactcatac tcttcctttt   3780
tcaatattat tgaagcattt atcagggtta ttgtctcatg agcggataca tatttgaatg   3840
tatttagaaa aataaacaaa tagggggttcc gcgcacattt ccccgaaaag tgccacctga   3900
cgtctaagaa accattatta tcatgacatt aacctataaa aataggcgta tcacgaggcc   3960
ctttcgtctc gcgcgtttcg gtgatgacgg tgaaaacctc tgacacatgc agctcccgga   4020
gacggtcaca gcttgtctgt aagcggatgc cgggagcaga caagcccgtc agggcgcgtc   4080
agcgggtgtt ggcgggtgtc ggggctggct taactatgcg gcatcagagc agattgtact   4140
```

```
gagagtgcac catatgcggt gtgaaatacc gcacagatgc gtaaggagaa aataccgcat    4200
caggcgccat tcgccattca ggctgcgcaa ctgttgggaa gggcgatcgg tgcgggcctc    4260
ttcgctatta cgccagctgg cgaaagggggg atgtgctgca aggcgattaa gttgggtaac    4320
gccagggttt tcccagtcac gacgttgtaa aacgacggcc agtgaattac caactttgta    4380
caaaaaagca gattaccctg ttatccctac atcatcaata atataccttta ttttggattg    4440 aagccaatat gataatgagg gggtggagtt tgtgacgtgg cgcggggcgt gggaacgggg    4500
cgggtgacgt agtagtgtgg cggaagtgtg atgttgcaag tgtggcggaa cacatgtaag    4560
cgacggatgt ggcaaaagtg acgttttttgg tgtgcgccgg tgtacacagg aagtgacaat    4620
tttcgcgcgg ttttaggcgg atgttgtagt aaatttgggc gtaaccgagt aagatttggc    4680
cattttcgcg ggaaaactga ataagaggaa gtgaaatctg aataattttg tgttactcat    4740
agcgcgtaat atttgtctag ggccgcgggg actttgaccg tttacgtgga gactcgccca    4800 ggtgttttc tcaggtgttt tccgcgttcc gggtcaaagt tggcgtttta ttattaatta    4860
agtttaaact tgaatcaata ttggcaatta gccatattag tcattggtta tatagcataa    4920
atcaatattg gctattggcc attgcatacg ttgtatctat atcataatat gtacatttat    4980
attggctcat gtccaatatg accgccatgt tgacattgat tattgactag ttattaatag    5040
taatcaatta cgggtcatt agttcatagc ccatatatgg agttccgcgt tacataactt    5100
acggtaaatg gcccgcctgg ctgaccgccc aacgacccc gcccattgac gtcaataatg    5160
acgtatgttc ccatagtaac gccaataggg actttccatt gacgtcaatg ggtggagtat    5220
ttacggtaaa ctgcccactt ggcagtacat caagtgtatc atatgccaag tccgccccct    5280
attgacgtca atgacggtaa atggcccgcc tggcattatg cccagtacat gaccttacgg    5340 gacttttccta cttggcagta catctacgta ttagtcatcg ctattaccat ggtgatgcgg    5400
ttttggcagt acaccaatgg gcgtggatag cggtttgact cacggggatt tccaagtctc    5460 cacccccattg acgtcaatgg gagtttgttt tggcaccaaa atcaacggga ctttccaaaa    5520
tgtcgtaata accccgcccc gttgacgcaa atgggcggta ggcgtgtacg gtgggaggtc    5580
tatataagca gagctcgttt agtgaaccgt cagaattttg taatacgact cactataggg    5640
cggccgggaa ttcgtcgact ggatccggta ccgaggagat ctgccgccgc gatcgccatg    5700
gaaaaccaca gcaagcaaac tgaggctccc cacccgggaa catatatgcc agctgggtat    5760 cccctccgt atccaccagc agctttccaa ggaccttcag accatgctgc ttaccccata    5820
ccccaggctg gctaccaagg gcctccgggc ccctatccag ggcccaacc tggctaccca    5880 gtcccaccag gaggttatgc aggtggtggc cctagtggct ttcctgtcca aaatcagcca    5940
gcatataatc atccaggtgg gcctgggggg accccatgga tgccagcccc cccacctcca    6000
ctgaactgtc caccggggct ggaatactta gctcagattg atcagcttct ggttcatcag    6060
caaattgagc ttctgaagt cttaacaggc tttgaaacaa ataacaaata tgaaatcaag    6120
aacagcctcg ggcagagagt ttactttgca gtggaagata ctgactgctg tacccgaaac    6180
tgctgtgggg cgtctagacc tttcacctttg aggatcctgg ataatctggg ccgagaagtc    6240
atgactctgg agcgacctct gagatgcagt agctgctgct tcccctgctg cctccaggag    6300
atagaaatcc aggctcctcc tgggtgcca gtaggttatg tgactcagac ctggcaccca    6360
tgtctgccca gttcactct ccaaaatgag aagaagcagg atgtcctgaa agtagttggt    6420
ccgtgtgttt tgtgtagctg ctgttccgac attgactttg agctcaaatc tctagatgaa    6480
gaatcagtag ttggcaaaat ttctaagcag tggtctggtt ttgtgagaga ggccttcacg    6540
```

| | |
|---|---|
| gatgcagcca actttgggat ccagttcccg ctagacctgg atgtgaagat gaaagctgtg | 6600 |
| atgcttggtg cttgtttcct catagatttc atgttttttg aaagaactgg aaacgaggaa | 6660 |
| caaagatcag gagtatggac gcgtacgcgg ccgctcgagc agaaactcat ctcagaagag | 6720 |
| gatctggcag caaatgatat cctggattac aaggatgacg acgataaggt tggatccgga | 6780 |
| gccacgaact tctctctgtt aaagcaagca ggagacgtgg aagaaaaccc cggtcctaga | 6840 |
| tctatggtga gcaagggcga ggaggtcatc aaagagttca tgcgcttcaa ggtgcgcatg | 6900 |
| gagggctcca tgaacggcca cgagttcgag atcgagggcg agggcgaggg ccgcccctac | 6960 |
| gagggcaccc agaccgccaa gctgaaggtg accaagggcg cccccctgcc cttcgcctgg | 7020 |
| gacatcctgt cccccagtt catgtacggc tccaaggcgt acgtgaagca ccccgccgac | 7080 |
| atccccgatt acaagaagct gtccttcccc gagggcttca gtgggagcg cgtgatgaac | 7140 |
| ttcgaggacg gcggtctggt gaccgtgacc caggactcct ccctgcagga cggcacgctg | 7200 |
| atctacaagg tgaagatgcg cggcaccaac ttcccccccg acggcccgt aatgcagaag | 7260 |
| aagaccatgg gctgggaggc ctccaccgag cgcctgtacc ccgcgacgg cgtgctgaag | 7320 |
| ggcgagatcc accaggccct gaagctgaag gacggcggcc actacctggt ggagttcaag | 7380 |
| accatctaca tggccaagaa gcccgtgcaa ctgcccggct actactacgt ggacaccaag | 7440 |
| ctggacatca cctcccacaa cgaggactac accatcgtgg aacagtacga gcgctccgag | 7500 |
| ggccgccacc acctgttcct ggggcatggc accggcagca ccggcagcgg cagctccggc | 7560 |
| accgcctcct ccgaggacaa caacatggcc gtcatcaaag agttcatgcg cttcaaggtg | 7620 |
| cgcatggagg gctccatgaa cggccacgag ttcgagatcg agggcgaggg cgagggccgc | 7680 |
| ccctacgagg gcacccagac cgccaagctg aaggtgacca agggcggccc cctgcccttc | 7740 |
| gcctgggaca tcctgtcccc ccagttcatg tacggctcca aggcgtacgt gaagcacccc | 7800 |
| gccgacatcc ccgattacaa gaagctgtcc ttccccgagg gcttcaagtg ggagcgcgtg | 7860 |
| atgaacttcg aggacggcgg tctggtgacc gtgacccagg actcctccct gcaggacggc | 7920 |
| acgctgatct acaaggtgaa gatgcgcggc accaacttcc cccccgacgg ccccgtaatg | 7980 |
| cagaagaaga ccatgggctg ggaggcctcc accgagcgcc tgtaccccg cgacggcgtg | 8040 |
| ctgaagggcg agatccacca ggccctgaag ctgaaggacg gcggccgcta cctggtggag | 8100 |
| ttcaagacca tctacatggc caagaagccc gtgcaactgc ccggctacta ctacgtggac | 8160 |
| accaagctgg acatcacctc ccacaacgag gactacacca tcgtggaaca gtacgagcgc | 8220 |
| tccgagggcc gccaccacct gttcctgtac ggcatggacg agctgtacaa gtaaggccgc | 8280 |
| aagaggtaag ggtttaaggg atggtcggtt ggtggggtat taatgtttaa ttacctggag | 8340 |
| cacctgcctg aaatcacttt ttttcaggtt ggaatcgata atcaacctct ggattacaaa | 8400 |
| atttgtgaaa gattgactgg tattcttaac tatgttgctc cttttacgct atgtggatac | 8460 |
| gctgctttaa tgcctttgta tcatgctatt gcttcccgta tggctttcat tttctcctcc | 8520 |
| ttgtataaat cctggttgct gtctctttat gaggagttgt ggcccgttgt caggcaacgt | 8580 |
| ggcgtggtgt gcactgtgtt tgctgacgca accccactg gttggggcat gccaccacc | 8640 |
| tgtcagctcc tttccgggac tttcgctttc ccctcccta ttgccacggc ggaactcatc | 8700 |
| gccgcctgcc ttgcccgctg ctggacaggg gctcggctgt tgggcactga caattccgtg | 8760 |
| gtgttgtcgg ggaagctgac gtcctttcca tggctgctcg cctgtgttgc cacctggatt | 8820 |
| ctgcgcggga cgtccttctg ctacgtccct tcggccctca atccagcgga ccttccttcc | 8880 |

```
cgcggcctgc tgccggctct gcggcctctt ccgcgtcttc gccttcgccc tcagacgagt    8940
cggatctccc tttgggccgc ctccccgcct gctgcagggc gccatcgtgg atgggagtcc    9000
gtgtgtgcct ggagattacc ctggacacct ctgctttttt tttttttactt tagcggttgc    9060
ctcctaggcc tgactccttc ccatgttgaa ctggaggcag ccacgttagg tgtcaatgtc    9120
ctggcatcag tatgaacagt cagtagtccc agggcagggc cacacttctc ccatcttctg    9180
cttccacccc agcttgtgat tgctagcctc ccagagctca attgctgtgc cttcagttg     9240
ccagccatct gttgtttgcc cctccccgt  gccttccttg accctggaag gtgccactcc    9300
cactgtcctt tcctaataaa atgaggaaat tgcatcgcat tgtctgagta ggtgtcattc    9360
tattctgggg ggtggggtgg ggcaggacag caaggggag  gattgggaag acaatagcag    9420
gcatgctggg gatgcggtgg gctctatgga cgcgtcggcc gctgcagctc gagtctagag    9480
ctgacggcgc gcctgaaatg tgtgggcgtg gcttaagggt gggaaagaat atataaggtg    9540
ggggtcttat gtagttttgt atctgttttg cagcagccgc cgccgccatg agcaccaact    9600
cgtttgatgg aagcattgtg agctcatatt tgacaacgcg catgccccca tgggccgggg    9660
tgcgtcagaa tgtgatgggc tccagcattg atggtcgccc cgtcctgccc gcaaactcta    9720
ctaccttgac ctacgagacc gtgtctggaa cgccgttgga gactgcagcc tccgccgccg    9780
cttcagccgc tgcagccacc gcccgcggga ttgtgactga cttttgctttc ctgagcccgc    9840
ttgcaagcag tgcagcttcc cgttcatccg cccgcgatga caagttgacg gctcttttgg    9900
cacaattgga ttctttgacc cgggaactta atgtcgtttc tcagcagctg ttggatctgc    9960
gccagcaggt ttctgccctg aaggcttcct cccctcccaa tgcggtttaa acataaata    10020
aaaaaccaga ctctgtttgg atttggatca agcataagtg tcttgctgtc tttatttagg   10080
ggttttgcgc gcgcggtagg cccgggacca gcggtctcgg tcgttgaggg tcctgtgtat   10140
tttttccagg acgtggtaaa ggtgactctg gatgttcaga tacatgggca taagcccgtc   10200
tctggggtgg aggtagcacc actgcagagc ttcatgctgc ggggtggtgt tgtagatgat   10260
ccagtcgtag caggagcgct gggcgtggtg cctaaaaatg tctttcagta gcaagctgat   10320
tgccagggca aggcccttgg tgtaagtgtt tacaaagcgg ttaagctggg atgggtgcat   10380
acgtggggat atgagatgca tcttggactg tattttttagg ttggctatgt tcccagccat   10440
atccctccgg ggattcatgt tgtgcagaac caccagcaca gtgtatccgg tgcacttggg   10500
aaatttgtca tgtagcttag aaggaaatgc gtggaagaac ttggagacgc ccttgtgacc   10560
tccaagattt tccatgcatt cgtccataat gatggcaatg gcccacgggg cggcggcctg   10620
ggcgaagata tttctgggat cactaacgtc atagttgtgt tccaggatga gatcgtcata   10680
ggccattttt acaaagcgcg gcggaggggt gccagactgc ggtataatgg ttccatccgg   10740
cccaggggcg tagttaccct cacagatttg catttcccac gctttgagtt cagatggggg   10800
gatcatgtct acctgcgggg cgatgaagaa aacggtttcc ggggtagggg agatcagctg   10860
ggaagaaagc aggttcctga gcagctgcga cttaccgcag ccggtgggcc cgtaaatcac   10920
acctattacc gggtgcaact ggtagttaag agagctgcag ctgccgtcat ccctgagcag   10980
gggggccact tcgttaagca tgtccctgac tcgcatgttt tccctgacca aatccgccag   11040
aaggcgctcg ccgcccagcg atagcagttc ttgcaaggaa gcaaagtttt tcaacggttt   11100
gagaccgtcc gccgtaggca tgcttttgag cgttttgacca agcagttcca ggcggtccca   11160
cagctcggtc acctgctcta cggcatctcg atccagcata tctcctcgtt tcgcgggttg   11220
gggcggcttt cgctgtacgg cagtagtcgg tgctcgtcca gacgggccag ggtcatgtct   11280
```

```
ttccacgggc gcagggtcct cgtcagcgta gtctgggtca cggtgaaggg gtgcgctccg    11340
ggctgcgcgc tggccagggt gcgcttgagg ctggtcctgc tggtgctgaa gcgctgccgg    11400
tcttcgccct gcgcgtcggc caggtagcat ttgaccatgg tgtcatagtc cagcccctcc    11460
gcggcgtggc ccttggcgcg cagcttgccc ttggaggagg cgccgcacga ggggcagtgc    11520
agacttttga gggcgtagag cttgggcgcg agaaataccg attccgggga gtaggcatcc    11580
gcgccgcagg ccccgcagac ggtctcgcat tccacgagcc aggtgagctc tggccgttcg    11640
gggtcaaaaa ccaggtttcc cccatgcttt ttgatgcgtt tcttacctct ggtttccatg    11700
agccggtgtc cacgctcggt gacgaaaagg ctgtccgtgt ccccgtatac agacttgaga    11760
ggcctgtcct cgagcggtgt tccgcggtcc tcctcgtata gaaactcgga ccactctgag    11820
acaaaggctc gcgtccaggc cagcacgaag gaggctaagt gggaggggta gcggtcgttg    11880
tccactaggg ggtccactcg ctccagggtg tgaagacaca tgtcgccctc ttcggcatca    11940
aggaaggtga ttggtttgta ggtgtaggcc acgtgaccgg tgttcctga aggggggcta    12000
taaaaggggg tgggggcgcg ttcgtcctca ctctcttccg catcgctgtc tgcgagggcc    12060
agctgttggg gtgagtactc cctctgaaaa gcgggcatga cttctgcgct aagattgtca    12120
gtttccaaaa acgaggagga tttgatattc acctggcccg cggtgatgcc tttgagggtg    12180
gccgcatcca tctggtcaga aaagacaatc ttttgttgt caagcttggt ggcaaacgac    12240
ccgtagaggg cgttggacag caacttggcg atggagcgca gggtttggtt tttgtcgcga    12300
tcggcgcgct ccttggccgc gatgtttagc tgcacgtatt cgcgcgcaac gcaccgccat    12360
tcgggaaaga cggtggtgcg ctcgtcgggc accaggtgca cgcgccaacc gcggttgtgc    12420
agggtgacaa ggtcaacgct ggtggctacc tctccgcgta ggcgctcgtt ggtccagcag    12480
aggcggccgc ccttgcgcga gcagaatggc ggtaggggt ctagctgcgt ctcgtccggg    12540
gggtctgcgt ccacggtaaa gaccccgggc agcaggcgcg cgtcgaagta gtctatcttg    12600
catccttgca agtctagcgc ctgctgccat gcgcgggcgg caagcgcgcg ctcgtatggg    12660
ttgagtgggg gaccccatgg catggggtgg gtgagcgcgg aggcgtacat gccgcaaatg    12720
tcgtaaacgt agagggctc tctgagtatt ccaagatatg tagggtagca tcttccaccg    12780
cggatgctgg cgcgcacgta atcgtatagt tcgtgcgagg gagcgaggag gtcgggaccg    12840
aggttgctac gggcgggctg ctctgctcgg aagactatct gcctgaagat ggcatgtgag    12900
ttggatgata tggttggacg ctggaagacg ttgaagctgg cgtctgtgag acctaccgcg    12960
tcacgcacga aggaggcgta ggagtcgcgc agcttgttga ccagctcggc ggtgacctgc    13020
acgtctaggg cgcagtagtc cagggtttcc ttgatgatgt catacttatc ctgtcccttt    13080
ttttccaca gctcgcggtt gaggacaaac tcttcgcggt cttcagta ctcttggatc    13140
ggaaacccgt cggcctccga acggtaagag cctagcatgt agaactggtt gacggcctgg    13200
taggcgcagc atccctttc tacgggtagc gcgtatgcct gcgcggcctt ccggagcgag    13260
gtgtgggtga gcgcaaaggt gtccctgacc atgactttga ggtactggta tttgaagtca    13320
gtgtcgtcgc atccgccctg ctcccagagc aaaaagtccg tgcgcttttt ggaacgcgga    13380
tttggcaggg cgaaggtgac atcgttgaag agtatctttc ccgcgcgagg cataaagttg    13440
cgtgtgatgc ggaagggtcc cggcacctcg gaacggttgt taattacctg ggcggcgagc    13500
acgatctcgt caaagccgtt gatgttgtgg cccacaatgt aaagttccaa gaagcgcggg    13560
atgcccttga tggaaggcaa ttttttaagt tcctcgtagg tgagctcttc agggagctg    13620
```

```
agcccgtgct ctgaaagggc ccagtctgca agatgagggt tggaagcgac gaatgagctc   13680
cacaggtcac gggccattag catttgcagg tggtcgcgaa aggtcctaaa ctggcgacct   13740
atggccattt tttctggggt gatgcagtag aaggtaagcg ggtcttgttc ccagcggtcc   13800
catccaaggt tcgcggctag gtctcgcgcg gcagtcacta gaggctcatc tccgccgaac   13860
ttcatgacca gcatgaaggg cacgagctgc ttcccaaagg cccccatcca agtataggtc   13920
tctacatcgt aggtgacaaa gagacgctcg gtgcgaggat gcgagccgat cgggaagaac   13980
tggatctccc gccaccaatt ggaggagtgg ctattgatgt ggtgaaagta gaagtccctg   14040
cgacgggccg aacactcgtg ctggcttttg taaaaacgtg cgcagtactg gcagcggtgc   14100
acgggctgta catcctgcac gaggttgacc tgacgaccgc gcacaaggaa gcagagtggg   14160
aatttgagcc cctcgcctgg cgggtttggc tggtggtctt ctacttcggc tgcttgtcct   14220
tgaccgtctg gctgctcgag gggagttacg gtggatcgga ccaccacgcc gcgcgagccc   14280
aaagtccaga tgtccgcgcg cggcggtcgg agcttgatga caacatcgcg cagatgggag   14340
ctgtccatgg tctggagctc ccgcggcgtc aggtcaggcg ggagctcctg caggtttacc   14400
tcgcatagac gggtcagggc gcgggctaga tccaggtgat acctaatttc caggggctgg   14460 ttggtggcg cgtcgatggc ttgcaagagg ccgcatcccc gcggcgcgac tacggtaccg   14520
cgcggcgggc ggtgggccgc gggggtgtcc ttggatgatg catctaaaag cggtgacgcg   14580
ggcgagcccc cggaggtagg gggggctccg gacccgccgg gagaggggc aggggcacgt   14640 cggcgccgcg cgcgggcagg agctggtgct gcgcgcgtag gttgctggcg aacgcgacga   14700
cgcggcggtt gatctcctga atctggcgcc tctgcgtgaa gacgacgggc ccggtgagct   14760
tgagcctgaa agagagttcg acagaatcaa tttcggtgtc gttgacggcg gcctggcgca   14820
aaatctcctg cacgtctcct gagttgtctt gataggcgat ctcggccatg aactgctcga   14880
tctcttcctc ctggagatct ccgcgtccgg ctcgctccac ggtggcggcg aggtcgttgg   14940
aaatgcgggc catgagctgc gagaaggcgt tgaggcctcc ctcgttccag acgcggctgt   15000
agaccacgcc cccttcggca tcgcgggcgc gcatgaccac ctgcgcgaga ttgagctcca   15060
cgtgccgggc gaagacggcg tagttcgca ggcgctgaaa gaggtagttg agggtggtgg   15120
cggtgtgttc tgccacgaag aagtacataa cccagcgtcg caacgtggat tcgttgatat   15180
cccccaaggc ctcaaggcgc tccatggcct cgtagaagtc cacggcgaag ttgaaaaact   15240
gggagttgcg cgccgacacg gttaactcct cctccagaag acggatgagc tcggcgacag   15300
tgtcgcgcac ctcgcgctca aaggctacag gggcctcttc ttcttcttca atctcctctt   15360
ccataagggc ctccccttct tcttcttctg gcggcggtgg gggaggggg acacggcggc   15420 gacgacggcg caccgggagg cggtcgacaa agcgctcgat catctccccg cggcgacggc   15480
gcatggtctc ggtgacggcg cggccgttct cgcggggggcg cagttggaag acgccgcccg   15540
tcatgtcccg gttatggggtt ggcgggggc tgccatgcgg cagggatacg gcgctaacga   15600
tgcatctcaa caattgttgt gtaggtactc cgccgccgag ggacctgagc gagtccgcat   15660
cgaccggatc ggaaaaacctc tcgagaaagg cgtctaacca gtcacagtcg caaggtaggc   15720
tgagcaccgt ggcgggcggc agcggccggc ggtcgggtt gtttctggcg gaggtgctgc   15780
tgatgatgta attaaagtag gcggtcttga gacggcggat ggtcgacaga agcaccatgt   15840
ccttgggtcc ggcctgctga atgcgcaggc ggtcggccat gccccaggct tcgttttgac   15900 atcgcgcag gtctttgtag tagtcttgca tgagcctttc taccggcact tcttcttctc   15960
cttcctcttg tcctgcatct cttgcatcta tcgctgcggc ggcggcggag tttggccgta   16020
```

```
ggtggcgccc tcttcctccc atgcgtgtga ccccgaagcc cctcatcggc tgaagcaggg    16080
ctaggtcggc gacaacgcgc tcggctaata tggcctgctg cacctgcgtg agggtagact    16140
ggaagtcatc catgtccaca aagcggtggt atgcgcccgt gttgatggtg taagtgcagt    16200
tggccataac ggaccagtta acggtctggt gacccggctg cgagagctcg gtgtacctga    16260
gacgcgagta agccctcgag tcaaatacgt agtcgttgca agtccgcacc aggtactggt    16320
atcccaccaa aaagtgcggc ggcggctggc ggtagagggg ccagcgtagg gtggccgggg    16380
ctccgggggc gagatcttcc aacataaggc gatgatatcc gtagatgtac ctggacatcc    16440
aggtgatgcc ggcggcggtg gtggaggcgc gcggaaagtc gcggacgcgg ttccagatgt    16500
tgcgcagcgg caaaaagtgc tccatggtcg ggacgctctg gccggtcagg cgcgcgcaat    16560
cgttgacgct ctagaccgtg caaaggaga gcctgtaagc gggcactctt ccgtggtctg    16620
gtggataaat tcgcaagggt atcatggcgg acgaccgggg ttcgagcccc gtatccggcc    16680
gtccgccgtg atccatgcgg ttaccgcccg cgtgtcgaac ccaggtgtgc gacgtcagac    16740
aacgggggag tgctccttt ggcttccttc caggcgcggc ggctgctgcg ctagcttttt    16800
tggccactgg ccgcgcgcag cgtaagcggt taggctggaa agcgaaagca ttaagtggct    16860
cgctccctgt agccggaggg ttattttcca agggttgagt cgcgggaccc ccggttcgag    16920
tctcggaccg gccggactgc ggcgaacggg ggtttgcctc cccgtcatgc aagacccgc    16980
ttgcaaattc ctccggaaac agggacgagc cccttttttg cttttcccag atgcatccgg    17040
tgctgcggca gatgcgcccc cctcctcagc agcggcaaga gcaagagcag cggcagacat    17100
gcagggcacc ctcccctcct cctaccgcgt caggagggc gacatccgcg gttgacgcgg    17160
cagcagatgg tgattacgaa ccccgcggc gccgggcccg gcactacctg gacttggagg    17220
agggcgaggg cctggcgcgg ctaggagcgc cctctcctga gcggtaccca agggtgcagc    17280
tgaagcgtga tacgcgtgag gcgtacgtgc cgcggcagaa cctgtttcgc gaccgcgagg    17340
gagaggagcc cgaggagatg cgggatcgaa agttccacgc agggcgcgag ctgcggcatg    17400
gcctgaatcg cgagcggttg ctgcgcgagg aggactttga ccccgacgcg cgaaccggga    17460
ttagtcccgc gcgcgcacac gtggcggccg ccgacctggt aaccgcatac gagcagacgg    17520
tgaaccagga gattaacttt caaaaaagct ttaacaacca cgtgcgtacg cttgtggcgc    17580
gcgaggaggt ggctatagga ctgatgcatc tgtgggactt tgtaagcgcg ctggagcaaa    17640
acccaaatag caagccgctc atggcgcagc tgttccttat agtgcagcac agcagggaca    17700
acgaggcatt cagggatgcg ctgctaaaca tagtagagcc cgagggccgc tggctgctcg    17760
atttgataaa catcctgcag agcatagtgg tgcaggagcg cagcttgagc ctggctgaca    17820
aggtggccgc catcaactat tccatgctta gcctgggcaa gttttacgcc cgcaagatat    17880
accataccccc ttacgttccc atagacaagg aggtaaagat cgaggggttc tacatgcgca    17940
tggcgctgaa ggtgcttacc ttgagcgacg acctgggcgt ttatcgcaac gagcgcatcc    18000
acaaggccgt gagcgtgagc cggcggcgcg agctcagcga ccgcgagctg atgcacagcc    18060
tgcaaagggc cctggctggc acgggcagcg gcgatagaga ggccgagtcc tactttgacg    18120
cgggcgctga cctgcgctgg gccccaagcc gacgcgccct ggaggcagct ggggccggac    18180
ctgggctggc ggtggcaccc gcgcgcgctg gcaacgtcgg cggcgtggag gaatatgacg    18240
aggacgatga gtacgagcca gaggacgcg agtactaagc ggtgatgttt ctgatcagat    18300
gatgcaagac gcaacggacc cggcggtgcg ggcggcgctg cagagccagc cgtccggcct    18360
```

-continued

```
taactccacg gacgactggc gccaggtcat ggaccgcatc atgtcgctga ctgcgcgcaa   18420
tcctgacgcg ttccggcagc agccgcaggc caaccggctc tccgcaattc tggaagcggt   18480
ggtcccggcg cgcgcaaacc ccacgcacga aaggtgctg gcgatcgtaa acgcgctggc    18540
cgaaaacagg gccatccggc ccgacgaggc cggcctggtc tacgacgcgc tgcttcagcg   18600
cgtggctcgt tacaacagcg gcaacgtgca gaccaacctg gaccggctgg tgggggatgt   18660
gcgcgaggcc gtggcgcagc gtgagcgcgc gcagcagcag ggcaacctgg gctccatggt   18720
tgcactaaac gccttcctga gtacacagcc cgccaacgtg ccgcggggac aggaggacta   18780
caccaacttt gtgagcgcac tgcggctaat ggtgactgag acaccgcaaa gtgaggtgta   18840
ccagtctggg ccagactatt ttttccagac cagtagacaa ggcctgcaga ccgtaaacct   18900
gagccaggct ttcaaaaact tgcagggggct gtgggggggtg cgggctccca caggcgaccg  18960
cgcgaccgtg tctagcttgc tgacgcccaa ctcgcgcctg ttgctgctgc taatagcgcc   19020
cttcacggac agtggcagcg tgtcccggga cataccta ggtcacttgc tgacactgta    19080
ccgcgaggcc ataggtcagg cgcatgtgga cgagcatact ttccaggaga ttacaagtgt   19140
cagccgcgcg ctggggcagg aggacacggg cagcctggag gcaaccctaa actacctgct   19200
gaccaaccgg cggcagaaga tccccctcgtt gcacagttta aacagcgagg aggagcgcat  19260
tttgcgctac gtgcagcaga gcgtgagcct taacctgatg cgcgacgggg taacgcccag   19320
cgtggcgctg gacatgaccg cgcgcaacat ggaaccgggc atgtatgcct caaaccggcc   19380
gtttatcaac cgcctaatgg actacttgca tcgcgcggcc gccgtgaacc ccgagtattt   19440
caccaatgcc atcttgaacc cgcactggct accgcccct ggttttctaca ccgggggatt    19500 cgaggtgccc gagggtaacg atggattcct ctgggacgac atagacgaca gcgtgttttc   19560
cccgcaaccg cagaccctgc tagagttgca acagcgcgag caggcagagg cggcgctgcg   19620
aaaggaaagc ttccgcaggc caagcagctt gtccgatcta ggcgctgcgg ccccgcggtc   19680
agatgctagt agcccatttc caagcttgat agggtctctt accagcactc gcaccacccg   19740
cccgcgcctg ctgggcgagg aggagtacct aaacaactcg ctgctgcagc cgcagcgcga   19800
aaaaaacctg cctccggcat ttcccaacaa cgggatagag agcctagtgg acaagatgag   19860
tagatggaag acgtacgcgc aggagcacag ggacgtgcca ggcccgcgcc cgcccacccg   19920
tcgtcaaagg cacgaccgtc agcggggtct ggtgtgggag gacgatgact cggcagacga   19980
cagcagcgtc ctggatttgg gagggagtgg caacccgttt gcgcaccttc gccccaggct   20040
ggggagaatg ttttaaaaaa aaaaagcat gatgcaaaat aaaaaactca ccaaggccat    20100
ggcaccgagc gttggttttc ttgtattccc cttagtatgc ggcgcgcggc gatgtatgag   20160
gaaggtcctc ctccctccta cgagagtgtg gtgagcgcgg cgccagtggc ggcggcgctg   20220
ggttctccct tcgatgctcc cctggacccg ccgtttgtgc ctccgcggta cctgcggcct   20280
accgggggga gaaacagcat ccgttactct gagttggcac ccctattcga caccaccgt    20340 gtgtacctgg tggacaacaa gtcaacggat gtggcatccc tgaactacca gaacgaccac   20400
agcaactttc tgaccacggt cattcaaaac aatgactaca gcccggggga ggcaagcaca   20460
cagaccatca atcttgacga ccggtcgcac tgggcggcg acctgaaaac catcctgcat   20520
accaacatgc caaatgtgaa cgagttcatg tttaccaata gtttaaggc gcgggtgatg   20580 gtgtcgcgct tgcctactaa ggacaatcag gtggagctga atacgagtg gtggagttc    20640 acgctgcccg agggcaacta ctccgagacc atgaccatag accttatgaa caacgcgatc   20700
gtggagcact acttgaaagt gggcagacag aacgggggttc tggaaagcga catcggggta   20760
```

```
aagtttgaca cccgcaactt cagactgggg tttgacccg tcactggtct tgtcatgcct     20820
ggggtatata caaacgaagc cttccatcca gacatcattt tgctgccagg atgcggggtg    20880
gacttcaccc acagccgcct gagcaacttg ttgggcatcc gcaagcggca acccttccag    20940
gagggcttta ggatcaccta cgatgatctg gagggtggta acattcccgc actgttggat    21000
gtggacgcct accaggcgag cttgaaagat gacaccgaac agggcggggg tggcgcaggc    21060
ggcagcaaca gcagtggcag cggcgcggaa gagaactcca acgcggcagc cgcggcaatg    21120
cagccggtgg aggacatgaa cgatcatgcc attcgcggcg acacctttgc cacacgggct    21180
gaggagaagc gcgctgaggc cgaagcagcg gccgaagctg ccgcccccgc tgcgcaaccc    21240
gaggtcgaga agcctcagaa gaaaccggtg atcaaacccc tgacagagga cagcaagaaa    21300
cgcagttaca acctaataag caatgacagc accttcaccc agtaccgcag ctggtacctt    21360
gcatacaact acggcgaccc tcagaccgga atccgctcat ggaccctgct ttgcactcct    21420
gacgtaacct gcggctcgga gcaggtctac tggtcgttgc cagacatgat gcaagacccc    21480
gtgaccttcc gctccacgcg ccagatcagc aactttccgg tggtgggcgc cgagctgttg    21540
cccgtgcact ccaagagctt ctacaacgac caggccgtct actcccaact catccgccag    21600
tttacctctc tgacccacgt gttcaatcgc tttcccgaga accagatttt ggcgcgcccg    21660
ccagcccca ccatcaccac cgtcagtgaa aacgttcctg ctctcacaga tcacgggacg     21720
ctaccgctgc gcaacagcat cggaggagtc cagcgagtga ccattactga cgccagacgc    21780
cgcacctgcc cctacgttta caaggccctg ggcatagtct cgccgcgcgt cctatcgagc    21840
cgcacttttt gagcaagcat gtccatcctt atatcgccca gcaataacac aggctggggc    21900
ctgcgcttcc caagcaagat gtttggcggg gccaagaagc gctccgacca acacccagtg    21960
cgcgtgcgcg ggcactaccg cgcgccctgg ggcgcgcaca aacgcggccg cactgggcgc    22020
accaccgtcg atgacgccat cgacgcggtg gtggaggagg cgcgcaacta cacgcccacg    22080
ccgccaccag tgtccacagt ggacgcggcc attcagaccg tggtgcgcgg agcccggcgc    22140
tatgctaaaa tgaagagacg gcggaggcgc gtagcacgtc gccaccgccg ccgacccggc    22200
actgccgccc aacgcgcggc ggcggccctg cttaaccgcg cacgtcgcac cggccgacgg    22260
gcggccatgc gggccgctcg aaggctggcc gcgggtattg tcactgtgcc ccccaggtcc    22320
aggcgacgag cggccgccgc agcagccgcg gccattagtg ctatgactca gggtcgcagg    22380
ggcaacgtgt attgggtgcg cgactcggtt agcggcctgc gcgtgcccgt gcgcacccgc    22440
cccccgcgca actagattgc aagaaaaaac tacttagact cgtactgttg tatgtatcca    22500
gcggcggcgg cgcgcaacga agctatgtcc aagcgcaaaa tcaaagaaga gatgctccag    22560
gtcatcgcgc cggagatcta tggccccccg aagaaggaag agcaggatta caagcccga    22620
aagctaaagc gggtcaaaaa gaaaagaaa gatgatgatg atgaacttga cgacgaggtg    22680
gaactgctgc acgctaccgc gcccaggcga cgggtacagt ggaaaggtcg acgcgtaaaa    22740
cgtgttttgc gacccggcac caccgtagtc tttacgcccg tgagcgctc cacccgcacc    22800
tacaagcgcg tgtatgatga ggtgtacggc gacgaggacc tgcttgagca ggccaacgag    22860
cgcctcgggg agtttgccta cggaaagcgg cataaggaca tgctggcgtt gccgctggac    22920
gagggcaacc caacacctag cctaaagccc gtaacactgc agcaggtgct gcccgcgctt    22980
gcaccgtccg aagaaagcg cggcctaaag cgcgagtctg gtgacttggc acccaccgtg    23040
cagctgatgg tacccaagcg ccagcgactg gaagatgtct tggaaaaaat gaccgtggaa    23100
```

```
cctgggctgg agcccgaggt ccgcgtgcgg ccaatcaagc aggtggcgcc gggactgggc      23160
gtgcagaccg tggacgttca gatacccact accagtagca ccagtattgc caccgccaca      23220
gagggcatgg agacacaaac gtccccggtt gcctcagcgg tggcggatgc cgcggtgcag      23280
gcggtcgctg cggccgcgtc caagacctct acggaggtgc aaacggaccc gtggatgttt      23340
cgcgtttcag ccccccggcg cccgcgcggt tcgaggaagt acggcgccgc cagcgcgcta      23400
ctgcccgaat atgccctaca tccttccatt gcgcctaccc ccggctatcg tggctacacc      23460
taccgcccca gaagacgagc aactacccga cgccgaacca ccactggaac ccgccgccgc      23520
cgtcgccgtc gccagcccgt gctggcccga atttccgtgc gcagggtggc tcgcgaagga      23580
ggcaggaccc tggtgctgcc aacagcgcgc taccaccccca gcatcgttta aaagccggtc      23640
tttgtggttc ttgcagatat ggccctcacc tgccgcctcc gtttcccggt gccgggattc      23700
cgaggaagaa tgcaccgtag gagggcatg gccggccacg gcctgacggg cggcatgcgt      23760
cgtgcgcacc accggcggcg gcgcgcgtcg caccgtcgca tgcgcggcgg tatcctgccc      23820
ctccttattc cactgatcgc cgcggcgatt ggcgccgtgc ccggaattgc atccgtggcc      23880
ttgcaggcgc agagacactg attaaaaaca agttgcatgt ggaaaaatca aaataaaaag      23940
tctggactct cacgctcgct tggtcctgta actattttgt agaatggaag acatcaactt      24000
tgcgtctctg gccccgcgac acggctcgcg cccgttcatg ggaaactggc aagatatcgg      24060
caccagcaat atgagcggtg cgccttcag ctggggctcg ctgtggagcg gcattaaaaa      24120
tttcggttcc accgttaaga actatggcag caaggcctgg aacagcagca caggccagat      24180
gctgagggat aagttgaaag agcaaaattt ccaacaaaag gtggtagatg gcctggcctc      24240
tggcattagc ggggtggtgg acctggccaa ccaggcagtg caaaataaga ttaacagtaa      24300
gcttgatccc cgccctcccg tagaggagcc tccaccggcc gtggagacag tgtctccaga      24360
ggggcgtggc gaaaagcgtc gcgcccccga cagggaagaa actctggtga cgcaaataga      24420
cgagcctccc tcgtacgagg aggcactaaa gcaaggcctg cccaccaccc gtcccatcgc      24480
gcccatggct accggagtgc tgggccagca cacacccgta acgctggacc tgcctccccc      24540
cgccgacacc cagcagaaac ctgtgctgcc aggcccgacc gccgttgttg taacccgtcc      24600
tagccgcgcg tccctgcgcc gcgccgccag cggtcgcgca tcgttgcggc ccgtagccag      24660
tggcaactgg caaagcacac tgaacagcat cgtgggtctg ggggtgcaat ccctgaagcg      24720
ccgacgatgc ttctgaatag ctaacgtgtc gtatgtgtgt catgtatgcg tccatgtcgc      24780
cgccagagga gctgctgagc cgccgcgcgc ccgcttttcca agatggctac cccttcgatg      24840
atgccgcagt ggtcttacat gcacatctcg ggccaggacg cctcggagta cctgagcccc      24900
gggctggtgc agtttgcccg cgccaccgag acgtacttca gcctgaataa caagtttaga      24960
aaccccacgg tggcgcctac gcacgacgtg accacagacc ggtcccagcg tttgacgctg      25020
cggttcatcc ctgtggaccg tgaggatact gcgtactcgt acaaggcgcg gttcaccta      25080 gctgtgggtg ataaccgtgt gctggacatg gcttccacgt actttgacat ccgcggcgtg      25140
ctggacaggg gccctacttt taagccctac tctggcactg cctacaacgc cctggctccc      25200
aagggtgccc caaatccttg cgaatgggat gaagctgcta ctgctcttga aataaaccta      25260
gaagaagagg acgatgacaa cgaagacgaa gtagacgagc aagctgagca gcaaaaaact      25320
cacgtatttg gcaggcgcc ttattctggt ataaatatta caaggagggg tattcaaata      25380
ggtgtcgaag gtcaaacacc taaatatgcc gataaaacat ttcaacctga acctcaaata      25440
ggagaatctc agtggtacga aactgaaatt aatcatcag ctgggagagt ccttaaaaag      25500
```

```
actaccccaa tgaaaccatg ttacggttca tatgcaaaac ccacaaatga aaatggaggg    25560
caaggcattc ttgtaaagca acaaaatgga aagctagaaa gtcaagtgga aatgcaattt    25620
ttctcaacta ctgaggcgac cgcaggcaat ggtgataact tgactcctaa agtggtattg    25680
tacagtgaag atgtagatat agaaacccca gacactcata tttcttacat gcccactatt    25740
aaggaaggta actcacgaga actaatgggc caacaatcta tgcccaacag gcctaattac    25800
attgctttta gggacaattt tattggtcta atgtattaca acagcacggg taatatgggt    25860
gttctggcgg gccaagcatc gcagttgaat gctgttgtag atttgcaaga cagaaacaca    25920
gagctttcat accagctttt gcttgattcc attggtgata gaaccaggta cttttctatg    25980
tggaatcagg ctgttgacag ctatgatcca gatgttagaa ttattgaaaa tcatggaact    26040
gaagatgaac ttccaaatta ctgctttcca ctgggaggtg tgattaatac agagactctt    26100
accaaggtaa aacctaaaac aggtcaggaa aatggatggg aaaaagatgc tacagaattt    26160
tcagataaaa atgaaataag agttggaaat aattttgcca tggaaatcaa tctaaatgcc    26220
aacctgtgga gaaatttcct gtactccaac atagcgctgt atttgcccga caagctaaag    26280
tacagtcctt ccaacgtaaa aatttctgat aacccaaaca cctacgacta catgaacaag    26340
cgagtggtgg ctcccgggtt agtggactgc tacattaacc ttggagcacg ctggtccctt    26400
gactatatgg acaacgtcaa cccatttaac caccaccgca atgctggcct gcgctaccgc    26460
tcaatgttgc tgggcaatgg tcgctatgtg cccttccaca tccaggtgcc tcagaagttc    26520
tttgccatta aaaacctcct tctcctgccg ggctcataca cctacgagtg aacttcagg    26580 aaggatgtta acatggttct gcagagctcc ctaggaaatg acctaagggt tgacggagcc    26640
agcattaagt ttgatagcat ttgcctttac gccaccttct tccccatggc ccacaacacc    26700
gcctccacgc ttgaggccat gcttagaaac gacaccaacc accagtcctt taacgactat    26760
ctctccgccg ccaacatgct ctaccctata cccgccaacg ctaccaacgt gcccatatcc    26820
atcccctccc gcaactgggc ggcttttccgc ggctgggcct tcacgcgcct taagactaag    26880
gaaaccccat cactgggctc gggctacgac ccttattaca cctactctgg ctctataccc    26940
tacctagatg gaaccttta cctcaaccac acctttaaga aggtggccat tacctttgac    27000
tcttctgtca gctggcctgg caatgaccgc ctgcttaccc ccaacagagtt tgaaattaag    27060 cgctcagttg acggggaggg ttacaacgtt gcccagtgta acatgaccaa agactggttc    27120
ctggtacaaa tgctagctaa ctacaacatt ggctaccagg gcttctatat cccagagagc    27180
tacaaggacc gcatgtactc cttctttaga aacttccagc ccatgagccg tcaggtggtg    27240
gatgatacta aatacaagga ctaccaacag gtgggcatcc tacaccaaca caacaactct    27300
ggatttgttg gtaccttgc ccccaccatg cgcgaaggac aggcctaccc tgctaacttc    27360
ccctatccgc ttataggcaa gaccgcagtt gacagcatta cccagaaaaa gtttctttgc    27420
gatcgcaccc tttggcgcat cccattctcc agtaactta tgtccatggg cgcactcaca    27480
gacctgggcc aaaaccttct ctacgccaac tccgcccacg cgctagacat gacttttgag    27540
gtggatccca tggacgagcc caccttctt tatgttttgt ttgaagtctt tgacgtggtc    27600
cgtgtgcacc ggccgcaccg cggcgtcatc gaaaccgtgt acctgcgcac gcccttctcg    27660
gccggcaacg ccacaacata agaagcaag caacatcaac aacagctgcc gccatgggct    27720
ccagtgagca ggaactgaaa gccattgtca aagatcttgg ttgtgggcca tatttttgg    27780 gcacctatga caagcgcttt ccaggctttg tttctccaca caagctcgcc tgcgccatag    27840
```

```
tcaatacggc cggtcgcgag actgggggcg tacactggat ggcctttgcc tggaacccgc   27900
actcaaaaac atgctacctc tttgagccct ttggcttttc tgaccagcga ctcaagcagg   27960
tttaccagtt tgagtacgag tcactcctgc gccgtagcgc cattgcttct tcccccgacc   28020
gctgtataac gctggaaaag tccacccaaa gcgtacaggg gcccaactcg gccgcctgtg   28080
gactattctg ctgcatgttt ctccacgcct ttgccaactg gccccaaact cccatggatc   28140
acaaccccac catgaacctt attaccgggg tacccaactc catgctcaac agtccccagg   28200
tacagcccac cctgcgtcgc aaccaggaac agctctacag cttcctggag cgccactcgc   28260
cctacttccg cagccacagt gcgcagatta ggagcgccac ttcttttgt cacttgaaaa    28320
acatgtaaaa ataatgtact agagacactt tcaataaagg caaatgcttt tatttgtaca   28380
ctctcgggtg attatttacc ccacccttg ccgtctgcgc cgtttaaaaa tcaaggggt     28440
tctgccgcgc atcgctatgc gccactggca gggacacgtt gcgatactgg tgtttagtgc   28500
tccacttaaa ctcaggcaca accatccgcg gcagctcggt gaagttttca ctccacaggc   28560
tgcgcaccat caccaacgcg tttagcaggt cgggcgccga tatcttgaag tcgcagttgg   28620
ggcctccgcc ctgcgcgcgc gagttgcgat acacagggtt gcagcactgg aacactatca   28680
gcgccgggtg gtgcacgctg gccagcacgc tcttgtcgga gatcagatcc gcgtccaggt   28740
cctccgcgtt gctcagggcg aacggagtca actttggtag ctgccttccc aaaaagggcg   28800
cgtgcccagg ctttgagttg cactcgcacc gtagtggcat caaaaggtga ccgtgcccgg   28860
tctgggcgtt aggatacagc gcctgcataa aagccttgat ctgcttaaaa gccacctgag   28920
cctttgcgcc ttcagagaag aacatgccgc aagacttgcc ggaaaactga ttggccggac   28980
aggccgcgtc gtgcacgcag caccttgcgt cggtgttgga gatctgcacc acatttcggc   29040
cccaccggtt cttcacgatc ttggccttgc tagactgctc cttcagcgcg cgctgcccgt   29100
tttcgctcgt cacatccatt tcaatcacgt gctccttatt tatcataatg cttccgtgta   29160
gacacttaag ctcgccttcg atctcagcgc agcggtgcag ccacaacgcg cagcccgtgg   29220
gctcgtgatg cttgtaggtc acctctgcaa acgactgcag gtacgcctgc aggaatcgcc   29280
ccatcatcgt cacaaaggtc ttgttgctgg tgaaggtcag ctgcaacccg cggtgctcct   29340
cgttcagcca ggtcttgcat acggccgcca gagcttccac ttggtcaggc agtagtttga   29400
agttcgcctt tagatcgtta tccacgtggt acttgtccat cagcgcgcgc gcagcctcca   29460
tgcccttctc ccacgcagac acgatcggca cactcagcgg gttcatcacc gtaatttcac   29520
tttccgcttc gctgggctct tcctcttcct cttgcgtccg cataccacgc gccactgggt   29580
cgtcttcatt cagccgccgc actgtgcgct tacctccttt gccatgcttg attagcaccg   29640
gtgggttgct gaaacccacc atttgtagcg ccacatcttc tctttcttcc tcgctgtcca   29700
cgattacctc tggtgatggc gggcgctcgg gcttgggaga agggcgcttc ttttcttct    29760
tgggcgcaat ggccaaatcc gccgccgagg tcgatggccg cgggctgggt gtgcgcggca   29820
ccagcgcgtc ttgtgatgag tcttcctcgt cctcggactc gatacgccgc ctcatccgct   29880
tttttggggg cgcccgggga ggcggcggcg acggggacgg ggacgacacg tcctccatgg   29940
ttggggacg tcgcgccgca ccgcgtccgc gctcgggggt ggtttcgcgc tgctcctctt    30000
cccgactggc catttccttc tcctataggc agaaaaagat catggagtca gtcgagaaga   30060
aggacagcct aaccgccccc tctgagttcg ccaccaccgc ctccaccgat gccgccaacg   30120
cgcctaccac cttccccgtc gaggcacccc gcttgaggga ggaggaagtg attatcgagc   30180
aggacccagg ttttgtaagc gaagacgacg aggaccgctc agtaccaaca gaggataaaa   30240
```

```
agcaagacca ggacaacgca gaggcaaacg aggaacaagt cgggcggggg gacgaaaggc    30300
atggcgacta cctagatgtg ggagacgacg tgctgttgaa gcatctgcag cgccagtgcg    30360
ccattatctg cgacgcgttg caagagcgca gcgatgtgcc cctcgccata gcggatgtca    30420
gccttgccta cgaacgccac ctattctcac cgcgcgtacc ccccaaacgc caagaaaacg    30480
gcacatgcga gcccaacccg cgcctcaact tctaccccgt atttgccgtg ccagaggtgc    30540
ttgccaccta tcacatcttt ttccaaaact gcaagatacc cctatcctgc cgtgccaacc    30600
gcagccgagc ggacaagcag ctggccttgc ggcagggcgc tgtcatacct gatatcgcct    30660
cgctcaacga agtgccaaaa atctttgagg gtcttggacg cgacgagaag cgcgcggcaa    30720
acgctctgca acaggaaaac agcgaaaatg aaagtcactc tggagtgttg gtggaactcg    30780
agggtgacaa cgcgcgccta gccgtactaa aacgcagcat cgaggtcacc cactttgcct    30840
acccggcact taacctaccc cccaaggtca tgagcacagt catgagtgag ctgatcgtgc    30900
gccgtgcgca gccccctggag agggatgcaa atttgcaaga acaaacagag gagggcctac    30960
ccgcagttgg cgacgagcag ctagcgcgct ggcttcaaac gcgcgagcct gccgacttgg    31020
aggagcgacg caaactaatg atggccgcag tgctcgttac cgtggagctt gagtgcatgc    31080
agcggttctt tgctgacccg gagatgcagc gcaagctaga ggaaacattg cactacacct    31140
ttcgacaggg ctacgtacgc caggcctgca agatctccaa cgtggagctc tgcaacctgg    31200
tctcctacct tggaattttg cacgaaaacc gccttgggca aaacgtgctt cattccacgc    31260
tcaagggcga ggcgcgccgc gactacgtcc gcgactgcgt ttacttattt ctatgctaca    31320
cctggcagac ggccatgggc gtttggcagc agtgcttgga ggagtgcaac ctcaaggagc    31380 tgcagaaaact gctaaagcaa aacttgaagg acctatggac ggccttcaac gagcgctccg    31440
tggccgcgca cctggcggac atcattttcc ccgaacgcct gcttaaaacc ctgcaacagg    31500
gtctgccaga cttcaccagt caaagcatgt tgcagaactt taggaacttt atcctagagc    31560
gctcaggaat cttgcccgcc acctgctgtg cacttcctag cgactttgtg cccattaagt    31620
accgcgaatg ccctccgccg cttttggggcc actgctacct tctgcagcta gccaactacc    31680
ttgcctacca ctctgacata atggaagacg tgagcggtga cggtctactg gagtgtcact    31740
gtcgctgcaa cctatgcacc ccgcaccgct ccctggtttg caattcgcag ctgcttaacg    31800
aaagtcaaat tatcggtacc tttgagctgc agggtccctc gcctgacgaa aagtccgcgg    31860
ctccggggtt gaaactcact ccggggctgt ggacgtcggc ttaccttcgc aaatttgtac    31920
ctgaggacta ccacgcccac gagattaggt tctacgaaga ccaatcccgc ccgccaaatg    31980
cggagcttac cgcctgcgtc attacccagg ccacattct tggccaattg caagccatca    32040
acaaagcccg ccaagagttt ctgctacgaa agggacgggg ggtttacttg gaccccccagt    32100 ccggcgagga gctcaacccca atccccccgc cgccgcagcc ctatcagcag cagccgcggg    32160
cccttgcttc ccaggatggc acccaaaaag aagctgcagc tgccgccgcc acccacggac    32220
gaggaggaat actgggacag tcaggcagag gaggttttgg acgaggagga ggaggacatg    32280
atggaagact gggagagcct agacgaggaa gcttccgagg tcgaagaggt gtcagacgaa    32340
acaccgtcac cctcggtcgc attcccctcg ccggcgcccc agaaatcggc aaccggttcc    32400
agcatggcta caacctccgc tcctcaggcg ccgccggcac tgcccgttcg ccgacccaac    32460
cgtagatggg acaccactgg aaccagggcc ggtaagtcca agcagccgcc gccgttagcc    32520
caagagcaac aacagcgcca aggctaccgc tcatggcgcg ggcacaagaa cgccatagtt    32580
```

```
gcttgcttgc aagactgtgg gggcaacatc tccttcgccc gccgctttct tctctaccat    32640
cacggcgtgg ccttccccg  taacatcctg cattactacc gtcatctcta cagcccatac    32700
tgcaccggcg gcagcggcag cggcagcaac agcagcggcc acacagaagc aaaggcgacc    32760
ggatagcaag actctgacaa agcccaagaa atccacagcg gcggcagcag caggaggagg    32820
agcgctgcgt ctggcgccca acgaacccgt atcgacccgc gagcttagaa acaggatttt    32880
tcccactctg tatgctatat ttcaacagag caggggccaa gaacaagagc tgaaaataaa    32940
aaacaggtct ctgcgatccc tcacccgcag ctgcctgtat cacaaaagcg aagatcagct    33000
tcggcgcacg ctggaagacg cggaggctct cttcagtaaa tactgcgcgc tgactcttaa    33060
ggactagttt cgcgcccttt ctcaaattta agcgcgaaaa ctacgtcatc tccagcggcc    33120
acacccggcg ccagcacctg tcgtcagcgc catttatgag caaggaaatt cccacgccct    33180
acatgtggag ttaccagcca caatgggac  ttgcggctgg agctgccaa  gactactcaa    33240 cccgaataaa ctacatgagc gcggaccccc acatgatatc ccgggtcaac ggaatacgcg    33300
cccaccgaaa ccgaattctc ctggaacagg cggctattac caccacacct cgtaataacc    33360
ttaatccccg tagttggccc gctgccctgg tgtaccagga aagtcccgct cccaccactg    33420
tggtacttcc cagagacgcc caggccgaag ttcagatgac taactcaggg gcgcagcttg    33480
cgggcggctt tcgtcacagg gtgcggtcgc ccgggcaggg tataactcac ctgacaatca    33540
gagggcgagg tattcagctc aacgacgagt cggtgagctc ctcgcttggt ctccgtccgg    33600
acgggacatt tcagatcggc ggcgccggcc gctcttcatt cacgcctcgt caggcaatcc    33660
taactctgca gacctcgtcc tctgagccgc gctctggagg cattggaact ctgcaattta    33720
ttgaggagtt tgtgccatcg gtctacttta acccccttctc gggacctccc ggccactatc    33780
cggatcaatt tattcctaac tttgacgcgg taaaggactc ggcggacggc tacgactgaa    33840
tgttaagtgg agaggcagag caactgcgcc tgaaacacct ggtccactgt cgccgccaca    33900
agtgctttgc ccgcgactcc ggtgagtttt gctactttga attgcccgag gatcatatcg    33960
agggcccggc gcacggcgtc cggcttaccg cccagggaga gcttgcccgt agcctgattc    34020
gggagtttac ccagcgcccc ctgctagttg agcgggacag gggaccctgt gttctcactg    34080
tgatttgcaa ctgtcctaac cctggattac aatttaaatg cggtctcaaa gatcttattc    34140
cctttaacta ataaaaaaaa ataataaagc atcacttact taaaatcagt tagcaaattt    34200
ctgtccagtt tattcagcag cacctccttg ccctcctccc agctctggta ttgcagcttc    34260
ctcctggctg caaactttct ccacaatcta aatggaatgt cagtttcctc ctgttcctgt    34320
ccatccgcac ccactatctt catgttgttg cagatgaagc gcgcaagacc gtctgaagat    34380
accttcaacc ccgtgtatcc atatgacacg gaaaccggtc ctccaactgt gccttttctt    34440
actcctccct ttgtatcccc caatgggttt caagagagtc cccctggggt actctctttg    34500
cgcctatccg aacctctagt tacctccaat ggcatgcttg cgctcaaaat gggcaacggc    34560
ctctctctgg acgaggccgg caaccttacc tcccaaaatg taaccactgt gagcccacct    34620
ctcaaaaaaa ccaagtcaaa cataaacctg gaaatatctg caccccctcac agttacctca    34680 gaagccctaa ctgtggctgc cgccgcacct ctaatggtcg cgggcaacac actcaccatg    34740
caatcacagg ccccgctaac cgtgcacgac tccaaactta gcattgccac ccaaggaccc    34800
ctcacagtgt cagaaggaaa gctagccctg caaacatcag gcccctcac  caccaccgat    34860 agcagtaccc ttactatcac tgcctcaccc cctctaacta ctgccactgg tagcttgggc    34920
attgacttga aagagcccat ttatacacaa aatggaaaac taggactaaa gtacggggct    34980
```

```
cctttgcatg taacagacga cctaaacact ttgaccgtag caactggtcc aggtgtgact   35040
attaataata cttccttgca aactaaagtt actggagcct tgggttttga ttcacaaggc   35100
aatatgcaac ttaatgtagc aggaggacta aggattgatt ctcaaaacag acgccttata   35160
cttgatgtta gttatccgtt tgatgctcaa aaccaactaa atctaagact aggacagggc   35220
cctcttttta taaactcagc ccacaacttg gatattaact acaacaaagg cctttacttg   35280
tttacagctt caaacaattc caaaaagctt gaggttaacc taagcactgc caaggggttg   35340
atgtttgacg ctacagccat agccattaat gcaggagatg gcttgaatt tggttcacct    35400 aatgcaccaa acacaaatcc cctcaaaaca aaaattggcc atggcctaga atttgattca   35460
aacaaggcta tggttcctaa actaggaact ggccttagtt ttgacagcac aggtgccatt   35520
acagtaggaa acaaaaataa tgataagcta actttgtgga ccacaccagc tccatctcct   35580
aactgtagac taaatgcaga gaaagatgct aaactcactt tggtcttaac aaaatgtggc   35640
agtcaaatac ttgctacagt ttcagttttg gctgttaaag gcagtttggc tccaatatct   35700
ggaacagttc aaagtgctca tcttattata agatttgacg aaaatggagt gctactaaac   35760
aattccttcc tggacccaga atattggaac tttagaaatg gagatcttac tgaaggcaca   35820
gcctatacaa acgctgttgg atttatgcct aacctatcag cttatccaaa atctcacggt   35880
aaaactgcca aaagtaacat tgtcagtcaa gtttacttaa acggagacaa aactaaacct   35940
gtaacactaa ccattacact aaacggtaca caggaaacag gagacacaac tccaagtgca   36000
tactctatgt cattttcatg ggactggtct ggccacaact acattaatga aatatttgcc   36060
acatcctctt acactttttc atacattgcc caagaataaa gaatcgtttg tgttatgttt   36120
caacgtgttt attttcaat tgcagaaaat ttcaagtcat ttttcattca gtagtatagc    36180
cccaccacca catagcttat acagatcacc gtaccttaat caaactcaca gaaccctagt   36240
attcaacctg ccacctccct cccaacacac agagtacaca gtcctttctc cccggctggc   36300
cttaaaaagc atcatatcat gggtaacaga catattctta ggtgttatat tccacacggt   36360
ttcctgtcga gccaaacgct catcagtgat attaataaac tccccgggca gctcacttaa   36420
gttcatgtcg ctgtccagct gctgagccac aggctgctgt ccaacttgcg gttgcttaac   36480
gggcggcgaa ggagaagtcc acgcctacat gggggtagag tcataatcgt gcatcaggat   36540
agggcggtgg tgctgcagca gcgcgcgaat aaactgctgc cgccgccgct ccgtcctgca   36600
ggaatacaac atggcagtgg tctcctcagc gatgattcgc accgcccgca gcataaggcg   36660
ccttgtcctc cgggcacagc agcgcaccct gatctcactt aaatcagcac agtaactgca   36720
gcacagcacc acaatattgt tcaaaatccc acagtgcaag gcgctgtatc caaagctcat   36780 ggcgggggacc acagaaccca cgtggccatc ataccacaag cgcaggtaga ttaagtggcg   36840 accctcata aacacgctgg acataaacat tacctctttt ggcatgttgt aattcaccac    36900
ctcccggtac catataaacc tctgattaaa catggcgcca tccaccacca tcctaaacca   36960
gctggccaaa acctgcccgc cggctataca ctgcagggaa ccgggactgg aacaatgaca   37020
gtggagagcc caggactcgt aaccatggat catcatgctc gtcatgatat caatgttggc   37080
acaacacagg cacacgtgca tacacttcct caggattaca agctcctccc gcgttagaac   37140
catatcccag ggaacaaccc attcctgaat cagcgtaaat cccacactgc agggaagacc   37200
tcgcacgtaa ctcacgttgt gcattgtcaa agtgttacat tcgggcagca gcggatgatc   37260
ctccagtatg gtagcgcggg tttctgtctc aaaaggaggt agacgatccc tactgtacgg   37320
```

```
agtgcgccga gacaaccgag atcgtgttgg tcgtagtgtc atgccaaatg gaacgccgga    37380
cgtagtcata tttcctgaag caaaaccagg tgcgggcgtg acaaacagat ctgcgtctcc    37440
ggtctcgccg cttagatcgc tctgtgtagt agttgtagta tatccactct ctcaaagcat    37500
ccaggcgccc cctggcttcg ggttctatgt aaactccttc atgcgccgct gccctgataa    37560
catccaccac cgcagaataa gccacaccca gccaacctac acattcgttc tgcgagtcac    37620
acacgggagg agcgggaaga gctggaagaa ccatgttttt ttttttattc aaaagatta    37680 tccaaaacct caaaatgaag atctattaag tgaacgcgct cccctccggt ggcgtggtca    37740
aactctacag ccaaagaaca gataatggca tttgtaagat gttgcacaat ggcttccaaa    37800
aggcaaacgg ccctcacgtc caagtggacg taaaggctaa acccttcagg gtgaatctcc    37860
tctataaaca ttccagcacc ttcaaccatg cccaataat tctcatctcg ccaccttctc    37920
aatatatctc taagcaaatc ccgaatatta agtccggcca ttgtaaaaat ctgctccaga    37980
gcgccctcca ccttcagcct caagcagcga atcatgattg caaaaattca ggttcctcac    38040
agacctgtat aagattcaaa agcggaacat taacaaaaat accgcgatcc cgtaggtccc    38100
ttcgcagggc cagctgaaca taatcgtgca ggtctgcacg gaccagcgcg gccacttccc    38160
cgccaggaac catgacaaaa gaacccacac tgattatgac acgcatactc ggagctatgc    38220
taaccagcgt agccccgatg taagcttgtt gcatgggcgg cgatataaaa tgcaaggtgc    38280
tgctcaaaaa atcaggcaaa gcctcgcgca aaaagaaag cacatcgtag tcatgctcat    38340
gcagataaag gcaggtaagc tccggaacca ccacagaaaa agacaccatt tttctctcaa    38400
acatgtctgc gggtttctgc ataaacacaa aataaaataa caaaaaaaca tttaaacatt    38460
agaagcctgt cttacaacag gaaaaacaac ccttataagc ataagacgga ctacggccat    38520
gccggcgtga ccgtaaaaaa actggtcacc gtgattaaaa agcaccaccg acagctcctc    38580
ggtcatgtcc ggagtcataa tgtaagactc ggtaaacaca tcaggttgat tcacatcggt    38640
cagtgctaaa aagcgaccga aatagcccgg gggaatacat acccgcaggc gtagagacaa    38700
cattacagcc cccataggag gtataacaaa attaatagga gagaaaaaca cataaacacc    38760
tgaaaaaccc tcctgcctag gcaaaatagc accctcccgc tccagaacaa catacagcgc    38820
ttccacagcg gcagccataa cagtcagcct taccagtaaa aagaaaaacc tattaaaaaa    38880
acaccactcg acacggcacc agctcaatca gtcacagtgt aaaaaagggc caagtgcaga    38940
gcgagtatat ataggactaa aaaatgacgt aacggttaaa gtccacaaaa aacacccaga    39000
aaaccgcacg cgaacctacg cccagaaacg aaagccaaaa aacccacaac ttcctcaaat    39060
cgtcacttcc gttttcccac gttacgtcac ttcccatttt aagaaaacta caattcccaa    39120
cacatacaag ttactccgcc ctaaaaccta cgtcacccgc cccgttccca cgccccgcgc    39180
cacgtcacaa actccacccc ctcattatca tattggcttc aatccaaaat aaggtatatt    39240
attgatgatg tagggataac agggtaataa atccggggat cctctagagt cgacctgcag    39300
gcatgcaagc ttggcgtaat catggtcata gctgtttcct gtgtgaaatt gttatccgct    39360
cacaattcca cacaacatac gagccggaag cataaagtgt aaagcctggg gtgcctaatg    39420
agtgagcta                                                            39429
```

<210> SEQ ID NO 4
<211> LENGTH: 36699
<212> TYPE: DNA
<213> ORGANISM: Artificial Sequence
<220> FEATURE:
<223> OTHER INFORMATION: Synthetic adenovirus vector (CMV-Null)

<400> SEQUENCE: 4

```
gttccactga gcgtcagacc ccttaataag atgatcttct tgagatcgtt ttggtctgcg      60
cgtaatctct tgctctgaaa acgaaaaaac cgccttgcag ggcggttttt cgaaggttct     120
ctgagctacc aactctttga accgaggtaa ctggcttgga ggagcgcagt caccaaaact     180
tgtcctttca gtttagcctt aaccggcgca tgacttcaag actaactcct ctaaatcaat     240
taccagtggc tgctgccagt ggtgcttttg catgtctttc cgggttggac tcaagacgat     300
agttaccgga taaggcgcag cggtcggact gaacgggggg ttcgtgcata cagtccagct     360
tggagcgaac tgcctacccg gaactgagtg tcaggcgtgg aatgagacaa acgcggccat     420
aacagcggaa tgacaccggt aaaccgaaag gcaggaacag gagagcgcac gagggagccg     480
ccaggggaaa cgcctggtat ctttatagtc ctgtcgggtt tcgccaccac tgatttgagc     540
gtcagatttc gtgatgcttg tcaggggggc ggagcctatg gaaaaacggc tttgccgcgg     600
ccctctcact tccctgttaa gtatcttcct ggcatcttcc aggaaatctc cgccccgttc     660
gtaagccatt tccgctcgcc gcagtcgaac gaccgagcgt agcgagtcag tgagcgagga     720
agcggaatat atcctgtatc acatattctg ctgacgcacc ggtgcagcct tttttctcct     780
gccacatgaa gcacttcact gacaccctca tcagtgccaa catagtaagc cagtatacac     840
tccgctagcg ctgaggtctg cctcgtgaag aaggtgttgc tgactcatac caggcctgaa     900
tcgccccatc atccagccag aaagtgaggg agccacggtt gatgagagct tgttgtagg     960
tggaccagtt ggtgattttg aactttttgct ttgccacgga acggtctgcg ttgtcgggaa    1020
gatgcgtgat ctgatccttc aactcagcaa aagttcgatt tattcaacaa agccacgttg    1080
tgtctcaaaa tctctgatgt tacattgcac aagataaaaa tatatcatca tgaacaataa    1140
aactgtctgc ttacataaac agtaatacaa ggggtgttga tactctcagt acaatctgct    1200
ctgatgccgc atagttaagc cagtatctgc tccctgcttg tgtgttggag gtcgctgagt    1260
agtgcgcgag caaaatttaa gctacaacaa ggcaaggctt gaccgacaat tgcatgaaga    1320
atctgcttag ggttaggcgt tttgcgctgc ttcgcgatgt acgggccaga tatacgcgta    1380
tctgagggga ctagggtgtg tttaggcgaa aagcggggct tcggttgtac gcggttagga    1440
gtcccctcag gatatagtag tttcgctttt gcatagggag ggggaaatgt agtcttatgc    1500
aatactcttg tagtcttgca acatggtaac gatgagttag caacatgcct tacaaggaga    1560
gaaaaagcac cgtgcatgcc gattggtgga agtaaggtgg tacgatcgtg ccttattagg    1620
aaggcaacag acgggtctga catggattgg acgaaccact gaattccgca ttgcagagat    1680
attgtattta agtgcctagc tcgatacaat aaacgccatt tgaccattca ccacattggt    1740
gtgcacctcc aagctgggta cggatccggc cttgccggcc tcgagcggcc gctagcgccg    1800
ccactatggg atcaagatcg ccaaaaaaga agagaaaggt gccgaagaag catgcagcac    1860
caccaaaaaa aaaacgaaaa gtagaagacc cacgatttat gtaccatac gatgttcctg     1920
actatgcggg tatgaaaaac atcaaaaaaa accaggtaat gaacctgggt ccgaactcta    1980
aactgctgaa agaatacaaa tcccagctga tcgaactgaa catcgaacag ttcgaagcag    2040
gtatcggtct gatcctgggt gatgcttaca tccgttctcg tgatgaaggt aaaacctact    2100
gtatgcagtt cgagtggaaa aacaaagcat acatggacca cgtatgtctg ctgtacgatc    2160
agtgggtact gtccccgccg cacaaaaaag aacgtgttaa ccacctgggt aacctggtaa    2220
tcacctgggg cgcccagact ttcaaacacc aagctttcaa caaactggct aacctgttca    2280
```

```
tcgttaacaa caaaaaaacc atcccgaaca acctggttga aaactacctg accccgatgt    2340
ctctggcata ctggttcatg gatgatggtg gtaaatggga ttacaacaaa aactctacca    2400
acaaatcgat cgtactgaac acccagtctt tcactttcga agaagtagaa tacctggtta    2460
agggtctgcg taacaaattc caactgaact gttacgtaaa aatcaacaaa aacaaaccga    2520
tcatctacat cgattctatg tcttacctga tcttctacaa cctgatcaaa ccgtacctga    2580
tcccgcagat gatgtacaaa ctgccgaaca ctatctcctc cgaaactttc ctgaaataag    2640
gtaccgatcc agacatgata agatacattg atgagtttgg acaaaccaca actagaatgc    2700
agtgaaaaaa atgctttatt tgtgaaattt gtgatgctat tgctttattt gtaaccatta    2760
taagctgcaa taaacaagtt aacaacaaca attgcattca ttttatgttt caggttcagg    2820
gggaggtgtg ggaggttttt taaagcaagt aaaacctcta caaatgtggt atggctgatt    2880
atgatcatcg taaacttggt ctgacagtta ccaatgctta atcagtgagg cacctatctc    2940
agcgatctgt ctatttcgtt catccatagt tgcctgactc cccgtcgtgt agataactac    3000
gatacgggag ggcttaccat ctggcccag tgctgcaatg ataccgcgag acccacgctc    3060
accggctcca gatttatcag caataaacca gccagccgga agggccgagc gcagaagtgg    3120
tcctgcaact ttatccgcct ccatccagtc tattaattgt tgccgggaag ctagagtaag    3180
tagttcgcca gttaatagtt tgcgcaacgt tgttgccatt gctacaggca tcgtggtgtc    3240
acgctcgtcg tttggtatgg cttcattcag ctccggttcc caacgatcaa ggcgagttac    3300
atgatccccc atgttgtgca aaaaagcggt tagctccttc ggtcctccga tcgttgtcag    3360
aagtaagttg gccgcagtgt tatcactcat ggttatggca gcactgcata attctcttac    3420
tgtcatgcca tccgtaagat gcttttctgt gactggtgag tactcaacca agtcattctg    3480
agaatagtgt atgcggcgac cgagttgctc ttgcccggcg tcaatacggg ataataccgc    3540
gccacatagc agaactttaa aagtgctcat cattggaaaa cgttcttcgg ggcgaaaact    3600
ctcaaggatc ttaccgctgt tgagatccag ttcgatgtaa cccactcgtg cacccaactg    3660
atcttcagca tcttttactt tcaccagcgt ttctgggtga gcaaaaacag gaaggcaaaa    3720
tgccgcaaaa aagggaataa gggcgacacg gaaatgttga atactcatac tcttcctttt    3780
tcaatattat tgaagcattt atcagggtta ttgtctcatg agcggataca tatttgaatg    3840
tatttagaaa aataaacaaa tagggggttcc gcgcacattt ccccgaaaag tgccacctga    3900
cgtctaagaa accattatta tcatgacatt aacctataaa aataggcgta tcacgaggcc    3960
ctttcgtctc gcgcgtttcg gtgatgacgg tgaaaacctc tgacacatgc agctcccgga    4020
gacggtcaca gcttgtctgt aagcggatgc cgggagcaga caagcccgtc agggcgcgtc    4080
agcgggtgtt ggcgggtgtc ggggctggct taactatgcg gcatcagagc agattgtact    4140
gagagtgcac catatgcggt gtgaaatacc gcacagatgc gtaaggagaa ataccgcat    4200 caggcgccat tcgccattca ggctgcgcaa ctgttgggaa gggcgatcgg tgcgggcctc    4260
ttcgctatta cgccagctgg cgaaaggggg atgtgctgca aggcgattaa gttgggtaac    4320
gccagggttt tcccagtcac gacgttgtaa aacgacggcc agtgaattaa ccaactttgt    4380
acaaaaaagc agattaccct gttatcccta catcatcaat aatataccct attttggatt    4440
gaagccaata tgataatgag ggggtggagt ttgtgacgtg gcgcggggcg tgggaacggg    4500
gcgggtgacg tagtagtgtg gcggaagtgt gatgttgcaa gtgtggcgga acacatgtaa    4560
gcgacggatg tggcaaaagt gacgtttttg gtgtgcgccg gtgtacacag gaagtgacaa    4620
ttttcgcgcg gttttaggcg gatgttgtag taaatttggg cgtaaccgag taagatttgg    4680
```

```
ccattttcgc gggaaaactg aataagagga agtgaaatct gaataatttt gtgttactca    4740
tagcgcgtaa tatttgtcta gggccgcggg gactttgacc gtttacgtgg agactcgccc    4800
aggtgttttt ctcaggtgtt ttccgcgttc cgggtcaaag ttggcgtttt attattaatt    4860
aagtttaaac ggcgcgccta atagtaatca attacgggt cattagttca tagcccatat     4920
atggagttcc gcgttacata acttacggta aatggcccgc ctggctgacc gcccaacgac    4980
ccccgcccat tgacgtcaat aatgacgtat gttcccatag taacgccaat agggactttc    5040
cattgacgtc aatgggtgga gtatttacgg taaactgccc acttggcagt acatcaagtg    5100
tatcatatgc caagtacgcc ccctattgac gtcaatgacg gtaaatggcc cgcctggcat    5160
tatgcccagt acatgacctt atgggacttt cctacttggc agtacatcta cgtattagtc    5220
atcgctatta ccatggtgat gcggttttgg cagtacatca atgggcgtgg atagcggttt    5280
gactcacggg gatttccaag tctccacccc attgacgtca atgggagttt gttttggcac    5340
caaaatcaac gggactttcc aaaatgtcgt aacaactccg ccccattgac gcaaatgggc    5400
ggtaggcgtg tacggtggga ggtctatata agcagagctg gtttagtgaa ccgtcagatg    5460
gtaccggccc cgggagacgg cggcggtggc ggcgcgggca gagcaaggac gcggcggatc    5520
tatagatatc ataaccggta tagcggccgc aagaggtaag ggtttaaggg atggtcggtt    5580
ggtggggtat taatgtttaa ttacctggag cacctgcctg aaatcacttt ttttcaggtt    5640
ggaatcgata atcaacctct ggattacaaa atttgtgaaa gattgactgg tattcttaac    5700
tatgttgctc cttttacgct atgtggatac gctgctttaa tgcctttgta tcatgctatt    5760
gcttcccgta tggctttcat tttctcctcc ttgtataaat cctggttgct gtctctttat    5820
gaggagttgt ggcccgttgt caggcaacgt ggcgtggtgt gcactgtgtt tgctgacgca    5880
acccccactg gttgggcat tgccaccacc tgtcagctcc tttccgggac tttcgctttc      5940
cccctcccta ttgccacggc ggaactcatc gccgcctgcc ttgcccgctg ctggacaggg    6000
gctcggctgt tgggcactga caattccgtg gtgttgtcgg ggaagctgac gtccttttcca   6060 tggctgctcg cctgtgttgc cacctggatt ctgcgcggga cgtccttctg ctacgtccct    6120
tcggccctca atccagcgga ccttccttcc gcggcctgc tgccggctct gcggcctctt     6180
ccgcgtcttc gccttcgccc tcagacgagt cggatctccc tttgggccgc ctccccgcct    6240
gctgcagggc gccatcgtgg atgggagtcc gtgtgtgcct ggagattacc ctggacacct    6300 ctgcttttt ttttttactt tagcggttgc ctcctaggcc tgactccttc ccatgttgaa      6360
ctggaggcag ccacgttagg tgtcaatgtc ctggcatcag tatgaacagt cagtagtccc    6420
agggcagggc cacacttctc ccatcttctg cttccacccc agcttgtgat tgctagcctc    6480
ccagagctca attgctgtgc cttctagttg ccagccatct gttgtttgcc cctccccgt      6540 gccttccttg accctggaag gtgccactcc cactgtcctt tcctaataaa atgaggaaat    6600
tgcatcgcat tgtctgagta ggtgtcattc tattctgggg ggtggggtgg ggcaggacag    6660 caaggggggag gattgggaag acaatagcag gcatgctggg gatgcggtgg gctctatgga   6720
cgcgtcggcc gctgcagctc gagtctagag ctgacggcgc gcctgaaatg tgtgggcgtg    6780
gcttaagggt gggaaagaat atataaggtg ggggtcttat gtagttttgt atctgttttg    6840
cagcagccgc cgccgccatg agcaccaact cgtttgatgg aagcattgtg agctcatatt    6900
tgacaacgcg catgccccca tgggccgggg tgcgtcagaa tgtgatgggc tccagcattg    6960
atggtcgccc cgtcctgccc gcaaactcta ctaccttgac ctacgagacc gtgtctggaa    7020
```

```
cgccgttgga gactgcagcc tccgccgccg cttcagccgc tgcagccacc gcccgcggga    7080
ttgtgactga ctttgctttc ctgagcccgc ttgcaagcag tgcagcttcc cgttcatccg    7140
cccgcgatga caagttgacg gctcttttgg cacaattgga ttctttgacc cgggaactta    7200
atgtcgtttc tcagcagctg ttggatctgc gccagcaggt ttctgccctg aaggcttcct    7260
cccctcccaa tgcggtttaa aacataaata aaaaaccaga ctctgtttgg atttggatca    7320
agcataagtg tcttgctgtc tttatttagg ggttttgcgc gcgcggtagg cccgggacca    7380
gcggtctcgg tcgttgaggg tcctgtgtat ttttccagg acgtggtaaa ggtgactctg     7440
gatgttcaga tacatgggca taagcccgtc tctggggtgg aggtagcacc actgcagagc    7500
ttcatgctgc ggggtggtgt tgtagatgat ccagtcgtag caggagcgct gggcgtggtg    7560
cctaaaaatg tctttcagta gcaagctgat tgccaggggc aggcccttgg tgtaagtgtt    7620
tacaaagcgg ttaagctggg atgggtgcat acgtgggat atgagatgca tcttggactg     7680 tattttagg ttggctatgt tcccagccat atccctccgg ggattcatgt tgtgcagaac     7740
caccagcaca gtgtatccgg tgcacttggg aaatttgtca tgtagcttag aaggaaatgc    7800
gtggaagaac ttggagacgc ccttgtgacc tccaagattt tccatgcatt cgtccataat    7860
gatggcaatg ggcccacggg cggcggcctg ggcgaagata tttctgggat cactaacgtc    7920
atagttgtgt tccaggatga gatcgtcata ggccattttt acaaagcgcg ggcggagggt    7980
gccagactgc ggtataatgg ttccatccgg cccaggggcg tagttaccct cacagatttg    8040
catttcccac gctttgagtt cagatggggg gatcatgtct acctgcgggg cgatgaagaa    8100
aacggtttcc ggggtagggg agatcagctg ggaagaaagc aggttcctga gcagctgcga    8160
cttaccgcag ccggtgggcc cgtaaatcac acctattacc gggtgcaact ggtagttaag    8220
agagctgcag ctgccgtcat ccctgagcag gggggccact tcgttaagca tgtccctgac    8280
tcgcatgttt tccctgacca aatccgccag aaggcgctcg ccgcccagcg atagcagttc    8340
ttgcaaggaa gcaaagtttt tcaacggttt gagaccgtcc gccgtaggca tgcttttgag    8400
cgtttgacca agcagttcca ggcggtccca cagctcggtc acctgctcta cggcatctcg    8460
atccagcata tctcctcgtt tcgcgggttg gggcggcttt cgctgtacgg cagtagtcgg    8520
tgctcgtcca gacgggccag ggtcatgtct ttccacgggc gcagggtcct cgtcagcgta    8580
gtctgggtca cggtgaaggg gtgcgctccg ggctgcgcgc tggccagggt gcgcttgagg    8640
ctggtcctgc tggtgctgaa gcgctgccgg tcttcgccct gcgcgtcggc caggtagcat    8700
ttgaccatgg tgtcatagtc cagcccctcc gcggcgtggc ccttggcgcg cagcttgccc    8760
ttggaggagg cgccgcacga ggggcagtgc agacttttga gggcgtagag cttgggcgcg    8820
agaaataccg attccgggga gtaggcatcc gcgccgcagg ccccgcagac ggtctcgcat    8880
tccacgagcc aggtgagctc tggccgttcg gggtcaaaaa ccaggtttcc cccatgcttt    8940
ttgatgcgtt tcttacctct ggtttccatg agccggtgtc cacgctcggt gacgaaaagg    9000
ctgtccgtgt ccccgtatac agacttgaga ggcctgtcct cgagcggtgt tccgcggtcc    9060
tcctcgtata gaaactcgga ccactctgag acaaaggctc gcgtccaggc cagcacgaag    9120
gaggctaagt gggagggta gcggtcgttg tccactaggg ggtccactcg ctccaggttg    9180
tgaagacaca tgtcgccctc ttcggcatca aggaaggtga ttggtttgta ggtgtaggcc    9240
acgtgaccgg gtgttcctga agggggggcta taaaagggggg tggggcgcg ttcgtcctca    9300 ctctcttccg catcgctgtc tgcgagggcc agctgttggg gtgagtactc cctctgaaaa    9360
gcgggcatga cttctgcgct aagattgtca gtttccaaaa acgaggagga tttgatattc    9420
```

```
acctggcccg cggtgatgcc tttgagggtg gccgcatcca tctggtcaga aagacaatc     9480
tttttgttgt caagcttggt ggcaaacgac ccgtagaggg cgttggacag caacttggcg    9540
atggagcgca gggtttggtt tttgtcgcga tcggcgcgct ccttggccgc gatgtttagc    9600
tgcacgtatt cgcgcgcaac gcaccgccat tcgggaaaga cggtggtgcg ctcgtcgggc    9660
accaggtgca cgcgccaacc gcggttgtgc agggtgacaa ggtcaacgct ggtggctacc    9720
tctccgcgta ggcgctcgtt ggtccagcag aggcggccgc ccttgcgcga gcagaatggc    9780
ggtaggggt ctagctgcgt ctcgtccggg gggtctgcgt ccacggtaaa gaccccgggc     9840
agcaggcgcg cgtcgaagta gtctatcttg catccttgca agtctagcgc ctgctgccat    9900
gcgcgggcgg caagcgcgcg ctcgtatggg ttgagtgggg gaccccatgg catggggtgg    9960
gtgagcgcg aggcgtacat gccgcaaatg tcgtaaacgt agaggggctc tctgagtatt     10020
ccaagatatg tagggtagca tcttccaccg cggatgctgg cgcgcacgta atcgtatagt    10080
tcgtgcgagg gagcgaggag gtcgggaccg aggttgctac gggcgggctg ctctgctcgg    10140
aagactatct gcctgaagat ggcatgtgag ttggatgata tggttggacg ctggaagacg    10200
ttgaagctgg cgtctgtgag acctaccgcg tcacgcacga aggaggcgta ggagtcgcgc    10260
agcttgttga ccagctcggc ggtgacctgc acgtctaggg cgcagtagtc cagggtttcc    10320
ttgatgatgt catacttatc ctgtcccttt tttttccaca gctcgcggtt gaggacaaac    10380
tcttcgcggt ctttccagta ctcttggatc ggaaacccgt cggcctccga acggtaagag    10440
cctagcatgt agaactggtt gacggcctgg taggcgcagc atcccttttc tacgggtagc    10500
gcgtatgcct gcgcggcctt ccggagcgag gtgtgggtga gcgcaaaggt gtccctgacc    10560
atgactttga ggtactggta tttgaagtca gtgtcgtcgc atccgccctg ctcccagagc    10620
aaaaagtccg tgcgcttttt ggaacgcgga tttgcaggg cgaaggtgac atcgttgaag     10680
agtatctttc ccgcgcgagg cataaagttg cgtgtgatgc ggaagggtcc cggcacctcg    10740
gaacggttgt taattacctg ggcggcgagc acgatctcgt caaagccgtt gatgttgtgg    10800
cccacaatgt aaagttccaa gaagcgcggg atgcccttga tggaaggcaa ttttttaagt    10860
tcctcgtagg tgagctcttc aggggagctg agcccgtgct ctgaaagggc ccagtctgca    10920
agatgagggt tggaagcgac gaatgagctc cacaggtcac gggccattag catttgcagg    10980
tggtcgcgaa aggtcctaaa ctggcgacct atggccattt tttctggggt gatgcagtag    11040
aaggtaagcg ggtcttgttc ccagcggtcc catccaaggt tcgcggctag gtctcgcgcg    11100
gcagtcacta gaggctcatc tccgccgaac ttcatgacca gcatgaaggg cacgagctgc    11160
ttcccaaagg ccccccatcca agtataggtc tctacatcgt aggtgacaaa gagacgctcg   11220
gtgcgaggat gcgagccgat cgggaagaac tggatctccc gccaccaatt ggaggagtgg    11280
ctattgatgt ggtgaaagta gaagtccctg cgacgggccg aacactcgtg ctggcttttg    11340
taaaaacgtg cgcagtactg gcagcggtgc acggctgta catcctgcac gaggttgacc     11400
tgacgaccgc gcacaaggaa gcagagtggg aatttgagcc cctcgcctgg cgggtttggc    11460
tggtggtctt ctacttcggc tgcttgtcct tgaccgtctg gctgctcgag gggagttacg    11520
gtggatcgga ccaccacgcc gcgcgagccc aaagtccaga tgtccgcgcg cggcggtcgg    11580
agcttgatga caacatcgcg cagatgggag ctgtccatgg tctggagctc ccgcggcgtc    11640
aggtcaggcg ggagctcctg caggtttacc tcgcatagac gggtcagggc gcgggctaga    11700
tccaggtgat acctaatttc cagggggctgg ttggtggcgg cgtcgatggc ttgcaagagg   11760
```

```
ccgcatcccc gcggcgcgac tacggtaccg cgcggcgggc ggtgggccgc ggggggtgtcc   11820 ttggatgatg catctaaaag cggtgacgcg ggcgagcccc cggaggtagg ggggggctccg   11880 gacccgccgg gagaggggggc aggggcacgt cggcgccgcg cgcgggcagg agctggtgct   11940
gcgcgcgtag gttgctggcg aacgcgacga cgcggcggtt gatctcctga atctggcgcc   12000
tctgcgtgaa gacgacgggc ccggtgagct tgagcctgaa agagagttcg acagaatcaa   12060
tttcggtgtc gttgacggcg gcctggcgca aaatctcctg cacgtctcct gagttgtctt   12120
gataggcgat ctcggccatg aactgctcga tctcttcctc ctggagatct ccgcgtccgg   12180
ctcgctccac ggtggcggcg aggtcgttgg aaatgcgggc catgagctgc gagaaggcgt   12240
tgaggcctcc ctcgttccag acgcggctgt agaccacgcc cccttcggca tcgcgggcgc   12300
gcatgaccac ctgcgcgaga ttgagctcca cgtgccgggc gaagacgcg tagtttcgca   12360 ggcgctgaaa gaggtagttg agggtggtgg cggtgtgttc tgccacgaag aagtacataa   12420
cccagcgtcg caacgtggat tcgttgatat cccccaaggc ctcaaggcgc tccatggcct   12480
cgtagaagtc cacggcgaag ttgaaaaact gggagttgcg cgccgacacg gttaactcct   12540
cctccagaag acggatgagc tcggcgacag tgtcgcgcac ctcgcgctca aaggctacag   12600
gggcctcttc ttcttcttca atctcctctt ccataagggc ctcccctcct tcttcttctg   12660
gcggcggtgg gggagggggg acacggcggc gacgacggcg caccgggagg cggtcgacaa   12720
agcgctcgat catctccccg cggcgacggc gcatggtctc ggtgacgcg cggccgttct   12780 cgcggggggcg cagttggaag acgccgcccg tcatgtcccg gttatgggtt ggcggggggc   12840
tgccatgcgg cagggatacg gcgctaacga tgcatctcaa caattgttgt gtaggtactc   12900
cgccgccgag ggacctgagc gagtccgcat cgaccggatc ggaaaacctc tcgagaaagg   12960
cgtctaacca gtcacagtcg caaggtaggc tgagcaccgt ggcgggcggc agcgggcggc   13020 ggtcgggggtt gtttctggcg gaggtgctgc tgatgatgta attaaagtag gcggtcttga   13080
gacggcggat ggtcgacaga agcaccatgt ccttgggtcc ggcctgctga atgcgcaggc   13140
ggtcggccat gccccaggct tcgttttgac atcggcgcag gtctttgtag tagtcttgca   13200
tgagcctttc taccggcact tcttcttctc cttcctcttg tcctgcatct cttgcatcta   13260
tcgctgcggc ggcggcggag tttggccgta ggtggcgccc tcttcctccc atgcgtgtga   13320
ccccgaagcc cctcatcggc tgaagcaggg ctaggtcggc gacaacgcgc tcggctaata   13380
tggcctgctg cacctgcgtg agggtagact ggaagtcatc catgtccaca aagcggtggt   13440
atgcgcccgt gttgatggtg taagtgcagt tggcctaaac ggaccagtta acggtctggt   13500
gacccggctg cgagagctcg gtgtacctga gacgcgagta agccctcgag tcaaatacgt   13560
agtcgttgca agtccgcacc aggtactggt atcccaccaa aaagtgcggc ggcggctggc   13620
ggtagagggg ccagcgtagg gtggccgggg ctccgggggc gagatcttcc aacataaggc   13680
gatgatatcc gtagatgtac ctggacatca aggtgatgcc ggcggcggtg gtggaggcgc   13740
gcggaaagtc gcggacgcgg ttccagatgt tgcgcagcgg caaaaagtgc tccatggtcg   13800
ggacgctctg gccggtcagg cgcgcgcaat cgttgacgct ctagaccgtg caaaaggaga   13860
gcctgtaagc gggcactctt ccgtggtctg gtggataaat tcgcaagggt atcatgcggg   13920
acgaccgggg ttcgagcccc gtatccggcc gtccgccgtg atccatgcgg ttaccgcccg   13980
cgtgtcgaac ccaggtgtgc gacgtcagac aacgggggag tgctccttttt ggcttccttc   14040 caggcgcggg ggctgctgcg ctagcttttt tggccactgg ccgcgcgcag cgtaagcggt   14100
taggctggaa agcgaaagca ttaagtggct cgctccctgt agccggaggg ttattttcca   14160
```

```
agggttgagt cgcgggaccc ccggttcgag tctcggaccg gccggactgc ggcgaacggg    14220
ggtttgcctc cccgtcatgc aagacccgc ttgcaaattc ctccggaaac agggacgagc    14280 ccctttttg cttttcccag atgcatccgg tgctgcggca gatgcgcccc cctcctcagc    14340
agcggcaaga gcaagagcag cggcagacat gcagggcacc ctcccctcct cctaccgcgt    14400
caggaggggc gacatccgcg gttgacgcgg cagcagatgg tgattacgaa cccccgcggc    14460
gccgggcccg gcactacctg gacttggagg agggcgaggg cctggcgcgg ctaggagcgc    14520
cctctcctga gcggtaccca agggtgcagc tgaagcgtga tacgcgtgag gcgtacgtgc    14580
cgcggcagaa cctgtttcgc gaccgcgagg gagaggagcc cgaggagatg cgggatcgaa    14640
agttccacgc agggcgcgag ctgcggcatg gcctgaatcg cgagcggttg ctgcgcgagg    14700
aggactttga gcccgacgcg cgaaccggga ttagtcccgc gcgcgcacac gtggcggccg    14760
ccgacctggt aaccgcatac gagcagacgg tgaaccagga gattaacttt caaaaaagct    14820
ttaacaacca cgtgcgtacg cttgtggcgc gcgaggaggt ggctatagga ctgatgcatc    14880
tgtgggactt tgtaagcgcg ctggagcaaa acccaaatag caagccgctc atggcgcagc    14940
tgttccttat agtgcagcac agcagggaca acgaggcatt cagggatgcg ctgctaaaca    15000
tagtagagcc cgagggccgc tggctgctcg atttgataaa catcctgcag agcatagtgg    15060
tgcaggagcg cagcttgagc ctggctgaca aggtggccgc catcaactat tccatgctta    15120
gcctgggcaa gttttacgcc cgcaagatat accataccc ttacgttccc atagacaagg    15180
aggtaaagat cgaggggttc tacatgcgca tggcgctgaa ggtgcttacc ttgagcgacg    15240
acctgggcgt ttatcgcaac gagcgcatcc acaaggccgt gagcgtgagc cggcggcgcg    15300
agctcagcga ccgcgagctg atgcacagcc tgcaaagggc cctggctggc acgggcagcg    15360
gcgatagaga ggccgagtcc tactttgacg cgggcgctga cctgcgctgg gccccaagcc    15420
gacgcgccct ggaggcagct ggggccggac ctgggctggc ggtggcaccc gcgcgcgctg    15480
gcaacgtcgg cggcgtggag gaatatgacg aggacgatga gtacgagcca gaggacggcg    15540
agtactaagc ggtgatgttt ctgatcagat gatgcaagac gcaacggacc cggcggtgcg    15600
ggcggcgctg cagagccagc cgtccggcct taactccacg gacgactggc gccaggtcat    15660
ggaccgcatc atgtcgctga ctgcgcgcaa tcctgacgcg ttccggcagc agccgcaggc    15720
caaccggctc tccgcaattc tggaagcggt ggtcccggcg cgcgcaaacc ccacgcacga    15780
gaaggtgctg gcgatcgtaa acgcgctggc cgaaaacagg gccatccggc ccgacgaggc    15840
cggcctggtc tacgacgcgc tgcttcagcg cgtggctcgt tacaacagcg gcaacgtgca    15900
gaccaacctg gaccggctgg tgggggatgt gcgcgaggcc gtggcgcagc gtgagcgcgc    15960
gcagcagcag ggcaacctgg gctccatggt tgcactaaac gccttcctga gtacacagcc    16020
cgccaacgtg ccgcggggac aggaggacta caccaacttt gtgagcgcac tgcggctaat    16080
ggtgactgag acaccgcaaa gtgaggtgta ccagtctggg ccagactatt ttttccgagac    16140 cagtagacaa ggcctgcaga ccgtaaacct gagccaggct ttcaaaaact gcagggggct    16200 gtgggggtg cgggctccca caggcgaccg cgcgaccgtg tctagcttgc tgacgcccaa    16260
ctcgcgcctg ttgctgctgc taatagcgcc cttcacggac agtggcagcg tgtcccggga    16320
cacataccta ggtcacttgc tgacactgta ccgcgaggcc ataggtcagg cgcatgtgga    16380
cgagcatact ttccaggaga ttacaagtgt cagccgcgcg ctggggcagg aggacacggg    16440
cagcctggag gcaaccctaa actacctgct gaccaaccgg cggcagaaga tccccctcgtt    16500
```

```
gcacagttta aacagcgagg aggagcgcat tttgcgctac gtgcagcaga gcgtgagcct    16560
taacctgatg cgcgacgggg taacgcccag cgtggcgctg acatgaccg  cgcgcaacat    16620
ggaaccgggc atgtatgcct caaaccggcc gtttatcaac cgcctaatgg actacttgca    16680
tcgcgcggcc gccgtgaacc ccgagtattt caccaatgcc atcttgaacc cgcactggct    16740
accgcccccct ggtttctaca ccgggggatt cgaggtgccc gagggtaacg atggattcct   16800
ctgggacgac atagacgaca gcgtgttttc cccgcaaccg cagaccctgc tagagttgca    16860
acagcgcgag caggcagagg cggcgctgcg aaaggaaagc ttccgcaggc caagcagctt    16920
gtccgatcta ggcgctgcgg ccccgcggtc agatgctagt agcccatttc caagcttgat    16980
agggtctctt accagcactc gcaccacccg cccgcgcctg ctgggcgagg aggagtacct    17040
aaacaactcg ctgctgcagc cgcagcgcga aaaaaacctg cctccggcat ttcccaacaa    17100
cgggatagag agcctagtgg acaagatgag tagatggaag acgtacgcgc aggagcacag    17160
ggacgtgcca ggcccgcgcc cgcccacccg tcgtcaaagg cacgaccgtc agcggggtct    17220
ggtgtgggag gacgatgact cggcagacga cagcagcgtc ctggatttgg agggagtgg    17280
caacccgttt gcgcaccttc gccccaggct ggggagaatg ttttaaaaaa aaaaaagcat    17340
gatgcaaaat aaaaaactca ccaaggccat ggcaccgagc gttggttttc ttgtattccc    17400
cttagtatgc ggcgcgcggc gatgtatgag gaaggtcctc ctccctccta cgagagtgtg    17460
gtgagcgcgg cgccagtggc ggcggcgctg ggttctccct tcgatgctcc cctgacccg    17520
ccgtttgtgc ctccgcggta cctgcggcct accgggggga gaaacagcat ccgttactct    17580
gagttggcac ccctattcga caccacccgt gtgtacctgg tggacaacaa gtcaacggat    17640
gtggcatccc tgaactacca gaacgaccac agcaactttc tgaccacggt cattcaaaac    17700
aatgactaca gccggggga ggcaagcaca cagaccatca atcttgacga ccggtcgcac    17760
tggggcggcg acctgaaaac catcctgcat accaacatgc aaatgtgaa cgagttcatg    17820
tttaccaata agtttaaggc gcgggtgatg gtgtcgcgct tgcctactaa ggacaatcag    17880
gtggagctga atacgagtg ggtggagttc acgctgcccg agggcaacta ctccgagacc    17940
atgaccatag accttatgaa caacgcgatc gtggagcact acttgaaagt gggcagacag    18000
aacgggttc  tggaaagcga catcggggta aagtttgaca cccgcaactt cagactggg    18060
tttgaccccg tcactggtct tgtcatgcct ggggtatata caaacgaagc cttccatcca    18120
gacatcattt tgctgccagg atgcgggtg gacttcaccc acagccgcct gagcaacttg    18180
ttgggcatcc gcaagcggca accccttccag gagggcttta ggatcaccta cgatgatctg    18240
gagggtggta acattccgc  actgttggat gtggacgcct accaggcgag cttgaaagat    18300
gacaccgaac agggcgggg  tggcgcaggc ggcagcaaca gcagtggcag cggcgcggaa    18360
gagaactcca acgcggcagc cgcggcaatg cagccggtgg aggacatgaa cgatcatgcc    18420
attcgcggcg acacctttgc cacacgggct gaggagaagc gcgctgaggc cgaagcagcg    18480
gccgaagctg ccgcccccgc tgcgcaaccc gaggtcgaga agcctcagaa gaaaccggtg    18540
atcaaacccc tgacagagga cagcaagaaa cgcagttaca acctaataag caatgacagc    18600
accttcaccc agtaccgcag ctggtacctt gcatacaact acgcgaccc  tcagaccgga    18660
atccgctcat ggaccctgct ttgcactcct gacgtaacct gcggctcgga gcaggtctac    18720
tggtcgttgc cagacatgat gcaagacccc gtgaccttcc gctccacgcg ccagatcagc    18780
aactttccgg tggtgggcgc cgagctgttg cccgtgcact ccaagagctt ctacaacgac    18840
caggccgtct actcccaact catccgccag tttacctctc tgacccacgt gttcaatcgc    18900
```

```
tttcccgaga accagatttt ggcgcgcccg ccagccccca ccatcaccac cgtcagtgaa   18960
aacgttcctg ctctcacaga tcacgggacg ctaccgctgc gcaacagcat cggaggagtc   19020
cagcgagtga ccattactga cgccagacgc cgcacctgcc cctacgttta caaggccctg   19080
ggcatagtct cgccgcgcgt cctatcgagc cgcactttt gagcaagcat gtccatcctt    19140
atatcgccca gcaataacac aggctggggc ctgcgcttcc caagcaagat gtttggcggg   19200
gccaagaagc gctccgacca acacccagtg cgcgtgcgcg ggcactaccg cgcgccctgg   19260
ggcgcgcaca aacgcggccg cactgggcgc accaccgtcg atgacgccat cgacgcggtg   19320
gtggaggagg cgcgcaacta cacgcccacg ccgccaccag tgtccacagt ggacgcggcc   19380
attcagaccg tggtgcgcgg agcccggcgc tatgctaaaa tgaagagacg gcggaggcgc   19440
gtagcacgtc gccaccgccg ccgacccggc actgccgccc aacgcgcggc ggcggccctg   19500
cttaaccgcg cacgtcgcac cggccgacgg gcggccatgc gggccgctcg aaggctggcc   19560
gcgggtattg tcactgtgcc ccccaggtcc aggcgacgag cggccgccgc agcagccgcg   19620
gccattagtg ctatgactca gggtcgcagg ggcaacgtgt attgggtgcg cgactcggtt   19680
agcggcctgc gcgtgcccgt gcgcacccgc ccccgcgca actagattgc aagaaaaaac    19740
tacttagact cgtactgttg tatgtatcca gcggcggcgg cgcgcaacga agctatgtcc   19800
aagcgcaaaa tcaaagaaga gatgctccag gtcatcgcgc cggagatcta tggccccccg   19860
aagaaggaag agcaggatta caagccccga aagctaaagc gggtcaaaaa gaaaagaaa    19920 gatgatgatg atgaacttga cgacgaggtg gaactgctgc acgctaccgc gcccaggcga   19980
cgggtacagt ggaaaggtcg acgcgtaaaa cgtgttttgc gacccggcac caccgtagtc   20040
tttacgcccg gtgagcgctc caccgcacc tacaagcgcg tgtatgatga ggtgtacggc     20100
gacgaggacc tgcttgagca ggccaacgag cgcctcgggg agtttgccta cggaaagcgg   20160
cataaggaca tgctggcgtt gccgctggac gagggcaacc caacacctag cctaaagccc   20220
gtaacactgc agcaggtgct gccgcgcgct gcaccgtccg aagaaaagcg cggcctaaag   20280
cgcgagtctg tgacttggc acccaccgtg cagctgatgg tacccaagcg ccagcgactg   20340
gaagatgtct tggaaaaaat gaccgtgaa cctgggctgg agcccgaggt ccgcgtgcgg    20400
ccaatcaagc aggtggcgcc gggactgggc gtgcagaccg tggacgttca gatacccact   20460
accagtagca ccagtattgc caccgccaca gagggcatga agacacaaac gtccccggtt   20520
gcctcagcgg tggcggatgc cgcggtgcag gcggtcgctg cggccgcgtc caagacctct   20580
acggaggtgc aaacgcgaccc gtggatgttt cgcgtttcag ccccccggcg cccgcgcggt   20640
tcgaggaagt acggcgccgc cagcgcgcta ctgcccgaat atgccctaca tccttccatt   20700
gcgcctaccc ccggctatcg tggctacacc taccgcccca gaagacgagc aactaccga    20760 cgccgaacca ccactggaac ccgccgccgc cgtcgccgtc gccagcccgt gctggccccg   20820
atttccgtgc gcagggtggc tcgcgaagga ggcaggaccc tggtgctgcc aacagcgcgc   20880 taccaccca gcatcgttta aaagccggtc tttgtggttc ttgcagatat ggccctcacc    20940
tgccgcctcc gtttcccggt gccgggattc cgaggaagaa tgcaccgtag gaggggcatg   21000 gccgccacg gcctgacggg cggcatgcgt cgtgcgcacc accggcggcg gcgcgcgtcg    21060
caccgtcgca tgcgcggcgg tatcctgccc ctccttattc cactgatcgc cgcggcgatt   21120
ggcgccgtgc ccggaattgc atccgtggcc ttgcaggcgc agagacactg attaaaaaca   21180
agttgcatgt ggaaaaatca aaataaaaag tctggactct cacgctcgct tggtcctgta   21240
```

```
actattttgt agaatggaag acatcaactt tgcgtctctg gccccgcgac acggctcgcg   21300
cccgttcatg ggaaactggc aagatatcgg caccagcaat atgagcggtg gcgccttcag   21360
ctggggctcg ctgtggagcg gcattaaaaa tttcggttcc accgttaaga actatggcag   21420
caaggcctgg aacagcagca caggccagat gctgagggat aagttgaaag agcaaaattt   21480
ccaacaaaag gtggtagatg gcctggcctc tggcattagc ggggtggtgg acctggccaa   21540
ccaggcagtg caaaataaga ttaacagtaa gcttgatccc cgccctcccg tagaggagcc   21600
tccaccggcc gtggagacag tgtctccaga ggggcgtggc gaaaagcgtc cgcgccccga   21660
cagggaagaa actctggtga cgcaaataga cgagcctccc tcgtacgagg aggcactaaa   21720
gcaaggcctg cccaccaccc gtcccatcgc gcccatggct accggagtgc tgggccagca   21780
cacacccgta acgctggacc tgcctccccc cgccgacacc cagcagaaac ctgtgctgcc   21840
aggcccgacc gccgttgttg taacccgtcc tagccgcgcg tccctgcgcc gcgccgccag   21900
cggtccgcga tcgttgcggc ccgtagccag tggcaactgg caaagcacac tgaacagcat   21960
cgtgggtctg ggggtgcaat ccctgaagcg ccgacgatgc ttctgaatag ctaacgtgtc   22020
gtatgtgtgt catgtatgcg tccatgtcgc cgccagagga gctgctgagc cgccgcgcgc   22080 ccgcttttcca agatggctac cccttcgatg atgccgcagt ggtcttacat gcacatctcg   22140
ggccaggacg cctcggagta cctgagcccc gggctggtgc agtttgcccg cgccaccgag   22200
acgtacttca gcctgaataa caagtttaga aaccccacgg tggcgcctac gcacgacgtg   22260
accacagacc ggtcccagcg tttgacgctg cggttcatcc ctgtggaccg tgaggatact   22320
gcgtactcgt acaaggcgcg gttcacccta gctgtgggtg ataacgtgt gctggacatg   22380 gcttccacgt actttgacat ccgcggcgtg ctggacaggg gccctacttt taagccctac   22440
tctggcactc cctacaacgc cctggctccc aagggtgccc caaatccttg cgaatgggat   22500
gaagctgcta ctgctcttga aataaaccta gaagaagagg acgatgacaa cgaagacgaa   22560
gtagacgagc aagctgagca gcaaaaaact cacgtatttg ggcaggcgcc ttattctggt   22620
ataaatatta caaaggaggg tattcaaata ggtgtcgaag gtcaaacacc taaatatgcc   22680
gataaaacat ttcaacctga acctcaaata ggagaatctc agtggtacga aactgaaatt   22740
aatcatgcag ctgggagagt ccttaaaaag actaccccaa tgaaaccatg ttacggttca   22800
tatgcaaaac ccacaaatga aaatggaggg caaggcattc ttgtaaagca acaaaatgga   22860
aagctagaaa gtcaagtgga aatgcaattt ttctcaacta ctgaggcgac cgcaggcaat   22920
ggtgataact tgactcctaa agtggtattg tacagtgaag atgtagatat agaaacccca   22980
gacactcata tttcttacat gcccactatt aaggaaggta actcacgaga actaatgggc   23040
caacaatcta tgcccaacag gcctaattac attgctttta gggacaattt tattggtcta   23100
atgtattaca acagcacggg taatatgggt gttctggcgg gccaagcatc gcagttgaat   23160
gctgttgtag atttgcaaga cagaaacaca gagctttcat accagctttt gcttgattcc   23220
attggtgata gaaccaggta cttttctatg tggaatcagg ctgttgacag ctatgatcca   23280
gatgttagaa ttattgaaaa tcatggaact gaagatgaac ttccaaatta ctgctttcca   23340
ctgggaggtg tgattaatac agagactctt accaaggtaa aacctaaaac aggtcaggaa   23400
aatggatggg aaaaagatgc tacagaattt tcagataaaa atgaaataag agttggaaat   23460
aattttgcca tggaaatcaa tctaaatgcc aacctgtgga gaaatttcct gtactccaac   23520
atagcgctgt atttgcccga caagctaaag tacagtcctt ccaacgtaaa atttctgat   23580 aacccaaaca cctacgacta catgaacaag cgagtggtgg ctcccgggtt agtggactgc   23640
```

```
tacattaacc ttggagcacg ctggtccctt gactatatgg acaacgtcaa cccatttaac    23700
caccaccgca atgctggcct gcgctaccgc tcaatgttgc tgggcaatgg tcgctatgtg    23760
cccttccaca tccaggtgcc tcagaagttc tttgccatta aaacctcct tctcctgccg     23820 ggctcataca cctacgagtg gaacttcagg aaggatgtta acatggttct gcagagctcc    23880
ctaggaaatg acctaagggt tgacggagcc agcattaagt ttgatagcat ttgcctttac    23940
gccaccttct tccccatggc ccacaacacc gcctccacgc ttgaggccat gcttagaaac    24000
gacaccaacg accagtcctt taacgactat ctctccgccg ccaacatgct ctaccctata    24060
cccgccaacg ctaccaacgt gcccatatcc atcccctccc gcaactgggc ggctttccgc    24120
ggctgggcct tcacgcgcct taagactaag gaaacccat cactgggctc gggctacgac      24180
ccttattaca cctactctgg ctctataccc tacctagatg gaaccttta cctcaaccac      24240 accttttaaga aggtggccat tacctttgac tcttctgtca gctggcctgg caatgaccgc    24300
ctgcttaccc ccaacgagtt tgaaattaag cgctcagttg acggggaggg ttacaacgtt    24360
gcccagtgta acatgaccaa agactggttc ctggtacaaa tgctagctaa ctacaacatt    24420
ggctaccagg gcttctatat cccagagagc tacaaggacc gcatgtactc cttctttaga    24480
aacttccagc ccatgagccg tcaggtggtg gatgatacta aatacaagga ctaccaacag    24540
gtgggcatcc tacccaaca caacaactct ggatttgttg ctaccttgc ccccaccatg       24600 cgcgaaggac aggcctaccc tgctaacttc ccctatccgc ttataggcaa gaccgcagtt    24660
gacagcatta cccagaaaaa gtttctttgc gatcgcaccc tttggcgcat cccattctcc    24720
agtaacttta tgtccatggg cgcactcaca gacctgggcc aaaaccttct ctacgccaac    24780
tccgcccacg cgctagacat gacttttgag gtggatccca tggacgagcc caccttctt    24840 tatgttttgt ttgaagtctt tgacgtggtc cgtgtgcacc ggccgcaccg cggcgtcatc    24900
gaaaccgtgt acctgcgcac gcccttctcg gccggcaacg ccacaacata agaagcaag     24960 caacatcaac aacagctgcc gccatgggct ccagtgagca ggaactgaaa gccattgtca    25020
aagatcttgg ttgtgggcca tatttttgg gcacctatga caagcgcttt ccaggctttg     25080
tttctccaca caagctcgcc tgcgccatag tcaatacggc cggtcgcgag actggggcg     25140 tacactggat ggccttttgcc tggaacccgc actcaaaaac atgctacctc tttgagccct    25200
ttggcttttc tgaccagcga ctcaagcagg tttaccagtt tgagtacgag tcactcctgc    25260
gccgtagcgc cattgcttct tcccccgacc gctgtataac gctggaaaag tccacccaaa    25320
gcgtacaggg gcccaactcg gccgcctgtg gactattctg ctgcatgttt ctccacgcct    25380
ttgccaactg gcccaaaact cccatggatc acaaccccac catgaacctt attaccgggg    25440
tacccaactc catgctcaac agtccccagg tacagcccac cctgcgtcgc aaccaggaac    25500
agctctacag cttcctggag cgccactcgc cctacttccg cagccacagt gcgcagatta    25560
ggagcgccac ttcttttgt cacttgaaaa acatgtaaaa ataatgtact agagacactt      25620
tcaataaagg caaatgcttt tatttgtaca ctctcgggtg attatttacc cccaccttg     25680 ccgtctgcgc cgtttaaaaa tcaagggggt tctgccgcgc atcgctatgc gccactggca    25740
gggacacgtt gcgatactgg tgtttagtgc tccacttaaa ctcaggcaca accatccgcg    25800
gcagctcggt gaagttttca ctccacaggc tgcgcaccat caccaacgcg tttagcaggt    25860
cgggcgccga tatcttgaag tcgcagttgg ggctccgcc ctgcgcgcgc gagttgcgat     25920
acacagggtt gcagcactgg aacactatca gcgccgggtg gtgcacgctg gccagcacgc    25980
```

```
tcttgtcgga gatcagatcc gcgtccaggt cctccgcgtt gctcagggcg aacggagtca   26040
actttggtag ctgccttccc aaaaagggcg cgtgcccagg ctttgagttg cactcgcacc   26100
gtagtggcat caaaaggtga ccgtgcccgg tctgggcgtt aggatacagc gcctgcataa   26160
aagccttgat ctgcttaaaa gccacctgag ccttttgcgcc ttcagagaag aacatgccgc   26220
aagacttgcc ggaaaactga ttggccggac aggccgcgtc gtgcacgcag caccttgcgt   26280
cggtgttgga gatctgcacc acatttcggc cccaccggtt cttcacgatc ttggccttgc   26340
tagactgctc cttcagcgcg cgctgcccgt tttcgctcgt cacatccatt tcaatcacgt   26400
gctccttatt tatcataatg cttccgtgta gacacttaag ctcgccttcg atctcagcgc   26460
agcggtgcag ccacaacgcg cagcccgtgg gctcgtgatg cttgtaggtc acctctgcaa   26520
acgactgcag gtacgcctgc aggaatcgcc ccatcatcgt cacaaaggtc ttgttgctgg   26580
tgaaggtcag ctgcaacccg cggtgctcct cgttcagcca ggtcttgcat acggccgcca   26640
gagcttccac ttggtcaggc agtagtttga agttcgcctt tagatcgtta tccacgtggt   26700
acttgtccat cagcgcgcgc gcagcctcca tgcccttctc ccacgcagac acgatcggca   26760
cactcagcgg gttcatcacc gtaatttcac tttccgcttc gctgggctct tcctcttcct   26820
cttgcgtccg cataccacgc gccactgggt cgtcttcatt cagccgccgc actgtgcgct   26880
tacctccttt gccatgcttg attagcaccg gtgggttgct gaaacccacc atttgtagcg   26940
ccacatcttc tctttcttcc tcgctgtcca cgattacctc tggtgatggc gggcgctcgg   27000
gcttgggaga agggcgcttc ttttttcttct tgggcgcaat ggccaaatcc gccgccgagg   27060
tcgatggccg cgggctgggt gtgcgcggca ccagcgcgtc ttgtgatgag tcttcctcgt   27120
cctcggactc gatacgccgc ctcatccgct tttttggggg cgcccgggga ggcggcggcg   27180
acggggacgg ggacgacacg tcctccatgg ttggggacg tcgcgccgca ccgcgtccgc   27240
gctcggggt ggtttcgcgc tgctcctctt cccgactggc catttccttc tcctataggc   27300
agaaaaagat catggagtca gtcgagaaga aggacagcct aaccgccccc tctgagttcg   27360
ccaccaccgc ctccaccgat gccgccaacg cgcctaccac cttccccgtc gaggcacccc   27420
cgcttgagga ggaggaagtg attatcgagc aggacccagg ttttgtaagc gaagacgacg   27480
aggaccgctc agtaccaaca gaggataaaa agcaagacca ggacaacgca gaggcaaacg   27540
aggaacaagt cgggcggggg gacgaaaggc atggcgacta cctagatgtg ggagacgacg   27600
tgctgttgaa gcatctgcag cgccagtgcg ccattatctg cgacgcgttg caagagcgca   27660
gcgatgtgcc cctcgccata gcggatgtca gccttgccta cgaacgccac ctattctcac   27720
cgcgcgtacc ccccaaacgc caagaaaacg gcacatgcga gcccaacccg cgcctcaact   27780
tctaccccgt atttgccgtg ccagaggtgc ttgccaccta tcacatcttt ttccaaaact   27840
gcaagatacc cctatcctgc cgtgccaacc gcagccgagc ggacaagcag ctggccttgc   27900
ggcagggcgc tgtcatacct gatatcgcct cgctcaacga agtgccaaaa atctttgagg   27960
gtcttggacg cgacgagaag cgcgcggcaa acgctctgca caggaaaaac agcgaaaatg   28020
aaagtcactc tggagtgttg gtggaactcg agggtgacaa cgcgcgccta gccgtactaa   28080
aacgcagcat cgaggtcacc cactttgcct accggcact taacctaccc cccaaggtca   28140
tgagcacagt catgagtgag ctgatcgtgc gccgtgcgca gccctggag agggatgcaa   28200
atttgcaaga acaaacagag gagggcctac ccgcagttgg cgacgagcag ctagcgcgct   28260
ggcttcaaac gcgcgagcct gccgacttgg aggagcgacg caaactaatg atggccgcag   28320
tgctcgttac cgtggagctt gagtgcatgc agcggttctt tgctgacccg gagatgcagc   28380
```

```
gcaagctaga ggaaacattg cactacacct ttcgacaggg ctacgtacgc caggcctgca   28440
agatctccaa cgtggagctc tgcaacctgg tctcctacct tggaattttg cacgaaaacc   28500
gccttgggca aaacgtgctt cattccacgc tcaagggcga ggcgcgccgc gactacgtcc   28560
gcgactgcgt ttacttattt ctatgctaca cctggcagac ggccatgggc gtttggcagc   28620
agtgcttgga ggagtgcaac ctcaaggagc tgcagaaact gctaaagcaa aacttgaagg   28680
acctatggac ggccttcaac gagcgctccg tggccgcgca cctggcggac atcattttcc   28740
ccgaacgcct gcttaaaacc ctgcaacagg gtctgccaga cttcaccagt caaagcatgt   28800
tgcagaactt taggaacttt atcctagagc gctcaggaat cttgcccgcc acctgctgtg   28860
cacttcctag cgactttgtg cccattaagt accgcgaatg ccctccgccg ctttggggcc   28920
actgctacct tctgcagcta gccaactacc ttgcctacca ctctgacata atggaagacg   28980
tgagcggtga cggtctactg gagtgtcact gtcgctgcaa cctatgcacc ccgcaccgct   29040
ccctggtttg caattcgcag ctgcttaacg aaagtcaaat tatcggtacc tttgagctgc   29100
agggtccctc gcctgacgaa agtccgcgg ctccggggtt gaaactcact ccggggctgt   29160
ggacgtcggc ttaccttcgc aaatttgtac ctgaggacta ccacgcccac gagattaggt   29220
tctacgaaga ccaatcccgc ccgccaaatg cggagcttac cgcctgcgtc attcccagg   29280 gccacattct tggccaattg caagccatca acaaagcccg ccaagagttt ctgctacgaa   29340
agggacgggg ggtttacttg gaccccagt ccggcgagga gctcaaccca atcccccgc   29400 cgccgcagcc ctatcagcag cagccgcggg cccttgcttc ccaggatggc acccaaaaag   29460
aagctgcagc tgccgccgcc acccacggac gaggaggaat actgggacag tcaggcagag   29520
gaggttttgg acgaggagga ggaggacatg atggaagact gggagagcct agacgaggaa   29580
gcttccgagg tcgaagaggt gtcagacgaa acaccgtcac cctcggtcgc attccctcg   29640 ccggcgcccc agaaatcggc aaccggttcc agcatggcta caacctcgc tcctcaggcg   29700 ccgccggcac tgcccgttcg ccgacccaac cgtagatggg acaccactgg aaccagggcc   29760
ggtaagtcca agcagccgcc gccgttagcc caagagcaac aacagcgcca aggctaccgc   29820
tcatggcgcg ggcacaagaa cgccatagtt gcttgcttgc aagactgtgg gggcaacatc   29880
tccttcgccc ccgctttct tctctaccat cacggcgtgg ccttcccccg taacatcctg   29940
cattactacc gtcatctcta cagcccatac tgcaccggcg gcagcggcag cggcagcaac   30000
agcagcggcc acacagaagc aaaggcgacc ggatagcaag actctgacaa agcccaagaa   30060
atccacagcg gcggcagcag caggaggagg agcgctgcgt ctggcgccca acgaacccgt   30120
atcgacccgc gagcttagaa acaggatttt tcccactctg tatgctatat ttcaacagag   30180
caggggccaa gaacaagagc tgaaaataaa aaacaggtct ctgcgatccc tcacccgcag   30240
ctgcctgtat cacaaaagcg aagatcagct tcggcgcacg ctggaagacg cggaggctct   30300
cttcagtaaa tactgcgcgc tgactcttaa ggactagttt cgcgccctt ctcaaattta   30360 agcgcgaaaa ctacgtcatc tccagcggcc acacccggcg ccagcacctg tcgtcagcgc   30420
catttatgag caaggaaatt cccacgcccct acatgtggag ttaccagcca caaatgggac   30480
ttgcggctgg agctgcccaa gactactcaa cccgaataaa ctacatgagc gcggaccccc   30540
acatgatatc ccgggtcaac ggaatacgcg cccaccgaaa ccgaattctc ctggaacagg   30600
cggctattac caccacacct cgtaataacc ttaatcccg tagttggccc gctgccctgg   30660
tgtaccagga aagtcccgct cccaccactg tggtacttcc cagagacgcc caggccgaag   30720
```

```
ttcagatgac taactcaggg gcgcagcttg cgggcggctt tcgtcacagg gtgcggtcgc    30780
ccgggcaggg tataactcac ctgacaatca gagggcgagg tattcagctc aacgacgagt    30840
cggtgagctc ctcgcttggt ctccgtccgg acgggacatt tcagatcggc ggcgccggcc    30900
gctcttcatt cacgcctcgt caggcaatcc taactctgca gacctcgtcc tctgagccgc    30960
gctctggagg cattggaact ctgcaattta ttgaggagtt tgtgccatcg gtctacttta    31020
accccttctc gggacctccc ggccactatc cggatcaatt tattcctaac tttgacgcgg    31080
taaaggactc ggcggacggc tacgactgaa tgttaagtgg agaggcagag caactgcgcc    31140
tgaaacacct ggtccactgt cgccgccaca agtgctttgc ccgcgactcc ggtgagtttt    31200
gctactttga attgcccgag gatcatatcg agggcccggc gcacggcgtc cggcttaccg    31260
cccagggaga gcttgcccgt agcctgattc gggagtttac ccagcgcccc ctgctagttg    31320
agcgggacag gggaccctgt gttctcactg tgatttgcaa ctgtcctaac cctggattac    31380
aatttaaatg cggtctcaaa gatcttattc cctttaacta ataaaaaaaa ataataaagc    31440
atcacttact taaaatcagt tagcaaattt ctgtccagtt tattcagcag cacctccttg    31500
ccctcctccc agctctggta ttgcagcttc ctcctggctg caaactttct ccacaatcta    31560
aatggaatgt cagtttcctc ctgttcctgt ccatccgcac ccactatctt catgttgttg    31620
cagatgaagc gcgcaagacc gtctgaagat accttcaacc ccgtgtatcc atatgacacg    31680
gaaaccggtc ctccaactgt gccttttctt actcctccct ttgtatcccc caatgggttt    31740
caagagagtc cccctggggt actctctttg cgcctatccg aacctctagt tacctccaat    31800
ggcatgcttg cgctcaaaat gggcaacggc ctctctctgg acgaggccgg caaccttacc    31860
tcccaaaatg taaccactgt gagcccacct ctcaaaaaaa ccaagtcaaa cataaacctg    31920
gaaatatctg caccccctcac agttacctca gaagccctaa ctgtggctgc cgccgcacct    31980
ctaatggtcg cgggcaacac actcaccatg caatcacagg ccccgctaac cgtgcacgac    32040
tccaaactta gcattgccac ccaaggaccc ctcacagtgt cagaaggaaa gctagccctg    32100
caaacatcag gcccccctcac caccaccgat agcagtaccc ttactatcac tgcctcaccc    32160
cctctaacta ctgccactgg tagcttgggc attgacttga aagagcccat ttatacacaa    32220
aatggaaaac taggactaaa gtacggggct cctttgcatg taacagacga cctaaacact    32280
ttgaccgtag caactggtcc aggtgtgact attaataata cttccttgca aactaaagtt    32340
actggagcct tgggttttga ttcacaaggc aatatgcaac ttaatgtagc aggaggacta    32400
aggattgatt ctcaaaacag acgccttata cttgatgtta gttatccgtt tgatgctcaa    32460
aaccaactaa atctaagact aggacagggc cctcttttta taaactcagc ccacaacttg    32520
gatattaact acaacaaagg cctttacttg tttacagctt caaacaattc caaaagctt    32580 gaggttaacc taagcactgc caaggggttg atgtttgacg ctacagccat agccattaat    32640
gcaggagatg ggcttgaatt tggttcacct aatgcaccaa acacaaatcc cctcaaaaca    32700
aaaattggcc atgcctaga atttgattca acaaggcta tggttcctaa actaggaact    32760
ggccttagtt ttgacagcac aggtgccatt acagtaggaa acaaaaataa tgataagcta    32820
actttgtgga ccacaccagc tccatctcct aactgtagac taaatgcaga gaaagatgct    32880
aaactcactt tggtcttaac aaaatgtggc agtcaaatac ttgctacagt ttcagttttg    32940
gctgttaaag gcagttttggc tccaatatct ggaacagttc aaagtgctca tcttattata    33000 agattgacg aaaatggagt gctactaaac aattccttcc tggacccaga atattggaac    33060
tttagaaatg gagatcttac tgaaggcaca gcctatacaa acgctgttgg atttatgcct    33120
```

```
aacctatcag cttatccaaa atctcacggt aaaactgcca aaagtaacat tgtcagtcaa    33180
gtttacttaa acggagacaa aactaaacct gtaacactaa ccattacact aaacggtaca    33240
caggaaacag gagacacaac tccaagtgca tactctatgt cattttcatg ggactggtct    33300
ggccacaact acattaatga aatatttgcc acatcctctt acactttttc atacattgcc    33360
caagaataaa gaatcgtttg tgttatgttt caacgtgttt attttcaat tgcagaaaat     33420 ttcaagtcat ttttcattca gtagtatagc cccaccacca catagcttat acagatcacc    33480
gtaccttaat caaactcaca gaaccctagt attcaacctg ccacctccct cccaacacac    33540
agagtacaca gtcctttctc cccggctggc cttaaaaagc atcatatcat gggtaacaga    33600
catattctta ggtgttatat tccacacggt ttcctgtcga gccaaacgct catcagtgat    33660
attaataaac tccccgggca gctcacttaa gttcatgtcg ctgtccagct gctgagccac    33720
aggctgctgt ccaacttgcg gttgcttaac gggcggcgaa ggagaagtcc acgcctacat    33780
gggggtagag tcataatcgt gcatcaggat agggcggtgg tgctgcagca gcgcgcgaat    33840
aaactgctgc cgccgccgct ccgtcctgca ggaatacaac atggcagtgg tctcctcagc    33900
gatgattcgc accgcccgca gcataaggcg ccttgtcctc cgggcacagc agcgcaccct    33960
gatctcactt aaatcagcac agtaactgca gcacagcacc acaatattgt tcaaaatccc    34020
acagtgcaag gcgctgtatc caaagctcat ggcgggacc acagaaccca cgtgccatc     34080 ataccacaag cgcaggtaga ttaagtggcg acccctcata aacacgctgg acataaacat    34140
tacctctttt ggcatgttgt aattcaccac ctcccggtac catataaacc tctgattaaa    34200
catggcgcca tccaccacca tcctaaacca gctggccaaa acctgcccgc cggctataca    34260
ctgcagggaa ccgggactgg aacaatgaca gtggagagcc caggactcgt aaccatggat    34320
catcatgctc gtcatgatat caatgttggc acaacacagg cacacgtgca tacacttcct    34380
caggattaca agctcctccc gcgttagaac catatcccag ggaacaaccc attcctgaat    34440
cagcgtaaat cccacactgc agggaagacc tcgcacgtaa ctcacgttgt gcattgtcaa    34500
agtgttacat tcgggcagca gcggatgatc ctccagtatg gtagcgcggg tttctgtctc    34560
aaaaggaggt agacgatccc tactgtacgg agtgcgccga gacaaccgag atcgtgttgg    34620
tcgtagtgtc atgccaaatg gaacgccgga cgtagtcata tttcctgaag caaaaccagg    34680
tgcgggcgtg acaaacagat ctgcgtctcc ggtctcgccg cttagatcgc tctgtgtagt    34740
agttgtagta tatccactct ctcaaagcat ccaggcgccc cctggcttcg ggttctatgt    34800
aaactccttc atgcgccgct gccctgataa catccaccac cgcagaataa gccacaccca    34860
gccaacctac acattcgttc tgcgagtcac acacgggagg agcgggaaga gctggaagaa    34920
ccatgttttt tttttattc caaaagatta tccaaaacct caaatgaag atctattaag      34980 tgaacgcgct cccctccggt ggcgtggtca aactctacag ccaaagaaca gataatggca    35040
tttgtaagat gttgcacaat ggcttccaaa aggcaaacgg ccctcacgtc caagtggacg    35100
taaaggctaa acccttcagg gtgaatctcc tctataaaca ttccagcacc ttcaaccatg    35160
cccaaataat tctcatctcg ccaccttctc aatatatctc taagcaaatc ccgaatatta    35220
agtccggcca ttgtaaaaat ctgctccaga gcgcctcca ccttcagcct caagcagcga    35280
atcatgattg caaaaattca ggttcctcac agacctgtat aagattcaaa agcggaacat    35340
taacaaaaat accgcgatcc cgtaggtccc ttcgcagggc cagctgaaca taatcgtgca    35400
ggtctgcacg gaccagcgcg gccacttccc cgccaggaac catgacaaaa gaacccacac    35460
```

```
tgattatgac acgcatactc ggagctatgc taaccagcgt agccccgatg taagcttgtt    35520
gcatgggcgg cgatataaaa tgcaaggtgc tgctcaaaaa atcaggcaaa gcctcgcgca    35580
aaaaagaaag cacatcgtag tcatgctcat gcagataaag gcaggtaagc tccggaacca    35640
ccacagaaaa agacaccatt tttctctcaa acatgtctgc gggtttctgc ataaacacaa    35700
aataaaataa caaaaaaaca tttaaacatt agaagcctgt cttacaacag gaaaaacaac    35760
ccttataagc ataagacgga ctacggccat gccggcgtga ccgtaaaaaa actggtcacc    35820
gtgattaaaa agcaccaccg acagctcctc ggtcatgtcc ggagtcataa tgtaagactc    35880
ggtaaacaca tcaggttgat tcacatcggt cagtgctaaa aagcgaccga atagcccgg    35940 gggaatacat acccgcaggc gtagagacaa cattacagcc cccataggag gtataacaaa    36000
attaatagga gagaaaaaca cataaacacc tgaaaaaccc tcctgcctag gcaaaatagc    36060
accctcccgc tccagaacaa catacagcgc ttccacagcg gcagccataa cagtcagcct    36120
taccagtaaa aaagaaaacc tattaaaaaa acaccactcg acacggcacc agctcaatca    36180
gtcacagtgt aaaaaagggc caagtgcaga gcgagtatat ataggactaa aaaatgacgt    36240
aacggttaaa gtccacaaaa aacacccaga aaaccgcacg cgaacctacg cccagaaacg    36300
aaagccaaaa aacccacaac ttcctcaaat cgtcacttcc gttttcccac gttacgtcac    36360
ttcccatttt aagaaaacta caattcccaa cacatacaag ttactccgcc ctaaaaccta    36420
cgtcacccgc cccgttccca cgcccgcgc cacgtcacaa actccacccc ctcattatca    36480
tattggcttc aatccaaaat aaggtatatt attgatgatg tagggataac agggtaataa    36540
atccggggat cctctagagt cgacctgcag gcatgcaagc ttggcgtaat catggtcata    36600
gctgtttcct gtgtgaaatt gttatccgct cacaattcca cacaacatac gagccggaag    36660
cataaagtgt aaagcctggg gtgcctaatg agtgagcta                           36699
```

<210> SEQ ID NO 5
<211> LENGTH: 34267
<212> TYPE: DNA
<213> ORGANISM: Artificial Sequence
<220> FEATURE:
<223> OTHER INFORMATION: Synthetic adenovirus vector

<400> SEQUENCE: 5

```
gttccactga gcgtcagacc ccttaataag atgatcttct tgagatcgtt ttggtctgcg      60
cgtaatctct tgctctgaaa acgaaaaaac cgccttgcag ggcggttttt cgaaggttct     120
ctgagctacc aactctttga accgaggtaa ctggcttgga ggagcgcagt caccaaaact     180
tgtcctttca gtttagcctt aaccggcgca tgacttcaag actaactcct ctaaatcaat     240
taccagtggc tgctgccagt ggtgcttttg catgtctttc cgggttggac tcaagacgat     300
agttaccgga taaggcgcag cggtcggact gaacggggg ttcgtgcata cagtccagct     360
tggagcgaac tgcctacccg gaactgagtg tcaggcgtgg aatgagacaa acgcggccat     420
aacagcggaa tgacaccggt aaaccgaaag gcaggaacag gagagcgcac gagggagccg     480 ccagggggaaa cgcctggtat ctttatagtc ctgtcgggtt tcgccaccac tgatttgagc     540
gtcagatttc gtgatgcttg tcagggggc ggagcctatg gaaaaacggc tttgccgcgg     600
ccctctcact tccctgttaa gtatcttcct ggcatcttcc aggaaatctc cgccccgttc     660
gtaagccatt tccgctcgcc gcagtcgaac gaccgagcgt agcgagtcag tgagcgagga     720
agcggaatat atcctgtatc acatattctg ctgacgcacc ggtgcagcct ttttctcct     780 gccacatgaa gcacttcact gacacccctca tcagtgccaa catagtaagc cagtatacac     840
```

```
tccgctagcg ctgaggtctg cctcgtgaag aaggtgttgc tgactcatac caggcctgaa      900
tcgccccatc atccagccag aaagtgaggg agccacggtt gatgagagct ttgttgtagg      960
tggaccagtt ggtgattttg aacttttgct ttgccacgga acggtctgcg ttgtcgggaa     1020
gatgcgtgat ctgatccttc aactcagcaa aagttcgatt tattcaacaa agccacgttg     1080
tgtctcaaaa tctctgatgt tacattgcac aagataaaaa tatatcatca tgaacaataa     1140
aactgtctgc ttacataaac agtaatacaa ggggtgttga tactctcagt acaatctgct     1200
ctgatgccgc atagttaagc cagtatctgc tccctgcttg tgtgttggag gtcgctgagt     1260
agtgcgcgag caaaatttaa gctacaacaa ggcaaggctt gaccgacaat tgcatgaaga     1320
atctgcttag ggttaggcgt tttgcgctgc ttcgcgatgt acgggccaga tatacgcgta     1380
tctgagggga ctagggtgtg tttaggcgaa aagcggggct tcggttgtac gcggttagga     1440
gtcccctcag gatatagtag tttcgctttt gcatagggag ggggaaatgt agtcttatgc     1500
aatactcttg tagtcttgca acatggtaac gatgagttag caacatgcct tacaaggaga     1560
gaaaaagcac cgtgcatgcc gattggtgga agtaaggtgg tacgatcgtg ccttattagg     1620
aaggcaacag acgggtctga catggattgg acgaaccact gaattccgca ttgcagagat     1680
attgtattta agtgcctagc tcgatacaat aaacgccatt tgaccattca ccacattggt     1740
gtgcacctcc aagctgggta cggatccggc cttgccggcc tcgagcggcc gctagcgccg     1800
ccactatggg atcaagatcg ccaaaaaaga agagaaaggt gccgaagaag catgcagcac     1860
caccaaaaaa aaaacgaaaa gtagaagacc cacgatttat gtacccatac gatgttcctg     1920
actatgcggg tatgaaaaac atcaaaaaaa accaggtaat gaacctgggt ccgaactcta     1980
aactgctgaa agaatacaaa tcccagctga tcgaactgaa catcgaacag ttcgaagcag     2040
gtatcggtct gatcctgggt gatgcttaca tccgttctcg tgatgaaggt aaaacctact     2100
gtatgcagtt cgagtggaaa aacaaagcat acatggacca cgtatgtctg ctgtacgatc     2160
agtgggtact gtccccgccg cacaaaaaag aacgtgttaa ccacctgggt aacctggtaa     2220
tcacctgggg cgcccagact ttcaaacacc aagctttcaa caaactggct aacctgttca     2280
tcgttaacaa caaaaaaacc atcccgaaca acctggttga aaactacctg accccgatgt     2340
ctctggcata ctggttcatg gatgatggtg gtaaatggga ttacaacaaa aactctacca     2400
acaaatcgat cgtactgaac acccagtctt tcactttcga agaagtagaa tacctggtta     2460
agggtctgcg taacaaattc caactgaact gttacgtaaa aatcaacaaa aacaaaccga     2520
tcatctacat cgattctatg tcttacctga tcttctacaa cctgatcaaa ccgtacctga     2580
tcccgcagat gatgtacaaa ctgccgaaca ctatctcctc cgaaactttc ctgaaataag     2640
gtaccgatcc agacatgata agatacattg atgagtttgg acaaaccaca actagaatgc     2700
agtgaaaaaa atgctttatt tgtgaaattt gtgatgctat tgctttattt gtaaccatta     2760
taagctgcaa taaacaagtt aacaacaaca attgcattca ttttatgttt caggttcagg     2820
gggaggtgtg ggaggttttt taaagcaagt aaaacctcta caaatgtggt atggctgatt     2880
atgatcatcg taaacttggt ctgacagtta ccaatgctta atcagtgagg cacctatctc     2940
agcgatctgt ctatttcgtt catccatagt tgcctgactc cccgtcgtgt agataactac     3000
gatacgggag ggcttaccat ctggccccag tgctgcaatg ataccgcgag acccacgctc     3060
accggctcca gatttatcag caataaacca gccagccgga agggccgagc gcagaagtgg     3120
tcctgcaact ttatccgcct ccatccagtc tattaattgt tgccgggaag ctagagtaag     3180
```

```
tagttcgcca gttaatagtt tgcgcaacgt tgttgccatt gctacaggca tcgtggtgtc    3240
acgctcgtcg tttggtatgg cttcattcag ctccggttcc caacgatcaa ggcgagttac    3300
atgatccccc atgttgtgca aaaaagcggt tagctccttc ggtcctccga tcgttgtcag    3360
aagtaagttg gccgcagtgt tatcactcat ggttatggca gcactgcata attctcttac    3420
tgtcatgcca tccgtaagat gcttttctgt gactggtgag tactcaacca agtcattctg    3480
agaatagtgt atgcggcgac cgagttgctc ttgcccggcg tcaatacggg ataataccgc    3540
gccacatagc agaactttaa aagtgctcat cattggaaaa cgttcttcgg ggcgaaaact    3600
ctcaaggatc ttaccgctgt tgagatccag ttcgatgtaa cccactcgtg cacccaactg    3660
atcttcagca tcttttactt tcaccagcgt ttctgggtga gcaaaaacag gaaggcaaaa    3720
tgccgcaaaa aagggaataa gggcgacacg gaaatgttga atactcatac tcttcctttt    3780
tcaatattat tgaagcattt atcagggtta ttgtctcatg agcggataca tatttgaatg    3840
tatttagaaa aataaacaaa tagggggttcc gcgcacattt ccccgaaaag tgccacctga    3900
cgtctaagaa accattatta tcatgacatt aacctataaa aataggcgta tcacgaggcc    3960
ctttcgtctc gcgcgtttcg gtgatgacgg tgaaaacctc tgacacatgc agctcccgga    4020
gacggtcaca gcttgtctgt aagcggatgc cgggagcaga caagcccgtc agggcgcgtc    4080
agcgggtgtt ggcgggtgtc ggggctggct taactatgcg gcatcagagc agattgtact    4140
gagagtgcac catatgcggt gtgaaatacc gcacagatgc gtaaggagaa ataccgcat    4200
caggcgccat cgccattca ggctgcgcaa ctgttgggaa gggcgatcgg tgcgggcctc    4260
ttcgctatta cgccagctgg cgaaaggggg atgtgctgca aggcgattaa gttgggtaac    4320
gccagggttt tcccagtcac gacgttgtaa aacgacggcc agtgaattaa ttaaggtggg    4380
ggtcttatgt agttttgtat ctgttttgca gcagccgccg ccgccatgag caccaactcg    4440
tttgatggaa gcattgtgag ctcatatttg acaacgcgca tgcccccatg ggccggggtg    4500
cgtcagaatg tgatgggctc cagcattgat ggtcgccccg tcctgcccgc aaactctact    4560
accttgacct acgagaccgt gtctggaacg ccgttggaga ctgcagcctc cgccgccgct    4620
tcagccgctg cagccaccgc ccgcgggatt gtgactgact tgctttcct gagcccgctt     4680
gcaagcagtg cagcttcccg ttcatccgcc cgcgatgaca agttgacggc tcttttggca    4740
caattggatt ctttgacccg ggaacttaat gtcgtttctc agcagctgtt ggatctgcgc    4800
cagcaggttt ctgccctgaa ggcttcctcc cctcccaatg cggtttaaaa cataaataaa    4860
aaaccagact ctgtttggat ttggatcaag cataagtgtc ttgctgtctt tatttagggg    4920
ttttgcgcgc gcggtaggcc cgggaccagc ggtctcggtc gttgagggtc ctgtgtattt    4980
tttccaggac gtggtaaagg tgactctgga tgttcagata catgggcata agcccgtctc    5040
tggggtggag gtagcaccac tgcagagctt catgctgcgg ggtggtgttg tagatgatcc    5100
agtcgtagca ggagcgctgg gcgtggtgcc taaaaatgtc tttcagtagc aagctgattg    5160
ccaggggcag gcccttggtg taagtgttta caaagcggtt aagctgggat gggtgcatac    5220
gtggggatat gagatgcatc ttggactgta ttttaggtt ggctatgttc ccagccatat    5280
ccctccgggg attcatgttg tgcagaacca ccagcacagt gtatccgtg cacttgggaa    5340
atttgtcatg tagcttagaa ggaaatgcgt ggaagaactt ggagacgccc ttgtgacctc    5400
caagattttc catgcattcg tccataatga tggcaatggg cccacgggcg gcggcctggg    5460
cgaagatatt tctgggatca ctaacgtcat agttgtgttc caggatgaga tcgtcatagg    5520
ccattttta aaagcgcggg cggagggtgc cagactgcgg tataatggtt ccatccggcc    5580
```

```
cagggggcgta gttaccctca cagatttgca tttcccacgc tttgagttca gatgggggga    5640
tcatgtctac ctgcggggcg atgaagaaaa cggtttccgg ggtaggggag atcagctggg    5700
aagaaagcag gttcctgagc agctgcgact taccgcagcc ggtgggcccg taaatcacac    5760
ctattaccgg gtgcaactgg tagttaagag agctgcagct gccgtcatcc ctgagcaggg    5820
gggccacttc gttaagcatg tccctgactc gcatgttttc cctgaccaaa tccgccagaa    5880
ggcgctcgcc gcccagcgat agcagttctt gcaaggaagc aaagttttc aacgtttga     5940
gaccgtccgc cgtaggcatg cttttgagcg tttgaccaag cagttccagg cggtcccaca    6000
gctcggtcac ctgctctacg gcatctcgat ccagcatatc tcctcgtttc gcgggttggg    6060
gcggctttcg ctgtacggca gtagtcggtg ctcgtccaga cgggccaggg tcatgtcttt    6120
ccacgggcgc agggtcctcg tcagcgtagt ctgggtcacg gtgaagggt gcgctccggg     6180
ctgcgcgctg gccagggtgc gcttgaggct ggtcctgctg gtgctgaagc gctgccggtc    6240
ttcgccctgc gcgtcggcca ggtagcattt gaccatggtg tcatagtcca gcccctccgc    6300
ggcgtggccc ttggcgcgca gcttgcccct tggaggaggcg ccgcacgagg ggcagtgcag   6360
acttttgagg gcgtagagct tgggcgcgag aaataccgat tccggggagt aggcatccgc    6420
gccgcaggcc ccgcagacgg tctcgcattc cacgagccag gtgagctctg gccgttcggg    6480
gtcaaaaacc aggtttcccc catgcttttt gatgcgtttc ttacctctgg tttccatgag    6540
ccggtgtcca cgctcggtga cgaaaaggct gtccgtgtcc ccgtatacag acttgagagg    6600
cctgtcctcg agcggtgttc cgcggtcctc ctcgtataga aactcggacc actctgagac    6660
aaaggctcgc gtccaggcca gcacgaagga ggctaagtgg gaggggtagc ggtcgttgtc    6720
cactaggggg tccactcgct ccagggtgtg aagacacatg tcgccctctt cggcatcaag    6780
gaaggtgatt ggtttgtagg tgtaggccac gtgaccgggt gttcctgaag gggggctata    6840
aaaggggtg ggggcgcgtt cgtcctcact ctcttccgca tcgctgtctg cgagggccag     6900
ctgttggggt gagtactccc tctgaaaagc gggcatgact tctgcgctaa gattgtcagt    6960
ttccaaaaac gaggaggatt tgatattcac ctggcccgcg gtgatgcctt tgagggtggc    7020
cgcatccatc tggtcagaaa agacaatctt tttgttgtca agcttggtgg caaacgaccc    7080
gtagagggcg ttggacagca acttggcgat ggagcgcagg gttttggtttt tgtcgcgatc    7140
ggcgcgctcc ttggccgcga tgtttagctg cacgtattcg cgcgcaacgc accgccattc    7200
gggaaagacg gtggtgcgct cgtcgggcac caggtgcacg cgccaaccgc ggttgtgcag    7260
ggtgacaagg tcaacgctgg tggctacctc tccgcgtagg cgctcgttgg tccagcagag    7320
gcggccgccc ttgcgcgagc agaatggcgg tagggggtct agctgcgtct cgtccggggg    7380
gtctgcgtca acgtaaaga ccccgggcag caggcgcgcg tcgaagtagt ctatcttgca    7440
tccttgcaag tctagcgcct gctgccatgc gcgggcggca agcgcgcgct cgtatgggtt    7500
gagtggggga cccatggca tgggtgggt gagcgcggag gcgtacatgc cgcaaatgtc      7560
gtaaacgtag aggggctctc tgagtattcc aagatatgta gggtagcatc ttccaccgcg    7620
gatgctggcg cgcacgtaat cgtatagttc gtgcgaggga gcgaggaggt cgggaccgag    7680
gttgctacgg gcgggctgct ctgctcggaa gactatctgc ctgaagatgg catgtgagtt    7740
ggatgatatg gttggacgct ggaagacgtt gaagctggcg tctgtgagac ctaccgcgtc    7800
acgcacgaag gaggcgtagg agtcgcgcag cttgttgacc agctcggcgg tgacctgcac    7860
gtctagggcg cagtagtcca gggtttcctt gatgatgtca tacttatcct gtcccttttt    7920
```

```
tttccacagc tcgcggttga ggacaaactc ttcgcggtct ttccagtact cttggatcgg    7980
aaacccgtcg gcctccgaac ggtaagagcc tagcatgtag aactggttga cggcctggta    8040
ggcgcagcat ccctttttcta cgggtagcgc gtatgcctgc gcggccttcc ggagcgaggt    8100
gtgggtgagc gcaaaggtgt ccctgaccat gactttgagg tactggtatt tgaagtcagt    8160
gtcgtcgcat ccgccctgct cccagagcaa aaagtccgtg cgcttttttgg aacgcggatt   8220
tggcagggcg aaggtgacat cgttgaagag tatctttccc gcgcgaggca taaagttgcg    8280
tgtgatgcgg aagggtcccg gcacctcgga acggttgtta attacctggg cggcgagcac    8340
gatctcgtca aagccgttga tgttgtggcc cacaatgtaa agttccaaga agcgcgggat    8400
gcccttgatg aaggcaatt ttttaagttc ctcgtaggtg agctcttcag gggagctgag    8460
cccgtgctct gaaagggccc agtctgcaag atgaggttg gaagcgacga atgagctcca    8520
caggtcacgg gccattagca tttgcaggtg gtcgcgaaag gtcctaaact ggcgacctat    8580
ggccatttt tctggggtga tgcagtagaa ggtaagcggg tcttgttccc agcggtccca    8640
tccaaggttc gcggctaggt ctcgcgcggc agtcactaga ggctcatctc cgccgaactt    8700
catgaccagc atgaagggca cgagctgctt cccaaaggcc cccatccaag tataggtctc    8760
tacatcgtag gtgacaaaga gacgctcggt gcgaggatgc gagccgatcg ggaagaactg    8820
gatctcccgc caccaattgg aggagtggct attgatgtgg tgaaagtaga agtccctgcg    8880
acgggccgaa cactcgtgct ggcttttgta aaaacgtgcg cagtactggc agcggtgcac    8940
gggctgtaca tcctgcacga ggttgacctg acgaccgcgc acaaggaagc agagtgggaa    9000
tttgagcccc tcgcctggcg ggtttggctg gtggtcttct acttcggctg cttgtccttg    9060
accgtctggc tgctcgaggg gagttacggt ggatcggacc accacgccgc gcgagcccaa    9120
agtccagatg tccgcgcgcg gcggtcggag cttgatgaca acatcgcgca gatgggagct    9180
gtccatggtc tggagctccc gcggcgtcag gtcaggcggg agctcctgca ggtttacctc    9240
gcatagacgg gtcagggcgc gggctagatc caggtgatac ctaatttcca ggggctggtt    9300
ggtggcggcg tcgatggctt gcaagaggcc gcatcccgc ggcgcgacta cggtaccgcg    9360
cggcgggcgg tgggccgcgg gggtgtcctt ggatgatgca tctaaaagcg gtgacgcggg    9420
cgagcccccg gaggtagggg gggctccgga cccgccggga gaggggggcag gggcacgtcg    9480
gcgccgcgcg cgggcaggag ctggtgctgc gcgcgtaggt tgctggcgaa cgcgacgacg    9540
cggcggttga tctcctgaat ctggcgcctc tgcgtgaaga cgacgggccc ggtgagcttg    9600
agcctgaaag agagttcgac agaatcaatt tcggtgtcgt tgacggcggc ctggcgcaaa    9660
atctcctgca cgtctcctga gttgtcttga taggcgatct cggccatgaa ctgctcgatc    9720
tcttcctcct ggagatctcc gcgtccggct cgctccacgg tggcggcgag tcgttggaa    9780
atgcgggcca tgagctgcga gaaggcgttg aggcctccct cgttccagac gcggctgtag    9840
accacgcccc cttcggcatc gcgggcgcgc atgaccacct cgcgcgagatt gagctccacg    9900
tgccgggcga agacggcgta gtttcgcagg cgctgaaaga ggtagttgag ggtggtggcg    9960
gtgtgttctg ccacgaagaa gtacataacc cagcgtcgca acgtggattc gttgatatcc   10020
cccaaggcct caaggcgctc catggcctcg tagaagtcca cggcgaagtt gaaaaactgg   10080
gagttgcgcg ccgacacggt taactcctcc tccagaagac ggatgagctc ggcgacagtg   10140
tcgcgcacct cgcgctcaaa ggctacaggg gcctcttctt cttcttcaat ctcctcttcc   10200
ataagggcct cccccttcttc ttcttctggc ggcggtgggg gaggggggac acggcggcga   10260
cgacggcgca ccgggaggcg gtcgacaaag cgctcgatca tctccccgcg gcgacggcgc   10320
```

```
atggtctcgg tgacggcgcg gccgttctcg cggggggcgca gttggaagac gccgcccgtc    10380
atgtcccggt tatgggttgg cgggggggctg ccatgcggca gggatacggc gctaacgatg    10440
catctcaaca attgttgtgt aggtactccg ccgccgaggg acctgagcga gtccgcatcg    10500
accggatcgg aaaacctctc gagaaaggcg tctaaccagt cacagtcgca aggtaggctg    10560
agcaccgtgg cgggcggcag cgggcggcgg tcggggttgt ttctggcgga ggtgctgctg    10620
atgatgtaat taaagtaggc ggtcttgaga cggcggatgg tcgacagaag caccatgtcc    10680
ttgggtccgg cctgctgaat gcgcaggcgg tcggccatgc cccaggcttc gttttgacat    10740
cggcgcaggt ctttgtagta gtcttgcatg agcctttcta ccggcacttc ttcttctcct    10800
tcctcttgtc ctgcatctct tgcatctatc gctgcggcgg cggcggagtt tggccgtagg    10860
tggcgccctc ttcctcccat gcgtgtgacc ccgaagcccc tcatcggctg aagcagggct    10920
aggtcggcga caacgcgctc ggctaatatg gcctgctgca cctgcgtgag ggtagactgg    10980
aagtcatcca tgtccacaaa gcggtggtat gcgcccgtgt tgatggtgta agtgcagttg    11040
gccataacgg accagttaac ggtctggtga cccggctgcg agagctcggt gtacctgaga    11100
cgcgagtaag ccctcgagtc aaatacgtag tcgttgcaag tccgcaccag gtactggtat    11160
cccaccaaaa agtgcggcgg cggctggcgg tagaggggcc agcgtagggt ggccggggct    11220
ccgggggcga gatcttccaa cataaggcga tgatatccgt agatgtacct ggacatccag    11280
gtgatgccgg cggcggtggt ggaggcgcgc ggaaagtcgc ggacgcggtt ccagatgttg    11340
cgcagcggca aaagtgctc catggtcggg acgtctggc cggtcaggcg cgcgcaatcg    11400
ttgacgctct agaccgtgca aaaggagagc ctgtaagcgg gcactcttcc gtggtctggt    11460
ggataaattc gcaagggtat catggcggac gaccggggtt cgagcccgt atccggccgt    11520 ccgccgtgat ccatgcggtt accgcccgcg tgtcgaaccc aggtgtgcga cgtcagacaa    11580
cgggggagtg ctccttttgg cttccttcca ggcgcggcgg ctgctgcgct agcttttttg    11640
gccactggcc gcgcgcagcg taagcggtta ggctggaaag cgaaagcatt aagtggctcg    11700
ctccctgtag ccggagggtt attttccaag ggttgagtcg cgggaccccc ggttcgagtc    11760
tcggaccggc cggactgcgg cgaacggggg tttgcctccc cgtcatgcaa gaccccgctt    11820
gcaaattcct ccggaaacag ggacgagccc ctttttttgct tttcccagat gcatccggtg    11880
ctgcggcaga tgcgccccc tcctcagcag cggcaagagc aagagcagcg gcagacatgc    11940
agggcaccct ccccctcctcc taccgcgtca ggaggggcga catccgcggt tgacgcggca    12000
gcagatggtg attacgaacc cccgcggcgc cgggcccggc actacctgga cttggaggag    12060
ggcgagggcc tggcgcggct aggagcgccc tctcctgagc ggtacccaag ggtgcagctg    12120
aagcgtgata cgcgtgaggc gtacgtgccg cggcagaacc tgtttcgcga ccgcgaggga    12180
gaggagcccg aggagatgcg ggatcgaaag ttccacgcag ggcgcgagct gcggcatggc    12240
ctgaatcgcg agcggttgct gcgcgaggag gactttgagc ccgacgcgcg aaccgggatt    12300
agtcccgcgc gcgcacacgt ggcggccgcc gacctggtaa ccgcatacga gcagacggtg    12360
aaccaggaga ttaactttca aaaaagcttt aacaaccacg tgcgtacgct tgtggcgcgc    12420
gaggaggtgg ctataggact gatgcatctg tgggactttg taagcgcgct ggagcaaaac    12480
ccaaatagca agccgctcat ggcgcagctg ttccttatag tgcagcacag cagggacaac    12540
gaggcattca gggatgcgct gctaaacata gtagagcccg agggccgctg gctgctcgat    12600
ttgataaaca tcctgcagag catagtggtg caggagcgca gcttgagcct ggctgacaag    12660
```

-continued

```
gtggccgcca tcaactattc catgcttagc ctgggcaagt tttacgcccg caagatatac    12720
catacccctt acgttcccat agacaaggag gtaaagatcg aggggttcta catgcgcatg    12780
gcgctgaagg tgcttacctt gagcgacgac ctgggcgttt atcgcaacga gcgcatccac    12840
aaggccgtga gcgtgagccg gcggcgcgag ctcagcgacc gcgagctgat gcacagcctg    12900
caaagggccc tggctggcac gggcagcggc gatagagagg ccgagtccta ctttgacgcg    12960
ggcgctgacc tgcgctgggc cccaagccga cgcgccctgg aggcagctgg ggccggacct    13020
gggctggcgg tggcacccgc gcgcgctggc aacgtcggcg gcgtggagga atatgacgag    13080
gacgatgagt acgagccaga ggacggcgag tactaagcgg tgatgtttct gatcagatga    13140
tgcaagacgc aacggacccg gcggtgcggg cggcgctgca gagccagccg tccggcctta    13200
actccacgga cgactggcgc caggtcatgg accgcatcat gtcgctgact gcgcgcaatc    13260
ctgacgcgtt ccggcagcag ccgcaggcca accggctctc cgcaattctg gaagcggtgg    13320
tcccggcgcg cgcaaacccc acgcacgaga aggtgctggc gatcgtaaac gcgctggccg    13380
aaaacagggc catccggccc gacgaggccg gcctggtcta cgacgcgctg cttcagcgcg    13440
tggctcgtta caacagcggc aacgtgcaga ccaacctgga ccggctggtg ggggatgtgc    13500
gcgaggccgt ggcgcagcgt gagcgcgcgc agcagcaggg caacctgggc tccatggttg    13560
cactaaacgc cttcctgagt acacagcccg ccaacgtgcc gcggggacag gaggactaca    13620
ccaactttgt gagcgcactg cggctaatgg tgactgagac accgcaaagt gaggtgtacc    13680
agtctgggcc agactatttt ttccagacca gtagacaagg cctgcagacc gtaaacctga    13740
gccaggcttt caaaaacttg cagggctgt ggggggtgcg ggctcccaca ggcgaccgcg    13800
cgaccgtgtc tagcttgctg acgcccaact cgcgcctgtt gctgctgcta atagcgccct    13860
tcacggacag tggcagcgtg tcccgggaca catacctagg tcacttgctg acactgtacc    13920
gcgaggccat aggtcaggcg catgtggacg agcatacttt ccaggagatt acaagtgtca    13980
gccgcgcgct ggggcaggag gacacgggca gcctggaggc aaccctaaac tacctgctga    14040
ccaaccggcg gcagaagatc ccctcgttgc acagtttaaa cagcgaggag gagcgcattt    14100
tgcgctacgt gcagcagagc gtgagcctta acctgatgcg cgacgggta acgcccagcg    14160
tggcgctgga catgaccgcg cgcaacatgg aaccgggcat gtatgcctca aaccggccgt    14220
ttatcaaccg cctaatggac tacttgcatc gcgcggccgc cgtgaacccc gagtatttca    14280
ccaatgccat cttgaacccg cactggctac cgccccctgg tttctacacc gggggattcg    14340
aggtgcccga gggtaacgat ggattcctct gggacgacat agacgacagc gtgtttttccc    14400
cgcaaccgca gaccctgcta gagttgcaac agcgcgagca ggcagaggcg gcgctgcgaa    14460
aggaaagctt ccgcaggcca agcagcttgt ccgatctagg gctgcggcc ccgcggtcag    14520
atgctagtag cccatttcca agcttgatag ggtctcttac cagcactcgc accacccgcc    14580
cgcgcctgct gggcgaggag gagtacctaa caactcgct gctgcagccg cagcgcgaaa    14640
aaaacctgcc tccggcattt cccaacaacg ggatagagag cctagtggac aagatgagta    14700
gatggaagac gtacgcgcag gagcacaggg acgtgccagg cccgcgcccg cccacccgtc    14760
gtcaaaggca cgaccgtcag cggggtctgg tgtgggagga cgatgactcg gcagacgaca    14820
gcagcgtcct ggattggga gggagtggca acccgtttgc gcaccttcgc cccaggctgg    14880
ggagaatgtt taaaaaaaa aaagcatga tgcaaaataa aaaactcacc aaggccatgg    14940
caccgagcgt tggttttctt gtattcccct tagtatgcgg cgcgcggcga tgtatgagga    15000
aggtcctcct ccctcctacg agagtgtggt gagcgcggcg ccagtggcgg cggcgctggg    15060
```

```
ttctcccttc gatgctcccc tggacccgcc gtttgtgcct ccgcggtacc tgcggcctac    15120 cgggggggaga aacagcatcc gttactctga gttggcaccc ctattcgaca ccacccgtgt    15180
gtacctggtg gacaacaagt caacggatgt ggcatccctg aactaccaga acgaccacag    15240
caactttctg accacggtca ttcaaaacaa tgactacagc ccgggggagg caagcacaca    15300
gaccatcaat cttgacgacc ggtcgcactg gggcggcgac ctgaaaacca tcctgcatac    15360
caacatgcca aatgtgaacg agttcatgtt taccaataag tttaaggcgc gggtgatggt    15420
gtcgcgcttg cctactaagg acaatcaggt ggagctgaaa tacgagtggg tggagttcac    15480
gctgcccgag ggcaactact ccgagaccat gaccatagac cttatgaaca cgcgatcgt    15540 ggagcactac ttgaaagtgg gcagacagaa cggggttctg gaaagcgaca tcggggtaaa    15600
gtttgacacc cgcaacttca gactgggggtt tgaccccgtc actggtcttg tcatgcctgg    15660
ggtatataca aacgaagcct tccatccaga catcattttg ctgccaggat gcggggtgga    15720
cttcacccac agccgcctga gcaacttgtt gggcatccgc aagcggcaac ccttccagga    15780
gggctttagg atcacctacg atgatctgga gggtggtaac attcccgcac tgttggatgt    15840
ggacgcctac caggcgagct tgaaagatga caccgaacag ggcgggggtg gcgcaggcgg    15900
cagcaacagc agtggcagcg gcgcggaaga gaactccaac gcggcagccg cggcaatgca    15960
gccggtggag gacatgaacg atcatgccat tcgcggcgac acctttgcca cacgggctga    16020
ggagaagcgc gctgaggccg aagcagcggc cgaagctgcc gccccgctg cgcaacccga    16080 ggtcgagaag cctcagaaga aaccggtgat caaaccctg acagaggaca gcaagaaacg    16140
cagttacaac ctaataagca atgacagcac cttcacccag taccgcagct ggtaccttgc    16200
atacaactac ggcgaccctc agaccggaat ccgctcatgg accctgcttt gcactcctga    16260
cgtaacctgc ggctcggagc aggtctactg gtcgttgcca gacatgatgc aagacccgt    16320 gaccttccgc tccacgcgcc agatcagcaa ctttccggtg gtgggcgccg agctgttgcc    16380
cgtgcactcc aagagcttct acaacgacca ggccgtctac tcccaactca tccgccagtt    16440
tacctctctg acccacgtgt tcaatcgctt cccgagaac cagattttgg cgcgcccgcc    16500
agcccccacc atcaccaccg tcagtgaaaa cgttcctgct ctcacagatc acgggacgct    16560
accgctgcgc aacagcatcg gaggagtcca gcgagtgacc attactgacg ccagacgccg    16620
cacctgcccc tacgtttaca aggccctggg catagtctcg ccgcgcgtcc tatcgagccg    16680 cacttttttga gcaagcatgt ccatccttat atcgcccagc aataacacag gctggggcct    16740
gcgcttccca agcaagatgt ttggcggggc caagaagcgc tccgaccaac acccagtgcg    16800
cgtgcgcggg cactaccgcg cgccctgggg cgcgcacaaa cgcggccgca ctgggcgcac    16860
caccgtcgat gacgccatcg acgcggtggt ggaggaggcg cgcaactaca cgcccacgcc    16920
gccaccagtg tccacagtgg acgcggccat tcagaccgtg gtgcgcggag cccggcgcta    16980
tgctaaaatg aagagacggc ggaggcgcgt agcacgtcgc caccgccgcc gacccggcac    17040
tgccgcccaa cgcgcggcgg cggccctgct taaccgcgca cgtcgcaccg ccgacgggc    17100 ggccatgcgg gccgctcgaa ggctggccgc gggtattgtc actgtgcccc ccaggtccag    17160
gcgacgagcg gccgccgcag cagccgcggc cattagtgct atgactcagg gtcgcagggg    17220
caacgtgtat tgggtgcgcg actcggttag cggcctgcgc gtgcccgtgc gcacccgccc    17280
cccgcgcaac tagattgcaa gaaaaaacta cttagactcg tactgttgta tgtatccagc    17340
ggcggcggcg cgcaacgaag ctatgtccaa gcgcaaaatc aaagaagaga tgctccaggt    17400
```

```
catcgcgccg gagatctatg gccccccgaa gaaggaagag caggattaca agccccgaaa    17460
gctaaagcgg gtcaaaaaga aaagaaaga tgatgatgat gaacttgacg acgaggtgga     17520
actgctgcac gctaccgcgc ccaggcgacg ggtacagtgg aaaggtcgac gcgtaaaacg    17580
tgttttgcga cccggcacca ccgtagtctt tacgcccggt gagcgctcca cccgcaccta    17640
caagcgcgtg tatgatgagg tgtacggcga cgaggacctg cttgagcagg ccaacgagcg    17700
cctcggggag tttgcctacg gaaagcggca taaggacatg ctggcgttgc cgctggacga    17760
gggcaaccca acacctagcc taaagcccgt aacactgcag caggtgctgc ccgcgcttgc    17820
accgtccgaa gaaaagcgcg gcctaaagcg cgagtctggt gacttggcac ccaccgtgca    17880
gctgatggta cccaagcgcc agcgactgga agatgtcttg gaaaaaatga ccgtggaacc    17940
tgggctggag cccgaggtcc gcgtgcggcc aatcaagcag gtggcgccgg gactgggcgt    18000
gcagaccgtg gacgttcaga tacccactac cagtagcacc agtattgcca ccgccacaga    18060
gggcatggag acacaaacgt ccccggttgc ctcagcggtg gcggatgccg cggtgcaggc    18120
ggtcgctgcg gccgcgtcca agacctctac ggaggtgcaa acggacccgt ggatgtttcg    18180
cgtttcagcc ccccggcgcc cgcgcggttc gaggaagtac ggcgccgcca gcgcgctact    18240 gccccgaatat gccctacatc cttccattgc gcctaccccc ggctatcgtg gctacaccta    18300
ccgccccaga agacgagcaa ctacccgacg ccgaaccacc actggaaccc gccgccgccg    18360
tcgccgtcgc cagcccgtgc tggccccgat ttccgtgcgc agggtggctc gcgaaggagg    18420
caggaccctg gtgctgccaa cagcgcgcta ccaccccagc atcgtttaaa agccggtctt    18480
tgtggttctt gcagatatgg ccctcacctg ccgcctccgt ttcccggtgc cgggattccg    18540
aggaagaatg caccgtagga ggggcatggc cggccacggc ctgacgggcg gcatgcgtcg    18600
tgcgcaccac cggcggcggc gcgcgtcgca ccgtcgcatg cgcggcggta tcctgccccT    18660
ccttattcca ctgatcgccg cggcgattgg cgccgtgccc ggaattgcat ccgtggcctt    18720
gcaggcgcag agacactgat taaaaacaag ttgcatgtgg aaaaatcaaa ataaaaagtc    18780
tggactctca cgctcgcttg gtcctgtaac tattttgtag aatggaagac atcaactttg    18840
cgtctctggc cccgcgacac ggctcgcgcc cgttcatggg aaactggcaa gatatcggca    18900
ccagcaatat gagcggtggc gccttcagct ggggctcgct gtggagcggc attaaaaatt    18960
tcggttccac cgttaagaac tatggcagca aggcctggaa cagcagcaca ggccagatgc    19020
tgagggataa gttgaaagag caaaatttcc aacaaaaggt ggtagatggc ctggcctctg    19080
gcattagcgg ggtggtggac ctggccaacc aggcagtgca aaataagatt aacagtaagc    19140
ttgatccccg ccctcccgta gaggagcctc caccggccgt ggagacagtg tctccagagg    19200
ggcgtggcga aaagcgtccg cgccccgaca gggaagaaac tctggtgacg caaatagacg    19260
agcctccctc gtacgaggag gcactaaagc aaggcctgcc caccaccgt cccatcgcgc      19320 ccatggctac cggagtgctg ggccagcaca caccgtaac gctggacctg cctccccccg      19380
ccgacaccca gcagaaacct gtgctgccag gcccgaccgc cgttgttgta acccgtccta    19440
gccgcgcgtc cctgcgccgc gccgccagcg gtccgcgatc gttgcggccc gtagccagtg    19500
gcaactggca aagcacactg aacagcatcg tgggtctggg ggtgcaatcc ctgaagcgcc    19560
gacgatgctt ctgaatagct aacgtgtcgt atgtgtgtca tgtatgcgtc catgtcgccg    19620
ccagaggagc tgctgagccg ccgcgcgccc gctttccaag atggctaccc cttcgatgat    19680
gccgcagtgg tcttacatgc acatctcggg ccaggacgcc tcggagtacc tgagccccgg    19740
gctggtgcag tttgcccgcg ccaccgagac gtacttcagc ctgaataaca agtttagaaa    19800
```

```
ccccacggtg gcgcctacgc acgacgtgac cacagaccgg tcccagcgtt tgacgctgcg    19860
gttcatccct gtggaccgtg aggatactgc gtactcgtac aaggcgcggt tcaccctagc    19920
tgtgggtgat aaccgtgtgc tggacatggc ttccacgtac tttgacatcc gcggcgtgct    19980
ggacaggggc cctacttta agccctactc tggcactgcc tacaacgccc tggctcccaa    20040
gggtgcccca aatccttgcg aatgggatga agctgctact gctcttgaaa taaacctaga    20100
agaagaggac gatgacaacg aagacgaagt agacagagcaa gctgagcagc aaaaaactca    20160
cgtatttggg caggcgcctt attctggtat aaatattaca aaggagggta ttcaaatagg    20220
tgtcgaaggt caaacaccta aatatgccga taaaacattt caacctgaac tcaaatagg    20280
agaatctcag tggtacgaaa ctgaaattaa tcatgcagct gggagagtcc ttaaaaagac    20340
taccccaatg aaaccatgtt acggttcata tgcaaaaccc acaaatgaaa atggagggca    20400
aggcattctt gtaaagcaac aaaatggaaa gctagaaagt caagtggaaa tgcaattttt    20460
ctcaactact gaggcgaccg caggcaatgg tgataacttg actcctaaag tggtattgta    20520
cagtgaagat gtagatatag aaaccccaga cactcatatt tcttacatgc ccactattaa    20580
ggaaggtaac tcacgagaac taatgggcca acaatctatg cccaacaggc ctaattacat    20640
tgcttttagg gacaatttta ttggtctaat gtattacaac agcacgggta atatgggtgt    20700
tctggcgggc caagcatcgc agttgaatgc tgttgtagat ttgcaagaca gaaacacaga    20760
gctttcatac cagcttttgc ttgattccat tggtgataga accaggtact tttctatgtg    20820
gaatcaggct gttgacagct atgatccaga tgttagaatt attgaaaatc atggaactga    20880
agatgaactt ccaaattact gctttccact gggaggtgtg attaatacag agactcttac    20940
caaggtaaaa cctaaaacag gtcaggaaaa tggatgggaa aaagatgcta cagaattttc    21000
agataaaaat gaaataagag ttggaaataa ttttgccatg gaaatcaatc taaatgccaa    21060
cctgtggaga aatttcctgt actccaacat agcgctgtat ttgcccgaca agctaaagta    21120
cagtccttcc aacgtaaaaa tttctgataa cccaaacacc tacgactaca tgaacaagcg    21180
agtggtggct cccgggttag tggactgcta cattaacctt ggagcacgct ggtcccttga    21240
ctatatggac aacgtcaacc catttaacca ccaccgcaat gctggcctgc gctaccgctc    21300
aatgttgctg ggcaatggtc gctatgtgcc cttccacatc caggtgcctc agaagttctt    21360
tgccattaaa aacctccttc tcctgccggg ctcatacacc tacgagtgga cttcaggaa    21420
ggatgttaac atggttctgc agagctccct aggaaatgac ctaagggttg acggagccag    21480
cattaagttt gatagcattt gcctttacgc caccttcttc cccatggccc acaacaccgc    21540
ctccacgctt gaggccatgc ttagaaacga caccaacgac cagtcctta acgactatct    21600
ctccgccgcc aacatgctct accctatacc cgccaacgct accaacgtgc ccatatccat    21660
cccctcccgc aactgggcgg ctttccgcgg ctgggccttc acgcgcctta agactaagga    21720
aaccccatca ctgggctcgg gctacgaccc ttattacacc tactctggct ctataccta    21780
cctagatgga acctttacc tcaaccacac ctttaagaag gtggccatta cctttgactc    21840
ttctgtcagc tggcctggca atgaccgcct gcttaccccc aacgagtttg aaattaagcg    21900
ctcagttgac ggggagggtt acaacgttgc ccagtgtaac atgaccaaag actggttcct    21960
ggtacaaatg ctagctaact acaacattgg ctaccagggc ttctatatcc cagagagcta    22020
caaggaccgc atgtactcct tctttagaaa cttccagccc atgagccgtc aggtggtgga    22080
tgatactaaa tacaaggact accaacaggt gggcatccta caccaacaca caactctgg    22140
```

```
atttgttggc taccttgccc ccaccatgcg cgaaggacag gcctaccctg ctaacttccc   22200
ctatccgctt ataggcaaga ccgcagttga cagcattacc cagaaaaagt ttctttgcga   22260
tcgcacccTt tggcgcatcc cattctccag taactttatg tccatgggcg cactcacaga   22320
cctgggccaa aaccttctct acgccaactc cgcccacgcg ctagacatga cttttgaggt   22380
ggatcccatg gacgagccca cccttcttta tgttttgttt gaagtctttg acgtggtccg   22440
tgtgcaccgg ccgcaccgcg gcgtcatcga aaccgtgtac ctgcgcacgc ccttctcggc   22500
cggcaacgcc acaacataaa gaagcaagca acatcaacaa cagctgccgc catgggctcc   22560
agtgagcagg aactgaaagc cattgtcaaa gatcttggtt gtgggccata tttttgggc   22620
acctatgaca agcgctttcc aggctttgtt tctccacaca agctcgcctg cgccatagtc   22680
aatacggccg gtcgcgagac tgggggcgta cactggatgg cctttgcctg gaacccgcac   22740
tcaaaaacat gctacctctt tgagcccttt ggcttttctg accagcgact caagcaggtt   22800
taccagtttg agtacgagtc actcctgcgc cgtagcgcca ttgcttcttc ccccgaccgc   22860
tgtataacgc tggaaaagtc cacccaaagc gtacaggggc ccaactcggc cgcctgtgga   22920
ctattctgct gcatgtttct ccacgccttt gccaactggc cccaaactcc catggatcac   22980
aaccccacca tgaaccttat taccggggta cccaactcca tgctcaacag tccccaggta   23040
cagcccaccc tgcgtcgcaa ccaggaacag ctctacagct tcctggagcg ccactcgccc   23100
tacttccgca gccacagtgc gcagattagg agcgccactt cttttgtca cttgaaaaac   23160
atgtaaaaat aatgtactag agacactttc aataaaggca aatgctttta tttgtacact   23220
ctcgggtgat tatttacccc cacccttgcc gtctgcgccg tttaaaaatc aaaggggttc   23280
tgccgcgcat cgctatgcgc cactggcagg gacacgttgc gatactggtg tttagtgctc   23340
cacttaaact caggcacaac catccgcggc agctcggtga agttttcact ccacaggctg   23400
cgcaccatca ccaacgcgtt tagcaggtcg ggcgccgata tcttgaagtc gcagttgggg   23460
cctccgccct gcgcgcgcga gttgcgatac acagggttgc agcactggaa cactatcagc   23520
gccgggtggt gcacgctggc cagcacgctc ttgtcggaga tcagatccgc gtccaggtcc   23580
tccgcgttgc tcagggcgaa cggagtcaac tttggtagct gccttcccaa aaagggcgcg   23640
tgcccaggct ttgagttgca ctcgcaccgt agtggcatca aaaggtgacc gtgcccggtc   23700
tgggcgttag gatacagcgc ctgcataaaa gccttgatct gcttaaaagc cacctgagcc   23760
tttgcgcctt cagagaagaa catgccgcaa gacttgccgg aaaactgatt ggccggacag   23820
gccgcgtcgt gcacgcagca ccttgcgtcg gtgttggaga tctgcaccac atttcggccc   23880
caccggttct tcacgatctt ggccttgcta gactgctcct tcagcgcgcg ctgcccgttt   23940
tcgctcgtca catccatttc aatcacgtgc tccttattta tcataatgct tccgtgtaga   24000
cacttaagct cgccttcgat ctcagcgcag cggtgcagcc acaacgcgca gcccgtgggc   24060
tcgtgatgct tgtaggtcac ctctgcaaac gactgcaggt acgcctgcag gaatcgcccc   24120
atcatcgtca caaggtcttg ttgctggtg aaggtcagct gcaacccgcg gtgctcctcg   24180
ttcagccagg tcttgcatac ggccgccaga gcttccactt ggtcaggcag tagtttgaag   24240
ttcgccttta gatcgttatc cacgtggtac ttgtccatca gcgcgcgcgc agcctccatg   24300
cccttctccc acgcagacac gatcggcaca ctcagcgggt tcatcaccgt aatttcactt   24360
tccgcttcgc tgggctcttc ctcttcctct tgcgtccgca taccacgcgc cactgggtcg   24420
tcttcattca gccgccgcac tgtgcgctta cctccttttgc catgcttgat tagcaccggt   24480
gggttgctga aacccaccat ttgtagcgcc acatcttctc tttcttcctc gctgtccacg   24540
```

```
attacctctg gtgatggcgg gcgctcgggc ttgggagaag ggcgcttctt tttcttcttg   24600
ggcgcaatgg ccaaatccgc cgccgaggtc gatggccgcg ggctgggtgt gcgcggcacc   24660
agcgcgtctt gtgatgagtc ttcctcgtcc tcggactcga tacgccgcct catccgcttt   24720
tttggggggcg cccggggagg cggcggcgac ggggacgggg acgacacgtc ctccatggtt   24780
ggggggacgtc gcgccgcacc gcgtccgcgc tcggggggtgg tttcgcgctg ctcctcttcc   24840
cgactggcca tttccttctc ctataggcag aaaaagatca tggagtcagt cgagaagaag   24900
gacagcctaa ccgcccccctc tgagttcgcc accaccgcct ccaccgatgc cgccaacgcg   24960
cctaccacct tccccgtcga ggcaccccccg cttgaggagg aggaagtgat tatcgagcag   25020
gacccaggtt ttgtaagcga agacgacgag gaccgctcag taccaacaga ggataaaaag   25080
caagaccagg acaacgcaga ggcaaacgag gaacaagtcg ggcgggggga cgaaaggcat   25140
ggcgactacc tagatgtggg agacgacgtg ctgttgaagc atctgcagcg ccagtgcgcc   25200
attatctgcg acgcgttgca agagcgcagc gatgtgcccc tcgccatagc ggatgtcagc   25260
cttgcctacg aacgccacct attctcaccg cgcgtacccc ccaaacgcca agaaaacggc   25320
acatgcgagc ccaacccgcg cctcaacttc taccccgtat ttgccgtgcc agaggtgctt   25380
gccacctatc acatcttttt ccaaaactgc aagataccccc tatcctgccg tgccaaccgc   25440
agccgagcgg acaagcagct ggccttgcgg cagggcgctg tcatacctga tatcgcctcg   25500
ctcaacgaag tgccaaaaat ctttgagggt cttggacgcg acgagaagcg cgcggcaaac   25560
gctctgcaac aggaaaacag cgaaaatgaa agtcactctg gagtgttggt ggaactcgag   25620
ggtgacaacg cgcgcctagc cgtactaaaa cgcagcatcg aggtcaccca cttttgcctac   25680
ccggcactta acctaccccc caaggtcatg agcacagtca tgagtgagct gatcgtgcgc   25740
cgtgcgcagc ccctggagag ggatgcaaat ttgcaagaac aaacagagga gggcctaccc   25800
gcagttggcg acgagcagct agcgcgctgg cttcaaacgc gcgagcctgc cgacttggag   25860
gagcgacgca aactaatgat ggccgcagtg ctcgttaccg tggagcttga gtgcatgcag   25920
cggttctttg ctgaccccgga gatgcagcgc aagctagagg aaacattgca ctacacccttt   25980
cgacagggct acgtacgcca ggcctgcaag atctccaacg tggagctctg caacctggtc   26040
tcctaccttg aattttgca cgaaaaccgc cttgggcaaa acgtgcttca ttccacgctc   26100
aagggcgagg cgcgccgcga ctacgtccgc gactgcgttt acttattctct atgctacacc   26160
tggcagacgg ccatgggcgt ttggcagcag tgcttggagg agtgcaacct caaggagctg   26220
cagaaactgc taaagcaaaa cttgaaggac ctatggacgg ccttcaacga gcgctccgtg   26280
gccgcgcacc tggcggacat cattttcccc gaacgcctgc ttaaaaccct gcaacagggt   26340
ctgccagact tcaccagtca aagcatgttg cagaacttta ggaactttat cctagagcgc   26400
tcaggaatct tgcccgccac ctgctgtgca cttcctagcg actttgtgcc cattaagtac   26460
cgcgaatgcc ctccgccgct ttggggccac tgctacttc tgcagctagc caactaccctt   26520
gcctaccact ctgacataat ggaagacgtg agcggtgacg tctactggaa gtgtcactgt   26580
cgctgcaacc tatgcacccc gcaccgctcc ctggtttgca attcgcagct gcttaacgaa   26640
agtcaaatta tcggtacctt tgagctgcag ggtcccctcgc ctgacgaaaa gtccgcggct   26700
ccggggttga aactcactcc ggggctgtgg acgtcggctt accttcgcaa atttgtacct   26760
gaggactacc acgcccacga gattaggttc tacgaagacc aatcccgccc gccaaatgcg   26820
gagcttaccg cctgcgtcat tacccagggc cacattcttg ccaattgca agccatcaac   26880
```

```
aaagcccgcc aagagtttct gctacgaaag ggacgggggg tttacttgga cccccagtcc   26940
ggcgaggagc tcaacccaat cccccccgccg ccgcagccct atcagcagca gccgcgggcc   27000
cttgcttccc aggatggcac ccaaaaagaa gctgcagctg ccgccgccac ccacggacga   27060
ggaggaatac tgggacagtc aggcagagga ggttttggac gaggaggagg aggacatgat   27120
ggaagactgg gagagcctag acgaggaagc ttccgaggtc gaagaggtgt cagacgaaac   27180
accgtcaccc tcggtcgcat tcccctcgcc ggcgcccccag aaatcggcaa ccggttccag   27240
catggctaca acctccgctc ctcaggcgcc gccggcactg cccgttcgcc gacccaaccg   27300
tagatgggac accactggaa ccagggccgg taagtccaag cagccgccgc cgttagccca   27360
agagcaacaa cagcgccaag gctaccgctc atggcgcggg cacaagaacg ccatagttgc   27420
ttgcttgcaa gactgtgggg gcaacatctc cttcgcccgc cgctttcttc tctaccatca   27480
cggcgtggcc ttcccccgta acatcctgca ttactaccgt catctctaca gcccatactg   27540
caccggcggc agcggcagcg gcagcaacag cagcggccac acagaagcaa aggcgaccgg   27600
atagcaagac tctgacaaag cccaagaaat ccacagcggc ggcagcagca ggaggaggag   27660
cgctgcgtct ggcgcccaac gaacccgtat cgacccgcga gcttagaaac aggatttttc   27720
ccactctgta tgctatattt caacagagca ggggccaaga acaagagctg aaaataaaaa   27780
acaggtctct gcgatccctc acccgcagct gcctgtatca caaaagcgaa gatcagcttc   27840
ggcgcacgct ggaagacgcg gaggctctct tcagtaaata ctgcgcgctg actcttaagg   27900
actagtttcg cgcccttcct caaatttaag cgcgaaaact acgtcatctc cagcggccac   27960
acccggcgcc agcacctgtc gtcagcgcca tttatgagca aggaaattcc cacgccctac   28020
atgtggagtt accagccaca aatgggactt gcggctggag ctgcccaaga ctactcaacc   28080
cgaataaact acatgagcgc gggacccac atgatatccc gggtcaacgg aatacgcgcc   28140
caccgaaacc gaattctcct ggaacaggcg gctattacca ccacacctcg taataaacctt   28200 aatccccgta gttggcccgc tgccctggtg taccaggaaa gtcccgctcc caccactgtg   28260
gtacttccca gagacgccca ggccgaagtt cagatgacta actcaggggc gcagcttgcg   28320
ggcggctttc gtcacagggt gcggtcgccc gggcagggta taactcacct gacaatcaga   28380
gggcgaggta ttcagctcaa cgacgagtcg gtgagctcct cgcttggtct ccgtccggac   28440
gggacatttc agatcggcgg cgccggccgc tcttcattca cgcctcgtca ggcaatccta   28500
actctgcaga cctcgtcctc tgagccgcgc tctggaggca ttggaactct gcaatttatt   28560
gaggagtttg tgccatcggt ctactttaac cccttctcgg gacctcccgg ccactatccg   28620
gatcaattta ttcctaactt tgacgcggta aaggactcgg cggacggcta cgactgaatg   28680
ttaagtggag aggcagagca actgcgcctg aaacacctgg tccactgtcg ccgccacaag   28740
tgctttgccc gcgactccgg tgagttttgc tactttgaat tgcccgagga tcatatcgag   28800
ggcccggcgc acggcgtccg gcttaccgcc caggagagc ttgcccgtag cctgattcgg   28860
gagtttaccc agcgccccct gctagttgag cgggacaggg gaccctgtgt tctcactgtg   28920
atttgcaact gtcctaaccc tggattacaa tttaaatgcg gtctcaaaga tcttattccc   28980
tttaactaat aaaaaaaaat aataaagcat cacttactta aaatcagtta gcaaatttct   29040
gtccagttta ttcagcagca cctccttgcc ctcctcccag ctctggtatt gcagcttcct   29100
cctggctgca aactttctcc acaatctaaa tggaatgtca gtttcctcct gttcctgtcc   29160
atccgcaccc actatcttca tgttgttgca gatgaagcgc gcaagaccgt ctgaagatac   29220
cttcaacccc gtgtatccat atgacacgga aaccggtcct ccaactgtgc ctttcttac    29280
```

```
tcctccctt  gtatccccca  atgggtttca  agagagtccc  cctggggtac  tctctttgcg   29340
cctatccgaa  cctctagtta  cctccaatgg  catgcttgcg  ctcaaaatgg  gcaacggcct   29400
ctctctggac  gaggccggca  accttacctc  ccaaaatgta  accactgtga  gcccacctct   29460
caaaaaacc   aagtcaaaca  taaacctgga  aatatctgca  ccccctcacag ttacctcaga   29520
agccctaact  gtggctgccg  ccgcacctct  aatggtcgcg  ggcaacacac  tcaccatgca   29580
atcacaggcc  ccgctaaccg  tgcacgactc  caaacttagc  attgccaccc  aaggacccct   29640
cacagtgtca  gaaggaaagc  tagccctgca  aacatcaggc  ccctcacca   ccaccgatag   29700
cagtaccctt  actatcactg  cctcaccccc  tctaactact  gccactggta  gcttgggcat   29760
tgacttgaaa  gagcccattt  atacacaaaa  tggaaaacta  ggactaaagt  acggggctcc   29820
tttgcatgta  acagacgacc  taaacacttt  gaccgtagca  actggtccag  gtgtgactat   29880
taataatact  tccttgcaaa  ctaaagttac  tggagccttg  ggttttgatt  cacaaggcaa   29940
tatgcaactt  aatgtagcag  gaggactaag  gattgattct  caaaacagac  gccttatact   30000
tgatgttagt  tatccgtttg  atgctcaaaa  ccaactaaat  ctaagactag  acagggcccc   30060
tcttttata   aactcagccc  acaacttgga  tattaactac  aacaaaggcc  tttacttgtt   30120
tacagcttca  aacaattcca  aaaagcttga  ggttaaccta  agcactgcca  aggggttgat   30180
gtttgacgct  acagccatag  ccattaatgc  aggagatggg  cttgaatttg  gttcacctaa   30240
tgcaccaaac  acaaatcccc  tcaaaacaaa  aattggccat  ggcctagaat  ttgattcaaa   30300
caaggctatg  gttcctaaac  taggaactgg  ccttagtttt  gacagcacag  gtgccattac   30360
agtaggaaac  aaaaataatg  ataagctaac  tttgtggacc  acaccagctc  catctcctaa   30420
ctgtagacta  aatgcagaga  aagatgctaa  actcactttg  gtcttaacaa  aatgtggcag   30480
tcaaatactt  gctacagttt  cagttttggc  tgttaaaggc  agtttggctc  caatatctgg   30540
aacagttcaa  agtgctcatc  ttattataag  atttgacgaa  aatggagtgc  tactaaacaa   30600
ttccttcctg  gacccagaat  attggaactt  tagaaatgga  gatcttactg  aaggcacagc   30660
ctatacaaac  gctgttggat  ttatgcctaa  cctatcagct  tatccaaaat  ctcacggtaa   30720
aactgccaaa  agtaacattg  tcagtcaagt  ttacttaaac  ggagacaaaa  ctaaacctgt   30780
aacactaacc  attacactaa  acggtacaca  ggaaacagga  gacacaactc  caagtgcata   30840
ctctatgtca  ttttcatggg  actggtctgg  ccacaactac  attaatgaaa  tatttgccac   30900
atcctcttac  acttttttcat acattgccca  agaataaaga  atcgtttgtg  ttatgtttca   30960
acgtgtttat  ttttcaattg  cagaaaattt  caagtcattt  ttcattcagt  agtatagccc   31020
caccaccaca  tagcttatac  agatcaccgt  accttaatca  aactcacaga  accctagtat   31080
tcaacctgcc  acctccctcc  caacacacag  agtacacagt  cctttctccc  cggctggcct   31140
taaaaagcat  catatcatgg  gtaacagaca  tattcttagg  tgttatattc  cacacggttt   31200
cctgtcgagc  caaacgctca  tcagtgatat  taataaactc  cccgggcagc  tcacttaagt   31260
tcatgtcgct  gtccagctgc  tgagccacag  gctgctgtcc  aacttgcggt  tgcttaacgg   31320
gcggcgaagg  agaagtccac  gcctacatgg  gggtagagtc  ataatcgtgc  atcaggatag   31380
ggcggtggtg  ctgcagcagc  gcgcgaataa  actgctgccg  ccgccgctcc  gtcctgcagg   31440
aatacaacat  ggcagtggtc  tcctcagcga  tgattcgcac  cgcccgcagc  ataaggcgcc   31500
ttgtcctccg  ggcacagcag  cgcaccctga  tctcacttaa  atcagcacag  taactgcagc   31560
acagcaccac  aatattgttc  aaaatcccac  agtgcaaggc  gctgtatcca  aagctcatgg   31620
```

```
cggggaccac agaacccacg tggccatcat accacaagcg caggtagatt aagtggcgac    31680
ccctcataaa cacgctggac ataaacatta cctcttttgg catgttgtaa ttcaccacct    31740
cccggtacca tataaacctc tgattaaaca tggcgccatc caccaccatc ctaaaccagc    31800
tggccaaaac ctgcccgccg gctatacact gcagggaacc gggactggaa caatgacagt    31860
ggagagccca ggactcgtaa ccatggatca tcatgctcgt catgatatca atgttggcac    31920
aacacaggca cacgtgcata cacttcctca ggattacaag ctcctcccgc gttagaacca    31980
tatcccaggg aacaacccat tcctgaatca gcgtaaatcc cacactgcag ggaagacctc    32040
gcacgtaact cacgttgtgc attgtcaaag tgttacattc gggcagcagc ggatgatcct    32100
ccagtatggt agcgcgggtt tctgtctcaa aaggaggtag acgatcccta ctgtacggag    32160
tgcgccgaga caaccgagat cgtgttggtc gtagtgtcat gccaaatgga acgccggacg    32220
tagtcatatt tcctgaagca aaaccaggtg cgggcgtgac aaacagatct gcgtctccgg    32280
tctcgccgct tagatcgctc tgtgtagtag ttgtagtata tccactctct caaagcatcc    32340
aggcgccccc tggcttcggg ttctatgtaa actccttcat gcgccgctgc cctgataaca    32400
tccaccaccg cagaataagc cacacccagc caacctacac attcgttctg cgagtcacac    32460
acgggaggag cgggaagagc tggaagaacc atgtttttt ttttattcca aaagattatc    32520
caaaacctca aaatgaagat ctattaagtg aacgcgctcc cctccggtgg cgtggtcaaa    32580
ctctacagcc aaagaacaga taatggcatt tgtaagatgt tgcacaatgg cttccaaaag    32640
gcaaacggcc ctcacgtcca agtggacgta aaggctaaac ccttcagggt gaatctcctc    32700
tataaacatt ccagcacctt caaccatgcc caaataattc tcatctcgcc accttctcaa    32760
tatatctcta agcaaatccc gaatattaag tccggccatt gtaaaaatct gctccagagc    32820
gccctccacc ttcagcctca agcagcgaat catgattgca aaaattcagg ttcctcacag    32880
acctgtataa gattcaaaag cggaacatta acaaaaatac cgcgatcccg taggtccctt    32940
cgcagggcca gctgaacata atcgtgcagg tctgcacgga ccagcgcggc cacttccccg    33000
ccaggaacca tgacaaaaga acccacactg attatgacac gcatactcgg agctatgcta    33060
accagcgtag ccccgatgta agcttgttgc atgggcggcg atataaaatg caaggtgctg    33120
ctcaaaaaat caggcaaagc ctcgcgcaaa aagaaagca catcgtagtc atgctcatgc    33180
agataaaggc aggtaagctc cggaaccacc acagaaaaag acaccatttt tctctcaaac    33240
atgtctgcgg gtttctgcat aaacacaaaa taaaataaca aaaaaacatt taaacattag    33300
aagcctgtct tacaacagga aaaacaaccc ttataagcat aagacggact acggccatgc    33360
cggcgtgacc gtaaaaaaac tggtcaccgt gattaaaaag caccaccgac agctcctcgg    33420
tcatgtccgg agtcataatg taagactcgg taaacacatc aggttgattc acatcggtca    33480
gtgctaaaaa gcgaccgaaa tagcccgggg gaatacatac ccgcaggcgt agagacaaca    33540
ttacagcccc cataggaggt ataacaaaat taataggaga gaaaacacac taaacacctg    33600
aaaaaccctc ctgcctaggc aaaatagcac cctcccgctc cagaacaaca tacagcgctt    33660
ccacagcggc agccataaca gtcagcctta ccagtaaaaa agaaaaccta ttaaaaaaac    33720
accactcgac acggcaccag ctcaatcagt cacagtgtaa aaaagggcca agtgcagagc    33780
gagtatatat aggactaaaa aatgacgtaa cggttaaagt ccacaaaaaa cacccagaaa    33840
accgcacgcg aacctacgcc cagaaacgaa agccaaaaaa cccacaactt cctcaaatcg    33900
tcacttccgt tttcccacgt tacgtcactt cccattttaa gaaaactaca attcccaaca    33960
catacaagtt actccgccct aaaacctacg tcacccgccc cgttcccacg cccgcgcca    34020
```

```
cgtcacaaac tccaccccct cattatcata ttggcttcaa tccaaaataa ggtatattat    34080
tgatgatgta gggataacag ggtaataaat ccggggatcc tctagagtcg acctgcaggc    34140
atgcaagctt ggcgtaatca tggtcatagc tgtttcctgt gtgaaattgt tatccgctca    34200
caattccaca caacatacga gccggaagca taaagtgtaa agcctggggt gcctaatgag    34260
tgagcta                                                              34267
```

```
<210> SEQ ID NO 6
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 6
aucucgcuug ggcgagagua ag                                              22

<210> SEQ ID NO 7
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 7
gcuggaauac uuagcucaga uc                                              22

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 8
gatgcagcca actttgggat ccag                                            24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 9
aaagttggct gcatccgtga aggc                                            24

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 10
gccgatgacg agccctt                                                    17

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide primer
```

```
<400> SEQUENCE: 11
aagtcaccac cctggcaca                                          19

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
ctctcgcttt ctggagggtg                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
acgcgcttgt acccattgat                                         20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
gcgcagctag aggattcagg                                         20

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 15
aacagtttct gaggctcctt ct                                      22

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 16
cctctccagc caagcttcc                                          19

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 17
ctcatcagga cagcccaggt                                         20

<210> SEQ ID NO 18
<211> LENGTH: 20
```

```
<212> TYPE: DNA
<213> ORGANISM: Artificial Sequence
<220> FEATURE:
<223> OTHER INFORMATION: Synthetic oligonucleotide primer

<400> SEQUENCE: 18
gccaccacgc tcttctgtct                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 19
cagctgctcc tccacttggt                                                  20

<210> SEQ ID NO 20
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 20
caccatggtg agcaagggcg aggaggataa c                                     31

<210> SEQ ID NO 21
<211> LENGTH: 58
<212> TYPE: DNA
<213> ORGANISM: Artificial Sequence
<220> FEATURE:
<223> OTHER INFORMATION: Synthetic oligonucleotide primer

<400> SEQUENCE: 21
agtgatttaa tttataccat tttaattcag ctttgtaaaa atgtatcaaa gagatagc        58

<210> SEQ ID NO 22
<211> LENGTH: 37110
<212> TYPE: DNA
<213> ORGANISM: Artificial Sequence
<220> FEATURE:
<223> OTHER INFORMATION: Synthetic adenovirus vector

<400> SEQUENCE: 22
gttccactga gcgtcagacc ccttaataag atgatcttct tgagatcgtt ttggtctgcg      60
cgtaatctct tgctctgaaa acgaaaaaac cgccttgcag gcggtttttt cgaaggttct    120
ctgagctacc aactctttga accgaggtaa ctggcttgga ggagcgcagt caccaaaact    180
tgtcctttca gtttagcctt aaccggcgca tgacttcaag actaactcct ctaaatcaat    240
taccagtggc tgctgccagt ggtgcttttg catgtctttc cgggttggac tcaagacgat    300
agttaccgga taaggcgcag cggtcggact gaacggggggg ttcgtgcata cagtccagct    360
tggagcgaac tgcctacccg gaactgagtg tcaggcgtgg aatgagacaa acgcggccat    420
aacagcggaa tgacaccggt aaaccgaaag gcaggaacag gagagcgcac gagggagccg    480
ccaggggaaa cgcctggtat ctttatagtc ctgtcgggtt cgccaccac tgatttgagc     540 gtcagatttc gtgatgcttg tcagggggc ggagcctatg gaaaaacggc tttgccgcgg     600
ccctctcact tccctgttaa gtatcttcct ggcatcttcc aggaaatctc cgccccgttc    660
gtaagccatt tccgctcgcc gcagtcgaac gaccgagcgt agcgagtcag tgagcgagga    720
```

```
agcggaatat atcctgtatc acatattctg ctgacgcacc ggtgcagcct ttttctcct    780
gccacatgaa gcacttcact gacaccctca tcagtgccaa catagtaagc cagtatacac   840
tccgctagcg ctgaggtctg cctcgtgaag aaggtgttgc tgactcatac caggcctgaa  900
tcgccccatc atccagccag aaagtgaggg agccacggtt gatgagagct ttgttgtagg   960
tggaccagtt ggtgattttg aacttttgct ttgccacgga acggtctgcg ttgtcgggaa 1020
gatgcgtgat ctgatccttc aactcagcaa aagttcgatt tattcaacaa agccacgttg 1080
tgtctcaaaa tctctgatgt tacattgcac aagataaaaa tatatcatca tgaacaataa 1140
aactgtctgc ttacataaac agtaatacaa ggggtgttga tactctcagt acaatctgct 1200
ctgatgccgc atagttaagc cagtatctgc tccctgcttg tgtgttggag gtcgctgagt 1260
agtgcgcgag caaaatttaa gctacaacaa ggcaaggctt gaccgacaat tgcatgaaga 1320
atctgcttag ggttaggcgt tttgcgctgc ttcgcgatgt acgggccaga tatacgcgta 1380
tctgagggga ctagggtgtg tttaggcgaa aagcggggct tcggttgtac gcggttagga 1440
gtcccctcag gatatagtag tttcgctttt gcataggggag ggggaaatgt agtcttatgc 1500
aatactcttg tagtcttgca acatggtaac gatgagttag caacatgcct tacaaggaga 1560
gaaaaagcac cgtgcatgcc gattggtgga agtaaggtgg tacgatcgtg ccttattagg 1620
aaggcaacag acgggtctga catggattgg acgaaccact gaattccgca ttgcagagat 1680
attgtattta agtgcctagc tcgatacaat aaacgccatt tgaccattca ccacattggt 1740
gtgcacctcc aagctgggta cggatccggc cttgccggcc tcgagcggcc gctagcgccg 1800
ccactatggg atcaagatcg ccaaaaaaga agagaaaggt gccgaagaag catgcagcac 1860
caccaaaaaa aaaacgaaaa gtagaagacc cacgatttat gtacccatac gatgttcctg 1920
actatgcggg tatgaaaaac atcaaaaaaa accaggtaat gaacctgggt ccgaactcta 1980
aactgctgaa agaatacaaa tcccagctga tcgaactgaa catcgaacag ttcgaagcag 2040
gtatcggtct gatcctgggt gatgcttaca tccgttctcg tgatgaaggt aaaacctact 2100
gtatgcagtt cgagtggaaa aacaaagcat acatggacca cgtatgtctg ctgtacgatc 2160
agtgggtact gtccccgccg cacaaaaaag aacgtgttaa ccacctgggt aacctggtaa 2220
tcacctgggg cgcccagact ttcaaacacc aagctttcaa caaactggct aacctgttca 2280
tcgttaacaa caaaaaaacc atcccgaaca acctggttga aaactacctg accccgatgt 2340
ctctggcata ctggttcatg gatgatggtg gtaaatggga ttacaacaaa aactctacca 2400
acaaatcgat cgtactgaac acccagtctt tcactttcga agaagtagaa tacctggtta 2460
agggtctgcg taacaaattc caactgaact gttacgtaaa aatcaacaaa acaaaccga 2520
tcatctacat cgattctatg tcttacctga tcttctacaa cctgatcaaa ccgtacctga 2580
tcccgcagat gatgtacaaa ctgccgaaca ctatctcctc cgaaactttc ctgaaataag 2640
gtaccgatcc agacatgata agatacattg atgagtttgg acaaaccaca actgaaatgc 2700
agtgaaaaaa atgctttatt tgtgaaattt gtgatgctat tgctttattt gtaaccatta 2760
taagctgcaa taaacaagtt aacaacaaca attgcattca ttttatgttt caggttcagg 2820
gggaggtgtg ggaggttttt taaagcaagt aaaacctcta caaatgtggt atggctgatt 2880
atgatcatcg taaacttggt ctgacagtta ccaatgctta atcagtgagg cacctatctc 2940
agcgatctgt ctatttcgtt catccatagt tgcctgactc cccgtcgtgt agataactac 3000
gatacgggag ggcttaccat ctggccccag tgctgcaatg ataccgcgag acccacgctc 3060
accggctcca gatttatcag caataaacca gccagccgga agggccgagc gcagaagtgg 3120
```

```
tcctgcaact ttatccgcct ccatccagtc tattaattgt tgccgggaag ctagagtaag    3180
tagttcgcca gttaatagtt tgcgcaacgt tgttgccatt gctacaggca tcgtggtgtc    3240
acgctcgtcg tttggtatgg cttcattcag ctccggttcc caacgatcaa ggcgagttac    3300
atgatccccc atgttgtgca aaaaagcggt tagctccttc ggtcctccga tcgttgtcag    3360
aagtaagttg gccgcagtgt tatcactcat ggttatggca gcactgcata attctcttac    3420
tgtcatgcca tccgtaagat gcttttctgt gactggtgag tactcaacca agtcattctg    3480
agaatagtgt atgcggcgac cgagttgctc ttgcccggcg tcaatacggg ataataccgc    3540
gccacatagc agaactttaa aagtgctcat cattggaaaa cgttcttcgg ggcgaaaact    3600
ctcaaggatc ttaccgctgt tgagatccag ttcgatgtaa cccactcgtg cacccaactg    3660
atcttcagca tcttttactt tcaccagcgt ttctgggtga gcaaaaacag gaaggcaaaa    3720
tgccgcaaaa aagggaataa gggcgacacg gaaatgttga atactcatac tcttcctttt    3780
tcaatattat tgaagcattt atcagggtta ttgtctcatg agcggataca tatttgaatg    3840
tatttagaaa aataaacaaa tagggggttcc gcgcacattt ccccgaaaag tgccacctga    3900
cgtctaagaa accattatta tcatgacatt aacctataaa aataggcgta tcacgaggcc    3960
ctttcgtctc gcgcgtttcg gtgatgacgg tgaaaacctc tgacacatgc agctcccgga    4020
gacggtcaca gcttgtctgt aagcggatgc cgggagcaga caagcccgtc agggcgcgtc    4080
agcgggtgtt ggcgggtgtc ggggctggct taactatgcg gcatcagagc agattgtact    4140
gagagtgcac catatgcggt gtgaaatacc gcacagatgc gtaaggagaa ataccgcat    4200 caggcgccat tcgccattca ggctgcgcaa ctgttgggaa gggcgatcgg tgcgggcctc    4260
ttcgctatta cgccagctgg cgaaggggg atgtgctgca aggcgattaa gttgggtaac    4320
gccagggttt tcccagtcac gacgttgtaa aacgacggcc agtgaattac caactttgta    4380
caaaaaagca gattaccctg ttatccctac atcatcaata atataccttta ttttggattg    4440 aagccaatat gataatgagg gggtggagtt tgtgacgtgg cgcggggcgt gggaacgggg    4500
cgggtgacgt agtagtgtgg cggaagtgtg atgttcaag tgtggcggaa cacatgtaag    4560
cgacggatgt ggcaaaagtg acgttttttgg tgtgcgccgg tgtacacagg aagtgacaat    4620
tttcgcgcgg ttttaggcgg atgttgtagt aaatttgggc gtaaccgagt aagatttggc    4680
cattttcgcg ggaaaactga ataagaggaa gtgaaatctg aataattttg tgttactcat    4740
agcgcgtaat atttgtctag ggccgcgggg actttgaccg tttacgtgga gactcgccca    4800 ggtgttttc tcaggtgttt tccgcgttcc gggtcaaagt tggcgtttta ttattaatta    4860
agtttaaacg gcgcgcctaa tagtaatcaa ttacggggtc attagttcat agcccatata    4920
tggagttccg cgttacataa cttacggtaa atggcccgcc tggctgaccg cccaacgacc    4980
cccgcccatt gacgtcaata atgacgtatg ttcccatagt aacgccaata gggactttcc    5040
attgacgtca atgggtggag tatttacggt aaactgccca cttggcagta catcaagtgt    5100
atcatatgcc aagtacgccc cctattgacg tcaatgacgg taaatggccc gcctggcatt    5160
atgcccagta catgacctta tgggactttc ctacttggca gtacatctac gtattagtca    5220
tcgctattac catggtgatg cggttttggc agtacatcaa tgggcgtgga tagcggtttg    5280
actcacgggg atttccaagt ctccacccca ttgacgtcaa tgggagtttg ttttggcacc    5340
aaaatcaacg ggactttcca aaatgtcgta acaactccgc cccattgacg caaatgggcg    5400
gtaggcgtgt acggtgggag gtctatataa gcagagctgg tttagtgaac cgtcagatgg    5460
```

```
taccggcccc gggagacggc ggcggtggcg gcgcgggcag agcaaggacg cggcggatcc    5520
cactcgcaca gcagcgcact cggtgccccg cgcagggtcg gtaccgaatt gccaccaatt    5580
catactcgag atacatatga taagatctgt ttgaatgagg cttcagtact ttacagaatc    5640
gttgcctgca catcttggaa acacttgctg ggattacttc ttcaggttaa cccaacagaa    5700
ggctcgagaa ggtatattgc tgttgacagt gagcggctgg aatacttagc tcagatctag    5760
tgaagccaca gatgtagatc tgagctaagt attccagctg cctactgcct cggaattcaa    5820
ggggctactt taggagcaat tatcttgttt actaaaactg aataccttgc tatctctttg    5880
atacattttt acaaagctga attaaaatgg tataaattaa atcactagat ctatagatat    5940
cataaccggt atagcggccg caagaggtaa gggtttaagg gatggtcggt tggtggggta    6000
ttaatgttta attcctgga gcacctgcct gaaatcactt ttttcaggt tggaatcgat    6060 aatcaacctc tggattacaa aatttgtgaa agattgactg gtattcttaa ctatgttgct    6120
ccttttacgc tatgtggata cgctgcttta atgcctttgt atcatgctat tgcttcccgt    6180
atggctttca ttttctcctc cttgtataaa tcctggttgc tgtctcttta tgaggagttg    6240
tggcccgttg tcaggcaacg tggcgtggtg tgcactgtgt ttgctgacgc aacccccact    6300
ggttggggca ttgccaccac ctgtcagctc ctttccggga ctttcgcttt cccctccct    6360 attgccacgg cggaactcat cgccgcctgc cttgcccgct gctggacagg gctcggctg    6420 ttgggcactg acaattccgt ggtgttgtcg gggaagctga cgtcctttcc atggctgctc    6480
gcctgtgttg ccacctggat tctgcgcggg acgtccttct gctacgtccc ttcggccctc    6540
aatccagcgg accttccttc ccgcggcctg ctgccggctc tgcggcctct tccgcgtctt    6600
cgccttcgcc ctcagacgag tcggatctcc ctttgggccg cctccccgcc tgctgcaggg    6660
cgccatcgtg gatgggagtc cgtgtgtgcc tggagattac cctggacacc tctgcttttt    6720
tttttttact ttagcggttg cctcctaggc ctgactcctt cccatgttga actggaggca    6780
gccacgttag gtgtcaatgt cctggcatca gtatgaacag tcagtagtcc cagggcaggg    6840
ccacacttct cccatcttct gcttccaccc cagcttgtga ttgctagcct cccagagctc    6900
aattgctgtg ccttctagtt gccagccatc tgttgtttgc cctcccccg tgccttcctt    6960 gaccctggaa ggtgccactc ccactgtcct ttcctaataa aatgaggaaa ttgcatcgca    7020
ttgtctgagt aggtgtcatt ctattctggg ggtggggtg gggcaggaca gcaaggggga    7080
ggattgggaa gacaatagca ggcatgctgg ggatgcggtg ggctctatgg acgcgtcggc    7140
cgctgcagct cgagtctaga gctgacggcg cgcctgaaat gtgtgggcgt ggcttaaggg    7200
tgggaaagaa tatataaggt gggggtctta tgtagttttg tatctgtttt gcagcagccg    7260
ccgccgccat gagcaccaac tcgtttgatg gaagcattgt gagctcatat ttgcaacgc    7320 gcatgccccc atgggccggg gtgcgtcaga atgtgatggg ctccagcatt gatggtcgcc    7380
ccgtcctgcc cgcaaactct actaccttga cctacgagac cgtgtctgga acgccgttgg    7440
agactgcagc ctccgccgcc gcttcagccg ctgcagccac cgcccgcggg attgtgactg    7500
actttgcttt cctgagcccg cttgcaagca gtgcagcttc ccgttcatcc gcccgcgatg    7560
acaagttgac ggctctttg gcacaattgg attctttgac ccgggaactt aatgtcgttt    7620
ctcagcagct gttggatctg cgccagcagg tttctgccct gaaggcttcc tcccctccca    7680
atgcggttta aaacataaat aaaaaaccag actctgtttg gatttggatc aagcataagt    7740
gtcttgctgt ctttatttag ggttttgcg cgcgcggtag gcccgggacc agcggtctcg    7800
gtcgttgagg gtcctgtgta ttttttccag gacgtggtaa aggtgactct ggatgttcag    7860
```

```
atacatgggc ataagcccgt ctctggggtg gaggtagcac cactgcagag cttcatgctg   7920
cggggtggtg ttgtagatga tccagtcgta gcaggagcgc tgggcgtggt gcctaaaaat   7980
gtctttcagt agcaagctga ttgccagggg caggcccttg gtgtaagtgt ttacaaagcg   8040
gttaagctgg gatgggtgca tacgtgggga tatgagatgc atcttggact gtattttag    8100
gttggctatg ttcccagcca tatccctccg gggattcatg ttgtgcagaa ccaccagcac   8160
agtgtatccg gtgcacttgg gaaatttgtc atgtagctta aaggaaatg cgtggaagaa    8220
cttggagacg cccttgtgac ctccaagatt ttccatgcat tcgtccataa tgatggcaat   8280
gggcccacgg gcggcggcct gggcgaagat atttctggga tcactaacgt catagttgtg   8340
ttccaggatg agatcgtcat aggccatttt tacaaagcgc gggcggaggg tgccagactg   8400
cggtataatg gttccatccg gcccaggggc gtagttaccc tcacagattt gcatttccca   8460
cgctttgagt tcagatgggg ggatcatgtc tacctgcggg gcgatgaaga aaacggtttc   8520
cggggtaggg gagatcagct gggaagaaag caggttcctg agcagctgcg acttaccgca   8580
gccggtgggc ccgtaaatca cacctattac cgggtgcaac tggtagttaa gagagctgca   8640
gctgccgtca tccctgagca ggggggccac ttcgttaagc atgtccctga ctcgcatgtt   8700
ttccctgacc aaatccgcca gaaggcgctc gccgcccagc gatagcagtt cttgcaagga   8760
agcaaagttt ttcaacggtt tgagaccgtc cgccgtaggc atgcttttga gcgtttgacc   8820
aagcagttcc aggcggtccc acagctcggt cacctgctct acggcatctc gatccagcat   8880
atctcctcgt ttcgcgggtt ggggcggctt tcgctgtacg gcagtagtcg gtgctcgtcc   8940
agacgggcca gggtcatgtc tttccacggg cgcagggtcc tcgtcagcgt agtctgggtc   9000
acggtgaagg ggtgcgctcc gggctgcgcg ctggccaggg tgcgcttgag gctggtcctg   9060
ctggtgctga agcgctgccg gtcttcgccc tgcgcgtcgg ccaggtagca tttgaccatg   9120
gtgtcatagt ccagcccctc cgcggcgtgg cccttggcgc gcagcttgcc cttggaggag   9180
gcgccgcacg aggggcagtg cagactttg agggcgtaga gcttgggcgc gagaaatacc   9240
gattccgggg agtaggcatc cgcgccgcag gccccgcaga cggtctcgca ttccacgagc   9300
caggtgagct ctggccgttc ggggtcaaaa accaggtttc ccccatgctt tttgatgcgt   9360
ttcttacctc tggtttccat gagccggtgt ccacgctcgg tgacgaaaag gctgtccgtg   9420
tccccgtata cagacttgag aggcctgtcc tcgagcggtg ttccgcggtc ctcctcgtat   9480
agaaactcgg accactctga dacaaaggct cgcgtccagg ccagcacgaa ggaggctaag   9540
tgggaggggt agcggtcgtt gtccactagg gggtccactc gctccagggt gtgaagacac   9600
atgtcgccct cttcggcatc aaggaaggtg attggtttgt aggtgtaggc cacgtgaccg   9660
ggtgttcctg aagggggggct ataaaagggg gtggggcgc gttcgtcctc actctcttcc   9720
gcatcgctgt ctgcgagggc cagctgttgg ggtgagtact ccctctgaaa agcgggcatg   9780
acttctgcgc taagattgtc agtttccaaa aacgaggagg atttgatatt cacctggccc   9840
gcggtgatgc ctttgagggt ggccgcatcc atctggtcag aaaagacaat cttttttgttg  9900
tcaagcttgg tggcaaacga cccgtagagg gcgttggaca gcaacttggc gatggagcgc   9960
agggtttggt ttttgtcgcg atcggcgcgc tccttggccg cgatgtttag ctgcacgtat   10020
tcgcgcgcaa cgcaccgcca ttcgggaaag acggtggtgc gctcgtcggg caccaggtgc   10080
acgcgccaac cgcggttgtg cagggtgaca aggtcaacgc tggtggctac ctctccgcgt   10140
aggcgctcgt tggtccagca gaggcggccg cccttgcgcg agcagaatgg cggtaggggg   10200
```

```
tctagctgcg tctcgtccgg ggggtctgcg tccacggtaa agaccccggg cagcaggcgc    10260
gcgtcgaagt agtctatctt gcatccttgc aagtctagcg cctgctgcca tgcgcgggcg    10320
gcaagcgcgc gctcgtatgg gttgagtggg ggaccccatg gcatggggtg ggtgagcgcg    10380
gaggcgtaca tgccgcaaat gtcgtaaacg tagaggggct ctctgagtat tccaagatat    10440
gtagggtagc atcttccacc gcggatgctg gcgcgcacgt aatcgtatag ttcgtgcgag    10500
ggagcgagga ggtcgggacc gaggttgcta cgggcgggct gctctgctcg gaagactatc    10560
tgcctgaaga tggcatgtga gttggatgat atggttggac gctggaagac gttgaagctg    10620
gcgtctgtga gacctaccgc gtcacgcacg aaggaggcgt aggagtcgcg cagcttgttg    10680
accagctcgg cggtgacctg cacgtctagg gcgcagtagt ccagggtttc cttgatgatg    10740
tcatacttat cctgtccctt tttttccac agctcgcggt tgaggacaaa ctcttcgcgg     10800
tctttccagt actcttggat cggaaacccg tcggcctccg aacggtaaga gcctagcatg    10860
tagaactggt tgacgcctg gtaggcgcag catcccttttt ctacgggtag cgcgtatgcc   10920
tgcgcggcct tccggagcga ggtgtgggtg agcgcaaagg tgtccctgac catgactttg    10980
aggtactggt atttgaagtc agtgtcgtcg catccgccct gctcccagag caaaaagtcc    11040
gtgcgctttt tggaacgcgg atttggcagg gcgaaggtga catcgttgaa gagtatcttt    11100
cccgcgcgag gcataaagtt gcgtgtgatg cggaagggtc ccggcacctc ggaacggttg    11160
ttaattacct gggcggcgag cacgatctcg tcaaagccgt tgatgttgtg cccacaatg     11220 taaagttcca agaagcgcgg gatgcccttg atggaaggca attttttaag ttcctcgtag    11280
gtgagctctt caggggagct gagcccgtgc tctgaaaggg cccagtctgc aagatgaggg    11340
ttggaagcga cgaatgagct ccacaggtca cgggccatta gcatttgcag gtggtcgcga    11400
aaggtcctaa actggcgacc tatggccatt ttttctgggg tgatgcagta gaaggtaagc    11460
gggtcttgtt cccagcggtc ccatccaagg ttcgcggcta ggtctcgcgc ggcagtcact    11520
agaggctcat ctccgccgaa cttcatgacc agcatgaagg gcacgagctg cttcccaaag    11580
gcccccatcc aagtataggt ctctacatcg taggtgacaa agagacgctc ggtgcgagga    11640
tgcgagccga tcgggaagaa ctggatctcc cgccaccaat tggaggagtg gctattgatg    11700
tggtgaaagt agaagtccct gcgacgggcc gaacactcgt gctggctttt gtaaaaacgt    11760
gcgcagtact ggcagcggtg cacgggctgt acatcctgca cgaggttgac ctgacgaccg    11820
cgcacaagga agcagagtgg gaatttgagc ccctcgcctg gcgggtttgg ctggtggtct    11880
tctacttcgg ctgcttgtcc ttgaccgtct ggctgctcga ggggagttac ggtggatcgg    11940
accaccacgc cgcgcgagcc caaagtccag atgtccgcgc gcggcggtcg gagcttgatg    12000
acaacatcgc gcagatggga gctgtccatg gtctggagct cccgcggcgt caggtcaggc    12060
gggagctcct gcaggtttac ctcgcataga cgggtcaggg cgcgggctag atccaggtga    12120
tacctaattt ccaggggctg gttggtggcg gcgtcgatgg cttgcaagag gccgcatccc    12180
cgcggcgcga ctacggtacc gcgcggcggg cgtggggccg cggggtgtc cttgatgat    12240 gcatctaaaa gcggtgacgc gggcgagccc ccggaggtag ggggggctcc ggacccgccg    12300
ggagaggggg caggggcacg tcggcgccgc gcgcgggcag gagctggtgc tgcgcgcgta    12360
ggttgctggc gaacgcgacg acgcggcggt tgatctcctg aatctggcgc ctctgcgtga    12420
agacgacggg cccggtgagc ttgagcctga aagagagttc gacagaatca atttcggtgt    12480
cgttgacggc ggcctggcgc aaaatctcct gcacgtctcc tgagttgtct tgataggcga    12540
tctcggccat gaactgctcg atctcttcct cctggagatc tccgcgtccg gctcgctcca    12600
```

```
cggtggcggc gaggtcgttg gaaatgcggg ccatgagctg cgagaaggcg ttgaggcctc   12660
cctcgttcca gacgcggctg tagaccacgc cccttcggc  atcgcgggcg cgcatgacca   12720
cctgcgcgag attgagctcc acgtgccggg cgaagacggc gtagtttcgc aggcgctgaa   12780
agaggtagtt gagggtggtg gcggtgtgtt ctgccacgaa gaagtacata acccagcgtc   12840
gcaacgtgga ttcgttgata tcccccaagg cctcaaggcg ctccatggcc tcgtagaagt   12900
ccacggcgaa gttgaaaaac tgggagttgc gcgccgacac ggttaactcc tcctccagaa   12960
gacggatgag ctcggcgaca gtgtcgcgca cctcgcgctc aaaggctaca ggggcctctt   13020
cttcttcttc aatctcctct tccataaggg cctccccttc ttcttcttct ggcggcggtg   13080
ggggaggggg gacacggcgg cgacgacggc gcaccgggag gcggtcgaca aagcgctcga   13140
tcatctcccc gcggcgacgg cgcatggtct cggtgacggc gcggccgttc tcgcgggggc   13200
gcagttggaa gacgccgccc gtcatgtccc ggttatgggt tggcggggg  ctgccatgcg   13260
gcagggatac ggcgctaacg atgcatctca acaattgttg tgtaggtact ccgccgccga   13320
gggacctgag cgagtccgca tcgaccggat cggaaaacct ctcgagaaag gcgtctaacc   13380
agtcacagtc gcaaggtagg ctgagcaccg tggcgggcgg cagcgggcgg cggtcggggt   13440
tgtttctggc ggaggtgctg ctgatgatgt aattaaagta ggcggtcttg agacggcgga   13500
tggtcgacag aagcaccatg tccttgggtc cggcctgctg aatgcgcagg cggtcggcca   13560
tgccccaggc ttcgttttga catcggcgca ggtctttgta gtagtcttgc atgagccttt   13620
ctaccggcac ttcttcttct ccttcctctt gtcctgcatc tcttgcatct atcgctgcgg   13680
cggcggcgga gtttggccgt aggtggcgcc ctcttcctcc catgcgtgtg accccgaagc   13740
ccctcatcgg ctgaagcagg gctaggtcgg cgacaacgcg ctcggctaat atggcctgct   13800
gcacctgcgt gagggtagac tggaagtcat ccatgtccac aaagcggtgg tatgcgcccg   13860
tgttgatggt gtaagtgcag ttggccataa cggaccagtt aacggtctgg tgacccggct   13920
gcgagagctc ggtgtacctg agacgcgagt aagccctcga gtcaaatacg tagtcgttgc   13980
aagtccgcac caggtactgg tatcccacca aaaagtgcgg cggcggctgg cggtagaggg   14040
gccagcgtag ggtggccggg gctccggggg cgagatcttc aacataagg  cgatgatatc   14100
cgtagatgta cctggacatc caggtgatgc cggcggcggt ggtggaggcg cgcggaaagt   14160
cgcggacgcg gttccagatg ttgcgcagcg gcaaaaagtg ctccatggtc gggacgctct   14220
ggccggtcag gcgcgcgcaa tcgttgacgc tctagaccgt gcaaaaggag agcctgtaag   14280
cgggcactct tccgtggtct ggtggataaa ttcgcaaggg tatcatggcg gacgaccggg   14340
gttcgagccc cgtatccggc cgtccgccgt gatccatgcg gttaccgccc gcgtgtcgaa   14400
cccaggtgtg cgacgtcaga caacggggga gtgctccttt tggcttcctt ccaggcgcgg   14460
cggctgctgc gctagctttt ttggccactg gccgcgcgca gcgtaagcgg ttaggctgga   14520
aagcgaaagc attaagtggc tcgctccctg tagccggagg gttattttcc aagggttgag   14580
tcgcgggacc cccggttcga gtctcggacc ggccggactg cggcgaacgg gggtttgcct   14640
ccccgtcatg caagacccCg cttgcaaatt cctccggaaa cagggacgag ccccttttt    14700
gcttttccca gatgcatccg gtgctgcggc agatgcgccc cctcctcag  cagcggcaag   14760
agcaagagca gcggcagaca tgcagggcac cctcccctcc tcctaccgcg tcaggagggg   14820
cgacatccgc ggttgacgcg gcagcagatg gtgattacga acccccgcgg cgccgggccc   14880
ggcactacct ggacttggag gagggcgagg gcctggcgcg gctaggagcg ccctctcctg   14940
```

```
agcggtaccc aagggtgcag ctgaagcgtg atacgcgtga ggcgtacgtg ccgcggcaga   15000
acctgtttcg cgaccgcgag ggagaggagc ccgaggagat gcgggatcga aagttccacg   15060
cagggcgcga gctgcggcat ggcctgaatc gcgagcggtt gctgcgcgag gaggactttg   15120
agcccgacgc gcgaaccggg attagtcccg cgcgcgcaca cgtggcggcc gccgacctgg   15180
taaccgcata cgagcagacg gtgaaccagg agattaactt tcaaaaaagc tttaacaacc   15240
acgtgcgtac gcttgtggcg cgcgaggagg tggctatagg actgatgcat ctgtgggact   15300
ttgtaagcgc gctggagcaa aacccaaata gcaagccgct catggcgcag ctgttcctta   15360
tagtgcagca cagcagggac aacgaggcat tcagggatgc gctgctaaac atagtagagc   15420
ccgagggccg ctggctgctc gatttgataa acatcctgca gagcatagtg gtgcaggagc   15480
gcagcttgag cctggctgac aaggtggccg ccatcaacta ttccatgctt agcctgggca   15540
agttttacgc ccgcaagata taccataccc cttacgttcc catagacaag gaggtaaaga   15600
tcgaggggtt ctacatgcgc atggcgctga aggtgcttac cttgagcgac gacctgggcg   15660
tttatcgcaa cgagcgcatc cacaaggccg tgagcgtgag ccggcggcgc gagctcagcg   15720
accgcgagct gatgcacagc ctgcaaaggg ccctggctgg cacgggcagc ggcgatagag   15780
aggccgagtc ctactttgac gcgggcgctg acctgcgctg gccccaagc cgacgcgccc    15840
tggaggcagc tggggccgga cctgggctgg cggtggcacc cgcgcgcgct ggcaacgtcg   15900
gcggcgtgga ggaatatgac gaggacgatg agtacgagcc agaggacggc gagtactaag   15960
cggtgatgtt tctgatcaga tgatgcaaga cgcaacggac ccggcggtgc gggcggcgct   16020
gcagagccag ccgtccggcc ttaactccac ggacgactgg cgccaggtca tggaccgcat   16080
catgtcgctg actgcgcgca atcctgacgc gttccggcag cagccgcagg ccaaccggct   16140
ctccgcaatt ctggaagcgg tggtcccggc gcgcgcaaac cccacgcacg agaaggtgct   16200
ggcgatcgta aacgcgctgg ccgaaaacag ggccatccgg cccgacgagg ccggcctggt   16260
ctacgacgcg ctgcttcagc gcgtggctcg ttacaacagc ggcaacgtgc agaccaacct   16320
ggaccggctg gtgggggatg tgcgcgaggc cgtggcgcag cgtgagcgcg cgcagcagca   16380
gggcaacctg ggctccatgg ttgcactaaa cgccttcctg agtacacagc ccgccaacgt   16440
gccgcgggga caggaggact acaccaactt tgtgagcgca ctgcggctaa tggtgactga   16500
gacaccgcaa agtgaggtgt accagtctgg gccagactat ttttccaga ccagtagaca     16560
aggcctgcag accgtaaacc tgagccaggc tttcaaaaac ttgcaggggc tgtgggggt     16620
gcgggctccc acaggcgacc gcgcgaccgt gtctagcttg ctgacgccca actcgcgcct   16680
gttgctgctg ctaatagcgc ccttcacgga cagtggcagc gtgtcccggg acacatacct   16740
aggtcacttg ctgacactgt accgcgaggc cataggtcag gcgcatgtgg acgagcatac   16800
tttccaggag attacaagtg tcagccgcgc gctggggcag gaggacacgg gcagcctgga   16860
ggcaacccta aactacctgc tgaccaaccg gcggcagaag atccctctcgt tgcacagttt   16920
aaacagcgag gaggagcgca tttttgcgcta cgtgcagcag agcgtgagcc ttaacctgat   16980
gcgcgacggg gtaacgccca gcgtggcgct ggacatgacc gcgcgcaaca tggaaccggg   17040
catgtatgcc tcaaaccggc cgtttatcaa ccgcctaatg gactacttgc atcgcgcggc   17100
cgccgtgaac cccgagtatt tcaccaatgc catcttgaac ccgcactggc taccgccccc   17160
tggtttctac accggggggat tcgaggtgcc cgagggtaac gatggattcc tctgggacga   17220
catagacgac agcgtgttt ccccgcaacc gcagaccctg ctagagttgc aacagcgcga   17280
gcaggcagag gcggcgctgc gaaaggaaag cttccgcagg ccaagcagct tgtccgatct   17340
```

```
aggcgctgcg gccccgcggt cagatgctag tagcccattt ccaagcttga tagggtctct  17400
taccagcact cgcaccaccc gcccgcgcct gctgggcgag gaggagtacc taaacaactc  17460
gctgctgcag ccgcagcgcg aaaaaaacct gcctccggca tttcccaaca acgggataga  17520
gagcctagtg gacaagatga gtagatggaa gacgtacgcg caggagcaca gggacgtgcc  17580
aggcccgcgc ccgcccaccc gtcgtcaaag gcacgaccgt cagcggggtc tggtgtggga  17640
ggacgatgac tcggcagacg acagcagcgt cctggatttg ggagggagtg gcaacccgtt  17700
tgcgcacctt cgccccaggc tggggagaat gttttaaaaa aaaaaagca tgatgcaaaa  17760
taaaaaactc accaaggcca tggcaccgag cgttggtttt cttgtattcc ccttagtatg  17820
cggcgcgcgg cgatgtatga ggaaggtcct cctccctcct acgagagtgt ggtgagcgcg  17880
gcgccagtgg cggcggcgct gggttctccc ttcgatgctc ccctggaccc gccgtttgtg  17940
cctccgcggt acctgcggcc taccgggggg agaaacagca tccgttactc tgagttggca  18000
cccctattcg acaccacccg tgtgtacctg gtggacaaca agtcaacgga tgtggcatcc  18060
ctgaactacc agaacgacca cagcaacttt ctgaccacgg tcattcaaaa caatgactac  18120
agcccggggg aggcaagcac acagaccatc aatcttgacg accggtcgca ctggggcggc  18180
gacctgaaaa ccatcctgca taccaacatg ccaaatgtga acgagttcat gtttaccaat  18240
aagtttaagg cgcgggtgat ggtgtcgcgc ttgcctacta aggacaatca ggtggagctg  18300
aaatacgagt gggtggagtt cacgctgccc gagggcaact actccgagac catgaccata  18360
gaccttatga caacgcgat cgtggagcac tacttgaaag tgggcagaca gaacggggtt  18420
ctggaaagcg acatcggggt aaagtttgac acccgcaact tcagactggg gtttgacccc  18480
gtcactggtc ttgtcatgcc tgggtatat acaaacgaag ccttccatcc agacatcatt  18540
ttgctgccag gatgcggggt ggacttcacc cacagccgcc tgagcaactt gttgggcatc  18600
cgcaagcggc aacccttcca ggagggcttt aggatcacct acgatgatct ggagggtggt  18660
aacattcccg cactgttgga tgtggacgcc taccaggcga gcttgaaaga tgacaccgaa  18720
cagggcgggg gtggcgcagg cggcagcaac agcagtggca gcggcgcgga agagaactcc  18780
aacgcggcag ccgcggcaat gcagccggtg gaggacatga acgatcatgc cattcgcggc  18840
gacaccttg ccacgcgggc tgaggagaag cgcgctgagg ccgaagcagc ggccgaagct  18900
gccgccccg ctgcgcaacc cgaggtcgag aagcctcaga gaaaccggt gatcaaacccc  18960
ctgacagagg acagcaagaa acgcagttac aacctaataa gcaatgacag caccttcacc  19020
cagtaccgca gctggtacct tgcatacaac tacggcgacc ctcagaccgg aatccgctca  19080
tggaccctgc tttgcactcc tgacgtaacc tgcggctcgg agcaggtcta ctggtcgttg  19140
ccagacatga tgcaagaccc cgtgaccttc cgctccacgc gccagatcag caactttccg  19200
gtggtgggcg ccgagctgtt gcccgtgcac tccaagagct tctacaacga ccaggccgtc  19260
tactcccaac tcatccgcca gtttacctct ctgacccacg tgttcaatcg ctttcccgag  19320
aaccagattt tggcgcgccc gccagccccc accatcacca ccgtcagtga aaacgttcct  19380
gctctcacag atcacgggac gctaccgctg cgcaacagca tcggaggagt ccagcgagtg  19440
accattactg acgccagacg ccgcacctgc ccctacgttt acaaggccct gggcatagtc  19500
tcgccgcgcg tcctatcgag ccgcacttt tgagcaagca tgtccatcct tatatcgccc  19560
agcaataaca caggctgggg cctgcgcttc ccaagcaaga tgtttggcgg ggccaagaag  19620
cgctccgacc aacacccagt gcgcgtgcgc gggcactacc gcgcgccctg ggcgcgcac  19680
```

```
aaacgcggcc gcactgggcg caccaccgtc gatgacgcca tcgacgcggt ggtggaggag   19740
gcgcgcaact acacgccac gccgccacca gtgtccacag tggacgcggc cattcagacc    19800
gtggtgcgcg agcccggcg ctatgctaaa atgaagagac ggcggaggcg cgtagcacgt    19860
cgccaccgcc gccgacccgg cactgccgcc aacgcgcgg cggcggccct gcttaaccgc    19920
gcacgtcgca ccggccgacg ggcggccatg cgggccgctc gaaggctggc cgcgggtatt   19980
gtcactgtgc cccccaggtc caggcgacga gcggccgccg cagcagccgc ggccattagt    20040
gctatgactc agggtcgcag gggcaacgtg tattgggtgc gcgactcggt tagcggcctg    20100
cgcgtgcccg tgcgcacccg ccccccgcgc aactagattg caagaaaaaa ctacttagac    20160
tcgtactgtt gtatgtatcc agcggcggcg gcgcgcaacg aagctatgtc caagcgcaaa    20220
atcaaagaag agatgctcca ggtcatcgcg ccggagatct atggcccccc gaagaaggaa    20280
gagcaggatt acaagccccg aaagctaaag cgggtcaaaa agaaaaagaa agatgatgat    20340
gatgaacttg acgacgaggt ggaactgctg cacgctaccg cgcccaggcg acgggtacag    20400
tggaaaggtc gacgcgtaaa acgtgttttg cgacccggca ccaccgtagt ctttacgccc    20460
ggtgagcgct ccacccgcac ctacaagcgc gtgtatgatg aggtgtacgg cgacgaggac    20520
ctgcttgagc aggccaacga gcgcctcggg gagtttgcct acgaaagcg gcataaggac    20580 atgctggcgt tgccgctgga cgagggcaac ccaacaccta gcctaaagcc cgtaacactg    20640
cagcaggtgc tgcccgcgct tgcaccgtcc gaagaaaagc gcggcctaaa gcgcgagtct    20700
ggtgacttgg cacccaccgt gcagctgatg gtacccaagc gccagcgact ggaagatgtc    20760
ttggaaaaaa tgaccgtgga acctgggctg gagcccgagg tccgcgtgcg gccaatcaag    20820
caggtggcgc cgggactggg cgtgcagacc gtggacgttc agatacccac taccagtagc    20880
accagtattg ccaccgccac agagggcatg gagacacaaa cgtccccggt tgcctcagcg    20940
gtggcggatg ccgcggtgca ggcggtcgct gcggccgcgt ccaagacctc tacggaggtg    21000 caaacgggacc cgtggatgtt tcgcgtttca gccccccggc gcccgcgcgg ttcgaggaag    21060
tacggcgccg ccagcgcgct actgcccgaa tatgccctac atccttccat tgcgcctacc    21120
cccggctatc gtggctacac ctaccgcccc agaagacgag caactacccg acgccgaacc    21180
accactggaa cccgccgccg ccgtcgccgt cgccagcccg tgctggcccc gatttccgtg    21240
cgcagggtgg ctcgcgaagg aggcaggacc ctggtgctgc caacagcgcg ctaccacccc    21300
agcatcgttt aaaagccggt cttttgtggtt cttgcagata tggccctcac ctgccgcctc    21360
cgtttcccgg tgccgggatt ccgaggaaga atgcaccgta ggaggggcat ggccggccac    21420
ggcctgacgg gcggcatgcg tcgtgcgcac caccggcggc ggcgcgcgtc gcaccgtcgc    21480
atgcgcggcg gtatcctgcc cctccttatt ccactgatcg ccgcggcgat tggcgccgtg    21540
cccggaattg catccgtggc cttgcaggcg cagagacact gattaaaaac aagttgcatg    21600
tggaaaaatc aaaataaaaa gtctggactc tcacgctcgc ttggtcctgt aactattttg    21660
tagaatggaa gacatcaact ttgcgtctct ggccccgcga cacggctcgc gcccgttcat    21720
gggaaactgg caagatatcg gcaccagcaa tatgagcggt ggcgccttca gctgggctc    21780 gctgtggagc ggcattaaaa atttcggttc caccgttaag aactatggca gcaaggcctg    21840
gaacagcagc acaggccaga tgctgaggga taagttgaaa gagcaaaatt ccaacaaaa    21900 ggtggtagat ggcctggcct ctggcattag cggggtggtg gacctggcca accaggcagt    21960
gcaaaataag attaacagta agcttgatcc ccgcctccc gtagaggagc ctccaccggc    22020
cgtggagaca gtgtctccag aggggcgtgg cgaaaagcgt ccgcgccccg acaggaaga    22080
```

```
aactctggtg acgcaaatag acgagcctcc ctcgtacgag gaggcactaa agcaaggcct    22140
gcccaccacc cgtcccatcg cgcccatggc taccggagtg ctgggccagc acacacccgt    22200
aacgctggac ctgcctcccc ccgccgacac ccagcagaaa cctgtgctgc caggcccgac    22260
cgccgttgtt gtaacccgtc ctagccgcgc gtccctgcgc cgcgccgcca gcggtccgcg    22320
atcgttgcgg cccgtagcca gtggcaactg gcaaagcaca ctgaacagca tcgtgggtct    22380
gggggtgcaa tccctgaagc gccgacgatg cttctgaata gctaacgtgt cgtatgtgtg    22440
tcatgtatgc gtccatgtcg ccgccagagg agctgctgag ccgccgcgcg cccgctttcc    22500
aagatggcta ccccttcgat gatgccgcag tggtcttaca tgcacatctc gggccaggac    22560
gcctcggagt acctgagccc cgggctggtg cagtttgccc gcgccaccga cgtacttc    22620 agcctgaata caagtttag aaaccccacg gtggcgccta cgcacgacgt gaccacagac    22680
cggtcccagc gtttgacgct gcggttcatc cctgtggacc gtgaggatac tgcgtactcg    22740
tacaaggcgc ggttcaccct agctgtgggt gataaccgtg tgctggacat ggcttccacg    22800
tactttgaca tccgcggcgt gctggacagg ggccctactt ttaagcccta ctctggcact    22860
gcctacaacg ccctggctcc caagggtgcc ccaaatcctt gcgaatggga tgaagctgct    22920
actgctcttg aaataaacct agaagaagag gacgatgaca acgaagacga agtagacgag    22980
caagctgagc agcaaaaaac tcacgtattt gggcaggcgc cttattctgg tataaatatt    23040
acaaaggagg gtattcaaat aggtgtcgaa ggtcaaacac ctaaatatgc cgataaaaca    23100
tttcaacctg aacctcaaat aggagaatct cagtggtacg aaactgaaat taatcatgca    23160
gctgggagag tccttaaaaa gactacccca atgaaaccat gttacggttc atatgcaaaa    23220
cccacaaatg aaaatggagg gcaaggcatt cttgtaaagc aacaaaatgg aaagctagaa    23280
agtcaagtgg aaatgcaatt tttctcaact actgaggcga ccgcaggcaa tggtgataac    23340
ttgactccta aagtggtatt gtacagtgaa gatgtagata tagaaacccc agacactcat    23400
atttcttaca tgcccactat taaggaaggt aactcacgag aactaatggg ccaacaatct    23460
atgcccaaca ggcctaatta cattgctttt agggacaatt ttattggtct aatgtattac    23520
aacagcacgg gtaatatggg tgttctggcg ggccaagcat cgcagttgaa tgctgttgta    23580
gatttgcaag acagaaacac agagctttca taccagcttt tgcttgattc cattggtgat    23640
agaaccaggt acttttctat gtggaatcag gctgttgaca gctatgatcc agatgttaga    23700
attattgaaa atcatggaac tgaagatgaa cttccaaatt actgctttcc actgggaggt    23760
gtgattaata cagagactct taccaaggta aaacctaaaa caggtcagga aaatggatgg    23820
gaaaaagatg ctacagaatt ttcagataaa aatgaaataa gagttggaaa taattttgcc    23880
atggaaatca atctaaatgc caacctgtgg agaaatttcc tgtactccaa catagcgctg    23940
tatttgcccg acaagctaaa gtacagtcct tccaacgtaa aaatttctga taacccaaac    24000
acctacgact acatgaacaa gcgagtggtg gctcccgggt tagtggactg ctacattaac    24060
cttggagcac gctggtccct tgactatatg gacaacgtca acccatttaa ccaccaccgc    24120
aatgctggcc tgcgctaccg ctcaatgttg ctgggcaatg gtcgctatgt gcccttccac    24180
atccaggtgc ctcagaagtt ctttgccatt aaaaacctcc ttctcctgcc gggctcatac    24240
acctacgagt ggaacttcag gaaggatgtt aacatggttc tgcagagctc cctaggaaat    24300
gacctaaggg ttgacggagc cagcattaag tttgatagca tttgccttta cgccaccttc    24360
ttccccatgg cccacaacac cgcctccacg cttgaggcca tgcttagaaa cgacaccaac    24420
```

```
gaccagtcct ttaacgacta tctctccgcc gccaacatgc tctaccctat acccgccaac   24480
gctaccaacg tgcccatatc catccctcc cgcaactggg cggctttccg cggctgggcc    24540
ttcacgcgcc ttaagactaa ggaaacccca tcactgggct cgggctacga cccttattac   24600
acctactctg gctctatacc ctacctagat ggaaccttt acctcaacca cacctttaag    24660
aaggtggcca ttacctttga ctcttctgtc agctggcctg gcaatgaccg cctgcttacc   24720
cccaacgagt ttgaaattaa gcgctcagtt gacggggagg gttacaacgt tgcccagtgt   24780
aacatgacca aagactggtt cctggtacaa atgctagcta actacaacat tggctaccag   24840
ggcttctata tcccagagag ctacaaggac cgcatgtact ccttctttag aaacttccag   24900
cccatgagcc gtcaggtggt ggatgatact aaatacaagg actaccaaca ggtgggcatc   24960
ctacaccaac acaacaactc tggatttgtt ggctaccttg cccccaccat gcgcgaagga   25020
caggcctacc ctgctaactt ccctatccg cttataggca agaccgcagt tgacagcatt    25080
acccagaaaa agtttctttg cgatcgcacc ctttggcgca tcccattctc cagtaacttt   25140
atgtccatgg gcgcactcac agacctgggc caaaaccttc tctacgccaa ctccgcccac   25200
gcgctagaca tgacttttga ggtggatccc atggacgagc ccacccttct ttatgttttg   25260
tttgaagtct ttgacgtggt ccgtgtgcac cggccgcacc gcggcgtcat cgaaaccgtg   25320
tacctgcgca cgcccttctc ggccggcaac gccacaacat aaagaagcaa gcaacatcaa   25380
caacagctgc cgccatgggc tccagtgagc aggaactgaa agccattgtc aaagatcttg   25440
gttgtgggcc atattttttg ggcacctatg acaagcgctt tccaggcttt gtttctccac   25500
acaagctcgc ctgcgccata gtcaatacgg ccggtcgcga gactggggc gtacactgga    25560 tggcctttgc ctggaacccg cactcaaaaa catgctacct ctttgagccc tttggctttt   25620
ctgaccagcg actcaagcag gtttaccagt ttgagtacga gtcactcctg cgccgtagcg   25680
ccattgcttc ttcccccgac cgctgtataa cgctggaaaa gtccacccaa agcgtacagg   25740
ggcccaactc ggccgcctgt ggactattct gctgcatgtt tctccacgcc tttgccaact   25800
ggccccaaac tcccatggat cacaacccca ccatgaacct tattaccggg gtacccaact   25860
ccatgctcaa cagtccccag gtacagccca ccctgcgtcg caaccaggaa cagctctaca   25920
gcttcctgga gcgccactcg ccctacttcc gcagccacag tgcgcagatt aggagcgcca   25980
cttctttttg tcacttgaaa aacatgtaaa aataatgtac tagagacact ttcaataaag   26040
gcaaatgctt ttatttgtac actctcgggt gattatttac ccccacccctt gccgtctgcg   26100 ccgtttaaaa atcaaagggg ttctgccgcg catcgctatg cgccactggc agggacacgt   26160
tgcgatactg gtgtttagtg ctccacttaa actcaggcac aaccatccgc ggcagctcgg   26220
tgaagttttc actccacagg ctgcgcacca tcaccaacgc gtttagcagg tcggcgcccg   26280
atatcttgaa gtcgcagttg gggcctccgc cctgcgcgcg cgagttgcga tacacagggt   26340
tgcagcactg gaacactatc agcgccgggt ggtgcacgct ggccagcacg ctcttgtcgg   26400
agatcagatc cgcgtccagg tcctccgcgt tgctcagggc gaacggagtc aactttggta   26460
gctgccttcc caaaagggc gcgtgccag gctttgagtt gcactcgcac cgtagtggca   26520
tcaaaaggtg accgtgcccg gtctgggcgt taggatacag cgcctgcata aaagccttga   26580
tctgcttaaa agccacctga gcctttgcgc cttcagagaa gaacatgccg caagacttgc   26640
cggaaaactg attggccgga caggccgcgt cgtgcacgca gcaccttgcg tcggtgttgg   26700
agatctgcac cacatttcgg ccccaccggt tcttcacgat cttggccttg ctagactgct   26760
ccttcagcgc gcgctgcccg ttttcgctcg tcacatccat ttcaatcacg tgctccttat   26820
```

```
ttatcataat gcttccgtgt agacacttaa gctcgccttc gatctcagcg cagcggtgca   26880
gccacaacgc gcagcccgtg ggctcgtgat gcttgtaggt cacctctgca aacgactgca   26940
ggtacgcctg caggaatcgc cccatcatcg tcacaaaggt cttgttgctg gtgaaggtca   27000
gctgcaaccc gcggtgctcc tcgttcagcc aggtcttgca tacggccgcc agagcttcca   27060
cttggtcagg cagtagtttg aagttcgcct ttagatcgtt atccacgtgg tacttgtcca   27120
tcagcgcgcg cgcagcctcc atgcccttct cccacgcaga cacgatcggc acactcagcg   27180
ggttcatcac cgtaatttca ctttccgctt cgctgggctc ttcctcttcc tcttgcgtcc   27240
gcataccacg cgccactggg tcgtcttcat tcagccgccg cactgtgcgc ttacctcctt   27300
tgccatgctt gattagcacc ggtgggttgc tgaaacccac catttgtagc gccacatctt   27360
ctctttcttc ctcgctgtcc acgattacct ctggtgatgg cgggcgctcg ggcttgggag   27420
aagggcgctt cttttcttc ttgggcgcaa tggccaaatc cgccgccgag gtcgatggcc   27480
gcgggctggg tgtgcgcggc accagcgcgt cttgtgatga gtcttcctcg tcctcggact   27540
cgatacgccg cctcatccgc ttttttgggg gcgcccgggg aggcggcggc gacggggacg   27600
gggacgacac gtcctccatg gttggggac gtcgcgccgc accgcgtccg cgctcggggg   27660
tggtttcgcg ctgctcctct tcccgactgg ccatttcctt ctcctatagg cagaaaaga    27720
tcatggagtc agtcgagaag aaggacagcc taaccgcccc ctctgagttc gccaccaccg   27780
cctccaccga tgccgccaac gcgcctacca ccttccccgt cgaggcaccc ccgcttgagg   27840
aggaggaagt gattatcgag caggacccag gttttgtaag cgaagacgac gaggaccgct   27900
cagtaccaac agaggataaa aagcaagacc aggacaacgc agaggcaaac gaggaacaag   27960
tcgggcgggg ggacgaaagg catggcgact acctagatgt gggagacgac gtgctgttga   28020
agcatctgca gcgccagtgc gccattatct gcgacgcgtt gcaagagcgc agcgatgtgc   28080
ccctcgccat agcggatgtc agccttgcct acgaacgcca cctattctca ccgcgcgtac   28140
cccccaaacg ccaagaaaac ggcacatgcg agcccaaccc gcgcctcaac ttctaccccg   28200
tatttgccgt gccagaggtg cttgccacct atcacatctt tttccaaaac tgcaagatac   28260
ccctatcctg ccgtgccaac cgcagccgag cggacaagca gctggccttg cggcagggcg   28320
ctgtcatacc tgatatcgcc tcgctcaacg aagtgccaaa aatctttgag ggtcttggac   28380
gcgacgagaa gcgcgcggca aacgctctgc aacaggaaaa cagcgaaaat gaaagtcact   28440
ctggagtgtt ggtggaactc gagggtgaca acgcgcgcct agccgtacta aaacgcagca   28500
tcgaggtcac ccactttgcc tacccggcac ttaacctacc ccccaaggtc atgagcacag   28560
tcatgagtga gctgatcgtg cgccgtgcgc agccctgga gagggatgca aatttgcaag   28620
aacaaacaga ggagggccta cccgcagttg gcgacgagca gctagcgcgc tggcttcaaa   28680
cgcgcgagcc tgccgacttg gaggagcgac gcaaactaat gatggccgca gtgctcgtta   28740
ccgtggagct tgagtgcatg cagcggttct ttgctgaccc ggagatgcag cgcaagctag   28800
aggaaacatt gcactacacc tttcgacagg gctacgtacg ccaggcctgc aagatctcca   28860
acgtggagct ctgcaacctg gtctcctacc ttggaatttt gcacgaaaac cgccttgggc   28920
aaaacgtgct tcattccacg ctcaagggcg aggcgcgccg cgactacgtc cgcgactgcg   28980
tttacttatt tctatgctac acctggcaga cggccatggg cgtttggcag cagtgcttgg   29040
aggagtgcaa cctcaaggag ctgcagaaac tgctaaagca aaacttgaag gacctatgga   29100
cggccttcaa cgagcgctcc gtggccgcgc acctggcgga catcatttc cccgaacgcc    29160
```

```
tgcttaaaac cctgcaacag ggtctgccag acttcaccag tcaaagcatg ttgcagaact   29220
ttaggaactt tatcctagag cgctcaggaa tcttgcccgc cacctgctgt gcacttccta   29280
gcgactttgt gcccattaag taccgcgaat gccctccgcc gctttggggc cactgctacc   29340
ttctgcagct agccaactac cttgcctacc actctgacat aatggaagac gtgagcggtg   29400
acggtctact ggagtgtcac tgtcgctgca acctatgcac cccgcaccgc tccctggttt   29460
gcaattcgca gctgcttaac gaaagtcaaa ttatcggtac ctttgagctg cagggtccct   29520
cgcctgacga aaagtccgcg gctccggggt tgaaactcac tccggggctg tggacgtcgg   29580
cttaccttcg caaatttgta cctgaggact accacgccca cgagattagg ttctacgaag   29640
accaatcccg cccgccaaat gcggagctta ccgcctgcgt cattacccag ggccacattc   29700
ttggccaatt gcaagccatc aacaaagccc gccaagagtt tctgctacga aagggacggg   29760
gggtttactt ggaccccagg tccggcgagg agctcaaccc aatccccccg ccgccgcagc   29820
cctatcagca gcagccgcgg gcccttgctt cccaggatgg cacccaaaaa gaagctgcag   29880
ctgccgccgc cacccacgga cgaggaggaa tactgggaca gtcaggcaga ggaggttttg   29940
gacgaggagg aggaggacat gatggaagac tgggagagcc tagacgagga agcttccgag   30000
gtcgaagagg tgtcagacga aacaccgtca ccctcggtcg cattcccctc gccggcgccc   30060
cagaaatcgg caaccggttc cagcatggct acaacctccg ctcctcaggc gccgccggca   30120
ctgcccgttc gccgacccaa ccgtagatgg gacaccactg gaaccagggc cggtaagtcc   30180
aagcagccgc cgccgttagc ccaagagcaa caacagcgcc aaggctaccg ctcatggcgc   30240
gggcacaaga acgccatagt tgcttgcttg caagactgtg ggggcaacat ctccttcgcc   30300
cgccgctttc ttctctacca tcacggcgtg gccttccccc gtaacatcct gcattactac   30360
cgtcatctct acagcccata ctgcaccggc ggcagcggca cggcagcaa cagcagcggc   30420 cacacagaag caaaggcgac cggatagcaa gactctgaca aagcccaaga aatccacagc   30480
ggcggcagca gcaggaggag gagcgctgcg tctggcgccc aacgaacccg tatcgacccg   30540
cgagcttaga aacaggattt ttcccactct gtatgctata tttcaacaga gcaggggcca   30600
agaacaagag ctgaaaataa aaaacaggtc tctgcgatcc ctcacccgca gctgcctgta   30660
tcacaaaagc gaagatcagc ttcggcgcac gctggaagac gcggaggctc tcttcagtaa   30720
atactgcgcg ctgactctta aggactagtt tcgcgccctt tctcaaattt aagcgcgaaa   30780
actacgtcat ctccagcggc cacacccggc gccagcacct gtcgtcagcg ccatttatga   30840
gcaaggaaat tccacgcccc tacatgtgga gttaccagcc acaaatggga cttgcggctg   30900
gagctgccca agactactca acccgaataa actacatgag cgcgggaccc cacatgatat   30960
cccgggtcaa cggaatacgc gcccaccgaa accgaattct cctggaacag gcggctatta   31020
ccaccacacc tcgtaataac cttaatcccc gtagttggcc cgctgccctg gtgtaccagg   31080
aaagtcccgc tcccaccact gtggtacttc ccagagacgc ccaggccgaa gttcagatga   31140
ctaactcagg ggcgcagctt gcgggcggct ttcgtcacag ggtgcggtcg cccgggcagg   31200
gtataactca cctgacaatc agagggcgag gtattcagct caacgacgag tcggtgagct   31260
cctcgcttgg tctccgtccg gacgggacat ttcagatcgg cggcgccggc cgctcttcat   31320
tcacgcctcg tcaggcaatc ctaactctgc agacctcgtc ctctgagccg cgctctggag   31380
gcattggaac tctgcaattt attgaggagt tgtgccatc ggtctacttt aaccccttct   31440
cgggacctcc cggccactat ccggatcaat ttattcctaa ctttgacgcg gtaaaggact   31500
cggcggacgg ctacgactga atgttaagtg gagaggcaga gcaactgcgc ctgaaacacc   31560
```

```
tggtccactg tcgccgccac aagtgctttg cccgcgactc cggtgagttt tgctactttg    31620
aattgcccga ggatcatatc gagggcccgg cgcacggcgt ccggcttacc gcccagggag    31680
agcttgcccg tagcctgatt cgggagttta cccagcgccc cctgctagtt gagcgggaca    31740
ggggaccctg tgttctcact gtgatttgca actgtcctaa ccctggatta caatttaaat    31800
gcggtctcaa agatcttatt ccctttaact aataaaaaaa aataataaag catcacttac    31860
ttaaaatcag ttagcaaatt tctgtccagt ttattcagca gcacctcctt gcctcctcc     31920 cagctctggt attgcagctt cctcctggct gcaaactttc tccacaatct aaatggaatg    31980
tcagtttcct cctgttcctg tccatccgca cccactatct tcatgttgtt gcagatgaag    32040
cgcgcaagac cgtctgaaga taccttcaac cccgtgtatc catatgacac ggaaaccggt    32100
cctccaactg tgccttttct tactcctccc tttgtatccc ccaatgggtt tcaagagagt    32160 cccccctgggg tactctcttt gcgcctatcc gaacctctag ttacctccaa tggcatgctt    32220
gcgctcaaaa tgggcaacgg cctctctctg gacgaggccg gcaaccttac ctcccaaaat    32280
gtaaccactg tgagcccacc tctcaaaaaa accaagtcaa acataaacct ggaaatatct    32340
gcacccctca cagttacctc agaagcccta actgtggctg ccgccgcacc tctaatggtc    32400
gcgggcaaca cactcaccat gcaatcacag gccccgctaa ccgtgcacga ctccaaactt    32460
agcattgcca cccaaggacc cctcacagtg tcagaaggaa agctagccct gcaaacatca    32520 ggcccccctca ccaccaccga tagcagtacc cttactatca ctgcctcacc ccctctaact    32580
actgccactg gtagcttggg cattgacttg aaagagccca tttatacaca aaatggaaaa    32640
ctaggactaa agtacggggc tcctttgcat gtaacagacg acctaaacac tttgaccgta    32700
gcaactggtc caggtgtgac tattaataat acttccttgc aaactaaagt tactggagcc    32760
ttgggttttg attcacaagg caatatgcaa cttaatgtag caggaggact aaggattgat    32820
tctcaaaaca gacgccttat acttgatgtt agttatccgt ttgatgctca aaaccaacta    32880
aatctaagac taggacaggg ccctctttt ataaactcag cccacaactt ggatattaac    32940
tacaacaaag gccttacttt gtttacagct tcaaacaatt ccaaaaagct tgaggttaac    33000
ctaagcactg ccaaggggtt gatgtttgac gctacagcca tagccattaa tgcaggagat    33060
gggcttgaat ttggttcacc taatgcacca aacacaaatc ccctcaaaac aaaaattggc    33120
catggcctag aatttgattc aaacaaggct atggttccta aactaggaac tggccttagt    33180
tttgacagca caggtgccat tacagtagga aacaaaaata atgataagct aactttgtgg    33240
accacaccag ctccatctcc taactgtaga ctaaatgcag agaaagatgc taaactcact    33300
ttggtcttaa caaaatgtgg cagtcaaata cttgctacag tttcagtttt ggctgttaaa    33360
ggcagtttgc tccaatatc tggaacagtt caaagtgctc atcttattat aagatttgac    33420
gaaaatggag tgctactaaa caattccttc ctggacccag aatattggaa ctttagaaat    33480
ggagatctta ctgaaggcac agcctataca acgctgttg gatttatgcc taacctatca    33540
gcttatccaa aatctcacgg taaaactgcc aaaagtaaca ttgtcagtca gtttacttta    33600
aacggagaca aaactaaacc tgtaacacta accattacac taaacggtac acaggaaaca    33660
ggagacacaa ctccaagtgc atactctatg tcattttcat gggactggtc tggccacaac    33720
tacattaatg aaatatttgc cacatcctct tacactttt catacattgc ccaagaataa    33780
agaatcgttt gtgttatgtt tcaacgtgtt tattttcaa ttgcagaaaa tttcaagtca    33840
tttttcattc agtagtatag ccccaccacc acatagctta tacagatcac cgtaccttaa    33900
```

```
tcaaactcac agaaccctag tattcaacct gccacctccc tcccaacaca cagagtacac  33960
agtcctttct ccccggctgg ccttaaaaag catcatatca tgggtaacag acatattctt  34020
aggtgttata ttccacacgg tttcctgtcg agccaaacgc tcatcagtga tattaataaa  34080
ctccccgggc agctcactta agttcatgtc gctgtccagc tgctgagcca caggctgctg  34140
tccaacttgc ggttgcttaa cgggcggcga aggagaagtc cacgcctaca tgggggtaga  34200
gtcataatcg tgcatcagga tagggcggtg gtgctgcagc agcgcgcgaa taaactgctg  34260
ccgccgccgc tccgtcctgc aggaatacaa catggcagtg gtctcctcag cgatgattcg  34320
caccgcccgc agcataaggc gccttgtcct ccgggcacag cagcgcaccc tgatctcact  34380
taaatcagca cagtaactgc agcacagcac cacaatattg ttcaaaatcc cacagtgcaa  34440
ggcgctgtat ccaaagctca tggcggggac cacagaaccc acgtggccat cataccacaa  34500
gcgcaggtag attaagtggc gaccctcat aaacacgctg gacataaaca ttacctcttt   34560
tggcatgttg taattcacca cctcccggta ccatataaac ctctgattaa acatggcgcc  34620
atccaccacc atcctaaacc agctggccaa aacctgcccg ccggctatac actgcaggga  34680
accgggactg gaacaatgac agtggagagc ccaggactcg taaccatgga tcatcatgct  34740
cgtcatgata tcaatgttgg cacaacacag gcacacgtgc atacacttcc tcaggattac  34800
aagctcctcc cgcgttagaa ccatatccca gggaacaacc cattcctgaa tcagcgtaaa  34860
tcccacactg cagggaagac ctcgcacgta actcacgttg tgcattgtca aagtgttaca  34920
ttcgggcagc agcggatgat cctccagtat ggtagcgcgg gtttctgtct caaaaggagg  34980
tagacgatcc ctactgtacg gagtgcgccg agacaaccga gatcgtgttg gtcgtagtgt  35040
catgccaaat ggaacgccgg acgtagtcat atttcctgaa gcaaaccag gtgcgggcgt   35100 gacaaacaga tctgcgtctc cggtctcgcc gcttagatcg ctctgtgtag tagttgtagt  35160
atatccactc tctcaaagca tccaggcgcc ccctggcttc gggttctatg taaactcctt  35220
catgcgccgc tgccctgata acatccacca ccgcagaata agccacaccc agccaaccta  35280
cacattcgtt ctgcgagtca cacacgggag gagcgggaag agctggaaga accatgtttt  35340 ttttttttatt ccaaaagatt atccaaaacc tcaaaatgaa gatctattaa gtgaacgcgc  35400
tcccctccgg tggcgtggtc aaactctaca gccaaagaac agataatggc atttgtaaga  35460
tgttgcacaa tggcttccaa aaggcaaacg gccctcacgt ccaagtggac gtaaaggcta  35520
aacccttcag ggtgaatctc ctctataaac attccagcac cttcaaccat gcccaaataa  35580
ttctcatctc gccaccttct caatatatct ctaagcaaat cccgaatatt aagtccggcc  35640
attgtaaaaa tctgctccag agcgccctcc accttcagcc tcaagcagcg aatcatgatt  35700
gcaaaaattc aggttcctca cagacctgta taagattcaa aagcggaaca ttaacaaaaa  35760
taccgcgatc ccgtaggtcc cttcgcaggg ccagctgaac ataatcgtgc aggtctgcac  35820
ggaccagcgc ggccacttcc ccgccaggaa ccatgacaaa agaacccaca ctgattatga  35880
cacgcatact cggagctatg ctaaccagcg tagccccgat gtaagcttgt tgcatgggcg  35940
gcgatataaa atgcaaggtg ctgctcaaaa aatcaggcaa agcctcgcgc aaaaaagaaa  36000
gcacatcgta gtcatgctca tgcagataaa ggcaggtaag ctccggaacc accacagaaa  36060
aagacaccat ttttctctca aacatgtctg cgggtttctg cataaacaca aataaaaata  36120
acaaaaaaac atttaaacat tagaagcctg tcttacaaca ggaaaaacaa cccttataag  36180
cataagacgg actacggcca tgccggcgtg accgtaaaaa aactggtcac cgtgattaaa  36240
aagcaccacc gacagctcct cggtcatgtc cggagtcata atgtaagact cggtaaacac  36300
```

```
atcaggttga ttcacatcgg tcagtgctaa aaagcgaccg aaatagcccg ggggaataca    36360
tacccgcagg cgtagagaca acattacagc ccccatagga ggtataacaa aattaatagg    36420
agagaaaaac acataaacac ctgaaaaacc ctcctgccta ggcaaaatag caccctcccg    36480
ctccagaaca acatacagcg cttccacagc ggcagccata acagtcagcc ttaccagtaa    36540
aaaagaaaac ctattaaaaa aacaccactc gacacggcac cagctcaatc agtcacagtg    36600
taaaaagggg ccaagtgcag agcgagtata taggacta aaaaatgacg taacggttaa       36660
agtccacaaa aaacacccag aaaaccgcac gcgaacctac gcccagaaac gaaagccaaa    36720
aaacccacaa cttcctcaaa tcgtcacttc cgttttccca cgttacgtca cttcccattt    36780
taagaaaact acaattccca acacatacaa gttactccgc cctaaaacct acgtcacccg    36840
ccccgttccc acgccccgcg ccacgtcaca aactccaccc cctcattatc atattggctt    36900
caatccaaaa taaggtatat tattgatgat gtagggataa cagggtaata aatccgggga    36960
tcctctagag tcgacctgca ggcatgcaag cttggcgtaa tcatggtcat agctgtttcc    37020
tgtgtgaaat tgttatccgc tcacaattcc acacaacata cgagccggaa gcataaagtg    37080
taaagcctgg ggtgcctaat gagtgagcta                                    37110
```

<210> SEQ ID NO 23
<211> LENGTH: 37999
<212> TYPE: DNA
<213> ORGANISM: Artificial Sequence
<220> FEATURE:
<223> OTHER INFORMATION: Synthetic adenovirus vector

<400> SEQUENCE: 23

```
agttccactg agcgtcagac cccttaataa gatgatcttc ttgagatcgt tttggtctgc      60
gcgtaatctc ttgctctgaa aacgaaaaaa ccgccttgca gggcggtttt tcgaaggttc     120
tctgagctac caactctttg aaccgaggta actggcttgg aggagcgcag tcaccaaaac     180
ttgtcctttc agtttagcct taaccggcgc atgacttcaa gactaactcc tctaaatcaa     240
ttaccagtgg ctgctgccag tggtgctttt gcatgtcttt ccgggttgga ctcaagacga     300
tagttaccgg ataaggcgca gcggtcggac tgaacggggg gttcgtgcat acagtccagc     360
ttggagcgaa ctgcctaccc ggaactgagt gtcaggcgtg gaatgagaca acgcggcca     420 taacagcgga atgacaccgg taaaccgaaa ggcaggaaca ggagagcgca cgagggagcc     480
gccaggggaa acgcctggta tctttatagt cctgtcgggt ttcgccacca ctgatttgag     540
cgtcagattt cgtgatgctt gtcagggggg cggagcctat ggaaaaacgg ctttgccgcg     600
gccctctcac ttccctgtta agtatcttcc tggcatcttc caggaaatct ccgccccgtt     660
cgtaagccat ttccgctcgc cgcagtcgaa cgaccgagcg tagcgagtca gtgagcgagg     720
aagcggaata tatcctgtat cacatattct gctgacgcac cggtgcagcc ttttttctcc     780
tgccacatga agcacttcac tgacaccctc atcagtgcca acatagtaag ccagtataca     840
ctccgctagc gctgaggtct gcctcgtgaa gaaggtgttg ctgactcata ccaggcctga     900
atcgccccat catccagcca gaaagtgagg gagccacggt tgatgagagc tttgttgtag     960
gtggaccagt tggtgatttt gaacttttgc tttgccacgg aacggtctgc gttgtcggga    1020
agatgcgtga tctgatcctt caactcagca aaagttcgat ttattcaaca agccacgtt    1080 gtgtctcaaa atctctgatg ttacattgca caagataaaa atatatcatc atgaacaata    1140
aaactgtctg cttacataaa cagtaataca aggggtgttg atactctcag tacaatctgc    1200
```

```
tctgatgccg catagttaag ccagtatctg ctccctgctt gtgtgttgga ggtcgctgag    1260
tagtgcgcga gcaaaattta agctacaaca aggcaaggct tgaccgacaa ttgcatgaag    1320
aatctgctta gggttaggcg ttttgcgctg cttcgcgatg tacgggccag atatacgcgt    1380
atctgagggg actagggtgt gtttaggcga aaagcgggc ttcggttgta cgcggttagg     1440
agtcccctca ggatatagta gtttcgcttt tgcataggga gggggaaatg tagtcttatg    1500
caatactctt gtagtcttgc aacatggtaa cgatgagtta gcaacatgcc ttacaaggag    1560
agaaaaagca ccgtgcatgc cgattggtgg aagtaaggtg gtacgatcgt gccttattag    1620
gaaggcaaca gacgggtctg acatggattg gacgaaccac tgaattccgc attgcagaga    1680
tattgtattt aagtgcctag ctcgatacaa taaacgccat ttgaccattc accacattgg    1740
tgtgcacctc caagctgggt acggatccgg ccttgccggc ctcgagcggc cgctagcgcc    1800
gccactatgg gatcaagatc gccaaaaaag aagagaaagg tgccgaagaa gcatgcagca    1860
ccaccaaaaa aaaacgaaa agtagaagac ccacgattta tgtacccata cgatgttcct     1920
gactatgcgg gtatgaaaaa catcaaaaaa aaccaggtaa tgaacctggg tccgaactct    1980
aaactgctga agaatacaa atcccagctg atcgaactga acatcgaaca gttcgaagca     2040
ggtatcggtc tgatcctggg tgatgcttac atccgttctc gtgatgaagg taaaacctac    2100
tgtatgcagt tcgagtggaa aaacaaagca tacatggacc acgtatgtct gctgtacgat    2160
cagtgggtac tgtccccgcc gcacaaaaaa gaacgtgtta accacctggg taacctggta    2220
atcacctggg gcgcccagac tttcaaacac caagctttca acaaactggc taacctgttc    2280
atcgttaaca caaaaaaac catcccgaac aacctggttg aaaactacct gaccccgatg     2340
tctctggcat actggttcat ggatgatggt ggtaaatggg attacaacaa aaactctacc    2400
aacaaatcga tcgtactgaa cacccagtct ttcacttttcg aagaagtaga ataccctggtt  2460
aagggtctgc gtaacaaatt ccaactgaac tgttacgtaa aaatcaacaa aaacaaaccg    2520
atcatctaca tcgattctat gtcttacctg atcttctaca acctgatcaa accgtacctg    2580
atcccgcaga tgatgtacaa actgccgaac actatctcct ccgaaacttt cctgaaataa    2640
ggtaccgatc cagacatgat aagatacatt gatgagtttg gacaaaccac aactagaatg    2700
cagtgaaaaa aatgctttat ttgtgaaatt tgtgatgcta ttgctttatt tgtaaccatt    2760
ataagctgca ataaacaagt taacaacaac aattgcattc attttatgtt tcaggttcag    2820
ggggaggtgt gggaggtttt ttaaagcaag taaaacctct acaaatgtgg tatggctgat    2880
tatgatcatc gtaaacttgg tctgacagtt accaatgctt aatcagtgag gcacctatct    2940
cagcgatctg tctatttcgt tcatccatag ttgcctgact ccccgtcgtg tagataacta    3000
cgatacggga gggcttacca tctggcccca gtgctgcaat gataccgcga gcccacgct    3060
caccggctcc agatttatca gcaataaacc agccagccgg aagggccgag cgcagaagtg    3120
gtcctgcaac tttatccgcc tccatccagt ctattaattg ttgccgggaa gctagagtaa    3180
gtagttcgcc agttaatagt ttgcgcaacg ttgttgccat tgctacaggc atcgtggtgt    3240
cacgctcgtc gtttggtatg gcttcattca gctccggttc caacgatca aggcgagtta     3300
catgatcccc catgttgtgc aaaaaagcgg ttagctcctt cggtcctccg atcgttgtca    3360
gaagtaagtt ggccgcagtg ttatcactca tggttatggc agcactgcat aattctctta    3420
ctgtcatgcc atccgtaaga tgcttttctg tgactggtga gtactcaacc aagtcattct    3480
gagaatagtg tatgcggcga ccgagttgct cttgcccggc gtcaatacgg gataataccg    3540
cgccacatag cagaacttta aaagtgctca tcattggaaa acgttcttcg ggcgaaaac    3600
```

```
tctcaaggat cttaccgctg ttgagatcca gttcgatgta acccactcgt gcacccaact    3660
gatcttcagc atcttttact ttcaccagcg tttctgggtg agcaaaaaca ggaaggcaaa    3720
atgccgcaaa aaagggaata agggcgacac ggaaatgttg aatactcata ctcttccttt    3780
ttcaatatta ttgaagcatt tatcagggtt attgtctcat gagcggatac atatttgaat    3840
gtatttagaa aaataaacaa ataggggttc cgcgcacatt tccccgaaaa gtgccacctg    3900
acgtctaaga aaccattatt atcatgacat taacctataa aaataggcgt atcacgaggc    3960
cctttcgtct cgcgcgtttc ggtgatgacg gtgaaaacct ctgacacatg cagctcccgg    4020
agacggtcac agcttgtctg taagcggatg ccgggagcag acaagcccgt cagggcgcgt    4080
cagcgggtgt tggcgggtgt cggggctggc ttaactatgc ggcatcagag cagattgtac    4140
tgagagtgca ccatatgcgg tgtgaaatac cgcacagatg cgtaaggaga aaataccgca    4200
tcaggcgcca ttcgccattc aggctgcgca actgttggga agggcgatcg gtgcgggcct    4260
cttcgctatt acgccagctg gcgaaagggg gatgtgctgc aaggcgatta agttgggtaa    4320
cgccagggtt ttcccagtca cgacgttgta aaacgacggc cagtgaatta ccaactttgt    4380
acaaaaaagc agattaccct gttatcccta catcatcaat aatataccct attttggatt    4440
gaagccaata tgataatgag ggggtggagt ttgtgacgtg gcgcggggcg tgggaacggg    4500
gcgggtgacg tagtagtgtg gcggaagtgt gatgttgcaa gtgtggcgga acacatgtaa    4560
gcgacggatg tggcaaaagt gacgttttg tgtgcgccg gtgtacacag gaagtgacaa    4620
ttttcgcgcg gttttaggcg gatgttgtag taaatttggg cgtaaccgag taagatttgg    4680
ccattttcgc gggaaaactg aataagagga agtgaaatct gaataatttt gtgttactca    4740
tagcgcgtaa tatttgtcta gggccgcggg gactttgacc gttacgtgg agactcgccc    4800 aggtgttttt ctcaggtgtt ttccgcgttc cgggtcaaag ttggcgtttt attattaatt    4860
aagtttaaac ttgaatcaat attggcaatt agccatatta gtcattggtt atatagcata    4920
aatcaatatt ggctattggc cattgcatac gttgtatcta tatcataata tgtacattta    4980
tattggctca tgtccaatat gaccgccatg ttgacattga ttattgacta gttattaata    5040
gtaatcaatt acggggtcat tagttcatag cccatatatg gagttccgcg ttacataact    5100
tacggtaaat ggcccgcctg gctgaccgcc caacgacccc cgcccattga cgtcaataat    5160
gacgtatgtt cccatagtaa cgccaatagg gactttccat tgacgtcaat gggtggagta    5220
tttacggtaa actgcccact tggcagtaca tcaagtgtat catatgccaa gtccgccccc    5280
tattgacgtc aatgacggta aatggcccgc ctggcattat gcccagtaca tgaccttacg    5340
ggactttcct acttggcagt acatctacgt attagtcatc gctattacca tggtgatgcg    5400
gttttggcag tacaccaatg ggcgtggata gcggtttgac tcacgggat ttccaagtct    5460 ccacccccatt gacgtcaatg ggagtttgtt ttggcaccaa aatcaacggg actttccaaa    5520
atgtcgtaat aaccccgccc cgttgacgca aatgggcggt aggcgtgtac ggtgggaggt    5580
ctatataagc agagctcgtt tagtgaaccg tcagaatttt gtaatacgac tcactatagg    5640
gcggccggga attcgtcgac tggatccggt accgaggaga tctgccgccg cgatcgccat    5700
ggaaaaccac agcaagcaaa ctgaggctcc ccacccggga acatatatgc cagctgggta    5760 tcccccctccg tatccaccag cagctttcca aggaccttca gaccatgctg cttacccccat    5820 accccaggct ggctaccaag ggcctccggg cccctatcca gggccccaac ctggctaccc    5880
agtcccacca ggaggttatg caggtggtgg ccctagtggc tttcctgtcc aaaatcagcc    5940
```

```
agcatataat catccaggtg ggcctggggg gaccccatgg atgccagccc ccccacctcc    6000
actgaactgt ccaccggggc tggaatactt agctcagatt gatcagcttc tggttcatca    6060
gcaaattgag cttctggaag tcttaacagg ctttgaaaca ataacaaat atgaaatcaa     6120 gaacagcctc gggcagagag tttactttgc agtggaagat actgactgct gtacccgaaa    6180
ctgctgtggg gcgtctagac cttttcacctt gaggatcctg gataatctgg gccgagaagt   6240
catgactctg gagcgacctc tgagatgcag tagctgctgc ttcccctgct gcctccagga    6300
gatagaaatc caggctcctc ctggggtgcc agtaggttat gtgactcaga cctggcaccc    6360
atgtctgccc aagttcactc tccaaaatga aagaagcag gatgtcctga aagtagttgg     6420
tccgtgtgtt gtgtgtagct gctgttccga cattgacttt gagctcaaat ctctagatga    6480
agaatcagta gttggcaaaa tttctaagca gtggtctggt tttgtgagag aggccttcac    6540
ggatgcagcc aactttggga tccagttccc gctagacctg gatgtgaaga tgaaagctgt    6600
gatgcttggt gcttgtttcc tcatagattt catgtttttt gaaagaactg gaaacgagga    6660
acaaagatca ggagtatgga cgcgtacgcg gccgctcgag cagaaactca tctcagaaga   6720
ggatctggca gcaaatgata tcctggatta caaggatgac gacgataagg ttggatccgg    6780
agccacgaac ttctctctgt taaagcaagc aggagacgtg gaagaaaacc ccggtcctag    6840
atctggccgc aagaggtaag ggtttaaggg atggtcggtt ggtggggtat taatgtttaa    6900
ttacctggag caccctgcct gaaatcacttt ttttcaggtt ggaatcgata atcaacctct   6960
ggattacaaa atttgtgaaa gattgactgg tattcttaac tatgttgctc cttttacgct    7020
atgtggatac gctgctttaa tgcctttgta tcatgctatt gcttcccgta tggctttcat    7080
tttctcctcc ttgtataaat cctggttgct gtctctttat gaggagttgt ggcccgttgt    7140
caggcaacgt ggcgtggtgt gcactgtgtt tgctgacgca accccactg gttgggcat      7200 tgccaccacc tgtcagctcc tttccgggac tttcgctttc ccctcccta ttgccacggc     7260 ggaactcatc gccgcctgcc ttgcccgctg ctggacaggg gctcggctgt tgggcactga    7320
caattccgtg gtgttgtcgg gaagctgac gtcctttcca tggctgctcg cctgtgttgc     7380
cacctggatt ctgcgcggga cgtccttctg ctacgtccct tcggccctca atccagcgga    7440
ccttccttcc cgcggcctgc tgccggctct gcggcctctt ccgcgtcttc gccttcgccc    7500
tcagacgagt cggatctccc tttgggccgc ctccccgcct gctgcagggc gcatcgtgg     7560 atgggagtcc gtgtgtgcct ggagattacc ctggacacct ctgcttttt tttttttactt    7620 tagcggttgc ctcctaggcc tgactccttc ccatgttgaa ctggaggcag ccacgttagg    7680
tgtcaatgtc ctggcatcag tatgaacagt cagtagtccc agggcagggc cacacttctc    7740
ccatcttctg cttccacccc agcttgtgat tgctagcctc ccagagctca attgctgtgc    7800
cttctagttg ccagccatct gttgtttgcc cctcccccgt gccttccttg accctggaag    7860
gtgccactcc cactgtcctt tcctaataaa atgaggaaat tgcatcgcat tgtctgagta    7920
ggtgtcattc tattctgggg ggtggggtgg ggcaggacag caaggggag gattgggaag     7980 acaatagcag gcatgctggg gatgcggtgg gctctatgga cgcgtcggcc gctgcagctc    8040
gagtctagag ctgacggcgc gcctgaaatg tgtgggcgtg gcttaagggt gggaaagaat    8100
atataaggtg ggggtcttat gtagttttgt atctgttttg cagcagccgc cgccgccatg    8160
agcaccaact cgtttgatgg aagcattgtg agctcatatt tgacaacgcg catgccccca    8220
tgggccgggg tgcgtcagaa tgtgatgggc tccagcattg atggtcgccc cgtcctgccc    8280
gcaaactcta ctaccttgac ctacgagacc gtgtctggaa cgccgttgga gactgcagcc    8340
```

```
tccgccgccg cttcagccgc tgcagccacc gcccgcggga ttgtgactga ctttgctttc   8400
ctgagcccgc ttgcaagcag tgcagcttcc cgttcatccg cccgcgatga caagttgacg   8460 gctctttttgg cacaattgga ttctttgacc cgggaactta atgtcgtttc tcagcagctg   8520
ttggatctgc gccagcaggt ttctgccctg aaggcttcct cccctcccaa tgcggtttaa   8580
aacataaata aaaaaccaga ctctgtttgg atttggatca agcataagtg tcttgctgtc   8640
tttatttagg ggttttgcgc gcgcggtagg cccgggacca gcggtctcgg tcgttgaggg   8700
tcctgtgtat tttttccagg acgtggtaaa ggtgactctg gatgttcaga tacatgggca   8760
taagcccgtc tctggggtgg aggtagcacc actgcagagc ttcatgctgc ggggtggtgt   8820
tgtagatgat ccagtcgtag caggagcgct gggcgtggtg cctaaaaatg tctttcagta   8880
gcaagctgat tgccaggggc aggcccttgg tgtaagtgtt tacaaagcgg ttaagctggg   8940
atgggtgcat acgtggggat atgagatgca tcttggactg tatttttagg ttggctatgt   9000
tcccagccat atccctccgg ggattcatgt tgtgcagaac caccagcaca gtgtatccgg   9060
tgcacttggg aaatttgtca tgtagcttag aaggaaatgc gtggaagaac ttggagacgc   9120
ccttgtgacc tccaagattt tccatgcatt cgtccataat gatggcaatg gcccacgggg   9180
cggcggcctg ggcgaagata tttctgggat cactaacgtc atagttgtgt tccaggatga   9240
gatcgtcata ggccattttt acaaagcgcg ggcggagggt gccagactgc ggtataatgg   9300
ttccatccgg cccaggggcg tagttaccct cacagatttg catttcccac gctttgagtt   9360 cagatgggg gatcatgtct acctgcgggg cgatgaagaa aacggtttcc ggggtagggg   9420
agatcagctg ggaagaaagc aggttcctga gcagctgcga cttaccgcag ccggtgggcc   9480
cgtaaatcac acctattacc gggtgcaact ggtagttaag agagctgcag ctgccgtcat   9540
ccctgagcag gggggccact tcgttaagca tgtccctgac tcgcatgttt tccctgacca   9600
aatccgccag aaggcgctcg ccgcccagcg atagcagttc ttgcaaggaa gcaaagtttt   9660
tcaacggttt gagaccgtcc gccgtaggca tgcttttgag cgtttgacca agcagttcca   9720
ggcggtccca cagctcggtc acctgctcta cggcatctcg atccagcata tctcctcgtt   9780
tcgcgggttg gggcggcttt cgctgtacgg cagtagtcgg tgctcgtcca gacgggccag   9840
ggtcatgtct ttccacgggc gcagggtcct cgtcagcgta gtctgggtca cggtgaaggg   9900
gtgcgctccg ggctgcgcgc tggccagggt gcgcttgagg ctggtcctgc tggtgctgaa   9960
gcgctgccgg tcttcgccct gcgcgtcggc caggtagcat ttgaccatgg tgtcatagtc  10020
cagcccctcc gcgcgtggc ccttggcgcg cagcttgccc ttggaggagg cgccgcacga  10080
ggggcagtgc agacttttga gggcgtagag cttgggcgcg agaaataccg attccgggga  10140
gtaggcatcc gcgccgcagg ccccgcagac ggtctcgcat tccacgagcc aggtgagctc  10200
tggccgttcg gggtcaaaaa ccaggttttcc cccatgcttt ttgatgcgtt tcttacctct  10260
ggtttccatg agccggtgtc cacgctcggt gacgaaaagg ctgtccgtgt ccccgtatac  10320
agacttgaga ggcctgtcct cgagcggtgt tccgcggtcc tcctcgtata gaaactcgga  10380
ccactctgag acaaaggctc gcgtccaggc cagcacgaag gaggctaagt gggaggggta  10440
gcggtcgttg tccactaggg ggtccactcg ctccaggggtg tgaagacaca tgtcgccctc  10500
ttcggcatca aggaaggtga ttggtttgta ggtgtaggcc acgtgaccgg tgttcctga  10560 agggggggcta taaaggggg tggggcgcg ttcgtcctca ctctcttccg catcgctgtc  10620
tgcgagggcc agctgttggg gtgagtactc cctctgaaaa gcgggcatga cttctgcgct  10680
```

-continued

```
aagattgtca gtttccaaaa acgaggagga tttgatattc acctggcccg cggtgatgcc    10740
tttgagggtg gccgcatcca tctggtcaga aaagacaatc tttttgttgt caagcttggt    10800
ggcaaacgac ccgtagaggg cgttggacag caacttggcg atggagcgca gggtttggtt    10860
tttgtcgcga tcgcgcgct ccttggccgc gatgtttagc tgcacgtatt cgcgcgcaac     10920
gcaccgccat tcgggaaaga cggtggtgcg ctcgtcgggc accaggtgca cgcgccaacc    10980
gcggttgtgc agggtgacaa ggtcaacgct ggtggctacc tctccgcgta ggcgctcgtt    11040
ggtccagcag aggcggccgc ccttgcgcga gcagaatggc ggtaggggt ctagctgcgt     11100 ctcgtccggg gggtctgcgt ccacggtaaa gaccccgggc agcaggcgcg cgtcgaagta    11160
gtctatcttg catccttgca agtctagcgc ctgctgccat gcgcgggcgg caagcgcgcg    11220
ctcgtatggg ttgagtgggg gaccccatgg catggggtgg gtgagcgcgg aggcgtacat    11280
gccgcaaatg tcgtaaacgt agaggggctc tctgagtatt ccaagatatg tagggtagca    11340
tcttccaccg cggatgctgg cgcgcacgta atcgtatagt tcgtgcgagg gagcgaggag    11400
gtcgggaccg aggttgctac gggcgggctg ctctgctcgg aagactatct gcctgaagat    11460
ggcatgtgag ttggatgata tggttggacg ctggaagacg ttgaagctgg cgtctgtgag    11520
acctaccgcg tcacgcacga aggaggcgta ggagtcgcgc agcttgttga ccagctcggc    11580
ggtgacctgc acgtctaggg cgcagtagtc caggggtttcc ttgatgatgt catacttatc   11640
ctgtcccttt tttttccaca gctcgcggtt gaggacaaac tcttcgcggt ctttccagta    11700
ctcttggatc ggaaacccgt cggcctccga acggtaagag cctagcatgt agaactggtt    11760
gacggcctgg taggcgcagc atcccttttc tacgggtagc gcgtatgcct gcgcggcctt    11820
ccggagcgag gtgtgggtga gcgcaaaggt gtccctgacc atgactttga ggtactggta    11880
tttgaagtca gtgtcgtcgc atccgccctg ctcccagagc aaaaagtccg tgcgcttttt    11940
ggaacgcgga tttggcaggg cgaaggtgac atcgttgaag agtatctttc ccgcgcgagg    12000
cataaagttg cgtgtgatgc ggaagggtcc cggcacctcg gaacggttgt taattacctg    12060
ggcggcgagc acgatctcgt caaagccgtt gatgttgtgg cccacaatgt aaagttccaa    12120
gaagcgcggg atgcccttga tggaaggcaa ttttttaagt tcctcgtagg tgagctcttc    12180
aggggagctg agcccgtgct ctgaaagggc ccagtctgca agatgagggt tggaagcgac    12240
gaatgagctc cacaggtcac gggccattag catttgcagg tggtcgcgaa aggtcctaaa    12300
ctggcgacct atggccattt tttctggggt gatgcagtag aaggtaagcg ggtcttgttc    12360
ccagcggtcc catccaaggt tcgcggctag gtctcgcgcg gcagtcacta gaggctcatc    12420
tccgccgaac ttcatgacca gcatgaaggg cacgagctgc ttcccaaagg cccccatcca    12480
agtataggtc tctacatcgt aggtgacaaa gagacgctcg gtgcgaggat gcgagccgat    12540
cgggaagaac tggatctccc gccaccaatt ggaggagtgg ctattgatgt ggtgaaagta    12600
gaagtccctg cgacgggccg aacactcgtg ctggcttttg taaaaacgtg cgcagtactg    12660
gcagcggtgc acgggctgta catcctgcac gaggttgacc tgacgaccgc gcacaaggaa    12720
gcagagtggg aatttgagcc cctcgcctgg cgggtttggc tggtggtctt ctacttcggc    12780
tgcttgtcct tgaccgtctg gctgctcgag gggagttacg gtggatcgga ccaccacgcc    12840
gcgcgagccc aaagtccaga tgtccgcgcg cggcggtcgg agcttgatga caacatcgcg    12900
cagatgggag ctgtccatgg tctggagctc ccgcggcgtc aggtcaggcg ggagctcctg    12960
caggtttacc tcgcatagac gggtcagggc gcgggctaga tccaggtgat acctaatttc    13020
caggggctgg ttggtggcgg cgtcgatggc ttgcaagagg ccgcatcccc gcggcgcgac    13080
```

| | | | | |
|---|---|---|---|---|
| tacggtaccg | cgcggcgggc | ggtgggccgc | ggggtgtcc | ttggatgatg catctaaaag | 13140 |
| cggtgacgcg | ggcgagcccc | cggaggtagg | ggggctccg | gacccgccgg gagaggggc | 13200 |
| agggcacgt | cggcgccgcg | cgcgggcagg | agctggtgct | gcgcgcgtag gttgctggcg | 13260 |
| aacgcgacga | cgcggcggtt | gatctcctga | atctggcgcc | tctgcgtgaa gacgacgggc | 13320 |
| ccggtgagct | tgagcctgaa | agagagttcg | acagaatcaa | tttcggtgtc gttgacggcg | 13380 |
| gcctggcgca | aaatctcctg | cacgtctcct | gagttgtctt | gataggcgat ctcggccatg | 13440 |
| aactgctcga | tctcttcctc | ctggagatct | ccgcgtccgg | ctcgctccac ggtggcggcg | 13500 |
| aggtcgttgg | aaatgcgggc | catgagctgc | gagaaggcgt | tgaggcctcc ctcgttccag | 13560 |
| acgcggctgt | agaccacgcc | cccttcggca | tcgcgggcgc | gcatgaccac ctgcgcgaga | 13620 |
| ttgagctcca | cgtgccgggc | gaagacgcg | tagtttcgca | ggcgctgaaa gaggtagttg | 13680 |
| agggtggtgg | cggtgtgttc | tgccacgaag | aagtacataa | cccagcgtcg caacgtggat | 13740 |
| tcgttgatat | cccccaaggc | ctcaaggcgc | tccatggcct | cgtagaagtc cacggcgaag | 13800 |
| ttgaaaaact | gggagttgcg | cgccgacacg | gttaactcct | cctccagaag acggatgagc | 13860 |
| tcggcgacag | tgtcgcgcac | ctcgcgctca | aaggctacag | ggcctcttc ttcttcttca | 13920 |
| atctcctctt | ccataagggc | ctccccttct | tcttcttctg | gcggcggtgg gggagggggg | 13980 |
| acacggcggc | gacgacggcg | caccgggagg | cggtcgacaa | agcgctcgat catctccccg | 14040 |
| cggcgacggc | gcatggtctc | ggtgacggcg | cggccgttct | cgcgggggcg cagttggaag | 14100 |
| acgccgcccg | tcatgtcccg | gttatgggtt | ggcggggggc | tgccatgcgg cagggatacg | 14160 |
| gcgctaacga | tgcatctcaa | caattgttgt | gtaggtactc | cgccgccgag ggacctgagc | 14220 |
| gagtccgcat | cgaccggatc | ggaaaacctc | tcgagaaagg | cgtctaacca gtcacagtcg | 14280 |
| caaggtaggc | tgagcaccgt | ggcgggcggc | agcgggcggc | ggtcggggtt gtttctggcg | 14340 |
| gaggtgctgc | tgatgatgta | attaaagtag | gcggtcttga | gacggcggat ggtcgacaga | 14400 |
| agcaccatgt | ccttgggtcc | ggcctgctga | atgcgcaggc | ggtcggccat gccccaggct | 14460 |
| tcgttttgac | atcggcgcag | gtctttgtag | tagtcttgca | tgagcctttc taccggcact | 14520 |
| tcttcttctc | cttcctcttg | tcctgcatct | cttgcatcta | tcgctgcggc ggcggcggag | 14580 |
| tttggccgta | ggtggcgccc | tcttcctccc | atgcgtgtga | ccccgaagcc cctcatcggc | 14640 |
| tgaagcaggg | ctaggtcggc | gacaacgcgc | tcggctaata | tggcctgctg cacctgcgtg | 14700 |
| agggtagact | ggaagtcatc | catgtccaca | aagcggtggt | atgcgcccgt gttgatggtg | 14760 |
| taagtgcagt | tggccataac | ggaccagtta | acggtctggt | gacccggctg cgagagctcg | 14820 |
| gtgtacctga | gacgcgagta | agccctcgag | tcaaatacgt | agtcgttgca agtccgcacc | 14880 |
| aggtactggt | atcccaccaa | aaagtgcggc | ggcggctggc | ggtagagggg ccagcgtagg | 14940 |
| gtggccgggg | ctccggggc | gagatcttcc | aacataaggc | gatgatatcc gtagatgtac | 15000 |
| ctggacatcc | aggtgatgcc | ggcggcgtg | gtggaggcgc | gcggaaagtc gcggacgcgg | 15060 |
| ttccagatgt | tgcgcagcgg | caaaaagtgc | tccatggtcg | ggacgctctg gccggtcagg | 15120 |
| cgcgcgcaat | cgttgacgct | ctagaccgtg | caaaaggaga | gcctgtaagc gggcactctt | 15180 |
| ccgtggtctg | tgtggataaat | tcgcaagggt | atcatgcgcg | acgaccgggg ttcgagcccc | 15240 |
| gtatccggcc | gtccgccgtg | atccatgcgg | ttaccgcccg | cgtgtcgaac ccaggtgtgc | 15300 |
| gacgtcagac | aacgggggag | tgctcctttt | ggcttcctc | caggcgcggc ggctgctgcg | 15360 |
| ctagcttttt | tggccactgg | ccgcgcgcag | cgtaagcggt | taggctggaa agcgaaagca | 15420 |

```
ttaagtggct cgctccctgt agccggaggg ttatttttcca agggttgagt cgcgggaccc   15480
ccggttcgag tctcggaccg gccggactgc ggcgaacggg ggtttgcctc cccgtcatgc   15540 aagacccgc ttgcaaattc ctccggaaac agggacgagc ccctttttg cttttcccag    15600 atgcatccgg tgctgcggca gatgcgcccc cctcctcagc agcggcaaga gcaagagcag   15660
cggcagacat gcagggcacc ctcccctcct cctaccgcgt caggaggggc gacatccgcg   15720
gttgacgcgg cagcagatgg tgattacgaa ccccgcggc gccgggcccg gcactacctg    15780
gacttggagg agggcgaggg cctggcgcgg ctaggagcgc cctctcctga gcggtaccca   15840
agggtgcagc tgaagcgtga tacgcgtgag gcgtacgtgc cgcggcagaa cctgtttcgc   15900
gaccgcgagg gagaggagcc cgaggagatg cgggatcgaa agttccacgc agggcgcgag   15960
ctgcggcatg gcctgaatcg cgagcggttg ctgcgcgagg aggactttga gcccgacgcg   16020
cgaaccggga ttagtcccgc gcgcgcacac gtggcggccg ccgacctggt aaccgcatac   16080
gagcagacgg tgaaccagga gattaacttt caaaaaagct ttaacaacca cgtgcgtacg   16140
cttgtggcgc gcgaggaggt ggctatagga ctgatgcatc tgtgggactt tgtaagcgcg   16200
ctggagcaaa acccaaatag caagccgctc atggcgcagc tgttccttat agtgcagcac   16260
agcagggaca acgaggcatt cagggatgcg ctgctaaaca tagtagagcc cgagggccgc   16320
tggctgctcg atttgataaa catcctgcag agcatagtgg tgcaggagcg cagcttgagc   16380
ctggctgaca aggtggccgc catcaactat tccatgctta gcctgggcaa gttttacgcc   16440
cgcaagatat accatacccc ttacgttccc atagacaagg aggtaaagat cgaggggttc   16500
tacatgcgca tggcgctgaa ggtgcttacc ttgagcgacg acctgggcgt ttatcgcaac   16560
gagcgcatcc acaaggccgt gagcgtgagc cggcggcgcg agctcagcga ccgcgagctg   16620
atgcacagcc tgcaaagggc cctggctggc acgggcagcg gcgatagaga ggccgagtcc   16680
tactttgacg cgggcgctga cctgcgctgg gccccaagcc gacgcgccct ggaggcagct   16740
ggggccggac ctgggctggc ggtggcaccc gcgcgcgctg gcaacgtcgg cggcgtggag   16800
gaatatgacg aggacgatga gtacgagcca gaggacggcg agtactaagc ggtgatgttt   16860
ctgatcagat gatgcaagac gcaacggacc cggcggtgcg ggcggcgctg cagagccagc   16920
cgtccggcct taactccacg gacgactggc gccaggtcat ggaccgcatc atgtcgctga   16980
ctgcgcgcaa tcctgacgcg ttccggcagc agccgcaggc caaccggctc tccgcaattc   17040
tggaagcggt ggtcccggcg cgcgcaaacc ccacgcacga gaaggtgctg gcgatcgtaa   17100
acgcgctggc cgaaaacagg gccatccggc ccgacgaggc cggcctggtc tacgacgcgc   17160
tgcttcagcg cgtggctcgt tacaacagcg gcaacgtgca gaccaacctg gaccggctgg   17220 tggggatgt gcgcgaggcc gtggcgcagc gtgagcgcgc gcagcagcag ggcaacctgg   17280
gctccatggt tgcactaaac gccttcctga gtacacagcc cgccaacgtg ccgcggggac   17340
aggaggacta caccaacttt gtgagcgcac tgcggctaat ggtgactgag acaccgcaaa   17400
gtgaggtgta ccagtctggg ccagactatt ttttccagac cagtagacaa ggcctgcaga   17460
ccgtaaacct gagccaggct ttcaaaaact gcagggggct gtgggggtg cgggctccca   17520 caggcgaccg cgcgaccgtg tctagcttgc tgacgcccaa ctcgcgcctg ttgctgctgc   17580
taatagcgcc cttcacggac agtggcagcg tgtcccggga cacatacctagtcacttgc    17640 tgacactgta ccgcgaggcc ataggtcagg cgcatgtgga cgagcatact ttccaggaga   17700
ttacaagtgt cagccgcgcg ctggggcagg aggacacggg cagcctggag gcaaccctaa   17760
actacctgct gaccaaccgg cggcagaaga tcccctcgtt gcacagttta aacagcgagg   17820
```

```
aggagcgcat tttgcgctac gtgcagcaga gcgtgagcct taacctgatg cgcgacgggg    17880
taacgcccag cgtggcgctg gacatgaccg cgcgcaacat ggaaccgggc atgtatgcct    17940
caaaccggcc gtttatcaac cgcctaatgg actacttgca tcgcgcggcc gccgtgaacc    18000
ccgagtattt caccaatgcc atcttgaacc cgcactggca accgcccct ggtttctaca     18060 ccggggggatt cgaggtgccc gagggtaacg atggattcct ctgggacgac atagacgaca   18120
gcgtgttttc cccgcaaccg cagaccctgc tagagttgca acagcgcgag caggcagagg    18180
cggcgctgcg aaaggaaagc ttccgcaggc caagcagctt gtccgatcta ggcgctgcgg    18240
ccccgcggtc agatgctagt agcccatttc caagcttgat agggtctctt accagcactc    18300
gcaccacccg cccgcgcctg ctgggcgagg aggagtacct aaacaactcg ctgctgcagc    18360
cgcagcgcga aaaaaacctg cctccggcat ttcccaacaa cgggatagag agcctagtgg    18420
acaagatgag tagatggaag acgtacgcgc aggagcacag ggacgtgcca ggcccgcgcc    18480
cgcccacccg tcgtcaaagg cacgaccgtc agcggggtct ggtgtgggag gacgatgact    18540
cggcagacga cagcagcgtc ctggatttgg gagggagtgg caacccgttt gcgcaccttc    18600
gccccaggct ggggagaatg ttttaaaaaa aaaaagcat gatgcaaaat aaaaaactca     18660
ccaaggccat ggcaccgagc gttggttttc ttgtattccc cttagtatgc ggcgcgcggc    18720
gatgtatgag gaaggtcctc ctccctccta cgagagtgtg gtgagcgcgg cgccagtggc    18780
ggcggcgctg ggttctccct tcgatgctcc cctggacccg ccgtttgtgc ctccgcggta    18840
cctgcggcct accgggggga gaaacagcat ccgttactct gagttggcac ccctattcga    18900
caccacccgt gtgtacctgg tggacaacaa gtcaacggat gtggcatccc tgaactacca    18960
gaacgaccac agcaactttc tgaccacggt cattcaaaac aatgactaca gcccggggga    19020
ggcaagcaca cagaccatca atcttgacga ccggtcgcac tggggcggcg acctgaaaac    19080
catcctgcat accaacatgc caaatgtgaa cgagttcatg tttaccaata gtttaaggc     19140 gcgggtgatg gtgtcgcgct tgcctactaa ggacaatcag gtggagctga atacgagtg     19200 ggtggagttc acgctgcccg agggcaacta ctccgagacc atgaccatag accttatgaa    19260
caacgcgatc gtggagcact acttgaaagt gggcagacag aacggggttc tggaaagcga    19320
catcggggta aagtttgaca cccgcaactt cagactgggg tttgaccccg tcactggtct    19380
tgtcatgcct ggggtatata caaacgaagc cttccatcca gacatcattt tgctgccagg    19440 atgcgggggtg gacttcaccc acagccgcct gagcaacttg ttgggcatcc gcaagcggca   19500 accccttccag gagggcttta ggatcaccta cgatgatctg gagggtggta acattcccgc   19560
actgttggat gtggacgcct accaggcgag cttgaaagat gacaccgaac agggcggggg   19620
tggcgcaggc ggcagcaaca gcagtggcag cggcgcggaa gagaactcca acgcggcagc    19680
cgcggcaatg cagccggtgg aggacatgaa cgatcatgcc attcgcggcg acacctttgc    19740
cacacgggct gaggagaagc gcgctgaggc cgaagcagcg gccgaagctg ccgccccgc     19800 tgcgcaaccc gaggtcgaga agcctcagaa gaaaccggtg atcaaacccc tgacagagga    19860
cagcaagaaa cgcagttaca acctaataag caatgacagc accttcaccc agtaccgcag    19920
ctggtacctt gcatacaact acggcgaccc tcagaccgga atccgctcat ggaccctgct    19980
ttgcactcct gacgtaacct gcggctcgga gcaggtctac tggtcgttgc cagacatgat    20040
gcaagacccc gtgaccttcc gctccacgcg ccagatcagc aactttccgg tggtgggcgc    20100
cgagctgttg cccgtgcact ccaagagctt ctacaacgac caggccgtct actcccaact    20160
```

```
catccgccag tttacctctc tgacccacgt gttcaatcgc tttcccgaga accagatttt   20220
ggcgcgcccg ccagcccccca ccatccaccac cgtcagtgaa aacgttcctg ctctcacaga   20280
tcacgggacg ctaccgctgc gcaacagcat cggaggagtc cagcgagtga ccattactga   20340
cgccagacgc cgcaccctgcc cctacgttta caaggccctg gcatagtct cgccgcgcgt   20400 cctatcgagc cgcactttt gagcaagcat gtccatcctt atatcgccca gcaataacac   20460 aggctgggc ctgcgcttcc caagcaagat gtttggcggg gccaagaagc gctccgacca   20520
acacccagtg cgcgtgcgcg ggcactaccg cgcgccctgg ggcgcgcaca aacgcggccg   20580
cactgggcgc accaccgtcg atgacgccat cgacgcggtg gtggaggagg cgcgcaacta   20640
cacgcccacg ccgccaccag tgtccacagt ggacgcggcc attcagaccg tggtgcgcgg   20700
agcccggcgc tatgctaaaa tgaagagacg gcggaggcgc gtagcacgtc gccaccgccg   20760
ccgacccggc actgccgccc aacgcgcggc ggcggccctg cttaaccgcg cacgtcgcac   20820
cggccgacgg gcggccatgc gggccgctcg aaggctggcc gcgggtattg tcactgtgcc   20880 cccaggtcc aggcgacgag cggccgccgc agcagccgcg gccattagtg ctatgactca   20940
gggtcgcagg ggcaacgtgt attgggtgcg cgactcggtt agcggcctgc gcgtgcccgt   21000
gcgcacccgc cccccgcgca actagattgc aagaaaaaac tacttagact cgtactgttg   21060
tatgtatcca gcggcggcgg cgcgcaacga agctatgtcc aagcgcaaaa tcaaagaaga   21120
gatgctccag gtcatcgcgc cggagatcta tggcccccg aagaaggaag agcaggatta   21180 caagcccga aagctaaagc gggtcaaaaa gaaaagaaa gatgatgatg atgaacttga   21240
cgacgaggtg gaactgctgc acgctaccgc gcccaggcga cgggtacagt ggaaaggtcg   21300
acgcgtaaaa cgtgtttgc gacccggcac caccgtagtc tttacgcccg gtgagcgctc   21360
cacccgcacc tacaagcgcg tgtatgatga ggtgtacggc gacgaggacc tgcttgagca   21420
ggccaacgag cgcctcgggg agtttgccta cggaaagcgg cataaggaca tgctggcgtt   21480
gccgctggac gagggcaacc caacacctag cctaaagccc gtaacactgc agcaggtgct   21540 gccccgcgctt gcaccgtccg aagaaaagcg cggcctaaag cgcgagtctg gtgacttggc   21600
acccaccgtg cagctgatgg tacccaagcg ccagcgactg gaagatgtct tggaaaaaat   21660
gaccgtggaa cctgggctgg agcccgaggt ccgcgtgcgg ccaatcaagc aggtggcgcc   21720
gggactgggc gtgcagaccg tggacgttca gataccact accagtagca ccagtattgc   21780
caccgccaca gagggcatgg agacacaaac gtccccggtt gcctcagcgg tggcggatgc   21840
cgcggtgcag gcggtcgctg cggccgcgtc caagacctct acggaggtgc aaacggaccc   21900
gtggatgttt cgcgtttcag ccccccggcg cccgcgcggt tcgaggaagt acggcgccgc   21960
cagcgcgcta ctgcccgaat atgcccctaca tccttccatt gcgcctaccc ccggctatcg   22020
tggctacacc taccgcccca agagacgagc aactacccga cgccgaacca ccactggaac   22080
ccgccgccgc cgtcgccgtc gccagcccgt gctggccccg atttccgtgc gcagggtggc   22140
tcgcgaagga ggcaggaccc tggtgctgcc aacagcgcgc taccacccca gcatcgttta   22200
aaagccggtc tttgtggttc ttgcagatat ggccctcacc tgccgcctcc gtttcccggt   22260
gccgggattc cgaggaagaa tgcaccgtag gagggcatg gccggccacg gcctgacggg   22320
cggcatgcgt cgtgcgcacc accggcggcg gcgcgcgtcg caccgtcgca tgcgcggcgg   22380
tatcctgccc ctccttattc cactgatcgc cgcggcgatt ggcgccgtgc ccggaattgc   22440
atccgtggcc ttgcaggcgc agagacactg attaaaaaca agttgcatgt ggaaaaatca   22500
aaataaaaag tctggactct cacgctcgct tggtcctgta actatttgt agaatggaag   22560
```

```
acatcaactt tgcgtctctg gccccgcgac acggctcgcg cccgttcatg ggaaactggc   22620
aagatatcgg caccagcaat atgagcggtg gcgccttcag ctggggctcg ctgtggagcg   22680
gcattaaaaa tttcggttcc accgttaaga actatggcag caaggcctgg aacagcagca   22740
caggccagat gctgagggat aagttgaaag agcaaaattt ccaacaaaag gtggtagatg   22800
gcctggcctc tggcattagc ggggtggtgg acctggccaa ccaggcagtg caaaataaga   22860
ttaacagtaa gcttgatccc cgccctcccg tagaggagcc tccaccggcc gtggagacag   22920
tgtctccaga ggggcgtggc gaaaagcgtc cgcgccccga cagggaagaa actctggtga   22980
cgcaaataga cgagcctccc tcgtacgagg aggcactaaa gcaaggcctg cccaccaccc   23040
gtcccatcgc gcccatggct accggagtgc tgggccagca cacccgta acgctggacc   23100 tgcctccccc cgccgacacc cagcagaaac ctgtgctgcc aggcccgacc gccgttgttg   23160
taacccgtcc tagccgcgcg tccctgcgcc gcgccgccag cggtccgcga tcgttgcggc   23220
ccgtagccag tggcaactgg caaagcacac tgaacagcat cgtgggtctg ggggtgcaat   23280
ccctgaagcg ccgacgatgc ttctgaatag ctaacgtgtc gtatgtgtgt catgtatgcg   23340
tccatgtcgc cgccagagga gctgctgagc cgccgcgcgc ccgctttcca agatggctac   23400
cccttcgatg atgccgcagt ggtcttacat gcacatctcg ggccaggacg cctcggagta   23460
cctgagcccc gggctggtgc agtttgcccg cgccaccgag acgtacttca gcctgaataa   23520
caagtttaga accccacgg tggcgcctac gcacgacgtg accacagacc ggtcccagcg   23580
tttgacgctg cggttcatcc ctgtggaccg tgaggatact gcgtactcgt acaaggcgcg   23640
gttcacccta gctgtgggtg ataaccgtgt gctggacatg gcttccacgt actttgacat   23700
ccgcggcgtg ctggacaggg gccctacttt taagccctac tctggcactg cctacaacgc   23760
cctggctccc aagggtgccc caaatccttg cgaatgggat gaagctgcta ctgctcttga   23820
aataaaccta gaagaagagg acgatgacaa cgaagacgaa gtagacgagc aagctgagca   23880
gcaaaaaact cacgtatttg ggcaggcgcc ttattctggt ataaatatta caaggaggg   23940 tattcaaata ggtgtcgaag gtcaaacacc taaatatgcc gataaaacat ttcaacctga   24000
acctcaaata ggagaatctc agtggtacga aactgaaatt aatcatgcag ctgggagagt   24060
ccttaaaaag actaccccaa tgaaaccatg ttacggttca tatgcaaaac ccacaaatga   24120
aaatggaggg caaggcattc ttgtaaagca acaaaatgga aagctagaaa gtcaagtgga   24180
aatgcaattt ttctcaacta ctgaggcgac cgcaggcaat ggtgataact tgactcctaa   24240
agtggtattg tacagtgaag atgtagatat agaaaccccca gacactcata tttcttacat   24300
gcccactatt aaggaaggta actcacgaga actaatgggc caacaatcta tgcccaacag   24360
gcctaattac attgctttta gggacaattt tattggtcta atgtattaca acagcacggg   24420
taatatgggt gttctggcgg gccaagcatc gcagttgaat gctgttgtag atttgcaaga   24480
cagaaacaca gagctttcat accagctttt gcttgattcc attggtgata gaaccaggta   24540
cttttctatg tggaatcagg ctgttgacag ctatgatcca gatgttagaa ttattgaaaa   24600
tcatggaact gaagatgaac ttccaaatta ctgctttcca ctgggaggtg tgattaatac   24660
agagactctt accaaggtaa aacctaaaac aggtcaggaa aatggatggg aaaaagatgc   24720
tacagaattt tcagataaaa atgaaataag agttggaaat aattttgcca tggaaatcaa   24780
tctaaatgcc aacctgtgga gaaatttcct gtactccaac atagcgctgt atttgcccga   24840
caagctaaag tacagtcctt ccaacgtaaa aatttctgat aacccaaaca cctacgacta   24900
```

```
catgaacaag cgagtggtgg ctcccgggtt agtggactgc tacattaacc ttggagcacg   24960
ctggtccctt gactatatgg acaacgtcaa cccatttaac caccaccgca atgctggcct   25020
gcgctaccgc tcaatgttgc tgggcaatgg tcgctatgtg cccttccaca tccaggtgcc   25080
tcagaagttc tttgccatta aaaacctcct tctcctgccg ggctcataca cctacgagtg   25140
gaacttcagg aaggatgtta acatggttct gcagagctcc ctaggaaatg acctaagggt   25200
tgacggagcc agcattaagt ttgatagcat ttgcctttac gccaccttct tccccatggc   25260
ccacaacacc gcctccacgc ttgaggccat gcttagaaac gacaccaacg accagtcctt   25320
taacgactat ctctccgccg ccaacatgct ctaccctata cccgccaacg ctaccaacgt   25380
gcccatatcc atccctccc gcaactgggc ggctttccgc ggctgggcct tcacgcgcct   25440
taagactaag gaaaccccat cactgggctc gggctacgac ccttattaca cctactctgg   25500
ctctataccc tacctagatg gaaccttta cctcaaccac acctttaaga aggtggccat   25560 taccttgac tcttctgtca gctggcctgg caatgaccgc ctgcttaccc caacgagtt   25620 tgaaattaag cgctcagttg acggggaggg ttacaacgtt gcccagtgta acatgaccaa   25680
agactggttc ctggtacaaa tgctagctaa ctacaacatt ggctaccagg gcttctatat   25740
cccagagagc tacaaggacc gcatgtactc ctttctttaga aacttccagc ccatgagccg   25800
tcaggtggtg gatgatacta aatacaagga ctaccaacag gtgggcatcc tacaccaaca   25860
caacaactct ggatttgttg gctaccttgc ccccaccatg cgcgaaggac aggcctaccc   25920
tgctaacttc ccctatccgc ttataggcaa gaccgcagtt gacagcatta cccagaaaaa   25980
gtttctttgc gatcgcaccc tttggcgcat cccattctcc agtaactta tgtccatggg   26040 cgcactcaca gacctgggcc aaaaccttct ctacgccaac tccgcccacg cgctagacat   26100
gacttttgag gtggatccca tggacagagcc caccttcct tatgtttgt ttgaagtctt   26160 tgacgtggtc cgtgtgcacc ggccgcaccg cggcgtcatc gaaaccgtgt acctgcgcac   26220
gcccttctcg gccggcaacg ccacaacata aagaagcaag caacatcaac aacagctgcc   26280
gccatgggct ccagtgagca ggaactgaaa gccattgtca agatcttgg ttgtgggcca   26340 tatttttggg gcacctatga caagcgcttt ccaggctttg tttctccaca caagctcgcc   26400
tgcgccatag tcaatacggc cggtcgcgag actgggggcg tacactggat ggcctttgcc   26460
tggaacccgc actcaaaaac atgctacctc tttgagccct ttggcttttc tgaccagcga   26520
ctcaagcagg tttaccagtt tgagtacgag tcactcctgc gccgtagcgc cattgcttct   26580
tcccccgacc gctgtataac gctggaaaag tccacccaaa gcgtacaggg gcccaactcg   26640
gccgcctgtg gactattctg ctgcatgttt ctccacgcct ttgccaactg gccccaaaact   26700 cccatggatc acaaccccac catgaacctt attaccgggg tacccaactc catgctcaac   26760
agtccccagg tacagcccac cctgcgtcgc aaccaggaac agctctacag cttcctggag   26820
cgccactcgc cctacttccg cagccacagt gcgcagatta ggagcgccac ttcttttgt   26880 cacttgaaaa acatgtaaaa ataatgtact agagacactt tcaataaagg caaatgcttt   26940
tatttgtaca ctctcgggtg attatttacc cccaccttg ccgtctgcgc cgtttaaaaa   27000
tcaaaggggt tctgccgcgc atcgctatgc gccactggca gggacacgtt gcgatactgg   27060
tgtttagtgc tccacttaaa ctcaggcaca accatccgcg gcagctcggt gaagttttca   27120
ctccacaggc tgcgcaccat caccaacgcg tttagcaggt cgggcgccga tatcttgaag   27180
tcgcagttgg ggcctccgcc ctgcgcgcgc gagttgcgat acacagggtt gcagcactgg   27240
aacactatca gcgccgggtg gtgcacgctg gccagcacgc tcttgtcgga gatcagatcc   27300
```

```
gcgtccaggt cctccgcgtt gctcagggcg aacggagtca actttggtag ctgccttccc   27360
aaaaagggcg cgtgcccagg ctttgagttg cactcgcacc gtagtggcat caaaaggtga   27420
ccgtgcccgg tctgggcgtt aggatacagc gcctgcataa agccttgat ctgcttaaaa    27480 gccacctgag cctttgcgcc ttcagagaag aacatgccgc aagacttgcc ggaaaactga   27540
ttggccggac aggccgcgtc gtgcacgcag caccttgcgt cggtgttgga gatctgcacc   27600
acatttcggc cccaccggtt cttcacgatc ttggccttgc tagactgctc cttcagcgcg   27660
cgctgcccgt tttcgctcgt cacatccatt tcaatcacgt gctccttatt tatcataatg   27720
cttccgtgta gacacttaag ctcgccttcg atctcagcgc agcggtgcag ccacaacgcg   27780
cagcccgtgg gctcgtgatg cttgtaggtc acctctgcaa acgactgcag gtacgcctgc   27840
aggaatcgcc ccatcatcgt cacaaaggtc ttgttgctgg tgaaggtcag ctgcaacccg   27900
cggtgctcct cgttcagcca ggtcttgcat acggccgcca gagcttccac ttggtcaggc   27960
agtagtttga agttcgcctt tagatcgtta tccacgtggt acttgtccat cagcgcgcgc   28020
gcagcctcca tgcccttctc ccacgcagac acgatcggca cactcagcgg gttcatcacc   28080
gtaatttcac tttccgcttc gctgggctct tcctcttcct cttgcgtccg cataccacgc   28140
gccactgggt cgtcttcatt cagccgccgc actgtgcgct tacctccttt gccatgcttg   28200
attagcaccg gtgggttgct gaaacccacc atttgtagcg ccacatcttc tctttcttcc   28260
tcgctgtcca cgattacctc tggtgatggc gggcgctcgg gcttgggaga agggcgcttc   28320
tttttcttct tgggcgcaat ggccaaatcc gccgccgagg tcgatggccg cgggctgggt   28380
gtgcgcggca ccagcgcgtc ttgtgatgag tcttcctcgt cctcggactc gatacgccgc   28440
ctcatccgct tttttggggg cgcccgggga ggcggcggcg acgggacgg ggacgacacg    28500 tcctccatgg ttgggggacg tcgcgccgca ccgcgtccgc gctcggggt ggtttcgcgc    28560 tgctcctctt cccgactggc catttccttc tcctataggc agaaaagat catggagtca    28620 gtcgagaaga aggacagcct aaccgccccc tctgagttcg ccaccaccgc ctccaccgat   28680
gccgccaacg cgcctaccac cttccccgtc gaggcacccc cgcttgagga ggaggaagtg   28740
attatcgagc aggacccagg ttttgtaagc gaagacgacg aggaccgctc agtaccaaca   28800
gaggataaaa agcaagacca ggacaacgca gaggcaaacg aggaacaagt cgggcggggg   28860
gacgaaaggc atggcgacta cctagatgtg ggagacgacg tgctgttgaa gcatctgcag   28920
cgccagtgcg ccattatctg cgacgcgttg caagagcgca gcgatgtgcc cctcgccata   28980
gcggatgtca gccttgccta cgaacgccac ctattctcac cgcgcgtacc ccccaaacgc   29040
caagaaaacg gcacatgcga gcccaacccg cgcctcaact tctacccgt atttgccgtg    29100 ccagaggtgc ttgccaccta tcacatcttt ttccaaaact gcaagatacc cctatcctgc   29160
cgtgccaacc gcagccgagc ggacaagcag ctggccttgc ggcagggcgc tgtcatacct   29220
gatatcgcct cgctcaacga agtgccaaaa atctttgagg gtcttggacg cgacgagaag   29280
cgcgcggcaa acgctctgca acaggaaaac agcgaaaatg aaagtcactc tggagtgttg   29340
gtggaactcg agggtgacaa cgcgcgccta gccgtactaa aacgcagcat cgaggtcacc   29400
cactttgcct acccggcact taacctaccc cccaaggtca tgagcacagt catgagtgag   29460
ctgatcgtgc gccgtgcgca gcccctggag agggatgcaa atttgcaaga acaaacagag   29520
gagggcctac ccgcagttgg cgacgagcag ctagcgcgct ggcttcaaac gcgcgagcct   29580
gccgacttgg aggagcgacg caaactaatg atggccgcag tgctcgttac cgtggagctt   29640
```

```
gagtgcatgc agcggttctt tgctgacccg gagatgcagc gcaagctaga ggaaacattg    29700
cactacacct ttcgacaggg ctacgtacgc caggcctgca agatctccaa cgtggagctc    29760
tgcaacctgg tctcctacct tggaattttg cacgaaaacc gccttgggca aaacgtgctt    29820
cattccacgc tcaagggcga ggcgcgccgc gactacgtcc gcgactgcgt ttacttattt    29880
ctatgctaca cctggcagac ggccatgggc gtttggcagc agtgcttgga ggagtgcaac    29940
ctcaaggagc tgcagaaact gctaaagcaa aacttgaagg acctatggac ggccttcaac    30000
gagcgctccg tggccgcgca cctggcggac atcatttttc ccgaacgcct gcttaaaacc    30060
ctgcaacagg gtctgccaga cttcaccagt caaagcatgt tgcagaactt taggaacttt    30120
atcctagagc gctcaggaat cttgcccgcc acctgctgtg cacttcctag cgactttgtg    30180
cccattaagt accgcgaatg ccctccgccg ctttggggcc actgctacct tctgcagcta    30240
gccaactacc ttgcctacca ctctgacata atggaagacg tgagcggtga cggtctactg    30300
gagtgtcact gtcgctgcaa cctatgcacc ccgcaccgct ccctggtttg caattcgcag    30360
ctgcttaacg aaagtcaaat tatcggtacc tttgagctgc agggtccctc gcctgacgaa    30420
aagtccgcgg ctccggggtt gaaactcact ccggggctgt ggacgtcggc ttaccttcgc    30480
aaatttgtac ctgaggacta ccacgcccac gagattaggt tctacgaaga ccaatcccgc    30540
ccgccaaatg cggagcttac cgcctgcgtc attacccagg ccacattct tggccaattg     30600
caagccatca acaaagcccg ccaagagttt ctgctacgaa agggacgggg ggtttacttg    30660
gaccccagt ccggcgagga gctcaaccca atccccccgc cgccgcagcc ctatcagcag     30720
cagccgcggg cccttgcttc ccaggatggc acccaaaaag aagctgcagc tgccgccgcc    30780
acccacggac gaggaggaat actgggacag tcaggcagag gaggttttgg acgaggagga    30840
ggaggacatg atggaagact gggagagcct agacgaggaa gcttccgagg tcgaagaggt    30900
gtcagacgaa acaccgtcac cctcggtcgc attcccctcg ccggcgcccc agaaatcggc    30960
aaccggttcc agcatggcta caacctccgc tcctcaggcg ccgccggcac tgcccgttcg    31020
ccgacccaac cgtagatggg acaccactgg aaccagggcc ggtaagtcca agcagccgcc    31080
gccgttagcc caagagcaac aacagcgcca aggctaccgc tcatggcgcg ggcacaagaa    31140
cgccatagtt gcttgcttgc aagactgtgg gggcaacatc tccttcgccc gccgctttct    31200
tctctaccat cacggcgtgg ccttcccccg taacatcctg cattactacc gtcatctcta    31260
cagcccatac tgcaccggcg gcagcggcag cggcagcaac agcagcggcc acacagaagc    31320
aaaggcgacc ggatagcaag actctgacaa agcccaagaa atccacagcg gcggcagcag    31380
caggaggagg agcgctgcgt ctggcgccca acgaacccgt atcgaccgc gagcttagaa     31440
acaggatttt tcccactctg tatgctatat ttcaacagag caggggccaa gaacaagagc    31500
tgaaaataaa aaacaggtct ctgcgatccc tcacccgcag ctgcctgtat cacaaaagcg    31560
aagatcagct tcggcgcacg ctggaagacg cggaggctct cttcagtaaa tactgcgcgc    31620
tgactcttaa ggactagttt cgcgcccttt ctcaaattta agcgcgaaaa ctacgtcatc    31680
tccagcggcc acaccggcg ccagcacctg tcgtcagcgc catttatgag caaggaaatt     31740
cccacgccct acatgtggag ttaccagcca caaatgggac ttgcggctgg agctgcccaa    31800
gactactcaa cccgaataaa ctacatgagc gcgggacccc acatgatatc ccgggtcaac    31860
ggaatacgcg cccaccgaaa ccgaattctc ctgaacagg cggctattac caccacacct     31920
cgtaataacc ttaatccccg tagttggccc gctgccctgg tgtaccagga aagtcccgct    31980
cccaccactg tggtacttcc cagagacgcc caggccgaag ttcagatgac taactcaggg    32040
```

```
gcgcagcttg cgggcggctt tcgtcacagg gtgcggtcgc ccgggcaggg tataactcac  32100
ctgacaatca gagggcgagg tattcagctc aacgacgagt cggtgagctc ctcgcttggt  32160
ctccgtccgg acgggacatt tcagatcggc ggcgccggcc gctcttcatt cacgcctcgt  32220
caggcaatcc taactctgca gacctcgtcc tctgagccgc gctctggagg cattggaact  32280
ctgcaattta ttgaggagtt tgtgccatcg gtctacttta accccttctc gggacctccc  32340
ggccactatc cggatcaatt tattcctaac tttgacgcgg taaaggactc ggcggacggc  32400
tacgactgaa tgttaagtgg agaggcagag caactgcgcc tgaaacacct ggtccactgt  32460
cgccgccaca agtgctttgc ccgcgactcc ggtgagtttt gctactttga attgcccgag  32520
gatcatatcg agggcccggc gcacggcgtc cggcttaccg cccagggaga gcttgcccgt  32580
agcctgattc gggagtttac ccagcgcccc ctgctagttg agcgggacag gggaccctgt  32640
gttctcactg tgatttgcaa ctgtcctaac cctggattac aatttaaatg cggtctcaaa  32700
gatcttattc cctttaacta ataaaaaaaa ataataaagc atcacttact taaaatcagt  32760
tagcaaattt ctgtccagtt tattcagcag cacctccttg ccctcctccc agctctggta  32820
ttgcagcttc ctcctggctg caaactttct ccacaatcta aatggaatgt cagtttcctc  32880
ctgttcctgt ccatccgcac ccactatctt catgttgttg cagatgaagc gcgcaagacc  32940
gtctgaagat accttcaacc ccgtgtatcc atatgacacg gaaaccggtc tccaactgt   33000 gcctttcctt actcctccct ttgtatcccc caatgggttt caagagagtc ccctggggt   33060 actctctttg cgcctatccg aacctctagt tacctccaat ggcatgcttg cgctcaaaat  33120
gggcaacggc ctctctctgg acgaggccgg caaccttacc tcccaaaatg taaccactgt  33180
gagcccacct ctcaaaaaaa ccaagtcaaa cataaacctg gaaatatctg caccccctcac 33240 agttacctca gaagccctaa ctgtggctgc cgccgcacct ctaatggtcg cgggcaacac  33300
actcaccatg caatcacagg ccccgctaac cgtgcacgac tccaaactta gcattgccac  33360
ccaaggaccc ctcacagtgt cagaaggaaa gctagccctg caaacatcag gccccctcac  33420
caccaccgat agcagtaccc ttactatcac tgcctcaccc cctctaacta ctgccactgg  33480
tagcttgggc attgacttga aagagcccat ttatacacaa aatggaaaac taggactaaa  33540
gtacggggct cctttgcatg taacagacga cctaaacact ttgaccgtag caactggtcc  33600
aggtgtgact attaataata cttccttgca aactaaagtt actggagcct tgggttttga  33660
ttcacaaggc aatatgcaac ttaatgtagc aggaggacta aggattgatt ctcaaaacag  33720
acgccttata cttgatgtta gttatccgtt tgatgctcaa aaccaactaa atctaagact  33780
aggacagggc cctctttta taaactcagc ccacaacttg gatattaact acaacaaagg  33840
cctttacttg tttacagctt caaacaattc caaaagctt gaggttaacc taagcactgc  33900
caaggggttg atgtttgacg ctacagccat agccattaat gcaggagatg ggcttgaatt  33960
tggttcacct aatgcaccaa acacaaatcc cctcaaaaca aaaattggcc atggcctaga  34020
atttgattca aacaaggcta tggttcctaa actaggaact ggccttagtt ttgacagcac  34080
aggtgccatt acagtaggaa acaaaaataa tgataagcta actttgtgga ccacaccagc  34140
tccatctcct aactgtagac taaatgcaga gaaagatgct aaactcactt tggtcttaac  34200
aaaatgtggc agtcaaatac ttgctacagt ttcagttttg gctgttaaag gcagtttggc  34260
tccaatatct ggaacagttc aaagtgctca tcttattata agatttgacg aaaatggagt  34320
gctactaaac aattccttcc tggacccaga atattggaac tttagaaatg gagatcttac  34380
```

```
tgaaggcaca gcctatacaa acgctgttgg atttatgcct aacctatcag cttatccaaa    34440
atctcacggt aaaactgcca aaagtaacat tgtcagtcaa gtttacttaa acggagacaa    34500
aactaaacct gtaacactaa ccattacact aaacggtaca caggaaacag gagacacaac    34560
tccaagtgca tactctatgt cattttcatg ggactggtct ggccacaact acattaatga    34620
aatatttgcc acatcctctt cacttttttc atacattgcc caagaataaa gaatcgtttg    34680
tgttatgttt caacgtgttt atttttcaat tgcagaaaat ttcaagtcat tttttcattca   34740 gtagtatagc cccaccacca catagcttat acagatcacc gtaccttaat caaactcaca    34800
gaaccctagt attcaacctg ccactcccct cccaacacac agagtacaca gtcctttctc    34860
cccggctggc cttaaaaagc atcatatcat gggtaacaga catattctta ggtgttatat    34920
tccacacggt ttcctgtcga gccaaacgct catcagtgat attaataaac tccccgggca    34980
gctcacttaa gttcatgtcg ctgtccagct gctgagccac aggctgctgt ccaacttgcg    35040
gttgcttaac gggcggcgaa ggagaagtcc acgcctacat gggggtagag tcataatcgt    35100
gcatcaggat agggcggtgg tgctgcagca gcgcgcgaat aaactgctgc cgccgccgct    35160
ccgtcctgca ggaatacaac atggcagtgg tctcctcagc gatgattcgc accgccgca    35220 gcataaggcg ccttgtcctc cgggcacagc agcgcaccct gatctcactt aaatcagcac    35280
agtaactgca gcacagcacc acaatattgt tcaaaatccc acagtgcaag gcgctgtatc    35340
caaagctcat ggcggggacc acagaaccca cgtggccatc ataccacaag cgcaggtaga    35400
ttaagtggcg accctcata aacacgctgg acataaacat tacctctttt ggcatgttgt     35460 aattccaccac ctcccggtac catataaacc tctgattaaa catggcgcca tccaccacca   35520 tcctaaaccca gctggccaaa acctgcccgc cggctataca ctgcagggaa ccgggactgg   35580
aacaatgaca gtggagagcc caggactcgt aaccatggat catcatgctc gtcatgatat    35640
caatgttggc acaacacagg cacacgtgca tacacttcct caggattaca agctcctccc    35700
gcgttagaac catatcccag ggaacaaccc attcctgaat cagcgtaaat cccacactgc    35760
agggaagacc tcgcacgtaa ctcacgttgt gcattgtcaa agtgttacat tcgggcagca    35820
gcggatgatc ctccagtatg gtagcgcggg tttctgtctc aaaaggaggt agacgatccc    35880
tactgtacgg agtgcgccga acaaccgag atcgtgttgg tcgtagtgtc atgccaaatg     35940
gaacgccgga cgtagtcata tttcctgaag caaaaccagg tgcgggcgtg acaaacagat    36000
ctgcgtctcc ggtctcgccg cttagatcgc tctgtgtagt agttgtagta tatccactct    36060
ctcaaagcat ccaggcgccc cctggcttcg ggttctatgt aaactccttc atgcgccgct    36120
gccctgataa catccaccac cgcagaataa gccacaccca gccaacctac acattcgttc    36180
tgcgagtcac acacgggagg agcgggaaga gctggaagaa ccatgttttt ttttttattc    36240
caaaagatta tccaaaacct caaaatgaag atcattaag tgaacgcgct cccctccggt     36300
ggcgtggtca aactctacag ccaaagaaca gataatggca tttgtaagat gttgcacaat    36360
ggcttccaaa aggcaaacgg ccctcacgtc caagtggacg taaaggctaa acccttcagg    36420
gtgaatctcc tctataaaca ttccagcacc ttcaaccatg cccaaataat tctcatctcg    36480
ccaccttctc aatatatctc taagcaaatc ccgaatatta agtccggcca ttgtaaaaat    36540
ctgctccaga gcgccctcca ccttcagcct caagcagcga atcatgattg caaaaattca    36600
ggttcctcac agacctgtat aagattcaaa agcggaacat taacaaaaat accgcgatcc    36660
cgtaggtccc ttcgcagggc cagctgaaca taatcgtgca ggtctgcacg gaccagcgcg    36720
gccacttccc cgccaggaac catgacaaaa gaacccacac tgattatgac acgcatactc    36780
```

```
ggagctatgc taaccagcgt agccccgatg taagcttgtt gcatgggcgg cgatataaaa  36840
tgcaaggtgc tgctcaaaaa atcaggcaaa gcctcgcgca aaaaagaaag cacatcgtag  36900
tcatgctcat gcagataaag gcaggtaagc tccggaacca ccacagaaaa agacaccatt  36960
tttctctcaa acatgtctgc gggtttctgc ataaacacaa aataaaataa caaaaaaaca  37020
tttaaacatt agaagcctgt cttacaacag gaaaaacaac ccttataagc ataagacgga  37080
ctacggccat gccggcgtga ccgtaaaaaa actggtcacc gtgattaaaa agcaccaccg  37140
acagctcctc ggtcatgtcc ggagtcataa tgtaagactc ggtaaacaca tcaggttgat  37200
tcacatcggt cagtgctaaa aagcgaccga aatagcccgg gggaatacat acccgcaggc  37260
gtagagacaa cattacagcc cccataggag gtataacaaa attaatagga gagaaaaaca  37320
cataaacacc tgaaaaaccc tcctgcctag gcaaaatagc accctcccgc tccagaacaa  37380
catacagcgc ttccacagcg gcagccataa cagtcagcct taccagtaaa aagaaaacc   37440 tattaaaaaa acaccactcg acacggcacc agctcaatca gtcacagtgt aaaaaagggc  37500
caagtgcaga gcgagtatat ataggactaa aaaatgacgt aacggttaaa gtccacaaaa  37560
aacacccaga aaaccgcacg cgaacctacg cccagaaacg aaagccaaaa aacccacaac  37620
ttcctcaaat cgtcacttcc gttttcccac gttacgtcac ttcccatttt aagaaaacta  37680
caattcccaa cacatacaag ttactccgcc ctaaaaccta cgtcacccgc cccgttccca  37740
cgccccgcgc cacgtcacaa actccacccc ctcattatca tattggcttc aatccaaaat  37800
aaggtatatt attgatgatg tagggataac agggtaataa atccggggat cctctagagt  37860
cgacctgcag gcatgcaagc ttggcgtaat catggtcata gctgtttcct gtgtgaaatt  37920
gttatccgct cacaattcca cacaacatac gagccggaag cataaagtgt aaagcctggg  37980
gtgcctaatg agtgagcta                                               37999
```

USE OF PHOSPHOLIPID SCRAMBLASE INHIBITORS FOR MODULATING INFLAMMATORY IMMUNE RESPONSES

CROSS REFERENCE TO RELATED APPLICATIONS

This application claims the benefit of U.S. Provisional Application No. 62/436,591, filed Dec. 20, 2016, which is herein incorporated by reference in its entirety.

ACKNOWLEDGMENT OF GOVERNMENT SUPPORT

This invention was made with government support under grant number NS083038 awarded by the National Institutes of Health. The government has certain rights in the invention.

FIELD

This disclosure concerns methods of inhibiting inflammatory responses induced by virus vectors, virus infection or inflammatory diseases/conditions. This disclosure further concerns methods of prolonging expression of virally encoded transgenes in tissue.

BACKGROUND

Microglia are the first responders to central nervous system (CNS) injury or disease (Ransohoff and Perry, *Annu Rev Immunol* 27, 119-145, 2009). As innate immune sensors, these cells are equipped with a suite of receptors that allow them to detect disturbances in their microenvironment through the presence or absence of soluble and membrane-bound signals whose expression may be triggered by intrinsic or extrinsic events (Kettenmann et al., *Physiol Rev* 91, 461-553, 2011; Tremblay et al., *Neurosci* 31, 16064-16069, 2011). Microglia activation leads to an inflammatory response typically aimed at restricting tissue injury or pathogen spread. Under certain conditions, maladaptive innate immune responses can lead to undesired cell loss through microglial phagocytosis (Brown and Neher, *Nat Rev Neurosci* 15, 209-216, 2014).

A key, so-called 'eat-me' signal for phagocytosis is phosphatidylserine (PtdSer) (Arandjelovic and Ravichandran, *Nat Immunol* 16, 907-917, 2015; Lemke, *Cold Spring Harb Perspect Biol* 5, a009076, 2013; Sierra et al., *Front Cell Neurosci* 7, 6, 2013). PtdSer is a phospholipid constituent of all eukaryotic cell membranes, but displays a remarkable asymmetry in its distribution, in that it is normally confined to the inner (cytoplasm-facing) leaflet of the plasma membrane. During apoptosis or cell stress, PtdSer is externalized, potentially serving as a tag for engulfment of these cells by microglia and other professional phagocytes (Arandjelovic and Ravichandran, *Nat Immunol* 16, 907-917, 2015; Brown and Neher, *Nat Rev Neurosci* 15, 209-216, 2014; Sierra et al., *Front Cell Neurosci* 7, 6, 2013). Microglia can detect tagged cells, for example, through contact-mediated sensing, enabled by continual extension and retraction of microglial cell processes (Davalos et al., *Nat Neurosci* 8, 752-758, 2005; Fourgeaud et al., *Nature* 532, 240-244, 2016; Nimmerjahn et al., *Science* 308, 1314-1318, 2005). PtdSer orientation in the plasma membrane is regulated by calcium-dependent and -independent phospholipid transporters (Frey and Gaipl, *Semin Immunopathol* 33, 497-516, 2011). High intracellular calcium concentrations may promote PtdSer externalization (Segawa and Nagata, *Trends Cell Biol* 25, 639-650, 2015). However, the circumstances that lead to intracellular calcium dysregulation, PtdSer externalization, and microglia activation in vivo are for the most part unknown.

Viral infections of the CNS trigger innate immune responses that can include microglia phagocytosis (Sierra et al., *Front Cell Neurosci* 7, 6, 2013; Swanson and McGavern, *Curr Opin Virol* 11, 44-54, 2015; Vasek et al., *Nature* 534, 538-543, 2016). In particular, adenovirus (Ad)-based expression vectors are reagents for gene transfer in the CNS. Ad5-based vectors are widely used vectors in basic research applications and gene therapy. They are particularly attractive agents in the CNS where cellular division is limited, which in principle, would enable long-term transgene expression. However, Ad5-based vectors can induce potent inflammatory responses and undesired cell loss (Castro et al., *Expert Opin Biol Ther* 14, 1241-1257, 2014; Hendrickx et al., *Hum Gene Ther* 25, 265-284, 2014; Tobias et al., *J Neurol Neurosurg Psychiatry* 84, 213-222, 2013; Wold and Toth, *Curr Gene Ther* 13, 421-433, 2013). The underlying effector mechanisms remain poorly understood.

SUMMARY

Disclosed herein is the finding that phosphatidylserine (PtdSer) exposure on the outer leaflet of virally transduced cells triggers their engulfment by resident immune cells through TAM receptor-dependent mechanisms. It is demonstrated herein that inhibition of phospholipid scramblase 1 (PLSCR1) activity reduces intracellular calcium dysregulation, prevents PtdSer externalization and enables prolonged protection of vector-transduced transgene-expressing cells from phagocytosis.

Provided herein is a method of inhibiting a virus vector-induced inflammatory response in tissue of a subject by administering to the subject the virus vector and an inhibitor of phospholipid scramblase 1 (PLSCR1). Also provided is a method of prolonging transgene expression in tissue of a subject by administering to the subject a virus vector comprising a transgene and an inhibitor of PLSCR1. In some embodiments, the tissue is tissue of the central nervous system (CNS). In some embodiments, the inhibitor of PLSCR1 is encoded by the virus vector. In other embodiments, the inhibitor of PLSCR1 is administered as a separate composition from the virus vector. In specific non-limiting examples, the virus vector is an adenovirus (Ad) vector or a herpes simplex virus (HSV) vector.

Further provided herein is a method of modulating an inflammatory response in tissue of a subject suffering from a viral infection, a bacterial infection, an autoimmune disease, or cancer, by administering an inhibitor of PLSCR1. In some embodiments, the tissue is tissue of the central nervous system (CNS).

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Serial coronal brain sections (z) from an adult mouse 17 days after intracortical injection of 5.35×10⁵ PFU of an adenovirus 5 (Ad5)-based vector that expresses tdTomato under control of the CMV promoter. Sections were co-stained with DAPI. Scale bar, 1 mm. (FIG. 1B) tdTomato transgene expression pattern (top left), Iba-1- and GFAP-immunoreactivity (top right and lower left), and fluorescence image overlay (lower right) from a central brain section area, similar to the one indicated in FIG. 1A (dashed box), 17 days after intracortical vector injection. Scale bars, 200 µm. (FIG. 1C) Population analysis showing that Ad5-transduced cells are progressively cleared from the center toward the edges of the transduced area. The graph shows 1-way ANOVA with Tukey's multiple comparisons test ($\alpha=0.05$; n≥5 animals per group). (FIG. 1D) Population data showing time-dependent Iba-1- and GFAP-immunoreactivity from the transduced and control hemisphere. The graph shows 1-way ANOVA with Dunnett's multiple comparisons test ($\alpha=0.05$; n≥5 animals per group). (FIG. 1E) Maximum-intensity projection image showing GFP-positive microglia and tdTomato-positive cells in an area close to the center of the transduced area (left), similar to the area indicated in FIG. 1B (dashed box). Three-dimensional image reconstruction confirms engulfment of Ad5-transduced cells by microglia (right). Scale bars, 30 µm (left) and 15 µm (center and right). (FIG. 1F) Brain section showing tdTomato-positive cells, Iba-1-positive microglia and CD68-positive lysosomes 3 days after vector injection (top). A subset of CD68- and Iba-1 double-positive cells are indicated (arrowheads). Three-dimensional image reconstruction of the indicated area (dashed box) confirms the presence of CD68-positive lysosomes inside microglia. Scale bars, 50 µm (top) and 10 µm (bottom).

(FIG. 2A) Fluorescence image showing transduced cells (top left) 3 days after intracortical Ad5 vector delivery. Phosphatidylserine on outer cell membranes was visualized using the annexin-based fluorescent indicator polarity sensitive indicator of viability and apoptosis (pSIVA) (center left). An image overlay is shown at the bottom. pSIVA staining was increased in the transduced region. Higher magnification images of the boxed regions are shown on the right. Near central regions, pSIVA staining appears punctate indicating cell fragmentation (open arrowhead). In more peripheral regions, circumferential somatic membrane staining predominates, indicating stressed but live transduced and non-transduced cells (filled arrowheads). Scale bars, 100 µm (left) and 30 µm (right). (FIG. 2B) Fluorescence image showing pSIVA staining 3 days after vehicle (TMN) injection. A higher magnification image of the boxed region is shown on the right. Scale bars, 100 µm (left) and 50 µm (right). (FIG. 2C) Example immunofluorescence images showing that 3 days after vector injection Mertk is upregulated on Iba-1-positive microglia near central regions of the transduced area (left) compared to cells in the contralateral control hemisphere (right). Image overlays are shown at the bottom. Population data is shown in FIG. 4H. Scale bars, 5 µm. (FIG. 2D) Example immunofluorescence images showing that Axl is also upregulated on Iba-1-positive microglia near central regions (left) compared to the control hemisphere (right). Population data is shown in FIG. 4H. Scale bars, 5 µm.

FIGS. 3A-3B: Microglia-mediated Cell Clearance Depends on TAM Receptors. (FIG. 3A) Fluorescence images showing Ad5 CMV-promoter-driven tdTomato expression (top), Iba-1-(center) and GFAP-immunoreactivity (bottom) in an Axl$^{-/-}$ Mertk$^{-/-}$ double knock out mouse 17 days after vector injection. Scale bar, 200 µm. (FIG. 3B) Population analysis showing cell clearance (top), Iba-1- (center) and GFAP-immunoreactivity (bottom) in Mertk$^{-/-}$ single and Axl$^{-/-}$ Mertk$^{-/-}$ double knock out mice 17 days after Ad5 injection. Contralateral hemispheres served as control regions. The graphs show 1-way ANOVA with Tukey's multiple comparisons test ($\alpha=0.05$; n≥3 animals per group).

(FIG. 4A) Serial coronal brain sections (z) from an adult mouse 17 days after intracortical injection of 5.35×10⁵ PFU of an Ad5 vector that expresses tdTomato and a miR30-based shRNA against mouse phospholipid scramblase 1 (PLSCR1) under control of the CMV promoter. Sections were co-stained with DAPI. Scale bar, 1 mm. (FIG. 4B) Transgene expression pattern (top left), Iba-1- and GFAP-immunoreactivity (top right and lower left), and fluorescence image overlay (lower right) from a central brain section area 17 days after intracortical vector injection. Scale bars, 200 µm. (FIG. 4C) Population analysis showing that CMV promoter-driven PLSCR1-shRNA expression can significantly reduce clearance of Ad5-transduced cells compared to a non-silencing control (NSC) shRNA at 17 days after transduction. The graph shows unpaired t-test (two-tailed) with Welch's correction, $p<0.001$, n≥4 animals per group. (FIG. 4D) Population data showing Iba-1- and GFAP-immunoreactivity for PLSCR1- and NSC-shRNA vectors. Contralateral hemispheres served as control regions. The graph shows 1-way ANOVA with Dunnett's multiple comparisons test ($\alpha=0.05$; n≥4 animals per group). (FIG. 4E) Schematic showing analysis regions. r denotes radial distance from the injection center. (FIG. 4F) Population data showing the number of CD68-positive puncta on Iba-1 positive cells as a function of radial distance from the injection site for PLSCR1- (right bars) and NSC-shRNA (left bars) vectors. Data was normalized using contralateral hemispheres as control regions. The graph shows unpaired t-test ($p<0.01$ for 0-100 µm; n=3 animals per group; N≥2 slices per animal). (FIG. 4G) Population data showing the number of pSIVA-positive puncta on tdTomato-positive transduced cells as a function of radial distance from the injection site for PLSCR1- (right bars) and NSC-shRNA (left bars) vectors. The graph shows unpaired t-test with Welch's correction ($p<0.01$ for 0-100 µm, 100-200 µm, and 200-350 n=3 animals per group; N≥3 slices per animal). (FIG. 4H) Population data showing the number of Mertk- and Iba-1-double-positive cells (left) or Axl- and Iba-1-double-positive cells (right) as a function of radial distance from the injection site for PLSCR1- (right bars) and NSC-shRNA (left bars) vectors. Data was normalized using contralateral hemispheres as control regions. The graph on the left shows unpaired t-test ($p<0.01$ and $p<0.05$ for 0-100 µm and 100-200 respectively; n=3 animals per group; N≥3 slices per animal); the graph on the right shows unpaired t-test ($p<0.01$ and $p<0.05$ for 100-200 µm and 200-350 respectively; n≥2 animals per group; N≥3 slices per animal). (FIG. 4I) qPCR population data showing PLSCR1-shRNA-mediated reduction in tissue levels of interleukin-1β (IL-1β; left) and tumor necrosis factor-α (TNF-α; right) compared to the NSC vector at 3 days (two left bars) and 17 days (two right bars) after intracortical Ad5 injection. Tissue punches included the transduced area and some uninfected cells in the immediate vicinity of this area. The graph on the left shows unpaired t-test (two-tailed), $p<0.05$ (n=2 animals per group); the graph on the right shows unpaired t-test (two-tailed), $p<0.05$ (n=2 animals per group).

(FIG. 5A) Two-photon fluorescence image showing Ad5-CMV-tdTomato-NSC-shRNA transduced and non-transduced cells in the cortex of a live transgenic mouse expressing the green fluorescent, genetically encoded calcium indicator GCaMP5G under control of the glial fibrillary acidic protein (GFAP) promoter 17 days after intracortical vector delivery. Recordings were made at various axial depths and lateral distances from the injection site. This example recording was made at the injection site 140 µm below the pia (injection depth, 200 µm). Scale bar, 100 µm. (FIG. 5B) Calcium activity of Ad5-transduced and non-transduced GCaMP5G-expressing cells in an awake head-restrained mouse on an exercise ball. Top, mouse running speed on the ball. Center and bottom, corresponding ΔF/F increases in 36 non-transduced and 62 transduced cells, respectively. Regions of interest (ROIs) used for analysis of calcium signals in transduced and non-transduced cells are indicated in FIG. 5A. Scale bars, 20 mm/s and 50 s. (FIG. 5C) Population data showing the running onset-triggered (vertical line) average ΔF/F increase across all Ad5-transduced and non-transduced GCaMP5G-positive cells. Each recording included 2-4 running bouts. Shaded areas represents 75% and 25% percentile of the mean. (FIG. 5D) Two-photon fluorescence image showing Ad5-CMV-tdTomato-PLSCR1-shRNA transduced and non-transduced cells in the cortex of a live transgenic mouse expressing GCaMP5G under control of the GFAP promoter 17 days after intracortical vector delivery (recording depth, 120 µm). Elongated dark regions are due to light absorption by surface blood vessels. Scale bar, 100 µm. (FIG. 5E) Calcium activity of Ad5-transduced and non-transduced GCaMP5G-positive cells in an awake head-restrained mouse on an exercise ball. Top, mouse running speed on the ball. Center and bottom, corresponding ΔF/F increases in 69 non-transduced and 60 transduced cells, respectively. ROIs used for analysis of transduced and non-transduced cells' calcium signals are indicated in FIG. 5D. Scale bars, 20 mm/s and 50 s. (FIG. 5F) Population data showing the running onset-triggered (vertical line) average ΔF/F increase across all Ad5-transduced and non-transduced GCaMP5G-positive cells. Each recording included 2-4 running bouts. Shaded areas represent 75% and 25% percentile of the mean. (FIG. 5G) Schematic showing analysis regions. r denotes radial distance from the injection center. (FIGS. 5H-5J) Running onset-triggered responsiveness, GCaMP5G baseline fluorescence, and tdTomato fluorescence, respectively, of Ad5-CMV-tdTomato-NSC-shRNA- or Ad5-CMV-tdTomato-PLSCR1-shRNA-transduced cells as a function of radial distance from the center of the injection site (from left to right bars represent r1, r2, r3 and untransduced cells as indicated in FIG. 5G). Data was normalized to non-transduced cells far away from the injection site (FIGS. 14H-14J). FIG. 5H shows paired t-test (Bonferroni corrected) for comparisons within the NSC (p<0.0001) or PLSCR1-shRNA group, and unpaired t-test (Bonferroni corrected) for comparison between the two groups (p<0.05); FIGS. 5I and 5J show unpaired t-test (Bonferroni corrected; p<0.05 and p<0.0001, respectively); the NSC or PLSCR1-shRNA group data in FIGS. 5H-5J is based on 25 recordings from 2 mice (1,208 non-transduced cells and 48, 337, 183 transduced cells within 0-100 µm, 100-200 µm, >200 µm, respectively) or 20 recordings from 3 mice, respectively (1,398 non-transduced cells and 130, 363, 290 transduced cells within 0-100 µm, 100-200 µm, >200 µm, respectively). Each recording included 2-4 running bouts.

(FIG. 6A) Fluorescence images showing Ad5-transduced tdTomato- and PLSCR1-shRNA-expressing cells 1 month (top), 3 months (center), and 6 months (bottom) after intracortical vector injection in three different mice. Close-ups show morphology of transduced cells near central regions of the transduced area. Scale bars, 200 µm (left) and 50 µm (right). (FIG. 6B) Population data showing cell clearance (top), Iba-1- (center) and GFAP-immunoreactivity (bottom) at 1 month, 3 months, or 6 months after intracortical injection of Ad5 with PLSCR1- or NSC-shRNA. The graphs show two-way ANOVA with Sidak's multiple comparisons test (α=0.05; n≥3 animals per group).

FIGS. 8A-8F: Microglia Are Activated by Adenoviral Vector Transduction. (FIG. 8A) Fluorescence images showing Iba-1- (top) and GFAP-immunoreactivity (bottom) in a wild type mouse 17 days after intracortical Ad5-CMV-Null injection. Iba-1 immunoreactivity is increased near the center of the injection site, while GFAP immunoreactivity is heightened near peripheral transduced regions, akin to immunoreactivity patterns in Ad5-CMV-tdTomato injected mice (FIG. 1B). Vehicle-injected mice (FIG. 8C) do not show these characteristic Iba-1 and GFAP immunoreactivity patterns. Scale bars, 200 µm. (FIG. 8B) Population data showing Iba-1- (top) and GFAP-immunoreactivity (bottom) in Ad5-CMV-Null- and Ad5-CMV-tdTomato-injected wild type mice 17 days after intracortical Ad5 delivery. The difference in particle to PFU ratio between the two vectors (Table 2) may, at least in part, account for the difference in GFAP immunoreactivity. The graphs show unpaired t-test with Welch's correction, p<0.0001, n≥3 animals per group. (FIG. 8C) Fluorescence images showing Iba-1- (top) and GFAP-immunoreactivity (bottom) in a wild type mouse 17 days after intracortical vehicle (TMN) injection. Scale bars, 200 µm. (FIG. 8D) Population data showing Iba-1- (top) and GFAP-immunoreactivity (bottom) from the vehicle (TMN) injected and control hemisphere (black). The graphs show paired t-test, p<0.05, n≥3 animals per group. (FIG. 8E) Fluorescence image showing transduced cells (top) 3 days after intracortical Ad5-CMV-tdTomato vector delivery. Center images show Iba-1-immunoreactivity and CD68-positive lysosomes from the same brain section. Right column images show boxed region at higher magnification. CD68 staining is increased near central regions. Image overlay is shown at the bottom. A subset of CD68- and Iba1-double-positive cells is indicated (arrowheads). Scale bars, 100 µm (left) and 50 µm (right). (FIG. 8F) Fluorescence images from the contralateral control hemisphere showing Iba1-positive microglia (top) and CD68-positive lysosomes (center). Right column images show boxed region at higher magnification. Image overlays are shown at the bottom. Scale bars, 100 µm (left) and 50 µm (right).

FIGS. 9A-9B: Multiple Immune Sensing Pathways Contribute to Microglia Activation and Cell Clearance. (FIG. 9A) Fluorescence images showing Ad5 CMV promoter-driven tdTomato expression pattern (top), Iba-1- (center) and GFAP-immunoreactivity (bottom) in wild type control (left), Toll-like receptor (TLR) 3, 4, or 9 knock out (TLR3/4/9$^{-/-}$; center), or TMEM173/stimulator of interferon gene mutant (STING$^{-/-}$; right) mice 17 days after intracortical vector injection. Scale bars, 200 µm. (FIG. 9B) Population data showing cell clearance (top), Iba-1-(center) and GFAP-immunoreactivity (bottom) in TLR3$^{-/-}$, TLR4$^{-/-}$, TLR9$^{-/-}$ knock out and STING$^{-/-}$ mutant compared to wild type control mice 17 days after intracortical Ad5 injection. The graphs show 1-way ANOVA with Dunnett's multiple comparisons test ($\alpha$=0.05, n≥3 animals per group).

FIGS. 10A-10B: Multiple Cytokine Signaling Pathways Contribute to Microglia Activation and Cell Clearance. (FIG. 10A) Fluorescence images showing Ad5 CMV promoter-driven tdTomato expression pattern (top), Iba-1- (center) and GFAP-immunoreactivity (bottom) in wild type control (left), type I interferon receptor knock out (IFNAR1$^{-/-}$; center left), interleukin-1 receptor 1 knock out (IL-1R1$^{-/-}$; center right), or tumor necrosis factor knock out (TNF$^{-/-}$; right) mice 17 days after intracortical vector injection. Scale bars, 200 µm. (FIG. 10B) Population data showing cell clearance (top), Iba-1- (center) and GFAP-immunoreactivity (bottom) in IFNAR1$^{-/-}$, IL-1R1$^{-/-}$ and TNF$^{-/-}$ knock out compared to wild type control mice 17 days after intracortical Ad5 injection. The graphs show 1-way ANOVA with Dunnett's multiple comparisons test ($\alpha$=0.05, n=3 animals per group).

(FIG. 11A) Quantitative PCR (qPCR) population data showing Ad5 CMV promoter-driven, shRNA-mediated knock down of mouse phospholipid scramblase 1 (PLSCR1) compared to the NSC vector at 48 hours after transduction of astrocyte-enriched cortical cultures using a multiplicity of infection (MOI) of 20. The graph shows 1-way ANOVA with Tukey's multiple comparisons test ($\alpha$=0.05, n=2 separate culture preparations from 5 animals each, and 2 separate virus infections each performed in triplicate). (FIG. 11B) Brain sections showing Ad5-CMV-tdTomato-NSC-shRNA- (left) or Ad5-CMV-tdTomato-PLSCR1-shRNA-transduced cells (right) in the cortex of transgenic mice expressing green fluorescent protein under control of transcriptional regulatory sequences of the human S100 calcium binding protein B (S100B) gene 17 days after intracortical vector delivery. Note that S100B is not exclusively expressed in cortical astrocytes, which likely accounts for the eGFP-positive, td-Tomato-negative cells within the transduced region. Scale bars, 200 µm. (FIG. 11C) Schematic showing analysis regions. r denotes radial distance from the injection center. (FIG. 11D) Population data showing the change in the number of eGFP-positive cells in PLSCR1- or NSC-shRNA vector transduced S100b-eGFP mice as a function of radial distance from the injection site. Data was normalized using contralateral hemispheres as control regions. The graph shows unpaired t-test (p<0.01 for 0-100 µm, n=3 animals per group; N=3 slices per animal). (FIG. 11E) Brain sections showing Ad5-CMV-tdTomato-NSC-shRNA- (left) or Ad5-CMV-tdTomato-PLSCR1-shRNA-transduced cells (right) in the cortex of wild type mice 17 days after intracortical vector delivery. Sections were stained with the neuronal marker NeuN. The majority of NeuN-positive cells are tdTomato-negative. Scale bars, 200 µm. (FIG. 11F) Population data showing the change in the number of NeuN-positive cells in vehicle (TMN) control, PLSCR1- and NSC-shRNA vector transduced mice as a function of radial distance from the injection site. Data was normalized using contralateral hemispheres as control regions. The graph shows 1-way ANOVA with Dunnett's multiple comparisons test ($\alpha$=0.05; n≥3 animals per group; N≥2 slices per animal). (FIG. 11G) Brain sections showing Ad5-CMV-tdTomato-NSC-shRNA- (left) or Ad5-CMV-tdTomato-PLSCR1-shRNA-transduced cells (right) in the cortex of wild type mice 17 days after intracortical vector delivery. Sections were stained with the nuclear marker DAPI. Scale bars, 200 µm. (FIG. 11H) Population data showing the change in the number of DAPI-positive cells in vehicle (TMN) control, PLSCR1- and NSC-shRNA vector transduced mice as a function of radial distance from the injection site. Data was normalized using contralateral hemispheres as control regions. The increase in microglial cell density (FIG. 1B; FIG. 11I) likely compensates, at least in part, for the reduced astrocyte and neuronal cell density seen in central regions of NSC-shRNA vector transduced mice (FIGS. 11D and 11F). The graph shows 1-way ANOVA with Dunnett's multiple comparisons test ($\alpha$=0.05; n≥3 animals per group; N≥2 slices per animal). (FIG. 11I) Population data showing the number of Iba-1-, GFAP- and tdTomato-positive cells in PLSCR1- and NSC-shRNA vector transduced mice as a function of radial distance from the injection site. The graph on the left shows unpaired t-test with Welch's correction (p<0.001 for 0-100 µm and 100-200 µm, n≥3 animals per group; N=3 slices per animal); the graph in the center shows unpaired t-test with Welch's correction (p<0.001 for 100-200 n≥3 animals per group; N=3 slices per animal); the graph on the right shows unpaired t-test with Welch's correction (p<0.001 and p<0.05 for 0-100 µm and 100-200 µm, n≥3 animals per group; N=3 slices per animal).

(FIG. 12A) Fluorescence image showing transduced cells (top left) 3 days after intracortical Ad5-CMV-tdTomato-PLSCR1-shRNA vector delivery. Center images show Iba-1-immunoreactivity and CD68-positive lysosomes from the same brain section. Image overlay is shown at the bottom. Right column images show boxed regions at higher magnification. CD68 staining is not significantly increased near central regions (FIG. 4F), despite transient morphological activation of microglia 3 days after vector injection. Scale bars, 100 µm (left) and 50 µm (right). (FIG. 12B) Fluorescence images from the contralateral control hemisphere showing Iba1-positive microglia (top) and CD68-positive lysosomes (center). Image overlay is shown at the bottom. Right column images show boxed regions at higher magnification. Scale bars, 100 µm (left) and 50 µm (right). (FIG. 12C) Fluorescence image showing transduced cells (top left) 3 days after intracortical Ad5-CMV-tdTomato-PLSCR1-shRNA vector delivery. Phosphatidylserine on outer cell membranes was visualized using pSIVA, an annexin-based fluorescent biosensor (center). Image overlay is shown at the bottom. Right column images show boxed regions at higher magnification. pSIVA staining is not significantly increased near central regions (FIG. 4G). Scale bars, 100 µm (left) and 50 µm (right). (FIG. 12D) Fluorescence image showing pSIVA staining 3 days after vehicle (TMN) injection. A higher magnification image of the boxed region is shown on the right. Scale bars, 100 µm (left) and 50 µm (right). (FIG. 12E) Example immunofluorescence images showing Mertk expression on Iba-1-positive microglia near central regions of the transduced area (left) 3 days after Ad5-CMV-tdTomato-PLSCR1-shRNA vector delivery, next to images from the contralateral control hemisphere (right). Image overlays are shown at the bottom. Mertk expression is reduced compared to NSC-shRNA vector transduced mice (FIGS. 2C and 4H). Scale bars, 5 µm. (FIG. 12F) Example immunofluorescence images showing Axl expression on Iba-1-positive microglia near central regions of the transduced area (left) 3 days after Ad5-CMV-tdTomato-PLSCR1-shRNA vector delivery, next to images from the contralateral control hemisphere (right). Image overlays are shown at the bottom. Population data is shown in FIG. 4H. Scale bars, 5 µm.

(FIG. 13A) tdTomato expression pattern (top left), Iba-1- (top right) and GFAP-immunoreactivity (lower left), and fluorescence image overlay (lower right) 17 days after intracortical injection of an Ad5 vector expressing calcium-insensitive $PLSCR1_{D284A}$ under control of a CMV promoter. Scale bars, 200 µm. (FIG. 13B) Population data showing cell clearance, Iba-1- and GFAP-immunoreactivity in mice injected with an Ad5 vector expressing calcium-insensitive $PLSCR1_{D284A}$. The graphs show unpaired t-test (two-tailed) with Welch's correction, p<0.0001, n=3 animals per group. (FIG. 13C) Fluorescence image showing transduced cells 3 days after intracortical Ad5-CMV-tdTomato-$PLSCR1_{D284A}$ vector delivery. Tissue was co-stained with pSIVA, an annexin-based fluorescent indicator that labels phosphatidylserine on outer cell membranes. A higher magnification image of the boxed regions is shown on the right. Scale bars, 200 µm (left) and 50 µm (right). (FIG. 13D) Population data showing the number of pSIVA-positive puncta on tdTomato-positive transduced cells as a function of radial distance from the injection site for $PLSCR1_{D284A}$ (right bars) and NSC-shRNA (left bars) vectors. The graph shows unpaired t-test with Welch's correction (p<0.05 for 100-200 µm and 200-350 µm, n=3 animals per group; N≥2 slices per animal).

(FIG. 14A) Two-photon fluorescence image showing Ad5-CMV-tdTomato-$PLSCR1_{D284A}$-transduced and non-transduced cells in the cortex of a live transgenic mouse expressing the green fluorescent, genetically encoded calcium indicator GCaMP5G under control of the glial fibrillary acidic protein (GFAP) promoter 17 days after intracortical vector delivery (recording depth, 82 µm). Scale bar, 100 µm. (FIG. 14B) Calcium activity of Ad5-transduced and non-transduced GCaMP5G-expressing cells in an awake head-restrained mouse on an exercise ball. Top, mouse running speed. Center and bottom, corresponding ΔF/F increases in 122 non-transduced and 52 transduced cells, respectively. Regions of interest (ROIs) used for analysis of calcium signals in transduced and non-transduced cells are indicated in FIG. 14A. Scale bars, 20 mm/s and 50 s. (FIG. 14C) Population data showing the running onset-triggered (vertical line) average ΔF/F increase across all Ad5-transduced and non-transduced GCaMP5G-positive cells. Each recording included 2-4 running bouts. Shaded areas represent 75% and 25% percentile of the mean. (FIG. 14D) Schematic showing analysis regions. r denotes radial distance from the injection center. (FIGS. 14E-14G) Running onset-triggered responsiveness, GCaMP5G baseline fluorescence, and tdTomato fluorescence, respectively, of Ad5-CMV-tdTomato-NSC-shRNA- (left) or Ad5-CMV-tdTomato-$PLSCR1_{D284A}$-transduced cells (right) as a function of radial distance from the center of the injection site (from left to right bars represent r1, r2, r3 and untransduced cells as indicated in FIG. 14D). Data was normalized to non-transduced cells far away from the injection site (FIGS. 14H-14J). FIG. 14E shows paired t-test (Bonferroni corrected) for comparisons within the NSC (p<0.0001) or $PLSCR1_{D284A}$ group (p<0.05), and unpaired t-test (Bonferroni corrected) for comparison between the two groups (p<0.05). FIGS. 14F and 14G show unpaired t-test (Bonferroni corrected; p<0.05 and p<0.0001, respectively). The NSC or $PLSCR1_{D284A}$ group data in FIGS. 14E-14G is based on 25 recordings from 2 mice (1,208 non-transduced cells and 48, 337, 183 transduced cells within 0-100 µm, 100-200 µm, >200 µm, respectively) or 11 recordings from 3 mice, respectively (814 non-transduced cells and 23, 91, 105 transduced cells within 0-100 µm, 100-200 µm, >200 respectively). (FIGS. 14H-14J) Running onset-triggered responsiveness, GCaMP5G baseline fluorescence, and tdTomato fluorescence, respectively, of non-transduced cells in Ad5-CMV-tdTomato-NSC-shRNA- (left bars), Ad5-CMV-tdTomato-PLSCR1-shRNA- (center bars) or Ad5-CMV-tdTomato-$PLSCR1_{D284A}$-injected mice (right bars) as a function of radial distance from the center of the injection site. For each group, the bars represent from left to right: r=300-600 µm, r=600-1000 µm and r>1000 µm. The data is based on 9, 8 or 4 recordings in 2-3 mice for the NSC, PLSCR1 or $PLSCR1_{D284A}$ group, respectively. Each recording included 2-4 running bouts. Non-transduced cell group data in FIGS. 14H-14J is based on 9, 8 or 4 recordings from 2, 3 or 3 NSC, PLSC1-shRNA or $PLSCR1_{D284A}$ injected mice, respectively (1,208, 1,398 or 814 total non-transduced cells, respectively); each recording included 2-4 running bouts.

FIGS. 15A-15B: PLSCR1 Inhibition Maintains Blood-brain Barrier Integrity after Adenoviral Vector Transduction. (FIG. 15A) Tight junction protein expression is reduced in eGFP-Claudin5 mice injected with Ad5-CMV-tdTomato-NSC. (FIG. 15B) PLSCR1 inhibition rescues this effect. Scale bars, 50 µm.

FIGS. 16A-16B: PLSCR1 Inhibition Protects from Cell Loss for a Range of Adenoviral Vector Doses. Serial coronal brain sections (z) from adult mice 17 days after intracortical delivery of $5.35 \times 10^5$ PFU (FIG. 16A) or $4.93 \times 10^6$ PFU (FIG. 16B) of an Ad5-CMV-tdTomato-PLSCR1-shRNA vector. Bottom images show boxed regions at higher magnification. Scale bars, 1 mm (top) and 200 µm (bottom).

(FIG. 17C) Quantitation of Iba-1 immunoreactivity indicating that PLSCR1 inhibition reduces HSV-1 vector-mediated inflammatory responses. Scale bars, 200 μm.

SEQUENCE LISTING

Figure 1A:
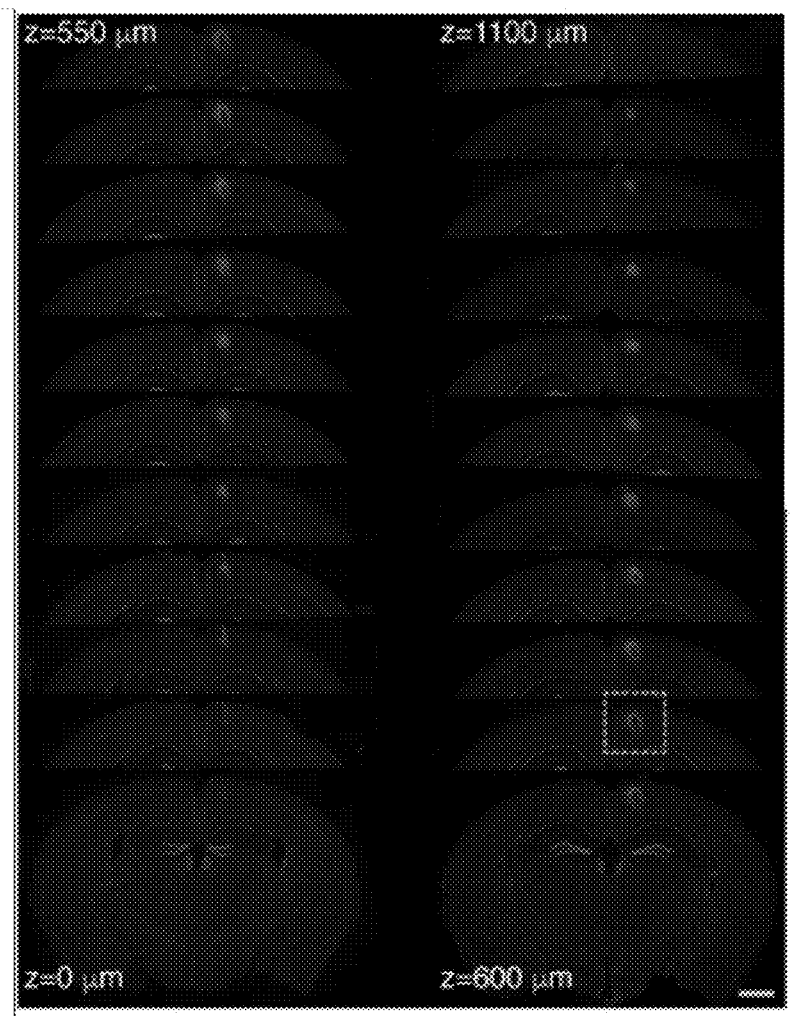
FIGS. 1A-1F: Microglia Engulf Adenoviral Vector-transduced Cells.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 18, 2017, 338 KB, which is incorporated by reference herein. In the accompanying sequence listing:

SEQ ID NO: 1 is the nucleotide sequence of adenovirus vector CMV-tdTomato-NSC-shRNA.

SEQ ID NO: 2 is the nucleotide sequence of adenovirus vector CMV-tdTomato-PLSCR1-shRNA.

SEQ ID NO: 3 is the nucleotide sequence of adenovirus vector CMV-PLSCR1$_{D284A}$-P2A-tdTomato.

SEQ ID NO: 4 is the nucleotide sequence of adenovirus vector CMV-Null.

SEQ ID NO: 5 is the nucleotide sequence of an E1/E3 deleted adenovirus vector.

SEQ ID NO: 6 is the nucleotide sequence of a non-silencing control RNA.

SEQ ID NO: 7 is the nucleotide sequence of a mouse PSCR1 shRNA.

SEQ ID NOs: 8 and 9 are PLSCR1 mutagenesis primer sequences.

SEQ ID NOs: 10 and 11 are cyclophilin A qRT-PCR primer sequences.

SEQ ID NOs: 12 and 13 are 36B4 qRT-PCR primer sequences.

SEQ ID NOs: 14 and 15 are mPLSCR1-3 qRT-PCR primer sequences.

SEQ ID NOs: 16 and 17 are IL-1β qRT-PCR primer sequences.

SEQ ID NOs: 18 and 19 are TNF-α qRT-PCR primer sequences.

SEQ ID NO: 20 is the TOPO/mCherry forward primer sequence.

SEQ ID NO: 21 is the TOPO/shRNA reverse primer sequence.

SEQ ID NO: 22 is the nucleotide sequence of adenovirus vector CMV-PLSCR1-shRNA.

SEQ ID NO: 23 is the nucleotide sequence of adenovirus vector CMV-PLSCR1$_{D284A}$-P2A.

DETAILED DESCRIPTION

I. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adenovirus: A non-enveloped virus with a linear, double-stranded DNA genome and an icosahedral capsid. There are currently 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G). Adenovirus-based vectors are commonly used in a variety of therapeutic and gene therapy applications.

Administration: To provide or give a subject an agent, such as a therapeutic agent (e.g. a virus vector), by any effective route. Exemplary routes of administration include, but are not limited to, injection (such as subcutaneous, intramuscular, intradermal, intraperitoneal, intratumoral, intrathecal, intracortical and intravenous), oral, intraductal, sublingual, rectal, transdermal, intranasal, vaginal and inhalation routes.

Gram-negative bacteria: Bacteria that loose or do not retain dark blue or violet stain during Gram staining, but instead are colored by a counterstain, such as safranin, and appear pink or ed. Gram-negative bacteria have a thin peptidoglycan layer. Exemplary Gram-negative bacteria include, but are not limited to:

| | |
|---|---|
| Acetic acid bacteria | *Fusobacterium necrophorum* |
| *Acinetobacter baumannii* | *Fusobacterium nucleatum* |
| *Agrobacterium tumefaciens* | *Fusobacterium polymorphum* |
| *Anaerobiospirillum* | *Haemophilus haemolyticus* |
| *Bacteroides* | *Haemophilus influenzae* |
| *Bacteroides fragilis* | *Helicobacter* |
| *Bdellovibrio* | *Helicobacter pylori* |
| *Brachyspira* | *Klebsiella pneumoniae* |
| *Cardiobacterium hominis* | *Legionella* |
| *Coxiella burnetii* | *Legionella pneumophila* |
| *Cyanobacteria* | *Leptotrichia buccalis* |
| *Cytophaga* | *Megamonas* |
| *Dialister* | *Megasphaera* |
| *Enterobacter* | *Moraxella* |
| *Enterobacter cloacae* | *Moraxella bovis* |
| *Enterobacteriaceae* | *Moraxella catarrhalis* |
| *Escherichia* | *Moraxella osloensis* |
| *Escherichia coli* | *Morganella morganii* |
| *Rickettsia rickettsii* | *Negativicutes* |
| *Salmonella* | *Neisseria gonorrhoeae* |
| *Salmonella enterica* | *Neisseria meningitidis* |
| *Salmonella enterica* | *Neisseria sicca* |
| *Selenomonadales* | *Pectinatus* |
| *Serratia marcescens* | *Propionispora* |
| *Shigella* | *Proteobacteria* |
| *Spirochaeta* | *Proteus mirabilis* |
| *Spirochaetaceae* | *Proteus penneri* |
| *Sporomusa* | *Pseudomonas* |
| *Stenotrophomonas* | *Pseudomonas aeruginosa* |
| *Streptococcus gordonii* | *Chlamydia trachomatis* |
| *Vampirococcus* | |
| *Verminephrobacter* | |
| *Vibrio cholerae* | |
| *Wolbachia* | |
| *Zymophilus* | |

Hepatitis B virus (HBV): A virus belonging to the Hepadnaviridae family of viruses that causes the disease hepatitis B. HBV is a double-stranded DNA virus with an icosahedral capsid and a lipid envelope.

Hepatitis C virus (HCV): A virus belonging to the Flaviviridae family of viruses. HCV is the causative agent of hepatitis C and can cause some types of cancer, including hepatocellular carcinoma and lymphoma. HCV is a positive-sense, single-stranded RNA virus with an icosahedral capsid and a lipid envelope.

Herpes simplex virus (HSV): A member of the Alphaherpesvirinae subfamily of the Herpesviridae family. Herpesviruses have a linear, double-stranded DNA genome that circularizes upon infection. The genome is contained within an icosahedral capsid, which is surrounded by a lipid envelope.

Heterologous: A heterologous protein or gene refers to a protein or gene derived from a different source or species.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents (e.g. a recombinant virus and/or PLSCR inhibitor).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospholipid scramblase (PLSCR): A family of proteins implicated in the translocation of phospholipids between the two monolayers of a lipid bilayer of a cell membrane. In humans, there are five PLSCR genes (PLSCR1-5). PLSCR1, PLSCR3 and PLSCR4 are expressed, for example, in the cortex and possess a conserved calcium ion binding domain and a putative transmembrane region (Zhang et al., 2014). PLSCR1 also contains a nuclear localization signal and a DNA binding domain, and is upregulated in response to inflammatory stimuli (Kodigepalli et al., 2015). PLSCR1 nucleotide and amino acid sequences are publically available, such as those provided under NCBI gene ID 5359. For example, GenBank Accession Nos. NM_021105 and NP_066928 provide mRNA and protein sequences, respectively, for human PLSCR1.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus. A recombinant cell includes cells that contain a non-naturally occurring nucleic acid molecule or protein, such as a recombinant nucleic acid molecule or protein.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Short hairpin RNA (shRNA): A sequence of RNA that makes a tight hairpin turn and can be used to silence gene expression via the RNAi pathway. The shRNA hairpin structure is cleaved by the cellular machinery into siRNA.

Subject: Living multi-cellular organisms, a category that includes both human and veterinary subjects, including human and non-human mammals.

Synthetic: Produced by artificial means in a laboratory, for example a synthetic nucleic acid or protein can be chemically synthesized in a laboratory.

Therapeutically effective amount: A quantity of a specified pharmaceutical or therapeutic agent (e.g. a virus vector and/or PLSCR inhibitor) sufficient to achieve a desired effect in a subject, or in a cell, being treated with the agent.

The effective amount of the agent can be dependent on several factors, including, but not limited to the subject or cells being treated, and the manner of administration of the therapeutic composition.

Transgene: A gene that has been inserted into the genome of a different organism (such as a virus). Transgenes can also be referred to as heterologous genes.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Vesicular stomatitis virus (VSV): A virus in the family Rhabdoviridae, genus *Vesiculovirus*. The VSV genome is comprised of non-segmented, negative-sense RNA. VSV vectors have been used for a variety of therapeutic applications, including as virus or cancer vaccine vectors.

Virus: An infectious agent that replicates itself only within cells of living hosts. Viruses are comprised of nucleic acid (DNA or RNA) surrounded by a protein coat. Examples of viruses include, but are not limited to those in the following virus families: Retroviridae (for example, human immunodeficiency virus (HIV), human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus, rubella viruses); Flaviridae (for example, hepatitis C virus, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxviridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Overview of Several Embodiments

Microglia are the intrinsic immune sentinels of the central nervous system. Their activation restricts tissue injury and pathogen spread, but in some settings, including viral infection, this response can contribute to cell death and disease. Mechanisms through which microglia recognize and respond to viral uptake using replication-incompetent adenovirus 5 (Ad5)-based vectors as a model were investigated. Transgenic, immunohistochemical, molecular genetic, and fluorescence imaging approaches revealed that phosphatidylserine (PtdSer) exposure on the outer leaflet of transduced cells triggers their engulfment by microglia through TAM receptor-dependent mechanisms. It is demonstrated herein that inhibition of phospholipid scramblase 1 (PLSCR1) activity, involved in antiviral responses, prevents PtdSer externalization and enables months-long protection of vector-transduced transgene-expressing cells from microglial phagocytosis. The present disclosure identifies PLSCR1 as a target through which the innate immune response to viral vectors, and other stimuli, can be controlled.

Provided herein is a method of reducing or inhibiting a virus vector-induced inflammatory response in tissue of a subject by administering to the subject the virus vector and an inhibitor of phospholipid scramblase 1 (PLSCR1). The virus vector-induced inflammatory response need not be completely eliminated for the treatment to be effective. In some examples, the virus vector-induced inflammatory response in the tissue of a subject is reduced by at least 20%, at least 30%, at least 40%, at least 50%, at least 75%, at least 80%, at least 90%, at least 95%, at least 99%, or even 100%, for example as compared to no administration of the PLSCR1 inhibitor. In some embodiments, the inhibitor of PLSCR1 is encoded by the virus vector. In other embodiments, the inhibitor of PLSCR1 is administered as a separate composition from the virus vector. When administered as a separate composition, the PLSCR1 inhibitor is generally administered about 24-72 hours prior to administration of the virus vector, such as about 72 hours, about 48 hours, or about 24 hours or prior to administration of the virus vector. The PLSCR1 inhibitor can be administered as frequently as necessary to maintain effective concentrations of the inhibitor in tissue (which depends on its half-life), and for as long as necessary to prevent immune activation and/or remain symptom-free. Thus, in some examples, the PLSCR1 inhibitor is administered in multiple doses (such as about 2, 3, 4, 5, 6, 7, 8, 9, or 10 doses) about 24-72 hours prior to administration of the virus vector. In some examples, the PLSCR1 inhibitor is further administered after administration of the virus vector, either in a single dose or in multiple doses (such as about 2, 3, 4, 5, 6, 7, 8, 9, or 10 doses).

In some embodiments, the virus vector is an adenovirus (Ad) vector. In some examples, the virus vector is an adenovirus type 5 (Ad5) vector. In some examples, the Ad vector is a replication-incompetent virus vector. In other examples, the Ad vector is replication competent in specific cell types, such as tumor cells. In specific non-limiting examples, the Ad vector is an oncolytic Ad that is specifically capable of replication in tumor cells.

In other embodiments, the virus vector is a herpes simplex virus (HSV) vector, such as an HSV-1 or HSV-2 vector.

In other embodiments, the virus vector is a canine adenovirus (CAV), a hepatitis B virus (HBV) vector, a hepatitis C virus (HCV) vector, or a vesicular stomatitis virus (VSV) vector.

In some embodiments, the virus vector comprises a transgene. In some examples, the transgene is a reporter gene. In particular examples, the reporter gene encodes a fluorescent protein, such as but not limited to, a green fluorescent protein (GFP), a yellow fluorescent protein (YFP), a cyan fluorescent protein (CFP), a red fluorescent protein (RFP), a blue fluorescent protein (BFP), or an orange fluorescent protein (for example, mOrange). In other particular examples, the reporter gene encodes an enzyme, such as but not limited to a luciferase.

In other examples, the transgene encodes a therapeutic protein or nucleic acid, such as a protein or nucleic acid useful for a gene therapy application. For example, the transgene may include any of the target genes listed in Table 2 or Table 3 of Shim et al. (*Acta Pharmacologica Sinica* 38:738-753, 2017, which is herein incorporated by reference in its entirety).

In some embodiments, the inhibitor of PLSCR1 is a short hairpin RNA (shRNA), a small interfering RNA (siRNA) or an antisense oligonucleotide that targets PLSCR1 mRNA. In some examples, the shRNA that targets PLSCR1 mRNA comprises a nucleotide sequence that is at least 80%, at least 85%, at least 90%, at least 95%, at least 96%, at least 97%, at least 98% or at least 99% identical to SEQ ID NO: 7. In specific examples, the shRNA targets human PLSCR1 mRNA. In other specific examples, the shRNA targets mouse PLSCR1 mRNA. In one non-limiting example, the shRNA that targets mouse PLSCR1 mRNA includes the nucleotide sequence of SEQ ID NO: 7.

In other embodiments, the inhibitor of PLSCR1 is a dominant-negative mutant PLSCR1. In specific examples, the dominant-negative mutant PLSCR1 is PLSCR1$_{D284A}$.

In other examples, the inhibitor of PLSCR1 is a small molecule, such as R5421 (ethanimidothioic acid N-[{5N-butylthio-N-methylamino]-carbonyloxy}-methyl ester; see Dekkers et al., *Blood* 91(6):2133-2138, 1998).

Also provided is a method of prolonging or increasing transgene expression in tissue of a subject by administering to the subject a virus vector that includes a transgene, and an inhibitor of PLSCR1. In some examples, transgene expression in the tissue of a subject is increased by at least 20%, at least 30%, at least 40%, at least 50%, at least 75%, at least 80%, at least 90%, at least 100%, at least 200%, at least 300%, at least 400%, or at least 500%, for example as compared to no administration of the PLSCR1 inhibitor. In some embodiments, the inhibitor of PLSCR1 is encoded by the virus vector. In other embodiments, the inhibitor of PLSCR1 is administered as a separate composition from the virus vector. When administered as a separate composition, the PLSCR1 inhibitor is generally administered about 24-72 hours prior to administration of the virus vector, such as about 72 hours, about 48 hours, or about 24 hours or prior to administration of the virus vector. The PLSCR1 inhibitor can be administered as frequently as necessary to maintain effective concentrations of the inhibitor in tissue (which depends on its half-life), and for as long as necessary to prevent immune activation and/or remain symptom-free. Thus, in some examples, the PLSCR1 inhibitor is administered in multiple doses (such as about 2, 3, 4, 5, 6, 7, 8, 9, or 10 doses) about 24-72 hours prior to administration of the virus vector. In some examples, the PLSCR1 inhibitor is further administered after administration of the virus vector, either in a single dose or in multiple doses (such as about 2, 3, 4, 5, 6, 7, 8, 9, or 10 doses).

In some embodiments, the virus vector is an Ad vector. In some examples, the virus vector is an Ad5 vector. In some examples, the Ad vector is a replication-incompetent virus vector. In other examples, the Ad vector is replication competent in specific cell types, such as tumor cells. In specific non-limiting examples, the Ad vector is an oncolytic Ad that is specifically capable of replication in tumor cells.

In other embodiments, the virus vector is a CAV, a HSV (such as an HSV-1), a HBV, a HCV or a VSV vector.

In some examples, the transgene is a reporter gene. In some examples, the reporter gene encodes a fluorescent protein, such as but not limited to, a GFP, a YFP, a CFP, an RFP, a BFP, or an orange fluorescent protein (for example, mOrange). In other examples, the reporter gene encodes an enzyme, such as but not limited to, a luciferase. In yet other examples, the transgene encodes a therapeutic protein or nucleic acid, such as a protein or nucleic acid useful for a gene therapy application.

In some embodiments, the inhibitor of PLSCR1 is a shRNA, a siRNA or an antisense oligonucleotide that targets PLSCR1 mRNA. In some examples, the shRNA that targets PLSCR1 mRNA comprises a nucleotide sequence that is at least 80%, at least 85%, at least 90%, at least 95%, at least 96%, at least 97%, at least 98% or at least 99% identical to SEQ ID NO: 7. In specific examples, the shRNA targets human PLSCR1 mRNA. In other specific examples, the shRNA targets mouse PLSCR1 mRNA. In one non-limiting example, the shRNA that targets mouse PLSCR1 mRNA includes the nucleotide sequence of SEQ ID NO: 7.

In other embodiments, the inhibitor of PLSCR1 is a dominant-negative mutant PLSCR1. In specific examples, the dominant-negative mutant PLSCR1 is PLSCR1$_{D284A}$.

The disclosure also provides viral vectors (such as an adenovirus vector or HSV vector) that includes an inhibitor of PLSCR1, such as a shRNA that targets PLSCR1 mRNA, a small interfering RNA (siRNA), an antisense oligonucleotide that targets PLSCR1 mRNA, or a dominant-negative mutant PLSCR1 (e.g., PLSCR1$_{D284A}$). Such vectors can further include a reporter molecule, such as encode a fluorescent protein. Such vectors can further include a therapeutic molecule, such as encode a therapeutic protein. In some examples, the shRNA that targets PLSCR1 mRNA comprises a nucleotide sequence that is at least 80%, at least 85%, at least 90%, at least 95%, at least 96%, at least 97%, at least 98% or at least 99% identical to SEQ ID NO: 7. In specific examples, the shRNA targets human PLSCR1 mRNA. In other specific examples, the shRNA targets mouse PLSCR1 mRNA. In one non-limiting example, the shRNA that targets mouse PLSCR1 mRNA includes the nucleotide sequence of SEQ ID NO: 7. In one example, the viral vector is a recombinant adenovirus vector that includes a nucleotide sequence at least 80%, at least 85%, at least 90%, at least 95%, at least 96%, at least 97%, at least 98% or at least 99% identical to SEQ ID NO: 2, SEQ ID NO: 3, SEQ ID NO: 22 or SEQ ID NO: 23 (the vectors of SEQ ID NO: 22 and SEQ ID NO: 23 correspond to the vectors of SEQ ID NO: 2 and SEQ ID NO: 3, respectively, without reporter gene TdTomato). In some embodiments, the recombinant adenovirus vector comprises or consists of the nucleotide sequence of SEQ ID NO: 2, SEQ ID NO: 3, SEQ ID NO: 22 or SEQ ID NO: 23.

Also provided are compositions that include a recombinant virus vector disclosed herein and a pharmaceutically acceptable carrier.

Further provided are compositions that include a PLSCR1 inhibitor and a viral vector encoding a transgene, wherein the PLSCR1 inhibitor is not encoded by the viral vector. The transgene can encode, for example, a reporter molecule or a therapeutic protein to nucleic acid molecule. In some embodiments, the inhibitor of PLSCR1 is a shRNA, a siRNA or an antisense oligonucleotide that targets PLSCR1 mRNA. In other embodiments, the inhibitor of PLSCR1 is a dominant-negative mutant PLSCR1, such as the dominant-negative mutant PLSCR1 is $PLSCR1_{D284A}$.

Also provided are recombinant (engineered) cells that include such a recombinant adenovirus vector, such as a mammalian cell, such as a human, mouse, or rat cell.

Also provided herein is a method of modulating (such as inhibiting) an inflammatory response in tissue of a subject suffering from a viral infection, a bacterial infection, an autoimmune disease, or cancer by administering an inhibitor of PLSCR1. In some embodiments, the tissue is CNS tissue.

In some embodiments, the viral infection is caused by an adenovirus, a HSV (such as HSV-1 or HSV-2), a hepatitis B virus (HBV), a hepatitis C virus (HCV), a vesicular stomatitis virus (VSV), a human immunodeficiency virus (HIV), an influenza virus, a varicella zoster virus (VZV), a human papillomavirus (HPV), an Epstein-Barr virus (EBV), a cytomegalovirus (CMV), an enterovirus, a togavirus (such as Eastern equine encephalitis virus, Western equine encephalitis virus, Chikungunya virus, or Sindbis virus) or a flavivirus (such as St. Louis encephalitis virus, West Nile encephalitis virus or Japanese encephalitis virus).

In some embodiments, the bacterial infection is caused by *Chlamydia trachomatis*, *Streptococcus agalactiae*, *Streptococcus pneumoniae*, *Escherichia coli*, *Listeria monocytogenes*, *Neisseria meningitides*, *Haemophilus influenza*, *Mycobacterium tuberculosis*, or *Borrelia burgdorferi*. In some embodiments, the bacterial infection is caused by Gram-negative bacteria.

In some embodiments, the autoimmune disease is antiphospholipid syndrome, multiple sclerosis, rheumatoid arthritis, systemic lupus erythematosus, inflammatory bowel disease, type 1 diabetes, Guillain-Barré syndrome, myasthenia gravis or Sjögren's syndrome.

In some embodiments, the cancer is of the central nervous system, such as a glioblastoma, astrocytoma, oligodendroglioma, ependymoma, meningioma or medulloblastoma.

In some embodiments, the virus infection, bacterial infection, autoimmune disease or cancer afflicts the CNS.

In some embodiments, the inhibitor of PLSCR1 is a shRNA, a siRNA or an antisense oligonucleotide that targets PLSCR1 mRNA. In some examples, the inhibitor of PLSCR1 is a shRNA that targets PLSCR1 mRNA. In particular examples, the shRNA that targets PLSCR1 mRNA comprises a nucleotide sequence that is at least 80%, at least 85%, at least 90%, at least 95%, at least 96%, at least 97%, at least 98% or at least 99% identical to SEQ ID NO: 7. In specific non-limiting examples, the shRNA targets human PLSCR1 mRNA. In other non-limiting examples, the shRNA targets mouse PLSCR1 mRNA. In one non-limiting example, the shRNA that targets mouse PLSCR1 mRNA includes the nucleotide sequence of SEQ ID NO: 7.

In other embodiments, the inhibitor of PLSCR1 is a dominant-negative mutant PLSCR1. In specific examples, the dominant-negative mutant PLSCR1 is $PLSCR1_{D284A}$.

In other embodiments, the inhibitor of PLSCR1 is a small molecule inhibitor. In one example, the small molecule inhibitor is R5421.

The PLSCR1 inhibitor can be administered in a single dose, or in multiple doses as necessary to maintain effective concentrations of the inhibitor in tissue (which depends on its half-life), and for as long as necessary to prevent immune activation and/or remain symptom-free.

The following examples are provided to illustrate certain particular features and/or embodiments. These examples should not be construed to limit the disclosure to the particular features or embodiments described.

EXAMPLES

In Examples 1 and 2, intracranial delivery of replication-incompetent Ad5-based vectors was used as a model to identify signaling pathways through which microglia recognize and respond to viral uptake, and to define target mechanisms for the modulation of innate immune responses. It is demonstrated herein that Ad5 delivery leads to dysregulation of intracellular calcium homeostasis and PtdSer externalization on the plasma membrane of transduced cells. Microglial TAM receptors (Tyro-3, Axl and Mer receptors) and their ligands were identified as key agents required for phagocytosis of PtdSer-tagged cells, and phospholipid scramblase 1 (PLSCR1) activity as an effective target for the control of intracellular calcium homeostasis, PtdSer externalization and microglia phagocytosis. Cells rescued from engulfment by microglia through PLSCR1 inhibition remained viable, resulting in prolonged transgene expression from Ad5 vectors. Together, the disclosed study identifies key molecular mechanisms mediating the interaction between Ad vector-transduced cells and innate immune sensors, which can be exploited for the construction of safer and more efficient Ad5-based vectors for both research and gene therapy applications. The study described in Example 3 demonstrates that PLSCR1 inhibition can also inhibit inflammatory responses induced following transduction of an HSV vector. Given the central and conserved role of PLSCR1 in signal transduction, these findings are relevant to other inflammatory conditions associated with intracellular calcium dysregulation, PtdSer externalization and microglia/macrophage phagocytosis in the CNS or the periphery.

Example 1: Materials and Methods

This example describes the experimental procedures used for the studies described in Example 2.

Animal Subjects

Mouse strains used in this study included wild type C57BL6/J (Jackson Laboratories) and transgenic mice (Table 1). Mice were typically group-housed at approximately 22° C. and provided with bedding and nesting material. Both male and female mice were used with a minimum age of 12 weeks.

Stereotactic Injections

Thin wall glass pipettes were pulled on a Sutter Flaming/Brown puller (Model P97). Pipette tips were carefully cut at an acute angle under 10× magnification using sterile techniques. Tip diameters were typically 10-15 μm. Pipettes that did not result with sharp bevels or had larger tip diameters were discarded. Adult mice (12-14 weeks old; typically male) were anesthetized with isoflurane (4% for induction; 1-2% during surgery). Mice were head-fixed in a computer-assisted stereotactic system with digital coordinate readout and atlas targeting (Leica Angle Two). Neocortical coordinates were AP −1.82-(−2.0) mm, ML 0.9-1.5 mm, DV 0.2-0.5 mm or AP −0.82 mm, ML 1-2 mm, DV 0.35-0.5 mm. Body temperature was maintained at 36-37° C. with a DC temperature controller, and ophthalmic ointment was used to prevent eyes from drying. A small amount of depilator cream (Nair) was used to thoroughly remove hair over dorsal areas of the skull. Skin was cleaned and sterilized with 70% ethanol and betadine. A midline incision (#15 scalpel blade) was made beginning just posterior to the eyes and ending just passed the lambda suture. The scalp was then pulled open and periosteum cleaned using scalpel and #3 forceps to expose desired hemisphere for calibrating the digital atlas and coordinate marking. Once reference points (bregma and lambda) were positioned using the pipette needle and entered into the program the desired target was set on the digital atlas. The injection pipette was carefully moved to the target site (using AP and ML coordinates). Next, the craniotomy site was marked and an electrical micro-drill with a fluted bit (0.5 mm tip diameter) was used to thin a 0.5-1 mm diameter part of the bone over the target injection site. Once the bone was thin enough to gently flex, a 30G needle with attached syringe was used to carefully cut and lift a very small (0.3-0.4 mm) segment of bone. Millimeter tick marks were made on each pulled capillary needle to measure volume of virus injected into the brain. A drop of virus was carefully pipetted onto parafilm (1-2 µL) in order to draw up the desired volume for injection. Once loaded with sufficient volume, the pipette needle was slowly lowered into the brain until the target depth was reached. Manual pressure was applied using a 30 mL syringe connected by shrink tubing and virus (0.4 or 0.8 µL for NSC-/PLSCR1-shRNA/Null or PLSCR1$_{D284A}$ vectors, respectively; 5.35×10$^5$ PFU for all vectors) or vehicle (TMN; 0.4 µL) was slowly injected over a period of 5-10 minutes. Once desired injection volume was delivered, the syringe's pressure valve was locked and position maintained for approximately 10 minutes to allow virus to spread and to avoid backflow upon needle retraction. Mice were then sutured along the incision on the scalp, given subcutaneous Buprenex SR (0.5 mg/kg) and allowed to recover before placement in their home cage.

Immunofluorescence

Mice were euthanized in their home cage at 3, 7, 17, 30, 90 or 180 days after injection using $CO_2$ asphyxiation at a 20% fill rate in accordance with IACUC guidelines. Mice were then quickly transcardially perfused with 10% sucrose followed by 4% paraformaldehyde (PFA). Brain tissue was carefully extracted to maintain structural integrity and allowed to incubate in 4% PFA overnight at 8° C. Brains were then thoroughly washed on a plate shaker with 1× phosphate buffered saline (PBS) three times over approximately 1 hour.

Perfused and PBS-washed brains were sectioned at 50 µm using a Leica VT1000s model vibratome. Immunostaining was performed on floating coronal sections using standard techniques. Primary antibodies included GFAP (1:250; Millipore Cat. # MAB3402) and Iba-1 (1:200; Wako Cat. #019-19741).

For CD68, NeuN, DAPI and Axl/Mertk receptor staining, brains were perfused as stated above. After 24 hours incubation in 4% PFA, brains were washed in 1×PBS for 10 minutes, repeated three times. Brains were then placed in 30% sucrose solution and left at 4° C. until they sank to the bottom of the conical storage tube. Brains were then frozen in O.C.T. compound-TissueTek media (Sakura #4583) over dry ice and ethanol mix. Frozen brain blocks were sectioned using a cryostat (Leica CM1800) at 12 µm thickness and collected on glass slides. For Axl/Mertk receptor staining a citrate buffer antigen retrieval protocol was applied followed by standard staining techniques. Primary antibodies included CD68 (1:200; Bio-Rad Cat. # MCA1957), NeuN (1:100; Millipore Cat. # ABN78), DAPI (1:1000; Thermo Fisher Scientific Cat. # D21490), anti-Axl (1:100; R&D Systems Cat. # AF854) and anti-Mertk (1:100 or 1:200; R&D Systems Cat. # AF591 or eBioscience Cat. #14-5751, respectively). Selected tissue was co-stained with Iba-1 for analysis of Axl/Mertk expression on microglia.

Secondary antibodies (1:100) included Oregon Green 488 goat anti-rabbit (Life Technologies Cat. #011038) and Alexa Fluor 633 goat anti-mouse (Life Technologies Cat. # A21052).

Cortical Cultures

Culture of cortical cells enriched for astrocytes was accomplished using methods provided by Life Technologies (Lifetechnologies.com; Derivation and culture of cortical astrocytes). Briefly, postnatal day 1-2 wild type mice were sacrificed, brains removed and thoroughly cleaned of meninges. All brain areas except cortices were removed using sterile techniques under a surgical stereoscope. Dissection was done in ice cold HBSS. Cells were dissociated, filtered and plated on collagen treated T-175 tissue culture flasks (Corning, Inc.). Cells were fed every 2 days with culture medium as described in the aforementioned protocol. Once confluent, cells were trypsinized and passed onto collagen-treated 35 mm glass bottom dishes (In Vitro Scientific; Cat. # D35-20-1.5-N) or standard plastic culture 10 cm dishes. When cultures reached confluency in these vessels (after approximately 1 week), astrocyte medium containing 0.25 mM dBcAMP and 0.2 ng/mL of EGF (Gibco; PHG0314) was used to induce differentiation and growth, respectively. Around 7 days after treatment with astrocyte medium, cultures were used for experiments. Transduction efficiency was ≥80%.

Live Animal Preparation

Under isoflurane anesthesia, mice were head-fixed with blunt ear bars on a custom surgical bed (Thorlabs) and kept at 36-37° C. with a DC temperature controller. Depilator cream was used to remove hair on top of the mouse's head. The scalp was thoroughly cleaned and sterilized with 70% ethanol and betadine. A portion of the scalp was surgically removed to expose frontal, parietal, and interparietal skull segments. The scalp edges were attached to the lateral sides of the skull using tissue compatible adhesive. A custom-machined aluminum or titanium head plate was then affixed to the skull with Optibond (31514; Kerr) and/or dental cement (H00335; Coltene Whaledent). Mice were given Buprenex SR (0.5 mg/kg) prior to relief from anesthesia and allowed to recover for 1-3 days before imaging or habituation.

Figure 2A:
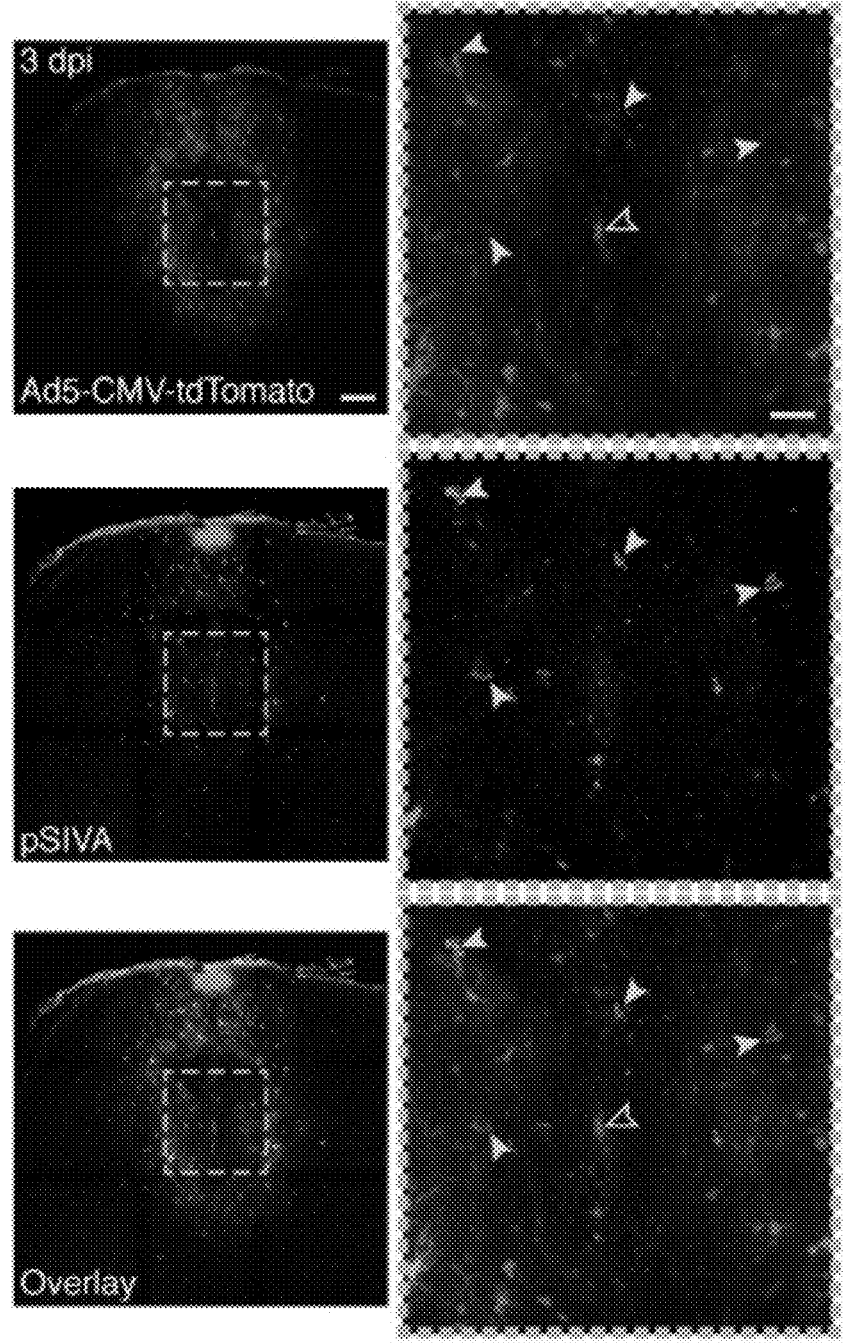
FIGS. 2A-2D: Adenoviral Vector Transduction Increases Phosphatidylserine Externalization and TAM Receptor Expression.
Figure 2B:
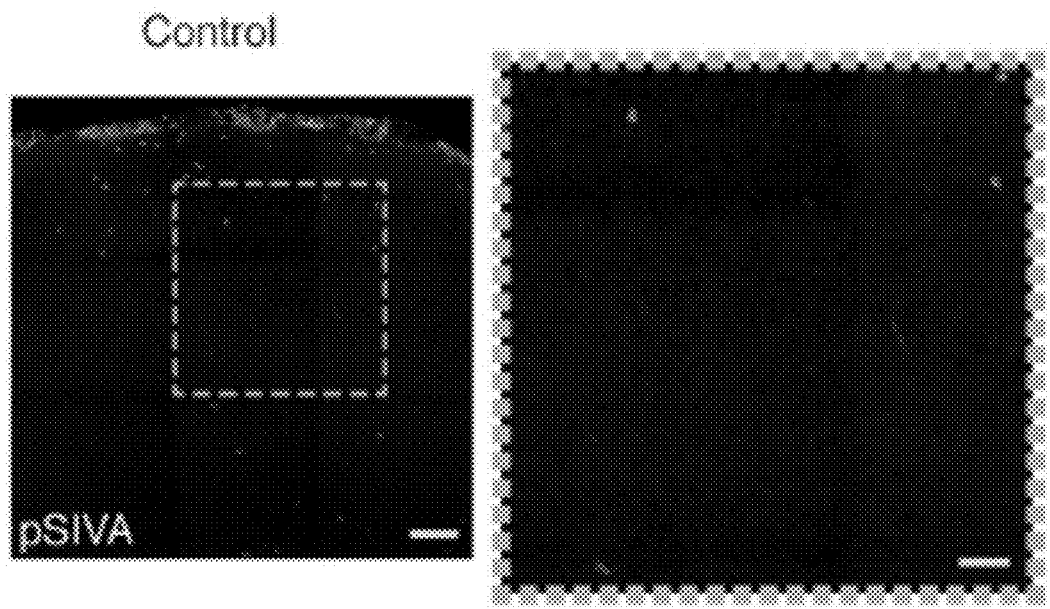
Figure 12A:
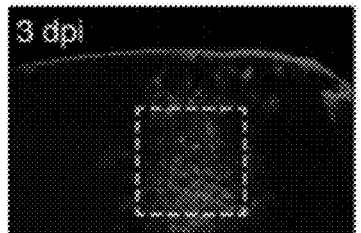
FIGS. 12A-12F: PLSCR1 Inhibition Reduces Phosphatidylserine Externalization and Microglia Phagocytosis.
Figure 12A:
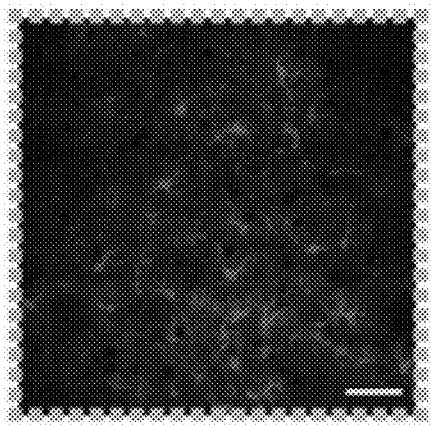
Figure 12A:
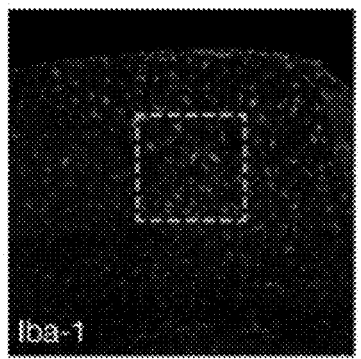
Figure 12A:
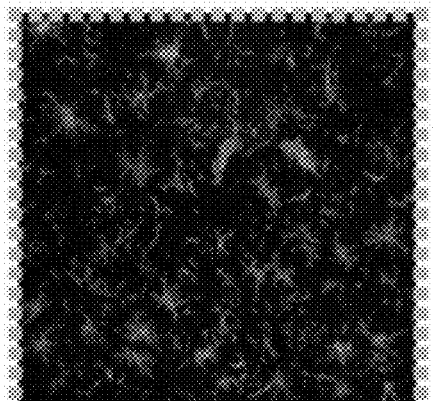
Figure 12A:
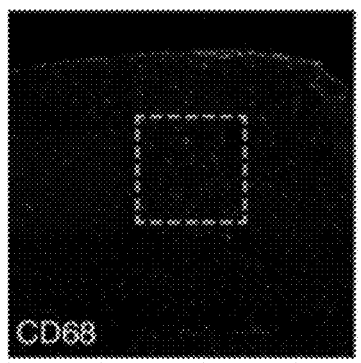
Figure 12A:
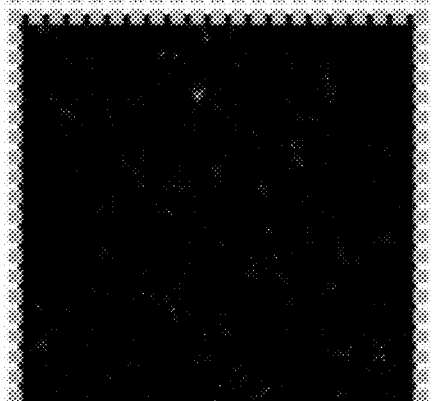
Figure 12A:
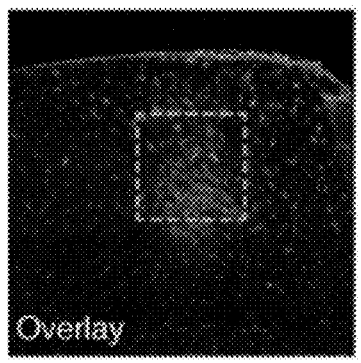
Figure 12A:
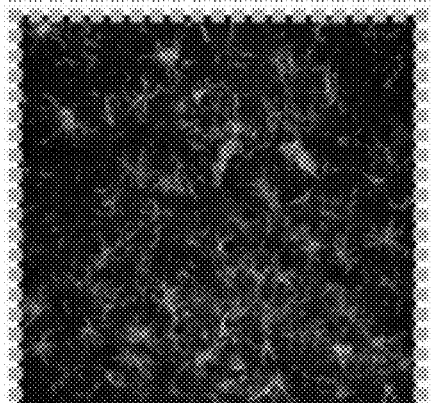
Figure 12B:
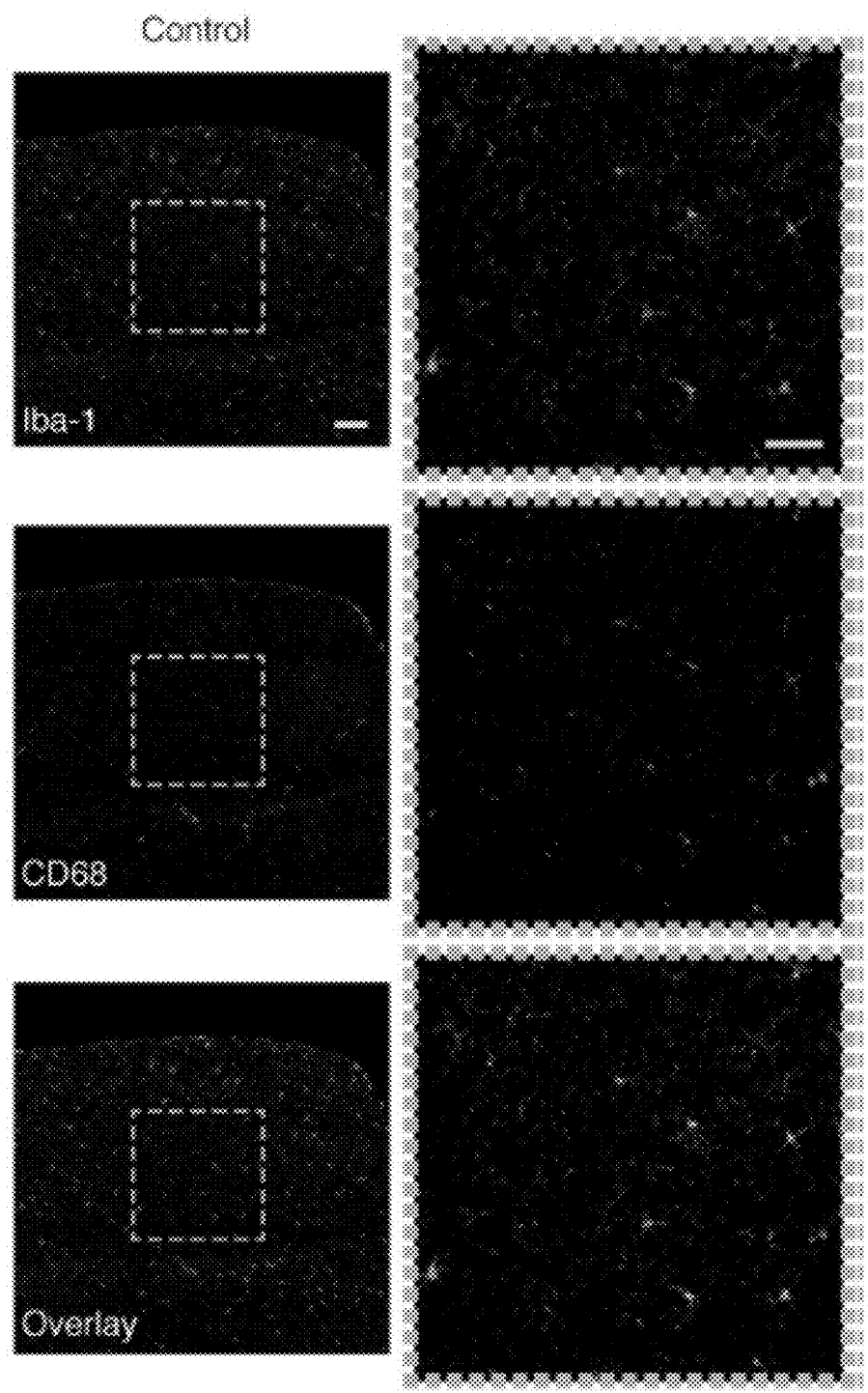
Figure 12C:
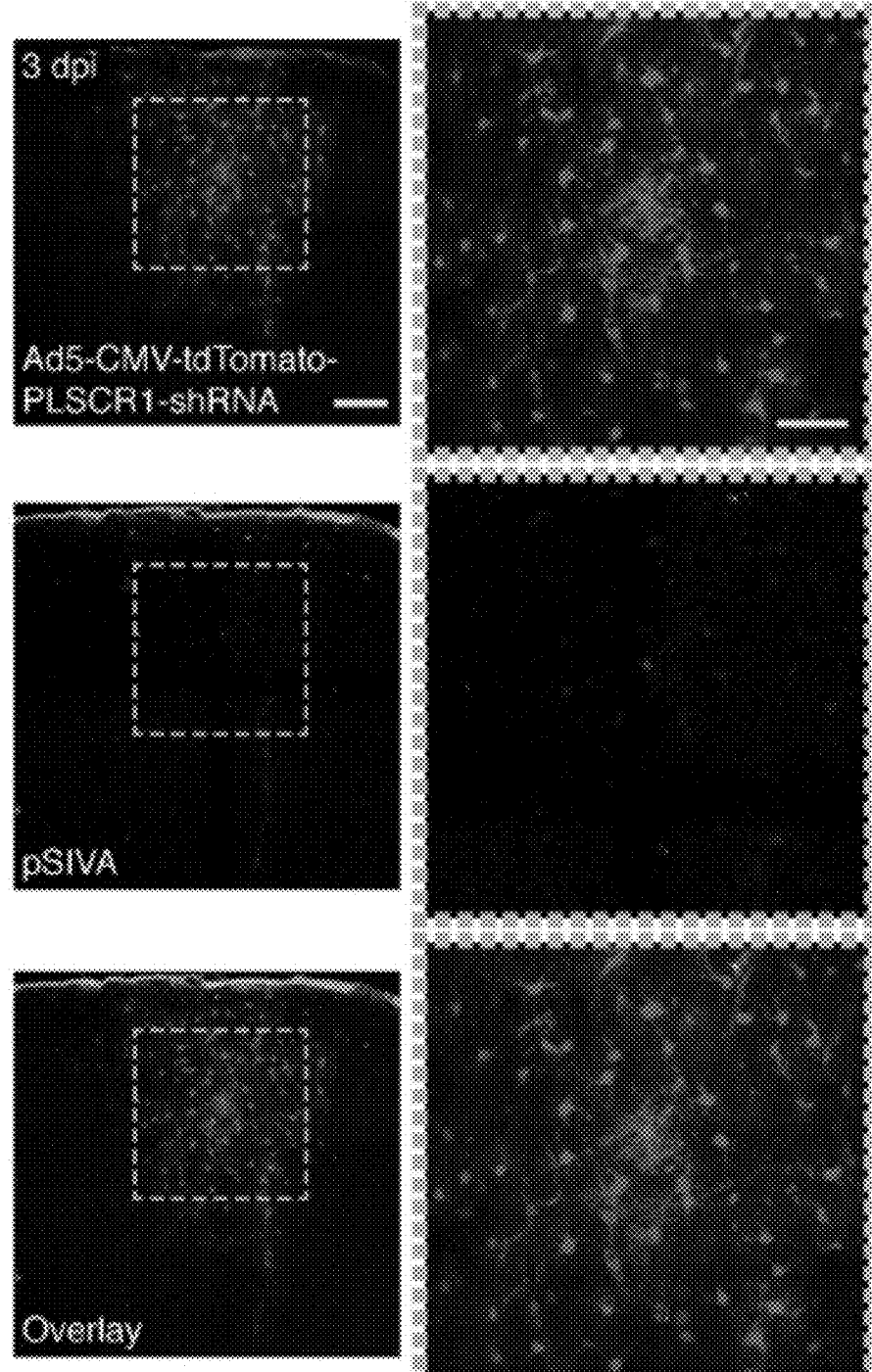
Figure 12D:
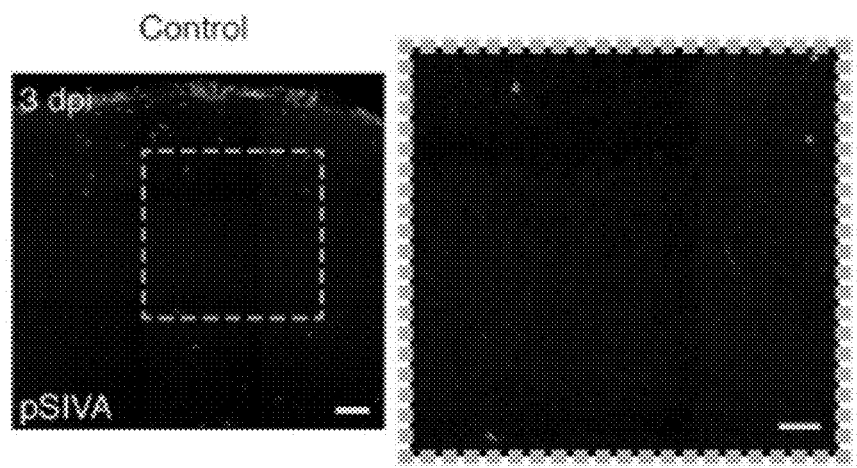
Figure 12E:
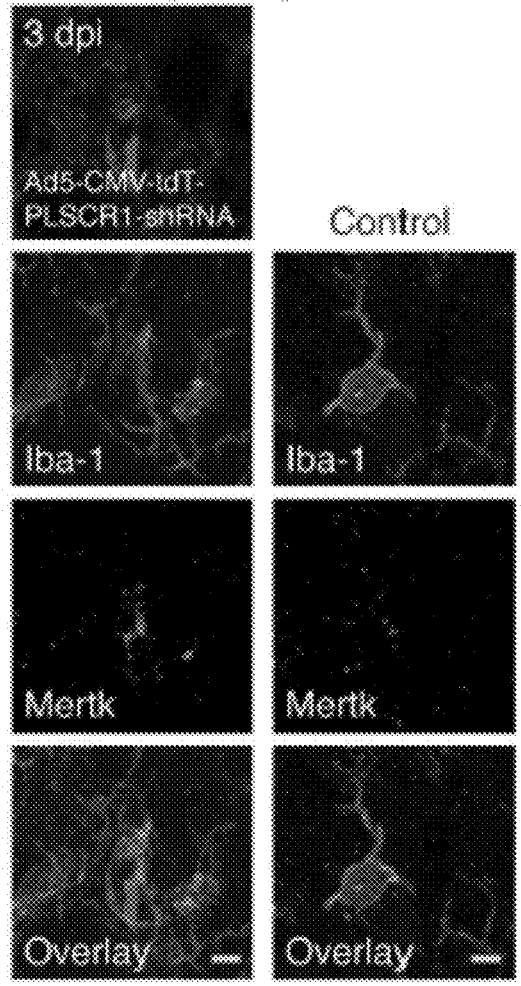
Figure 12F:
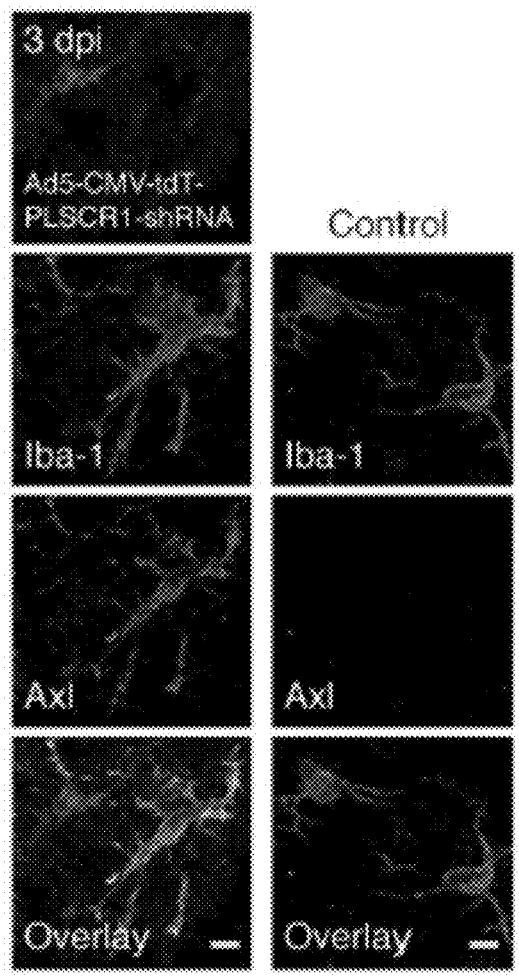
Figure 13A:
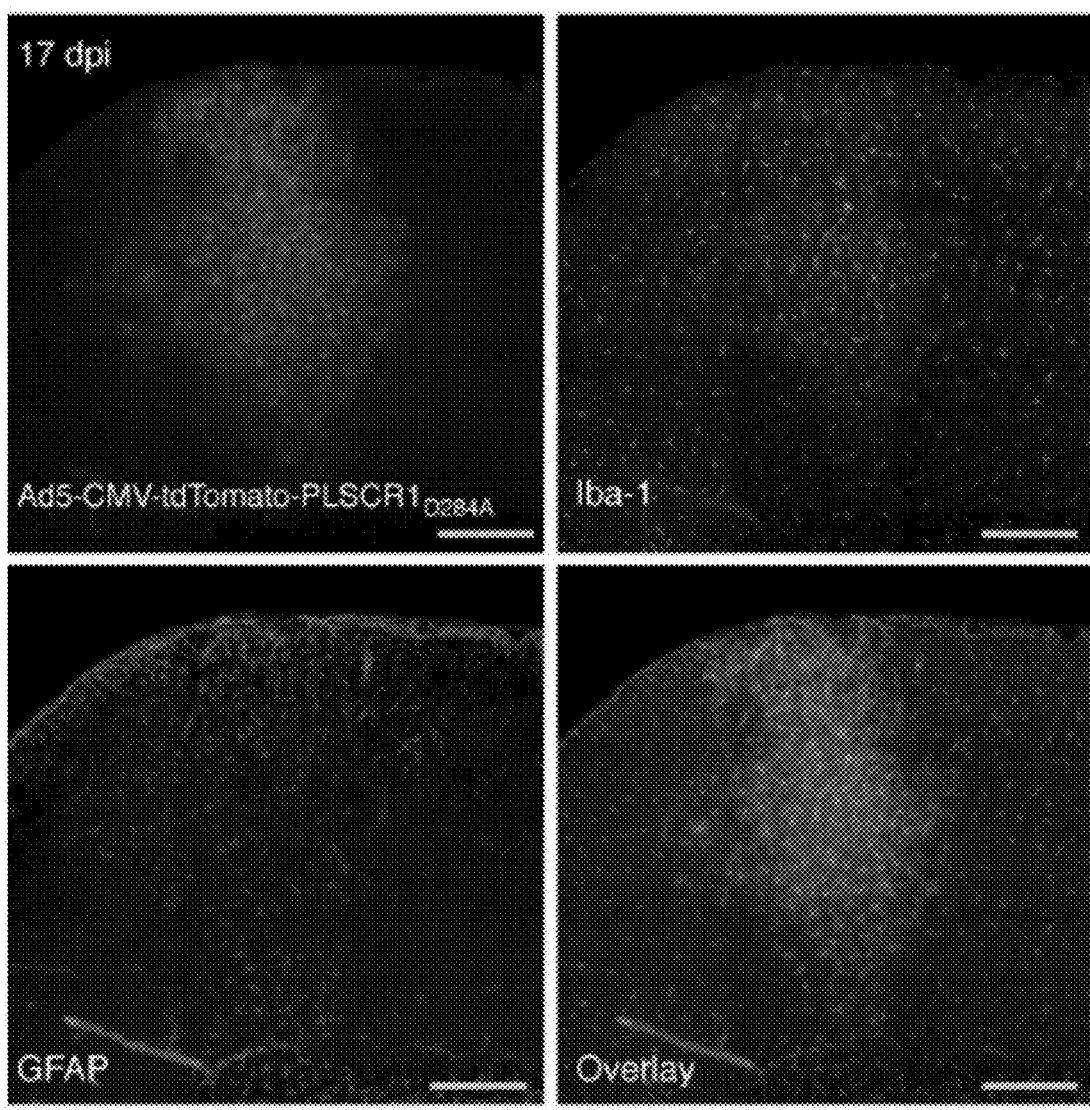
FIGS. 13A-13D: Expression of Calcium-insensitive $PLSCR1_{D284A}$ Inhibits Cell Clearance.
Figure 13B:
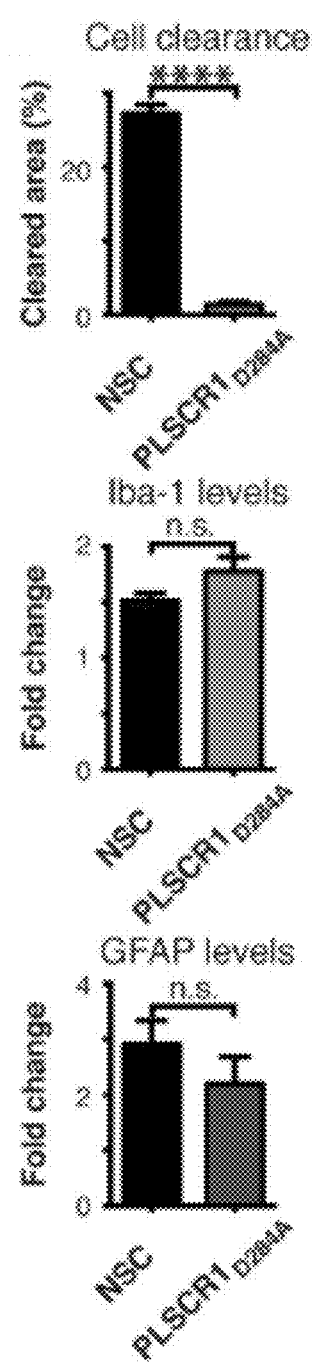
Figure 13C:
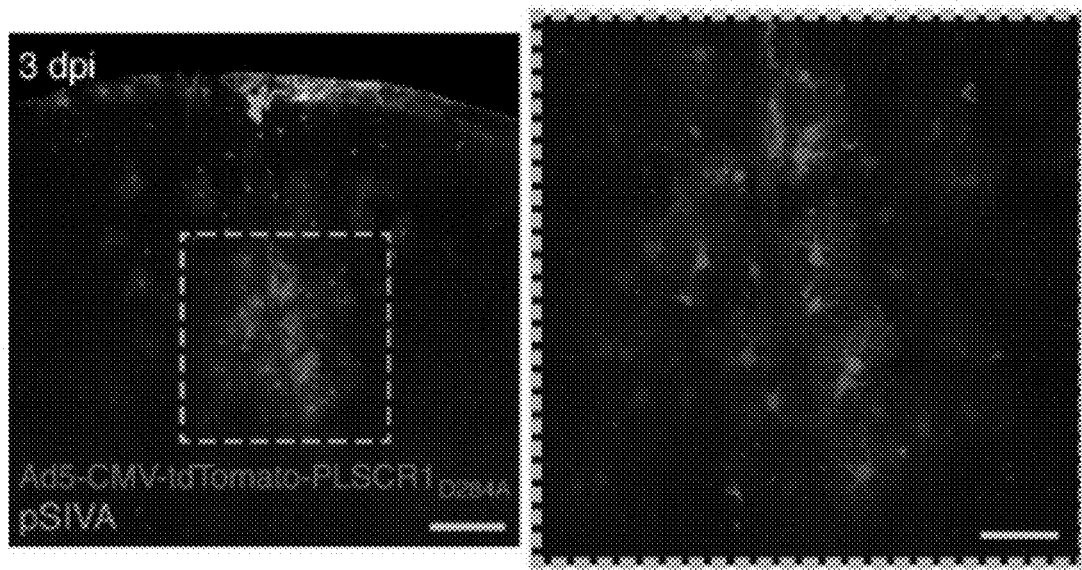

To visualize phosphatidylserine externalization in vivo (FIGS. 2A and 2B; FIGS. 12C-12D, 13C) mice were anesthetized with isoflurane and an approximately 3 mm diameter craniotomy was made over the vector injection site. The dura was carefully removed to facilitate dye penetration into the cortex. 200 µl of the fixable, green fluorescent polarity sensitive indicator of viability and apoptosis (pSIVA-IANBD; Novus Biologicals Cat. # NBP2-29382) (Kim et al., *Nat Methods* 7, 67-73, 2010) was applied topically for 90 min. Following this incubation period, mice were immediately perfused for tissue sectioning and immunostaining.

For imaging experiments, mice were anesthetized with isoflurane and a 2-3 mm diameter craniotomy was made over the original vector injection site. 2% agarose solution and a coverslip was used to seal the craniotomy, as previously described (Dittgen et al., *Proc Natl Acad Sci USA* 101, 18206-18211, 2004).

Confocal Microscopy

One-photon laser-scanning confocal microscopy was performed on a Zeiss LSM 780. Three channel tiled z-stacks (typically 10-40 images for 12-50 µm brain sections; 1 µm axial spacing) were acquired to produce images (laser lines: 488 nm, 561 nm, 633 nm). Image size was 512×512 pixels stitched into 3×3 tiles (frame scanning; 1.27 µs pixel dwell time; 2× averaging). Images were taken with an Olympus 20×0.8-NA air-matched or 63×1.4-NA oil objective.

Two-Photon Microscopy

In vivo two-photon imaging was performed as previously described (Nimmerjahn, *Cold Spring Harb Protoc* 2012, 594-603, 2012). A Sutter Movable Objective Microscope (MOM) equipped with a pulsed femtosecond Ti:Sapphire laser (Chameleon Vision or Ultra II, Coherent) with two fluorescence detection channels (dichroic, 565DXCR (Chroma); green emission filter, FF01-494/41 (Semrock); red emission filter, ET605/70M-2P (Chroma)) and H7422-40 GaAsP photomultiplier tubes (Hamamatsu) was used for imaging. Typical excitation wavelength was 880 nm. Data was acquired using an Olympus 20×1.0-NA or a Nikon 16×0.8-NA water immersion objective.

Fixed Tissue Immunofluorescence

Cell clearance (FIGS. 1C, 3B, 4C, 6B and FIGS. 9B, 10B, 13B) was quantified as the area (in %) devoid of tdTomato-positive cell bodies over the total area of the transduced region. Corresponding Iba-1 and GFAP expression changes (FIGS. 1D, 3B, 4D, 6B and FIGS. 8B, 8D, 9B, 10B, 13B) were assessed by measuring the average fluorescence per area, followed by calculating the background corrected fluorescence. Data was normalized to the respective control hemisphere. More specifically, a 3-channel (Iba-1/Ad5-CMV-tdTomato/GFAP) maximum-intensity projection image (.lsm file) was opened in Fiji software and a region of interest (ROI) was drawn around the extent of the tdTomato-positive transduced area. The image channel was then switched to display the Iba-1 staining while maintaining the same ROI and then selecting "Analyze:Measure" to display area, mean gray value and integrated density. Next, 2-3 separate smaller ROIs were made to analyze background fluorescence in the same manner. This procedure was repeated to measure the GFAP expression, but due to the expression profile extending beyond the limits of tdTomato-expressing cells, a custom-drawn ROI was made around the full field of view while avoiding GFAP expression from the white matter/corpus collosum, stained blood vessels, and the superficial pia mater. Total fluorescence was then calculated using the following equation:

Total fluorescence=Integrated density−(ROI×mean fluorescence of background) Data from all animals within each respective experimental group were pooled and normalized to controls (non-transduced hemispheres).

Changes in CD68, Mertk, Axl and pSIVA levels (FIGS. 4F-4H), and changes in the number of S100b-, NeuN-, DAPI-, Iba-1, GFAP- and tdTomato-positive cells (FIGS. 11D, 11F, 11H, 11I) were analyzed using Imaris (version 7 or 8; Bitplane). First, background subtraction was performed using a Gaussian filter (276 µm width) applied to each image within the three-channel tiled confocal z-stacks. We then used the creation wizard feature in Imaris to generate digital representations of immunostained cells/structures, so-called "Spots" or "Surfaces".

"Spots" were created for spherical-shaped entities such as NeuN- or DAPI-positive cell bodies (FIGS. 11E and 11G) and CD68-, pSIVA-, Mertk- or Axl-positive puncta (FIG. 1F, 2A-2D and FIGS. 8E-8F, 12A-12F, 13C-13D). The following "XY Diameter" spot size filter values were used: 10 µm, 8 µm or 3 µm for NeuN-, DAPI-, or CD68/pSIVA/Mertk-/Axl-positive structures, respectively. As "Quality" filter values we used: 1-3, 2-3, 2 or 1 for NeuN-, DAPI-, Mertk- or Axl-positive structures, respectively, depending on staining quality, to include the top 50% of spots. For CD68- and pSIVA-positive spots, the quality filter was set to include the top 1% of spots. "Quality" is the intensity value at the center of a spot in the channel the spots were detected. The same filter settings were used for corresponding control hemisphere images.

Figure 1B:
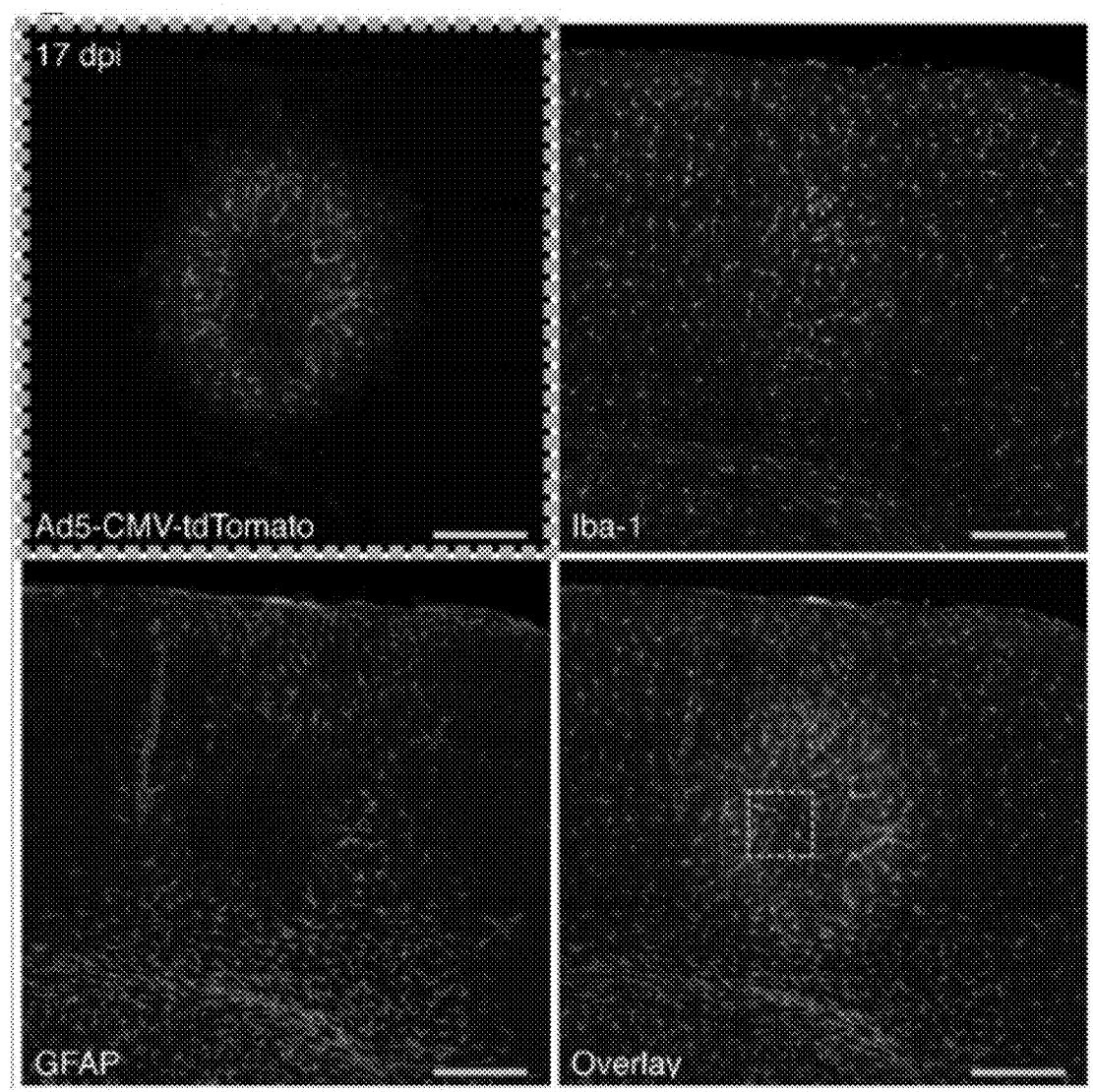
Figure 1C:
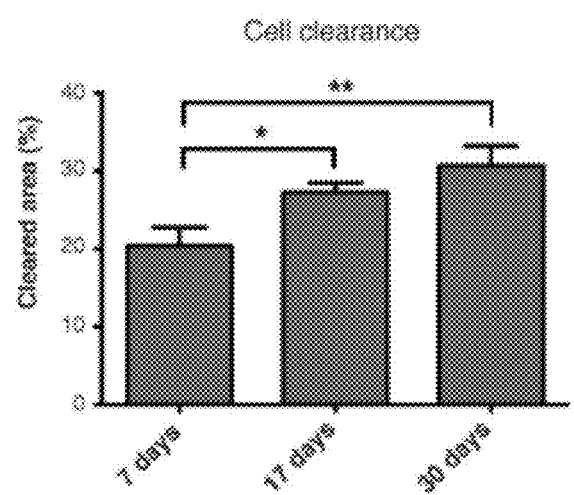
Figure 4A:
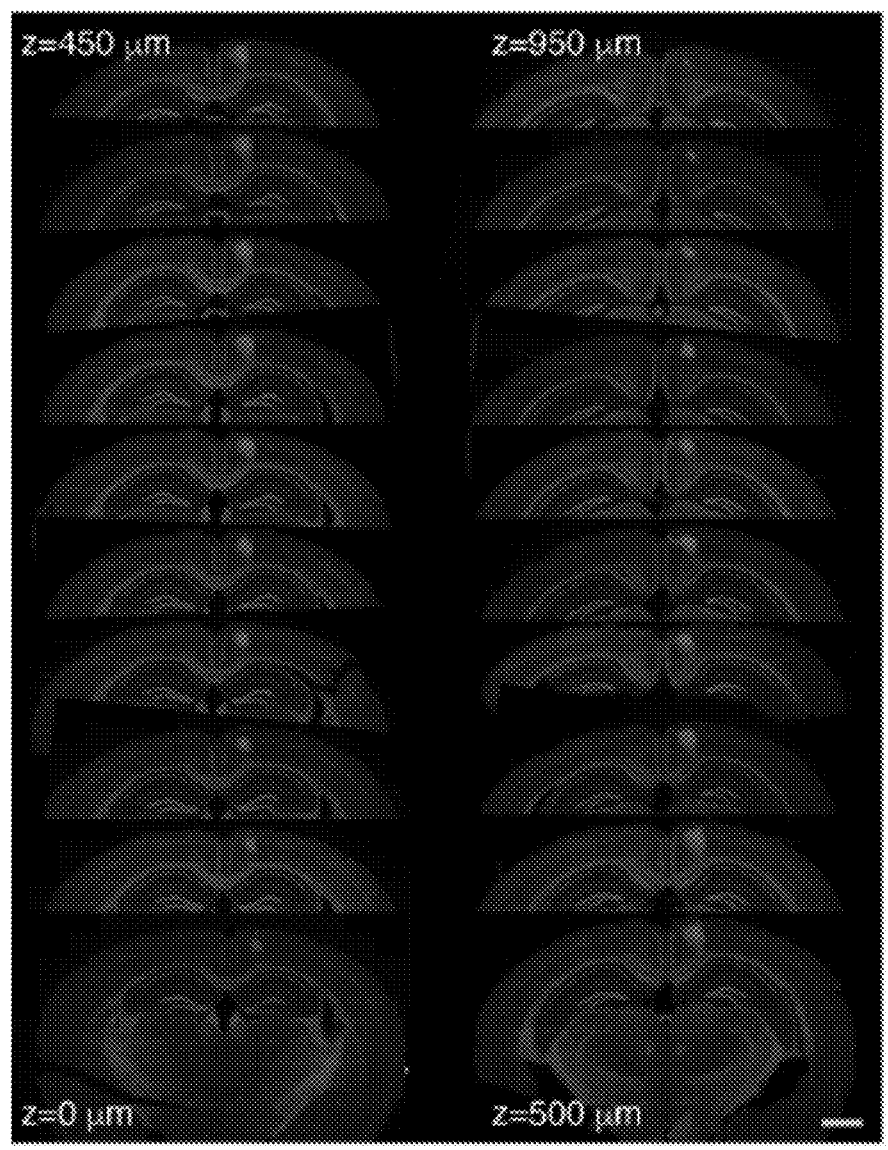
FIGS. 4A-4I: Phospholipid Scramblase 1 Inhibition Reduces Microglia-mediated Cell Clearance and Cytokine Levels.
Figure 4B:
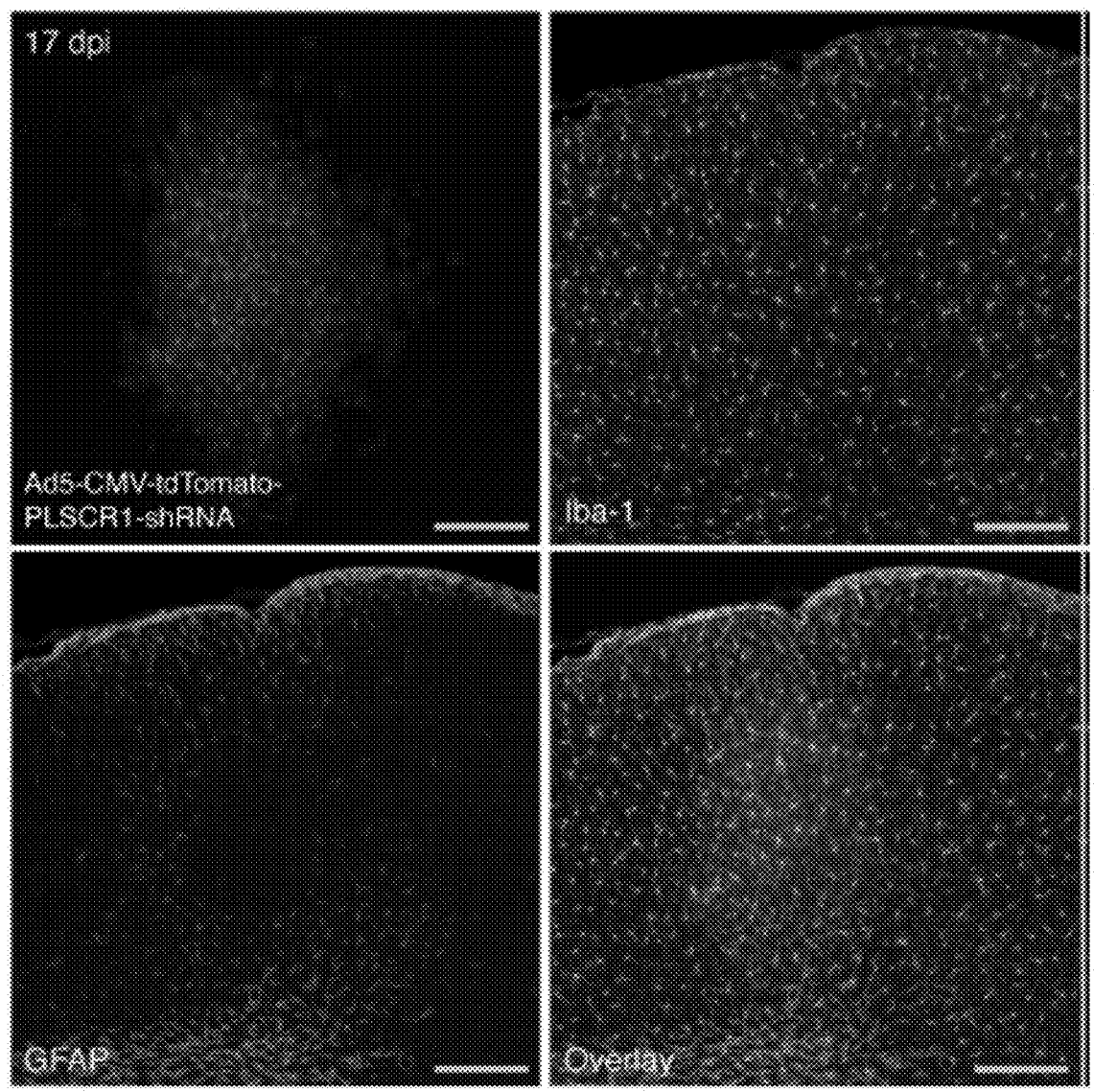
Figure 4D:
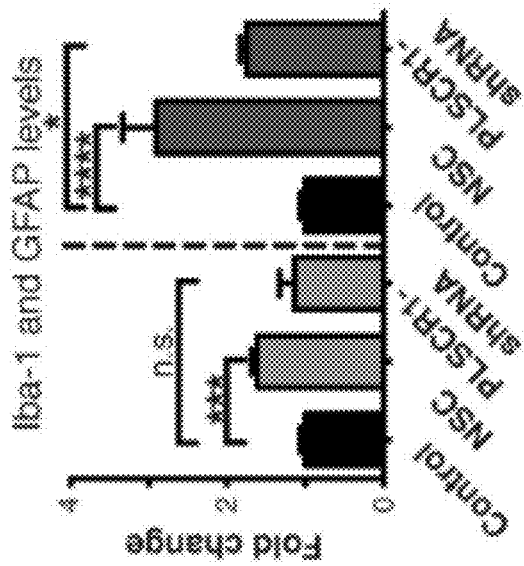
Figure 4C:
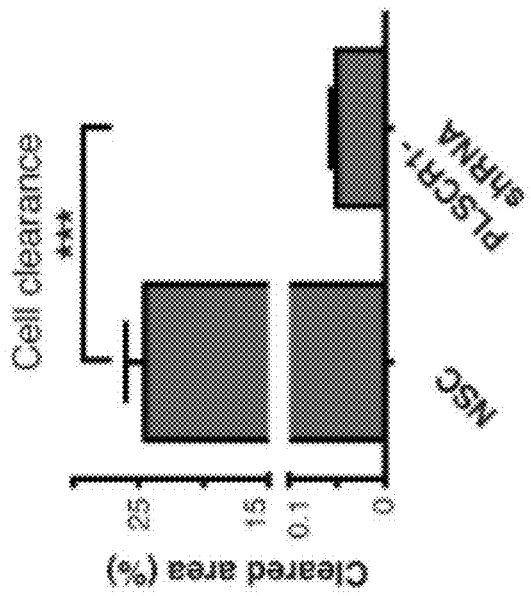
Figure 4E:
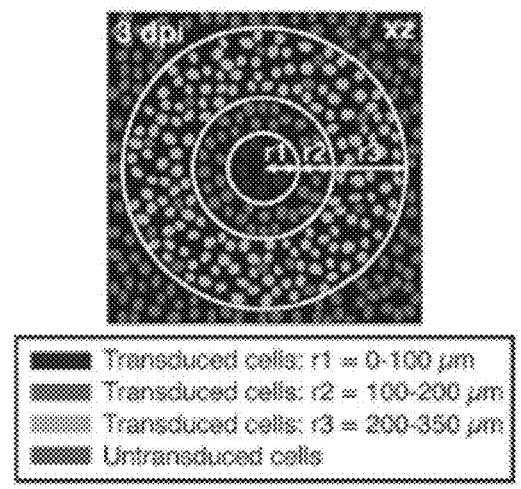
Figure 11A:
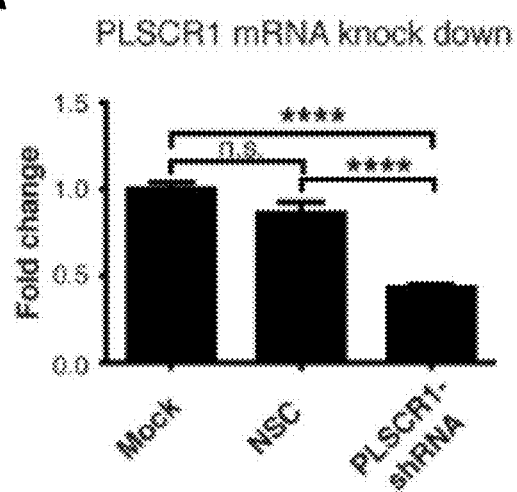
FIGS. 11A-11I: Phospholipid Scramblase 1 Inhibition Reduces Inflammatory Responses and Cell Loss.
Figure 11B:
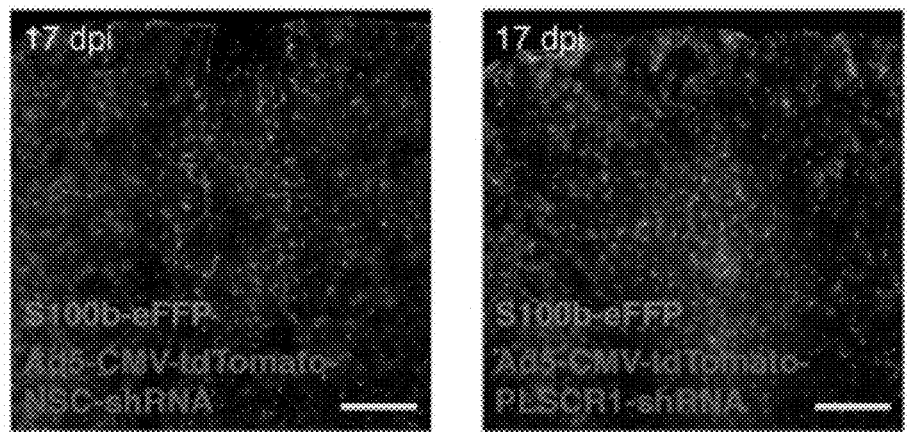
Figure 11C:
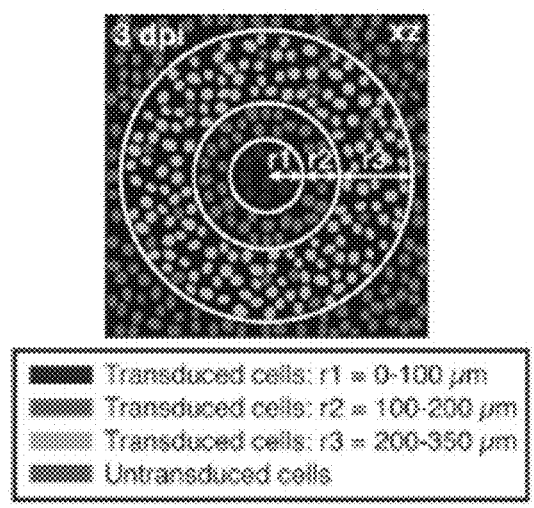
Figure 11D:
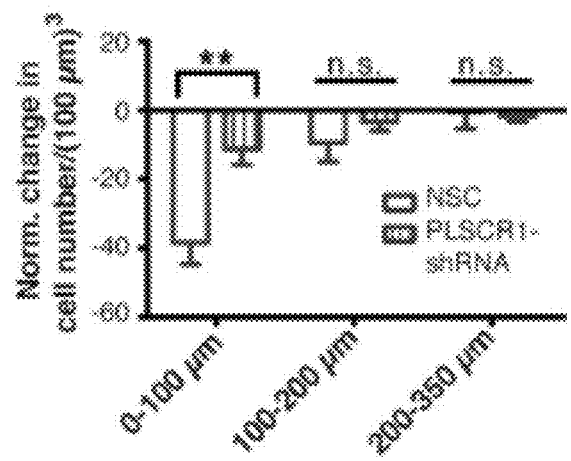
Figure 11E:
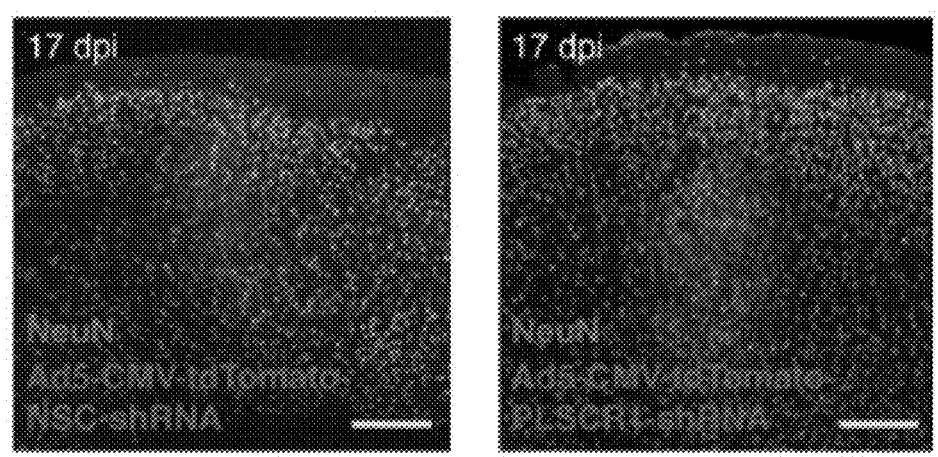
Figure 11F:
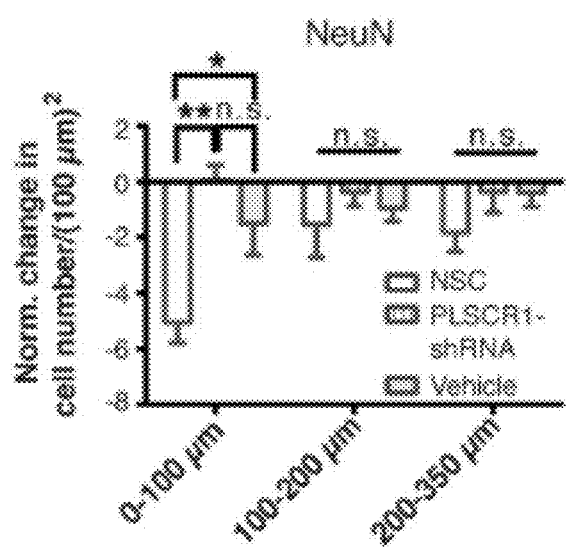
Figure 11G:
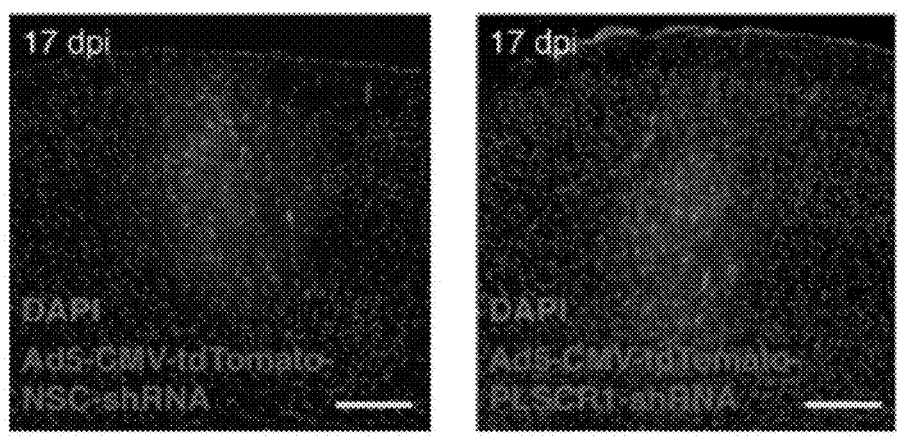
Figure 11H:
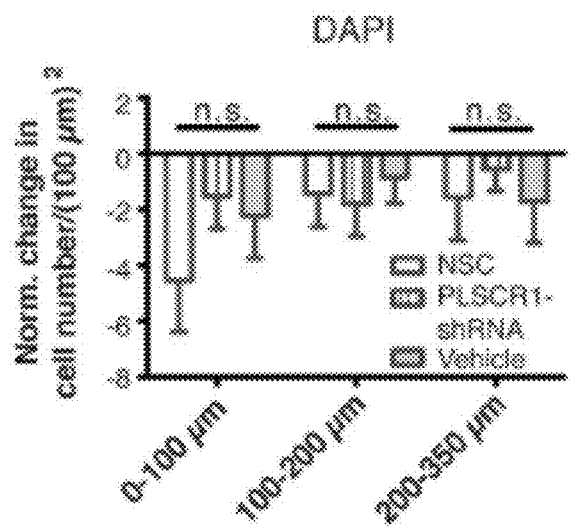
Figure 11I:
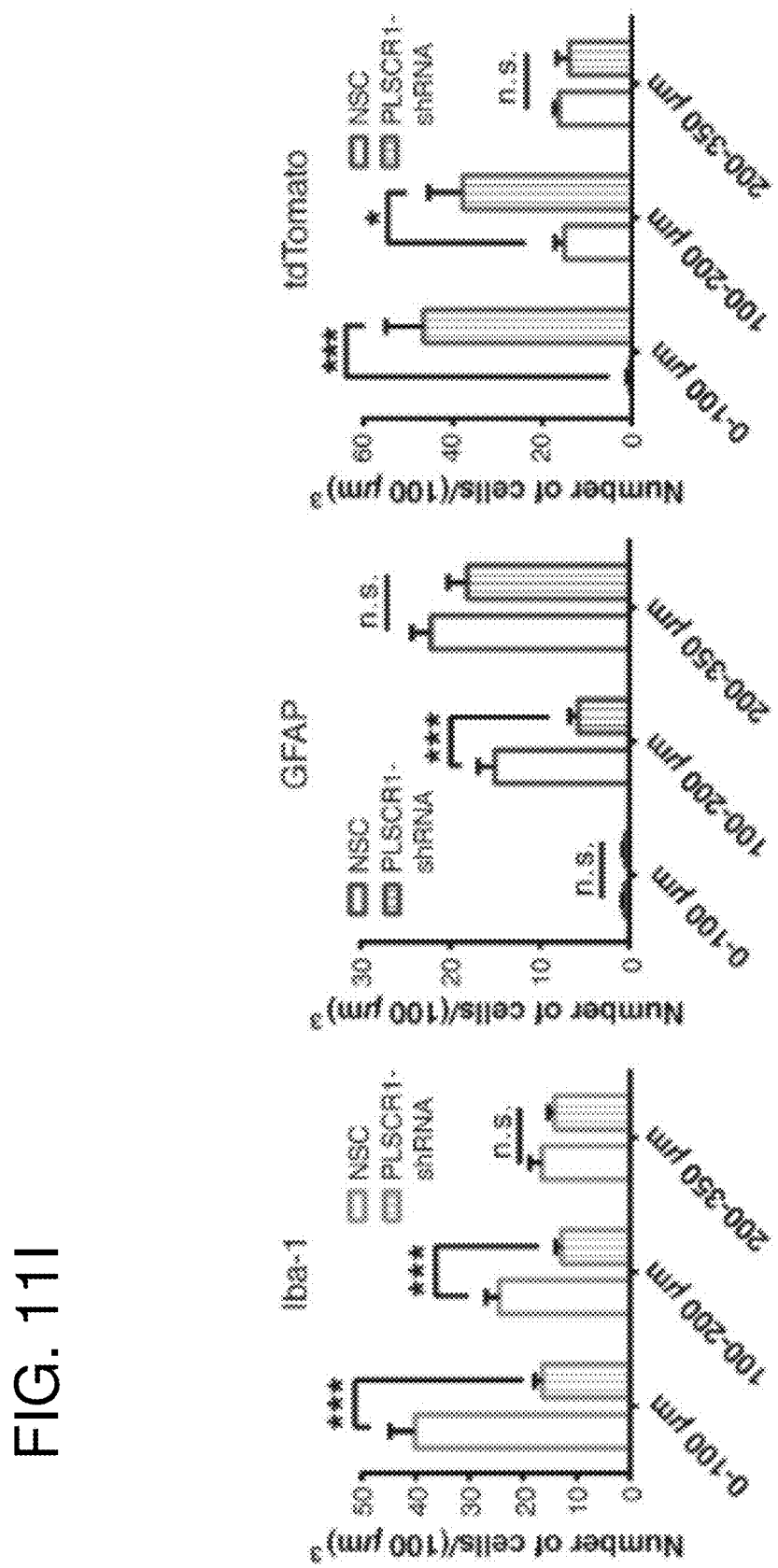

Spots were also created for quantifying the number of tdTomato-positive cell bodies (FIGS. 1B and 4B; FIG. 11I), using a spot size diameter of 10 µm and a quality filter to include the top 10% of spots. Non-spherical, tdTomato-positive structures such as astrocytic endfeet or polarized processes were excluded from cell counts. Dim cell bodies (e.g., near image stitching regions) were manually added to the cell counts.

Figure 13D:
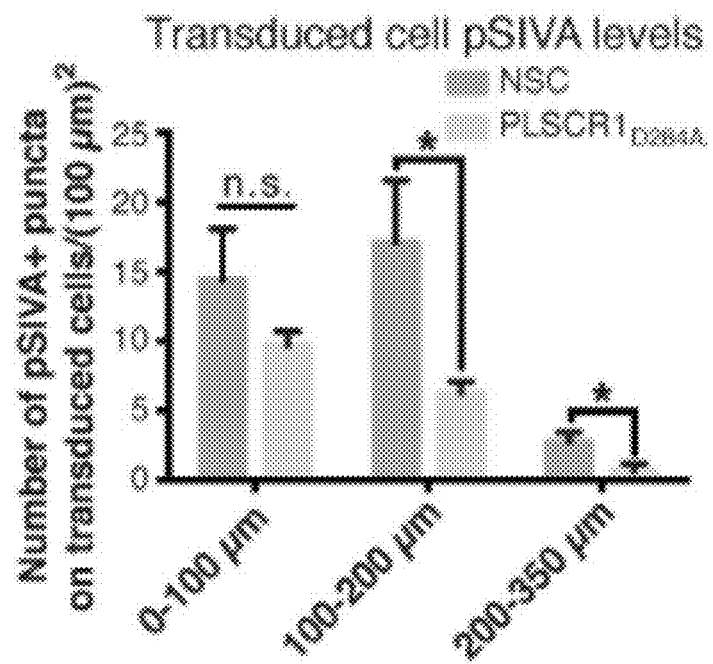

"Surfaces" were created for morphologically more complex structures such as Iba-1-, GFAP- or S100b-positive cells (FIGS. 1B, 1E-1F, 2C-2D, 4B and FIGS. 8E-8F, 11B, 12A-12B). These surfaces captured cell bodies and their major processes. Surfaces were also created for tdTomato-positive cells during colocalization analysis (FIG. 4G; FIG. 13D). First, a smoothing Gaussian filter (0.83 µm width) was applied to the channel of interest. Then, surface filers were used. Surface filters included "Surface grain size", "Diameter of the largest sphere which fits into object", "Seed points diameter" and/or "Quality for seed points" (e.g., to determine whether a structure belongs to the same or a neighboring cell). The surface grain size was set to 1 µm or 0.5 µm for Iba-1/pSIVA or GFAP/S100b/tdTomato-positive structures. The "Diameter of largest sphere" parameter was set to 7 µm, 5 µm or 10 µm for Iba-1, GFAP or pSIVA/S100b/tdTomato-positive structures, respectively. For the seed points diameter parameter we used 8 µm, 15 µm, 8.3 µm or 10 µm for Iba-1-, GFAP-, S100b or pSIVA-positive structures, respectively. The seed points quality filter was set to include the top 10%, 50%, 30% or 5% for Iba-1, GFAP, S100b or pSIVA-positive structures. Finally, a "Number of voxels" filter was applied to eliminate surfaces below 25 voxels, 90 voxels or 10 voxels for Iba-1, GFAP/S100b or pSIVA/tdTomato-positive structures.

Figure 4F:
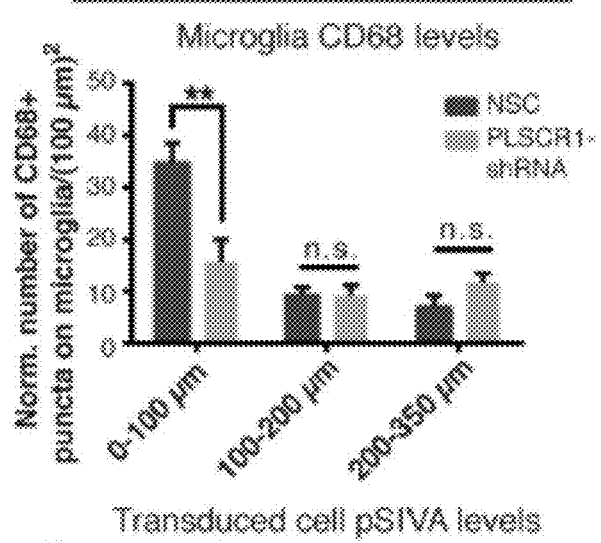
Figure 4G:
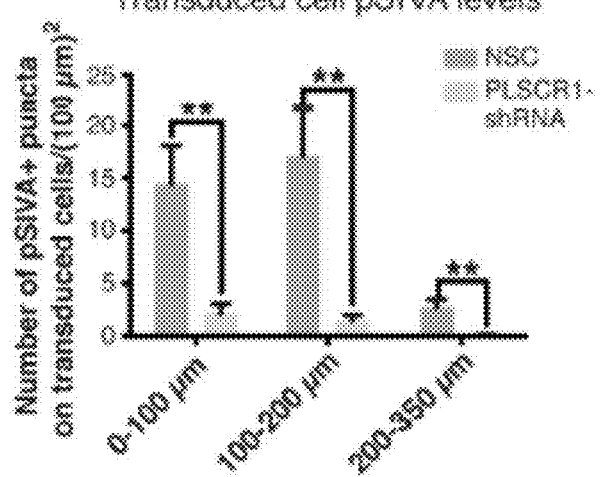
Figure 4H:
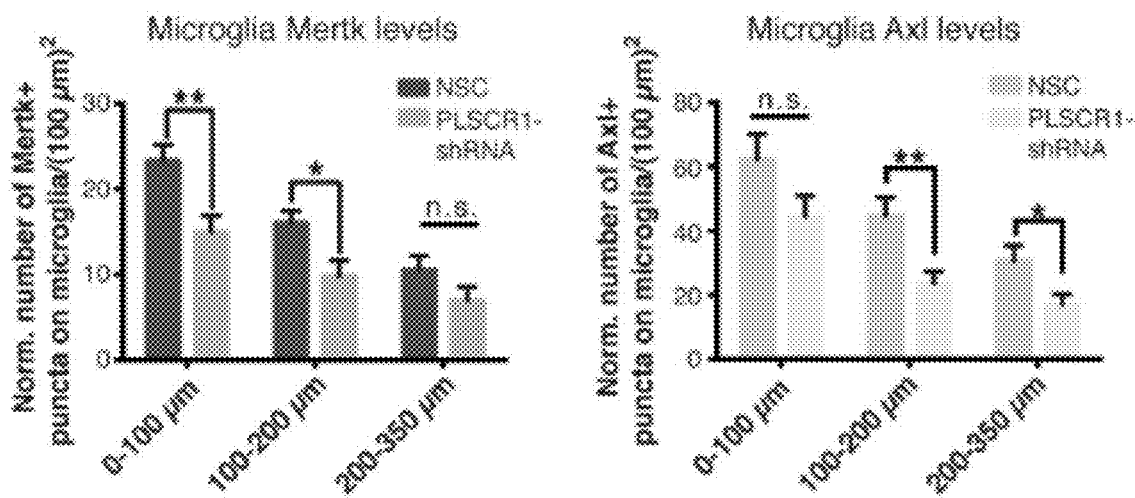

Created spots and surfaces were then used to determine colocalization with the MatLab function in Imaris (e.g., to quantify the levels of CD68, Mertk or Axl on Iba-1-positive cells; FIGS. 4F and 4H). Spots were considered colocalized with a surface if the distance between them was ≤0.5 µm.

Three analysis regions were defined (FIG. 4E, FIG. 11C): $r_1 \leq 100$ µm (the typical cell clearance region in Ad5-CMV-tdTomato-injected mice), 100 µm$<r_2 \leq 200$ µm (the adjacent region with generally the highest level of tdTomato expression), and 200 µm$<r_3 \leq 350$ µm from the injection center (the distal border region). These concentric regions were created manually in Imaris and then used as filters to determine the number of cells that fall within a given radial distance from the injection site. Cell counts were normalized to area/volume, taking brain slice thickness into account. To allow comparison across animals, data was normalized to control hemispheres, whenever possible (FIGS. 4F, 4H and FIGS. 11D, 11F, 11H). Contralateral hemispheres were analyzed using the same concentric regions placed over comparable cortical areas. This analysis approach was used for our S100b, Iba-1, GFAP, tdTomato, Mertk and Axl data (FIG. 4H; FIGS. 11D and 11I). To quantify changes in NeuN- and DAPI-positive cells, analysis regions were further narrowed. In particular, we restricted analysis to a 100 μm-wide band within the cortical layer that included the injection site. Layer 1, which contains only few cells bodies, was excluded from analysis (FIGS. 11E and 11G). Region-restricted analysis was also used to quantify our CD68 data. Specifically, the area along the injection needle tract was excluded from analysis. Likewise, for analysis of our pSIVA data we excluded the top 200 μm of the cortex from analysis to avoid artifacts due to surgical preparation. In vivo pSIVA staining required creation of a cranial window and dura removal, which may cause glial cell activation. Indeed, GFAP immunoreactivity in vehicle-injected mice with a cranial window and removed dura indicated elevated GFAP levels near surface regions (<200 μm from the pia).

In Vivo Calcium Imaging

Calcium imaging in awake head-restrained mice was performed as previously described (Mukamel et al., Neuron 63, 747-760, 2009; Nimmerjahn et al., Neuron 62, 400-412, 2009). Corresponding image data sets were analyzed using custom Matlab software.

Figure 14A:
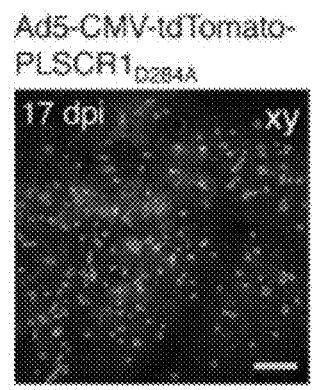
FIGS. 14A-14J: Expression of Calcium-insensitive $PLSCR1_{D284A}$ Reduces Intracellular Calcium Dysregulation.
Figure 14A:
Figure 14B:
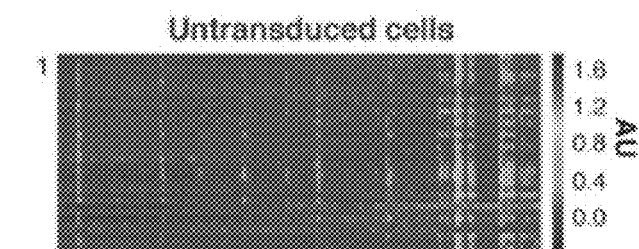
Figure 14B:
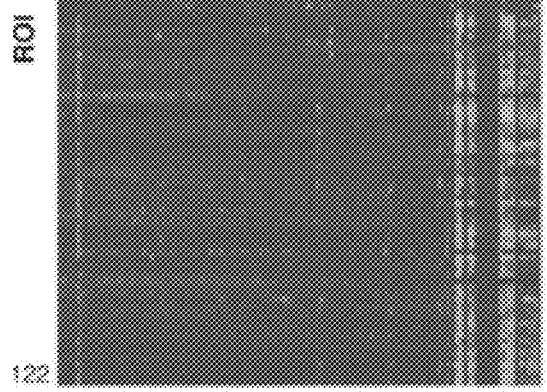
Figure 14B:
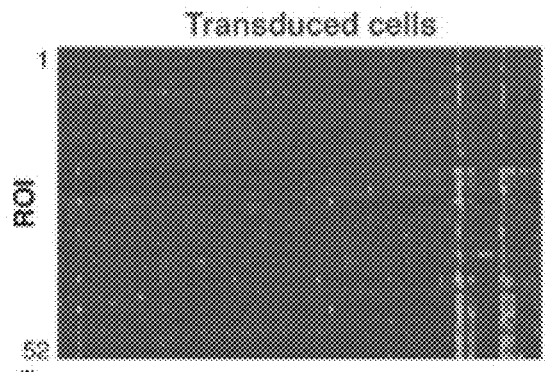
Figure 14C:
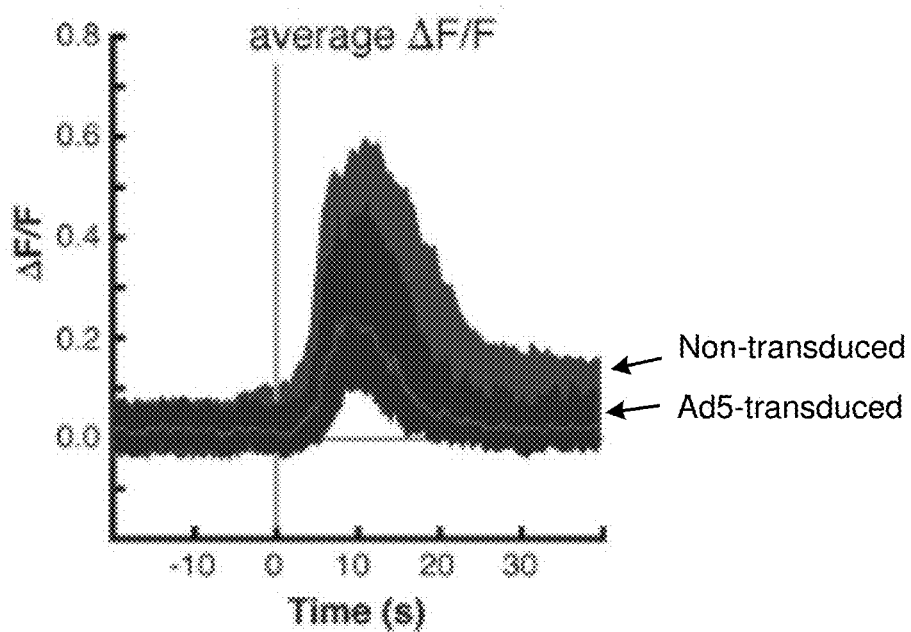
Figure 14D:
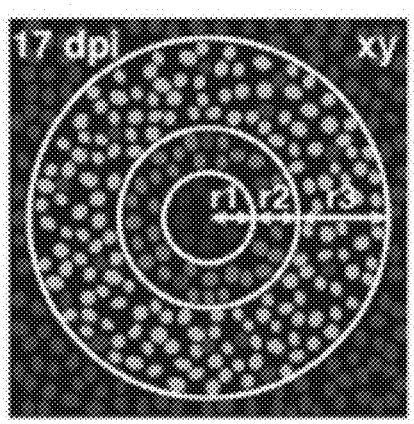
Figure 14D:
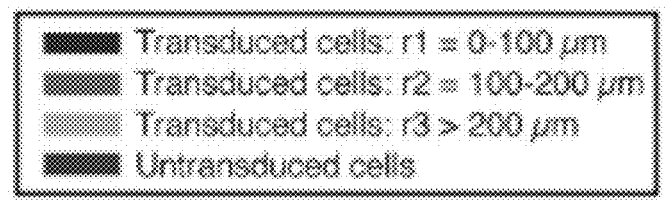
Figure 14E:
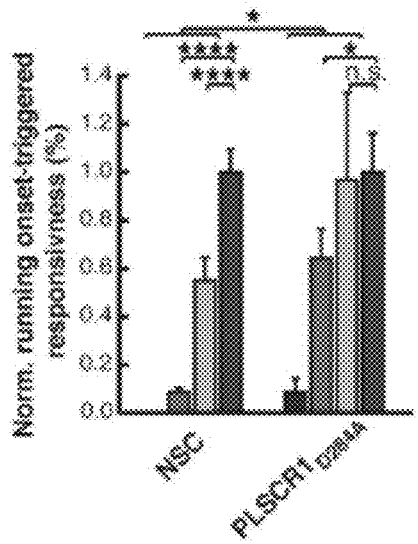
Figure 14F:
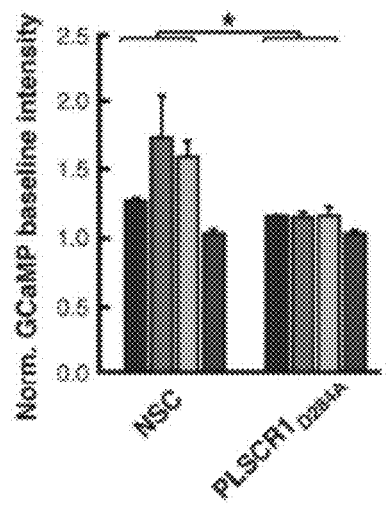
Figure 14G:
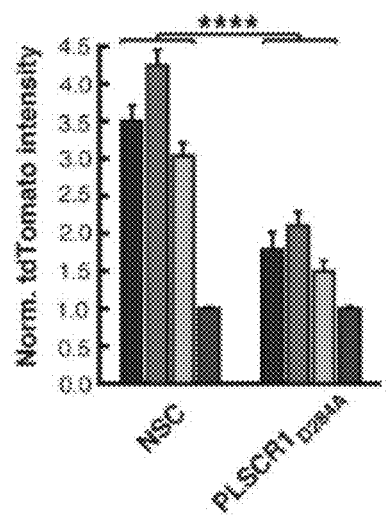
Figure 14H:
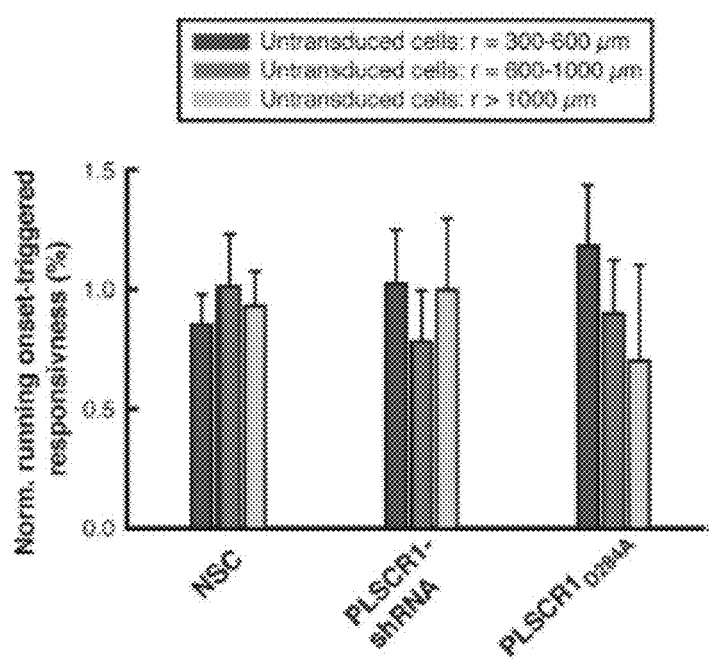

To determine whether and how calcium activity differs between Ad5-transduced and non-transduced cells we stereotactically injected either Ad5-CMV-tdTomato-NSC-shRNA, Ad5-CMV-tdTomato-PLSCR1-shRNA or Ad5-CMV-PLSCR1$_{D284A}$-P2A-tdTomato into transgenic mice with widespread expression of the green fluorescent, genetically encoded calcium indicator GCaMP5G. Because the majority of Ad5-transduced cells were astrocytes (FIG. 6A; FIGS. 11B and 11E) we generated Gfap-Cre (73.12) x CAG-GCaMP5G-IRES-tdTomato mice (Table 1). Imaging was performed 17 days after Ad5 vector delivery and following habituation of the animal to head restraint (typically 3 sessions, 30-90 min/session, 1 session/day on 3 consecutive days prior to imaging). Ad5-transduced cells were readily distinguishable from non-transduced cells based on their level and pattern of tdTomato expression (FIG. 5A, 5D, 5J; FIGS. 14A and 14G). Calcium activity was recorded in cortical areas at or near the depth of Ad5 vector injection (typically z=200 μm from the pia) and at different radial distances (r) from the injection site (FIG. 5G; FIGS. 14D and 14H). At each recording site, images were typically acquired for 20 min using a 2 Hz frame rate and 512×512 pixel resolution (560-700 μm field of view; 50 mW average laser power at z=125 μm) (FIGS. 5A-5F; FIGS. 14A-14C). No signs of phototoxicity, such as a gradual increase in baseline fluorescence, lasting changes in activity rate or blebbing of recorded cells were apparent in our recordings. The same PMT settings were used for all recordings and mice.

Figure 14I:
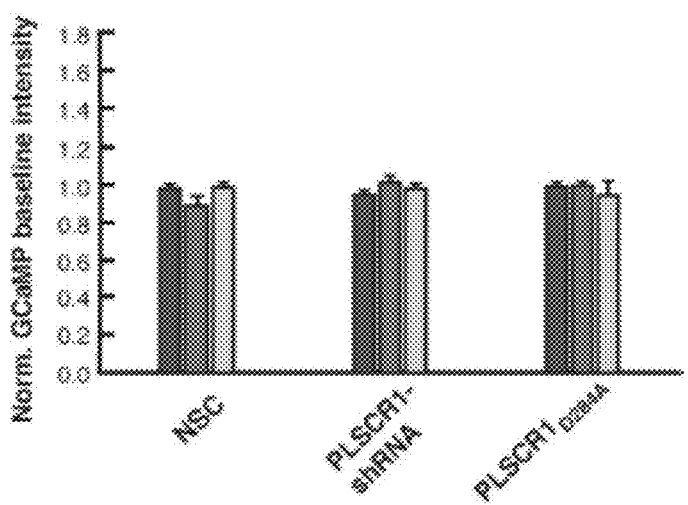
Figure 14J:
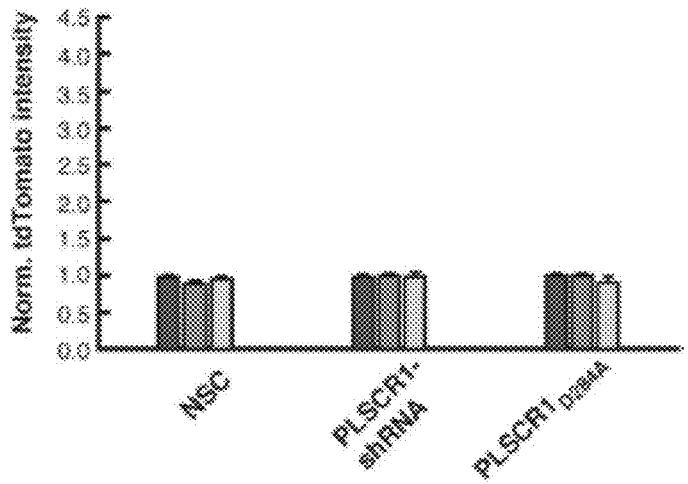

Based on the radial tdTomato expression profile typically found in Ad5-CMV-tdTomato-injected wild type mice (FIG. 1B), three main analysis regions were defined: $r_1 \leq 100$ μm (the typical cell clearance region), 100 μm$<r_2 \leq 200$ μm (the adjacent region with generally the highest level of tdTomato expression), and $r_3 > 200$ μm from the injection center (the distal border region) (FIGS. 5 and 14). Non-transduced cells included in analysis were located in regions with little to no GFAP activation (r>300 μm) (FIG. 1B). A comparison of non-transduced cells located at various distances from the injection site (r=300-600 μm, r=600-1,000 μm, or r>1,000 μm) revealed no significant effect of distance on calcium transients or GCaMP baseline expression (FIGS. 14H-14J).

Cells and analysis regions were computationally defined. For each two-channel recording we first calculated the maximum intensity projection image of the fluorescence recorded in the tdTomato channel. Next, we identified parameters suitable for automated segmentation of Ad5-transduced and non-transduced tdTomato-positive cells. Because Ad5-transduced cells showed consistently higher tdTomato levels compared to non-transduced cells (FIG. 5J; FIG. 14G) we used tdTomato levels as one parameter. In particular, for segmentation of Ad5-transduced cells we used the ~$95^{th}$ percentile of the tdTomato pixel intensity distribution recorded at the injection site. The corresponding threshold value differed between test groups (NSC, PLSCR1, PLSCR1$_{D284A}$). For Ad5-CMV-tdTomato-NSC-shRNA or -PLSCR1-shRNA transduced cells we used a threshold value of 14,000 in 16-bit unsigned grayscale images. For Ad5-CMV-PLSCR1$_{D284A}$-P2A-tdTomato transduced cells we used 8,000. For identification of non-transduced cells we used the ~$95^{th}$ percentile of the pixel intensity distribution recorded far away from the injection site (r>300 μm). This threshold varied between 4,000 and 7,000, depending on animal (e.g., optical window quality or brain surface blood vessel pattern).

A second parameter that we used to distinguish Ad5-transduced from non-transduced cells was the labeling pattern. Cellular processes/branches of transduced cells were more apparent than those of non-transduced cells, likely due to the higher levels of tdTomato expression. During segmentation, this resulted in a 'haze' around Ad5-transduced cells, i.e. larger cell segments for transduced compared to non-transduced cells. Cell segments determined using the 'non-transduced cell' threshold that appeared 10× larger in size than the same segment determined using the 'transduced cell' threshold were classified as 'transduced'. Otherwise, they were counted as 'non-transduced'. Segments that exceeded a size of 300 μm$^2$, likely representing more than one cell, were re-segmented with a higher threshold. For every such iteration the threshold was increased by 2,000. Segments >30 μm$^2$ were retained. Re-segmentation was repeated for a maximum of 10 iterations. All areas segmented with the 'transduced' threshold (or higher) were considered 'transduced'. All areas segmented with the 'non-transduced' threshold and non-overlapping with the transduced areas were considered 'non-transduced'. The radial distance of each identified segment from the injection center was calculated as the Euclidian distance of the segments' centroid to the injection center.

To verify that identified tdTomato-positive segments were also GCaMP-positive, we calculated the maximum intensity projection image of the fluorescence simultaneously recorded in the GCaMP channel and applied a threshold of 10,000 (corresponding to the approximately $50^{th}$ percentile of the pixel intensity distribution in that channel). Segments showing less than 80% overlap of tdTomato with GCaMP expression were excluded from analysis.

GCaMP fluorescence signals, F(t), were extracted from all identified segments and corresponding temporal traces were smoothed with a Gaussian filter (s.d., 0.2 s) (FIGS. 5A and 5B, FIGS. 5D and 5E, FIGS. 14A and 14B). ΔF(t)/F was calculated as (F(t)−baseline)/baseline. Cells were considered active when ΔF(t)/F crossed a threshold, defined as the $95^{th}$ percentile of the filtered signal distribution of the whole recording, for >4 s.

Figure 5A:
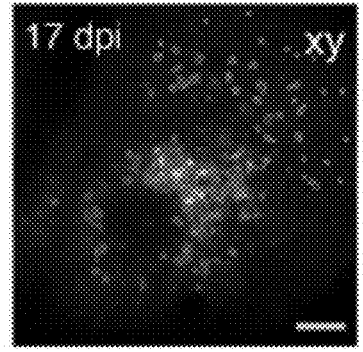
FIGS. 5A-5J: PLSCR1 Inhibition Reduces Intracellular Calcium Dysregulation.
Figure 5B:
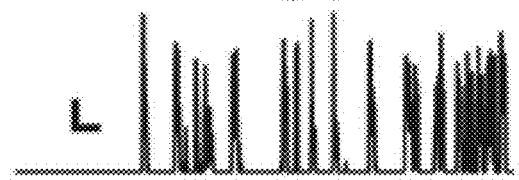
Figure 5B:
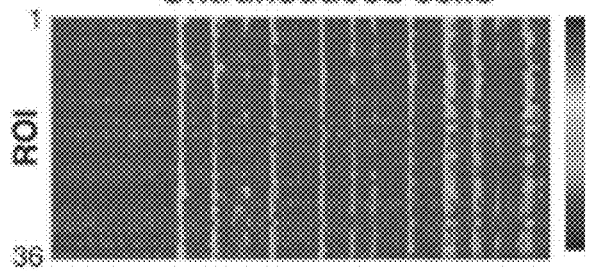
Figure 5B:
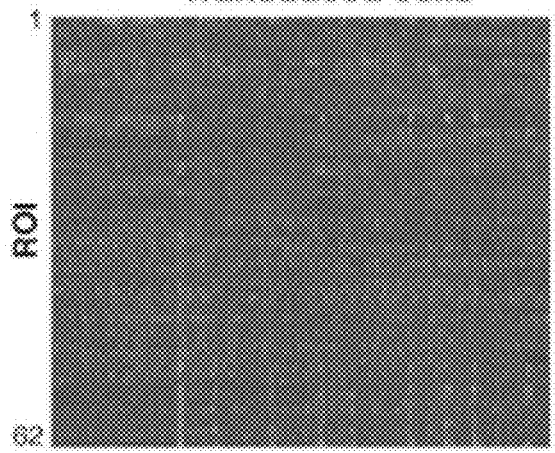
Figure 5C:
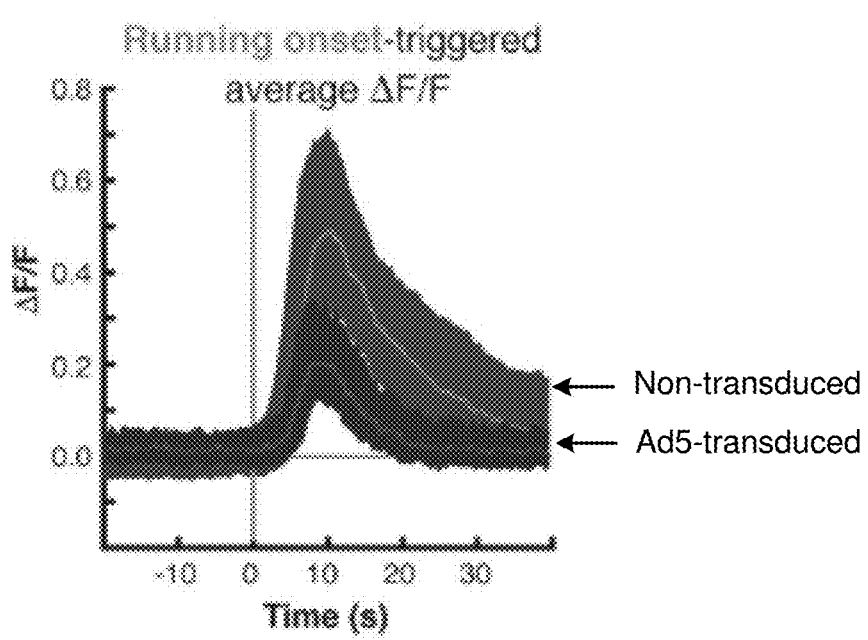
Figure 5D:
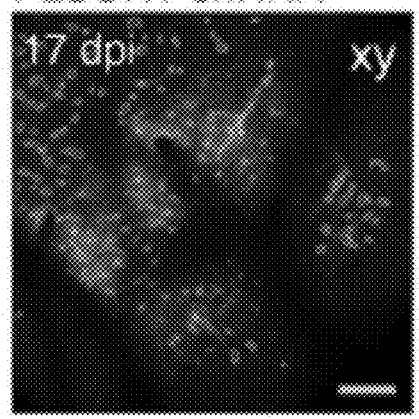
Figure 5E:
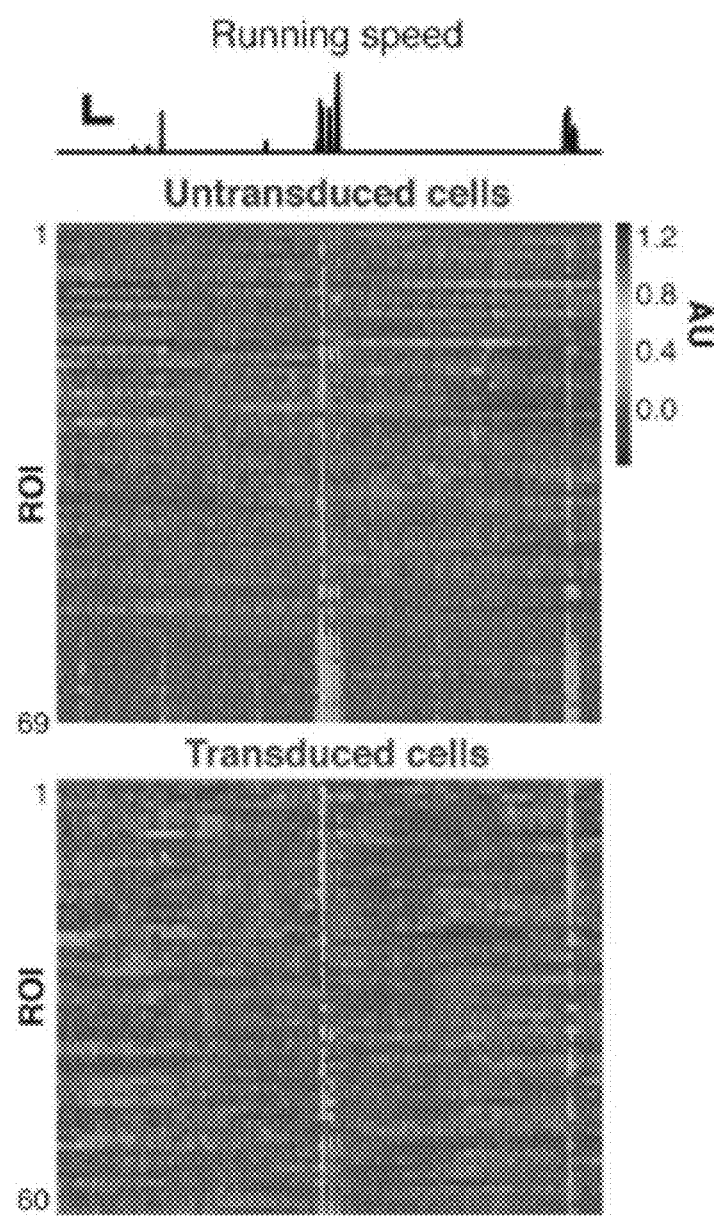
Figure 5F:
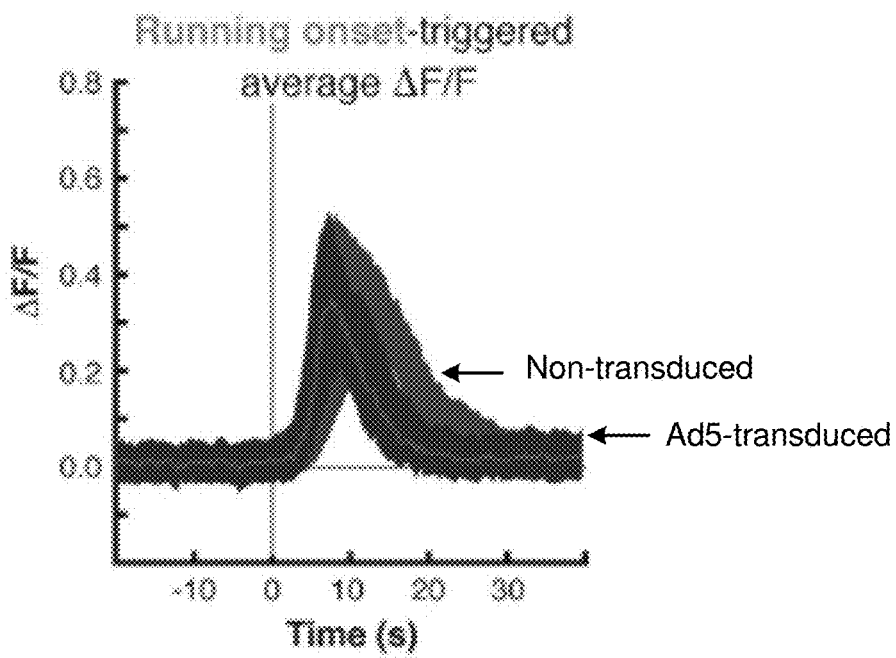
Figure 5G:
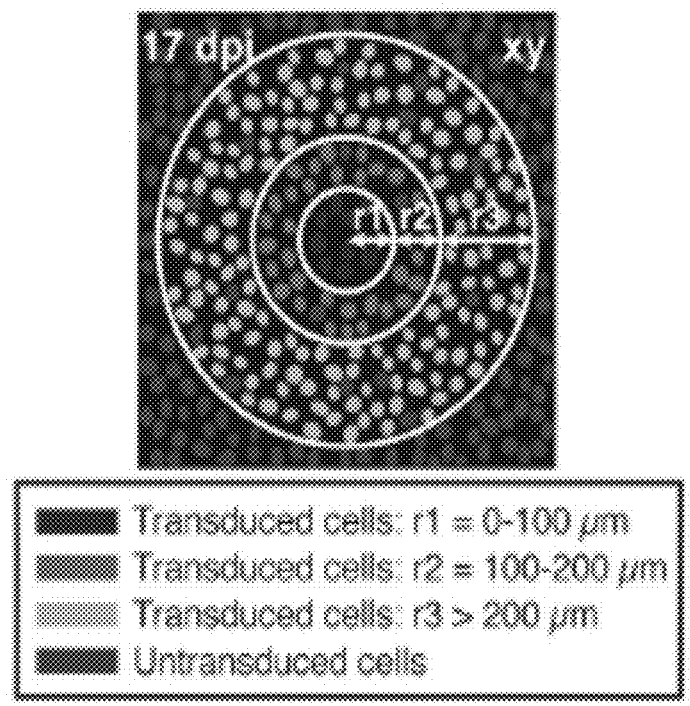
Figure 5H:
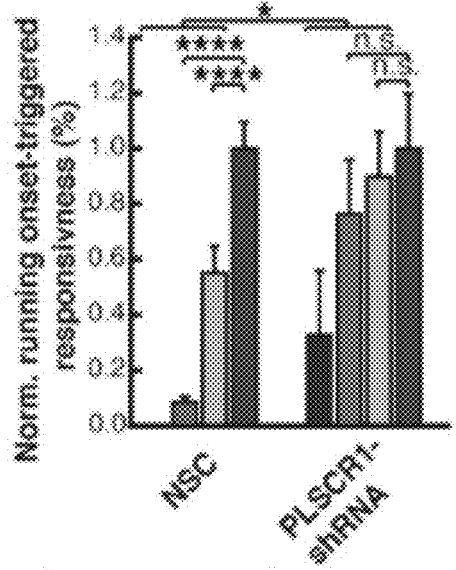
Figure 5I:
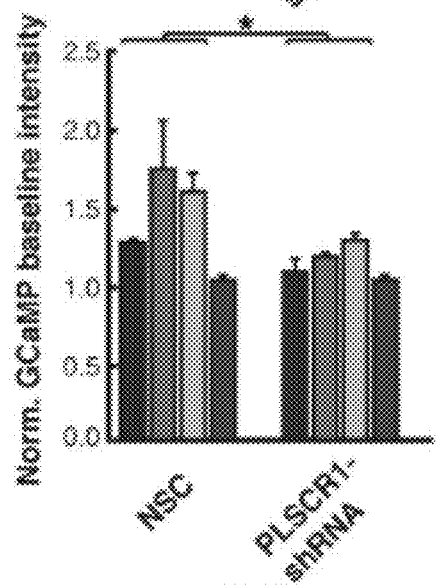

To quantify how GCaMP baseline expression differs across test groups and analysis regions (FIG. 5I; FIG. 14F)

we generated regions of interest (ROIs) of a fixed size (10 µm×10 µm) around the centroid of each identified segment. This served to minimize analysis biases that could arise from segmentation with different tdTomato thresholds. For each ROI the mean GCaMP intensity over time was used as a threshold to detect calcium activity on-/offset. For baseline calculation calcium activity starting 5 s prior to a detected onset and ending 5 s after a detected offset were excluded from the trace. If the remaining intervals were longer than 20 s, the corresponding GCaMP signal was temporally averaged to yield the calcium baseline. Baseline values for each ROI were normalized to the average baseline value of all non-transduced cell ROIs from the same mouse. For group analysis, baseline values were averaged for each recording and analysis region.

Figure 5J:
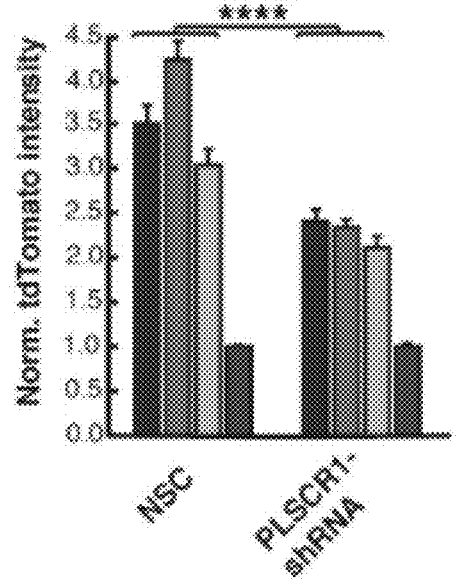

To quantify tdTomato expression differences across test groups and analysis regions (FIG. 5J; FIG. 14G), we applied the ROIs defined for quantifying GCaMP baseline expression differences to the maximum intensity projection image of fluorescence detected in the tdTomato channel. Pixel intensities for each ROI were averaged and then normalized to the average tdTomato intensity of all non-transduced cells from the same mouse. For group analysis, tdTomato intensities were averaged for each recording and analysis region.

Locomotor activity of head-restrained awake mice on the spherical treadmill was recorded using an optical encoder (E7PD-720-118; US Digital). Encoder signals were acquired at 10 kHz but, for analysis, down-sampled to 20 Hz and smoothed with a Gaussian filter (s.d., 0.7 s). Running onset or offset was defined as the time point at which running speed exceeded 10 mm/s or fell below 4 mm/s. Because astrocyte calcium transients are typically slow, lasting several seconds (FIGS. 5C and 5F; FIG. 14C), only calcium activity evoked by running bouts that were separated by at least 40 s from a previous running bout was included in analysis. Calcium activity was classified as running-evoked if it occurred between 5 s before and 10 s after running onset. To generate the plot of average running-evoked calcium activity, shown in FIGS. 5C, 5F and 14C (shaded area indicates 25% and 75% median), calcium traces were aligned to running onset. For a given recording, responsiveness of a cell to running (FIG. 5H; FIGS. 14E and 14H) was calculated as the proportion of running bouts that evoked astrocyte calcium activity in that cell. All cell responsiveness values were then normalized to the average responsiveness of non-transduced cells from the same mouse. For group analysis, responsiveness values were averaged for each recording and analysis region.

For the analysis of calcium baseline, tdTomato expression, and responsiveness to running events we used a two-way ANOVA with two fixed factors, namely test group (NSC, PLSCR1 or PLSCR1$_{D284A}$) and cell transduction state (transduced or non-transduced). All three comparisons showed significant effects for both factors ($p<0.01$). A t-test was used to compare calcium baseline, tdTomato expression and responsiveness to running events of transduced cells across test groups. The NSC group showed significantly higher tdTomato expression than the PLSCR1 and PLSCR1$_{D284A}$ group ($p<0.5$, Bonferroni corrected). To test for differences between transduced and non-transduced cells within test groups, we used a paired t-test. In the NSC group, the responsiveness to running events of transduced cells with 100 µm<$r_2$≤200 µm or $r_3$>200 µm was significantly lower than the responsiveness of non-transduced cells ($p<0.05$, Bonferroni corrected). In the PLSCR1 group, the responsiveness of transduced cells with 100 µm<$r_2$≤200 µm or $r_3$>200 µm was not significantly different compared to the responsiveness of non-transduced cells ($p>0.05$). In the PLSCR1$_{D284A}$ group, the responsiveness of transduced cells with 100 µm<$r_2$≤200 µm was significantly lower compared to the responsiveness of non-transduced cells ($p<0.05$, Bonferroni corrected). Transduced cells with $r_3$>200 µm showed responsiveness comparable to that of non-transduced cells ($p>0.05$, Bonferroni corrected). We also tested whether calcium baseline level, tdTomato expression and responsiveness to running events of non-transduced cells varied with distance from the injection site. We used a two-way ANOVA with a fixed factor 'test group' (NSC, PLSCR1 or PLSCR1$_{D284A}$) and a fixed continuous factor 'radial distance from the injection site' (r=300-600 µm, 600-1,000 µm, or >1,000 µm). No significant effect was found ($p>0.05$).

Molecular Cloning

To prepare the CMV-tdTomato construct, the CMV promoter was subcloned into the plasmid pUNISHER (Montesinos et al., *J Neurophysiol* 106, 3230-3244, 2011) replacing the hSYN promoter. The tdTomato gene was then subcloned into the EcoRI site downstream of the CMV promoter. The plasmid non-silencing pGIPZ shRNA miR control vector (pGIPZ-NSC) was purchased from Open Biosystems, Inc., Huntsville, Ala. It contained the non-silencing control (NSC) RNA sequence 5'-AUCUCGC-UUGGGCGAGAGUAAG-3' (SEQ ID NO: 6), in a 318-nt miR30 shRNA cassette. The sequence used for the mouse PLSCR1 (mPLSCR1)-shRNA was 5'-GCUGGAAUAC-UUAGCUCAGAUC-3' (SEQ ID NO: 7), corresponding to nt 321-342 of the mPLSCR1 ORF. The 318-nt cassette containing the shRNA was synthesized in the same context as the NSC-shRNA by Integrated DNA Technologies, Coralville, Iowa Both the mPLSCR1 and NSC miR30 shRNA cassettes were then subcloned into the EcoRV site in the 3'-utr region of the pUN-CMV-tdTomato plasmid to form the constructs pUN-CMV-tdTomato-mPLSCR1-shRNA and pUN-CMV-tdTomato-NSC-shRNA.

The vector pCMV6-mPLSCR1-myc-DDK containing the myc- and DDK-tagged mPLSCR1 cDNA was purchased from OriGene, Rockville, Md. A single nucleotide substitution was introduced which changed the amino acid at position 284 from aspartic acid to alanine by inverse PCR site-directed mutagenesis. The primers used for the mutagenesis were as follows: FWD 5'-GATGCAGC-CAACTTTGGGATCCAG-3' (SEQ ID NO: 8) and REV 5'-AAAGTTGGCTGCATCCGTGAAGGC-3' (SEQ ID NO: 9). The CMV-mutant (or wild type) mPLSCR1-myc-DDK cassettes were then PCR amplified and subcloned into the PmeI to BamHI sites of the pDE1/DE3-P2A-tdTomato vector, in-frame with the P2A-tdTomato cassette.

Adenovirus Production and Titering

All viruses were E1/E3 deleted and generated using the AdSyn method by sequence and ligation independent cloning (SLIC) (U.S. Publication No. 2013/0231267). First, the entire transcription cassette from each plasmid was PCR amplified and inserted by SLIC into AdSyn Ad5 E1 module pCOE1-038 that lacks the E1A/B region (Ad5 base pairs 448-3513). Next, the entire Ad5 E1 module with transcription cassette was PCR amplified and joined by SLIC with AdSyn Ad5 macromodule pCOASMM-025 that contains the remaining Ad5 genome (base pairs 3555-35938) except for a deletion of the E3 region (Ad5 base pairs 28599-30476). The E3 region was deleted for space. No transgenes or shRNAs were inserted into the deleted E3 region. All vectors were verified by sequencing. The vectors were then transfected into 293-H cells and the resultant viruses were amplified for three rounds and purified on two successive CsCl gradients. Titers of preparations ranged between $10^8$ and $10^{10}$ infectious units/ml (based on ELISA) and the particle to PFU ratios were typically ≤100:1 (Table 2).

All viruses described in this paper were grown and amplified on 293-H cells, but were titered on 293e4/ix cells. 293e4/ix cells were seeded into 96-well tissue-culture plates in 100 µl of complete growth media (CGM) with 2% fetal bovine serum (FBS) per well one hour prior to transduction. Each virus preparation was serially diluted 1:3 in CGM with 2% FBS seven times. For comparison, a standard human adenovirus serotype 5 viral stock was purchased from American Type Culture Collection, Manassas, Va. (# VR-1516FZ). This standard virus was diluted with CGM and 2% FBS down to $5 \times 10^5$ PFU/ml, then serially diluted 1:3 in the same medium seven times. The cells were then transduced with 100 µl per well of each serial dilution of viral preparation, standard Ad5, or CGM with 2% FBS alone (non-transduced control) in triplicate. Transduced cells were incubated at 37° C. and 5% $CO_2$ for 48 hours.

Following the incubation, the inoculum was removed and the cells were fixed with 200 µl per well of an ice-cold 95% ethanol with 5% glacial acetic acid solution at −20° C. for 15 minutes. The fixative was then removed and the wells were washed with PBS. After removing the PBS wash, 100 µl of Superblock Reagent (Life Technologies #37515) was added per well. The fixed cells were blocked at 4° C. overnight.

For ELISA, the anti-adenovirus serotype 5 antibody (Abcam; # ab6982) was diluted 1:2000 in BupH Phosphate Buffered Saline (Life Technologies; #28372) supplemented with 1.5% Normal Goat Serum (NGS, Jackson Labs). The Superblock was then decanted from each well and replaced with 75 µl per well of the diluted primary antibody. Plates were incubated in the primary antibody for 1 hour at room temperature with gentle rocking. The primary antibody was then decanted and the cells washed three times with ELISA wash buffer (20 mM Tris pH 7.5 with 150 mM NaCl and 0.1% Tween-20).

The secondary antibody, HRP conjugated goat anti-rabbit IgG (Thermo-Pierce; #31460) was diluted 1:1000 in BupH buffer with 1.5% NGS. The cells were incubated with 75 µl of secondary antibody per well for 1 hour at room temperature with gentle rocking. The cells were then washed again three times with ELISA wash buffer. Following the last wash, the buffer was decanted and replaced with 100 µl of Detection Reagent per well (1×PNPP [Thermo #34047] with 1× diethanolamine [Thermo 34064]). The cells were then incubated in the Detection Reagent for 10 minutes at room temperature in the dark. The ELISA was read on a Bio-Rad Model 680 Microplate reader using a 405 nM filter. Results were calculated from a standard curve prepared using the standard Ad5 readings.

Quantitative RT-PCR

Primary mouse liver cells or astrocyte-enriched cortical cultures were transduced with adenovirus constructs (MOI 20). 48 hours post-transduction, RNA was extracted according to the manufacturer's specifications (RNAeasy, Qiagen Cat. #74104 or #75142), and then reverse transcribed using an RT Transcriptor First Strand cDNA synthesis kit (Roche; Cat. #04379012001). qRT-PCR was performed (for primers see Table 3) on an Applied Biosystems 7900HT fast real-time PCR system using a 96- or 384-well plate format with 2×SYBR Green PCR master mix (Applied Biosystems; LifeTechnologies Cat. #4344463). Data was processed with AQ/RQ manager and analyzed using cloud-based software Symphony (LifeTechnologies).

For ex vivo brain tissue qRT-PCR experiments, 3 or 17 days after intracranial injection of Ad5, mice were $CO_2$ asphyxiated and quickly perfused with 1×PBS. Whole brains were carefully removed and surgically dissected in ice cold ACSF. Cortical tissue punches were made by using a sterile 2.0 mm inner diameter round glass capillary connected with flexible shrink tubing to a 10 mL syringe. The open end of the capillary was gently pressed onto the site of vector injection and depressed to collect approximately 1.2 mm thickness of tissue. Tissue punches were then quickly pressure ejected into sterile 1.5 mL Eppendorf tubes using the connected syringe. Tubes with tissue samples were then dropped into liquid nitrogen and stored at −80° C. until processed for RNA extraction, as described above.

Statistical Analysis

Data was analyzed and plotted using Matlab, Excel, or Prism software. All data sets displayed normal distribution and equal standard deviations unless indicated by unequal variance test (Welch's). The following convention was used to indicate P values in FIGS. 1, 3-6, 8-11, and 13-14: "n.s." indicates P>0.05, "*" indicates $0.01 < P \leq 0.05$, "" indicates $0.001 < P \leq 0.01$, "*" indicates $0.0001 < P \leq 0.001$, and "****" indicates $P \leq 0.0001$. All data are represented as mean±SEM.

TABLE 1

List of Mutant Mouse Lines

| Mouse strain | Source | Stock number(s) |
| --- | --- | --- |
| Cx3cr1$^{+/eGFP}$ | JAX | 005582 |
| S100b-eGFP | JAX | 005621 (cryopreserved) |
| Gfap-Cre (73.12) × CAG-GCaMP5G-IRES-tdTomato (heterozygous) | JAX | 012886, 024477 |
| Mertk$^{-/-}$ | Lemke laboratory | — |
| Axl$^{-/-}$ Mertk$^{-/-}$ | Lemke laboratory | — |
| TLR3$^{-/-}$ | JAX | 009675 |
| TLR4$^{-/-}$ | JAX | 007227 |
| TLR9$^{-/-}$ | MMRRC | 034329 |
| TMEM173$^{-/-}$ (STING$^{-/-}$) | JAX | 017537 |
| IFNAR1$^{-/-}$ | MMRRC | 032045 |
| IL-1R1$^{-/-}$ | JAX | 003018 |
| TNF$^{-/-}$ | JAX | 005540 |

TABLE 2

List of Custom Adenovirus 5 (Ad5)-based Vectors

| Ad5 | SEQ ID NO: | Titer (PFU/ml) | Particle to PFU ratio |
| --- | --- | --- | --- |
| CMV-tdTomato-NSC-shRNA | 1 | $2.97 \times 10^{10}$ | 11 |
| CMV-tdTomato-PLSCR1-shRNA | 2 | $6.16 \times 10^9$ | 22 |
| CMV-PLSCR1$_{D284A}$-P2A-tdTomato | 3 | $2.12 \times 10^8$ | 577 |
| CMV-Null | 4 | $4.88 \times 10^{10}$ | 24 |

TABLE 3

List of qRT-PCR Primers

| Target mRNA | | Primer sequence | SEQ ID NO: |
| --- | --- | --- | --- |
| Cyclophilin A | Forward primer | GCCGATGACGAGCCCTT | 10 |
| | Reverse primer | AAGTCACCACCCTGGCACA | 11 |
| 36B4 | Forward primer | CTCTCGCTTTCTGGAGGGTG | 12 |

TABLE 3-continued

List of qRT-PCR Primers

| Target mRNA | | Primer sequence | SEQ ID NO: |
|---|---|---|---|
| | Reverse primer | ACGCGCTTGTACCCATTGAT | 13 |
| mPLSCR1-3 | Forward primer | GCGCAGCTAGAGGATTCAGG | 14 |
| | Reverse primer | AACAGTTTCTGAGGCTCCTTCT | 15 |
| IL-1β | Forward primer | CCTCTCCAGCCAAGCTTCC | 16 |
| | Reverse primer | CTCATCAGGACAGCCCAGGT | 17 |
| TNF-α | Forward primer | GCCACCACGCTCTTCTGTCT | 18 |
| | Reverse primer | CAGCTGCTCCTCCACTTGGT | 19 |

Example 2: Phosphatidylserine Exposure Controls Viral Innate Immune Response by Microglia The example describes the finding that phosphatidylserine (PtdSer) exposure on the outer leaflet of virally transduced cells triggers their engulfment by microglia through TAM receptor-dependent mechanisms. It is further demonstrated that inhibition of phospholipid scramblase 1 (PLSCR1) activity, involved in antiviral responses, prevents PtdSer externalization and enables months-long protection of vector-transduced transgene-expressing cells from microglial phagocytosis.

Microglia Engulf Adenoviral Vector-Transduced Cells

Figure 1D:
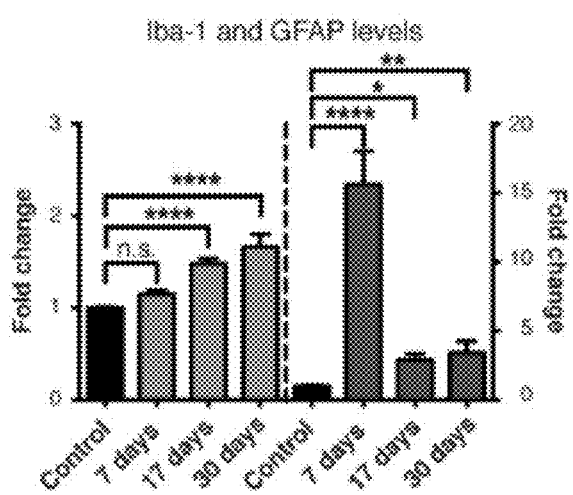
Figure 1E:
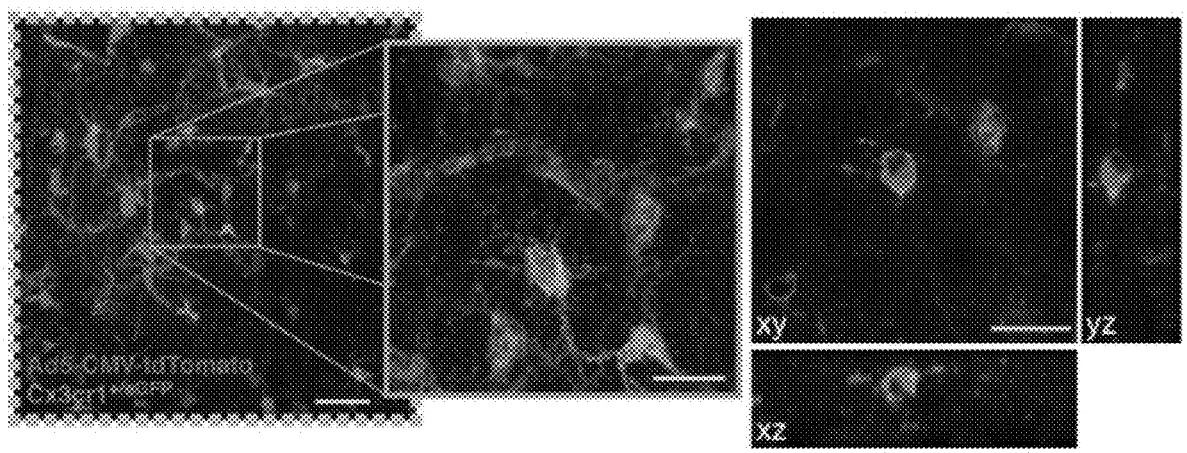
Figure 1F:
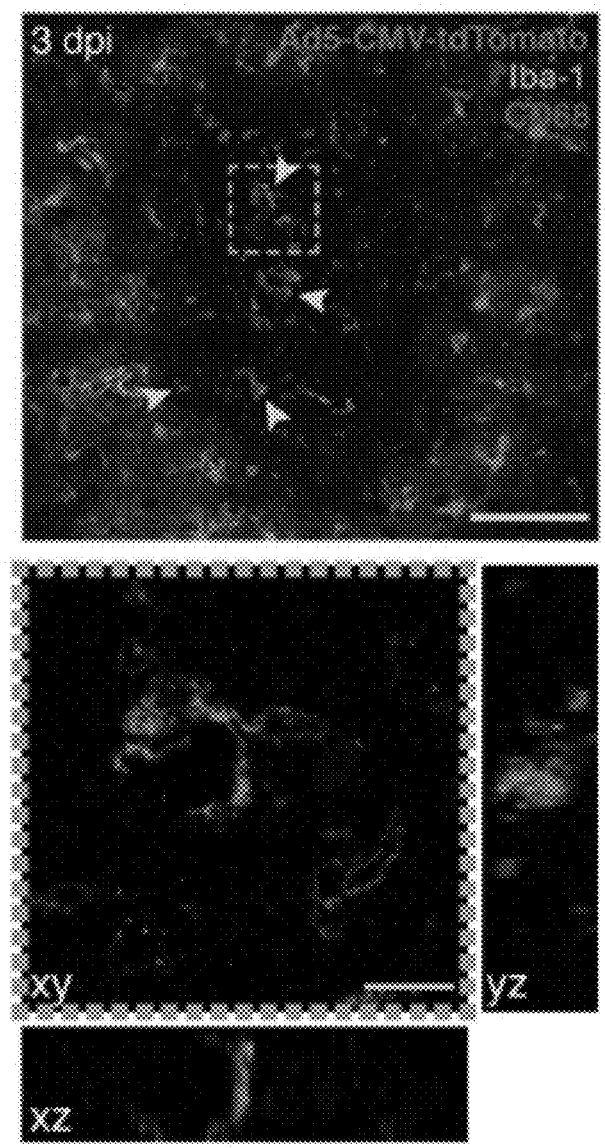
Figure 8C:
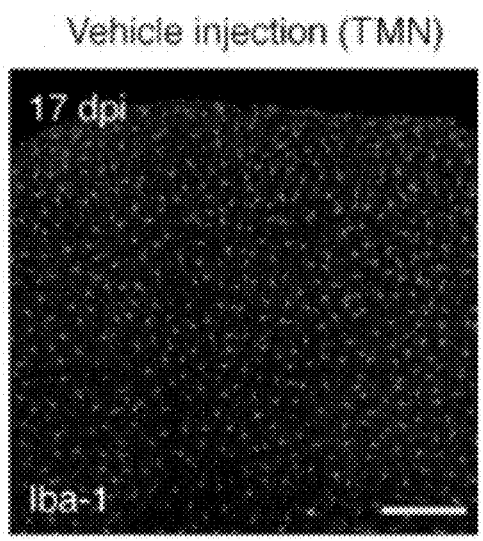
Figure 8D:
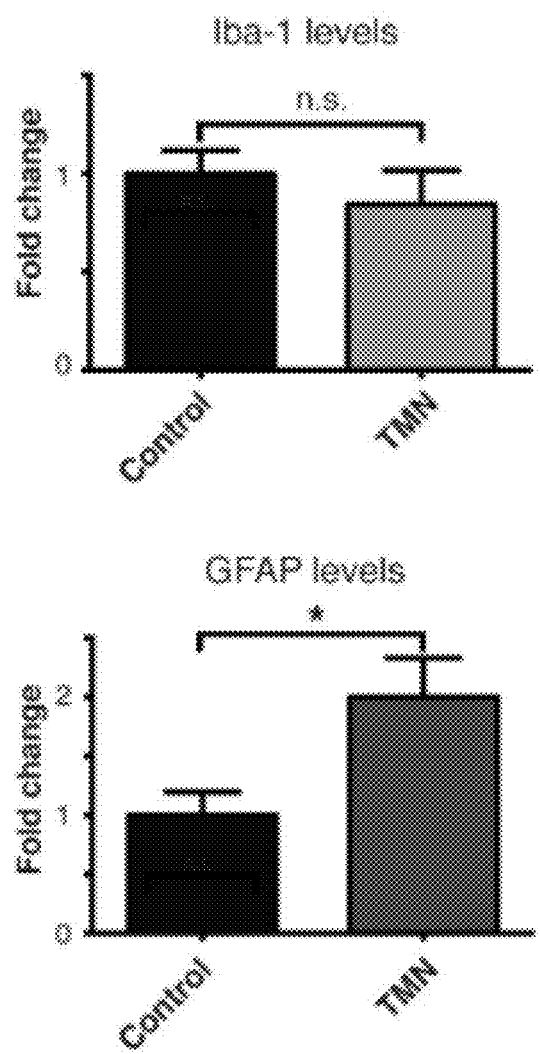
Figure 8E:
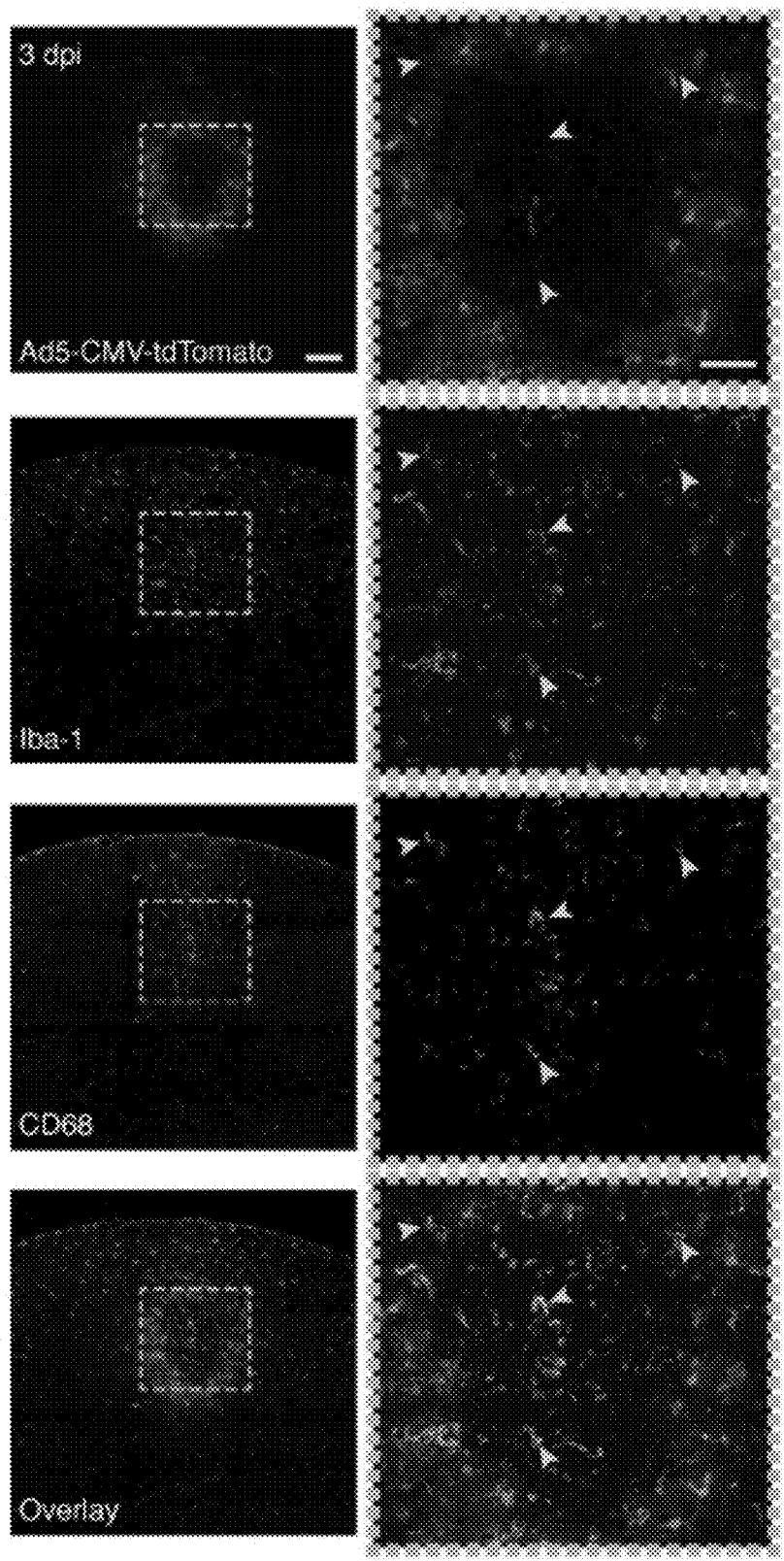
Figure 8F:
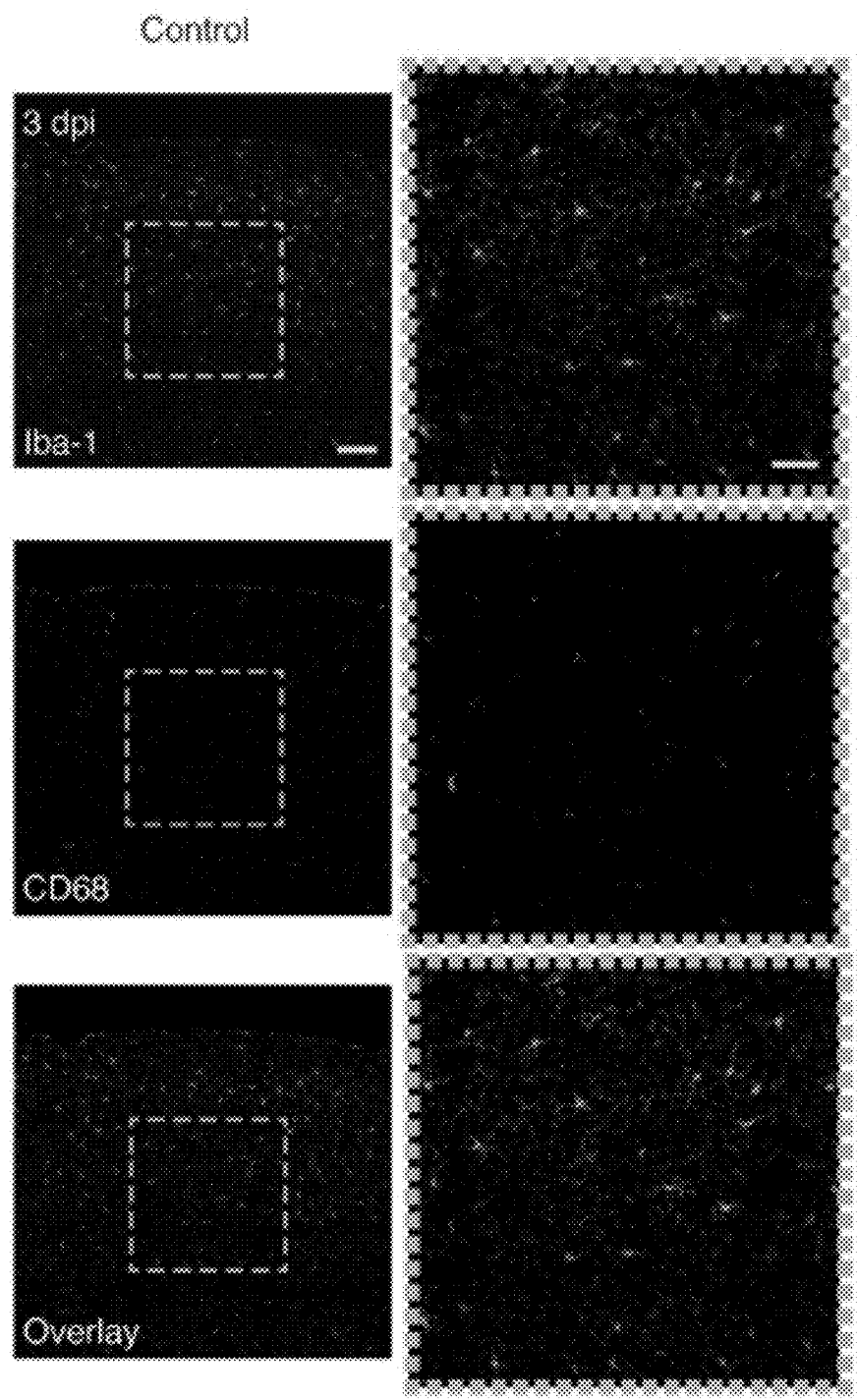

To analyze the spatiotemporal interaction of microglia with Ad5-transduced cells, a custom Ad5 vector expressing either the red fluorescent protein tdTomato (FIG. 1A) or no transgene (FIGS. 8A and 8B) under control of the cytomegalovirus (CMV) promoter was intracranially delivered in wild type or transgenic mice. Microglia showed markedly elevated expression of ionized calcium-binding adaptor Iba-1 and eGFP density in Cx3cr1$^{+/eGFP}$ mice, which express eGFP in microglia (Jung et al., Mol Cell Biol 20, 4106-4114, 2000), near central regions of the transduced area. In this central area, loss of tdTomato transgene expression was observed at 3, 7, 17, and 30 days after vector injection (FIGS. 1A-1C, 1E-1F). In contrast, expression of glial fibrillary acidic protein (GFAP) was preferentially elevated at the boundary surrounding the transduced area (FIGS. 1B and 1D). No such Iba-1 or GFAP activation pattern was seen in vehicle controls (FIGS. 8C and 8D), indicating that activation was associated with viral uptake and not with injection alone. While GFAP expression around the transduced region progressively decreased over time, Iba-1 levels increased or remained elevated (FIG. 1D). tdTomato-positive material within eGFP-positive cells in Cx3cr1$^{+/eGFP}$ mice indicated clearance of Ad5-transduced cells through microglial phagocytosis (FIG. 1E). Microglia phagocytosis of Ad5-transduced cells was confirmed by two-photon imaging in live Cx3cr1$^{+/eGFP}$ mice. Consistent with this data, microglia showed an increase in the lysosomal marker CD68 in central regions (FIG. 1F; FIGS. 8E and 8F).

Microglia-Mediated Cell Clearance Depends on Soluble and Membrane-Bound Factors

Figure 9B:
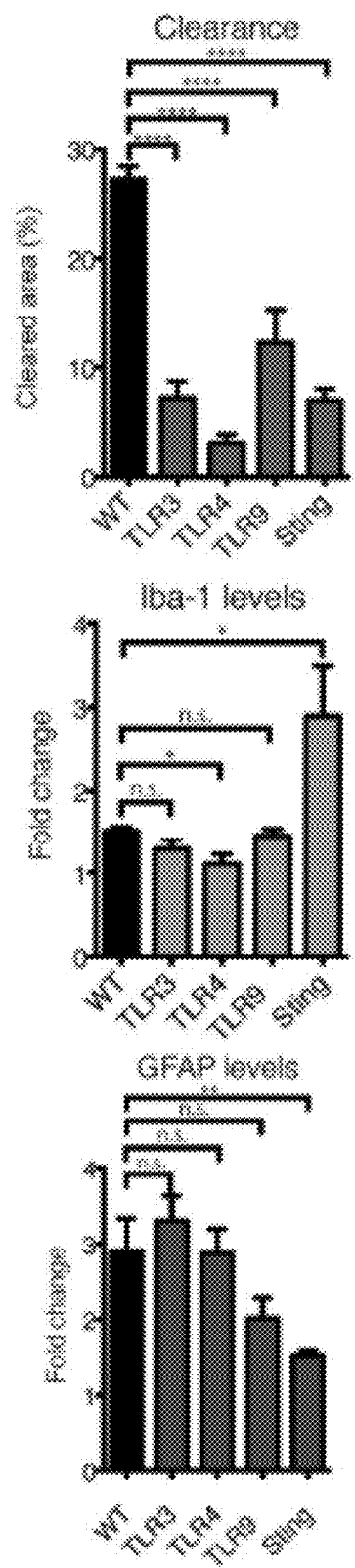
Figure 10B:
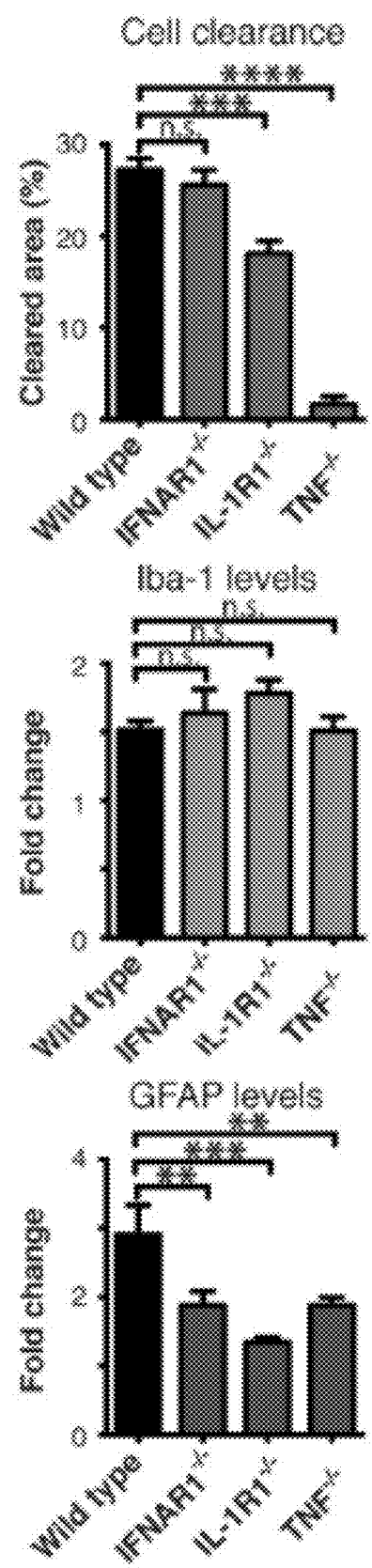

Given the chemotactic ability and process dynamics of microglia (Davalos et al., Nat Neurosci 8, 752-758, 2005; Fourgeaud et al., Nature 532, 240-244, 2016; Nimmerjahn et al., Science 308, 1314-1318, 2005), it was hypothesized that both soluble and membrane-bound factors contribute to innate immune recognition of Ad vector-transduced cells by microglia. As a first step in testing this hypothesis, Ad5 vector injection was performed in a series of mutant mice. It was found that in vivo transduction led to release of cytokines triggered, at least in part, by viral particle sensing during cell entry or intracellular trafficking, as indicated by reduced cell loss in Toll-like receptor (TLR) knock out and stimulator of interferon genes (STING) mutant mice (FIGS. 9A and 9B). Tumor necrosis factor (TNF) signaling played a particularly important role in cell clearance compared to other cytokines, such as interleukin-1 (IL-1), as demonstrated in TNF and IL-1 receptor 1 knock out mice (FIGS. 10A and 10B). Type I interferon signaling did not significantly contribute to cell clearance despite its effect on GFAP levels (FIGS. 10A and 10B).

Next, studies were conducted to determine which membrane-bound factors and receptors mediate microglia engulfment of Ad5 vector-transduced cells. Cell clearance requires display of an "eat-me" signal, such as PtdSer. To determine if PtdSer externalization might contribute to clearance of Ad5-transduced cells, experiments were conducted in live mice. Using a fixable polarity-sensitive indicator of cell viability and apoptosis (pSIVA), an Annexin B12 derivative that is membrane-impermeable and emits green fluorescence only upon reversible binding to exposed PtdSer on the0 external plasma membrane (Kim et al., Nat Methods 7, 67-73, 2010; Ruggiero et al., Proc Natl Acad Sci USA 109, 8145-8148, 2012), an increase in pSIVA-positive cells within the transduced region was demonstrated at 3 days after vector injection (FIGS. 2A and 2B). Near central regions punctate staining predominated, indicating cell fragmentation due to cell death or phagocytosis. In surrounding regions, membrane staining of morphologically intact cells was observed, suggesting the presence of stressed but live cells.

Figure 2C:
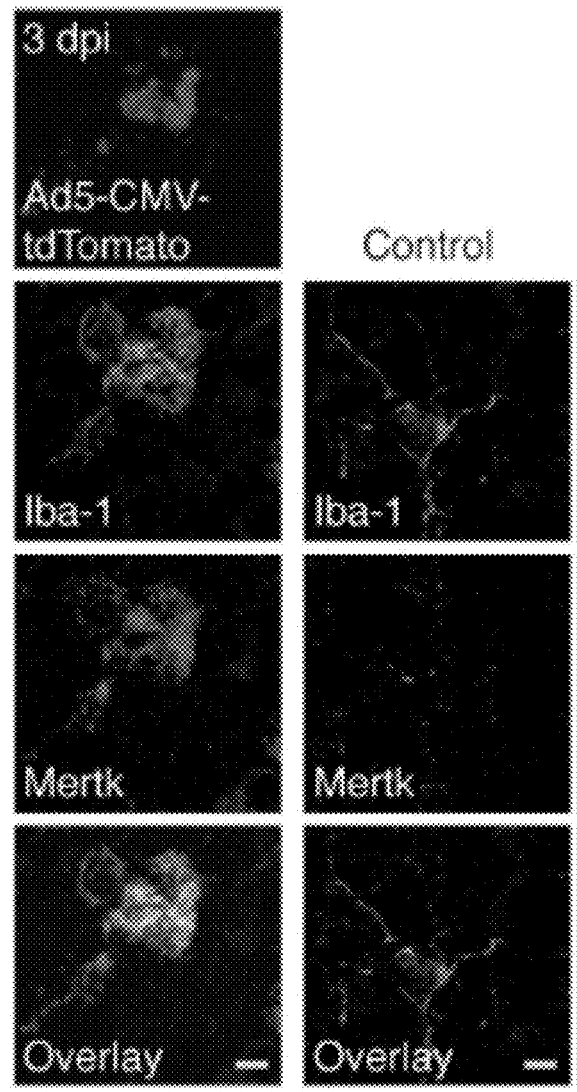
Figure 2D:
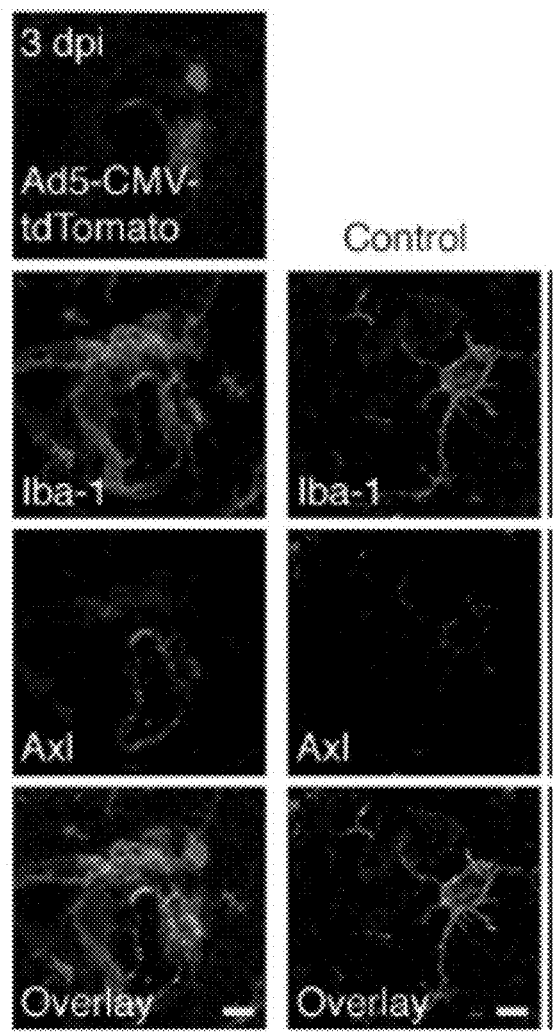

Externalized PtdSer can be recognized by a variety of receptors (Arandjelovic and Ravichandran, Nat Immunol 16, 907-917, 2015; Sierra et al., Front Cell Neurosci 7, 6, 2013). TAM receptor tyrosine kinases are known to mediate the phagocytosis of apoptotic cells and to regulate innate immune responses in professional phagocytes (Lemke, Cold Spring Harb Perspect Biol 5, a009076, 2013; Rothlin et al., Cell 131, 1124-1136, 2007; Zagorska et al., Nat Immunol 15, 920-928, 2014). TAM receptor activation is dependent on PtdSer exposure in the outer leaflet of apoptotic cells, since TAM ligands bind PtdSer and bridge this phospholipid to TAM receptors (Lemke, Cold Spring Harb Perspect Biol 5, a009076, 2013). While all TAM receptors (Tyro3, Axl, Mertk) are expressed in the adult CNS, Axl and Mertk are present in microglia (Fourgeaud et al., Nature 532, 240-244, 2016; Grommes et al., J Neuroimmune Pharmacol 3, 130-140, 2008). Using immunostaining, pronounced upregulation of Mertk and Axl was found in microglia near the cell clearance area at 3 days after vector injection (FIGS. 2C and 2D). Cell clearance was markedly reduced in Mertk$^{-/-}$ single or Axl$^{-/-}$ Mertk$^{-/-}$ double knock out mice (FIGS. 3A and 3B). While Axl$^{-/-}$ Mertk$^{-/-}$ double knock out mice showed increased Iba-1 expression levels, indicating an activated microglia phenotype, GFAP expression in astrocytes around the transduced area was reduced (FIGS. 3A and 3B).

Modulating PLSCR1 Activity Controls Innate Immune Responses by Microglia

To further test PtdSer's involvement in cell clearance, further studies were conducted to inhibit its externalization specifically in Ad5-transduced cells. Transmembrane movement of PtdSer across the plasma membrane's lipid bilayer is regulated by phospholipid transporters, particularly calcium-dependent scramblase(s) and ATP-dependent flippase(s)/translocase(s) (Frey and Gaipl, *Semin Immunopathol* 33, 497-516, 2011; Segawa and Nagata, *Trends Cell Biol* 25, 639-650, 2015). Because viral infection may affect intracellular calcium signaling (Chami et al., *Biochim Biophys Acta* 1763, 1344-1362, 2006), it was reasoned that altered scramblase activity due to dysregulated calcium homeostasis might contribute to increased PtdSer externalization (Zhao et al., *J Biol Chem* 273, 6603-6606, 1998).

Figure 4I:
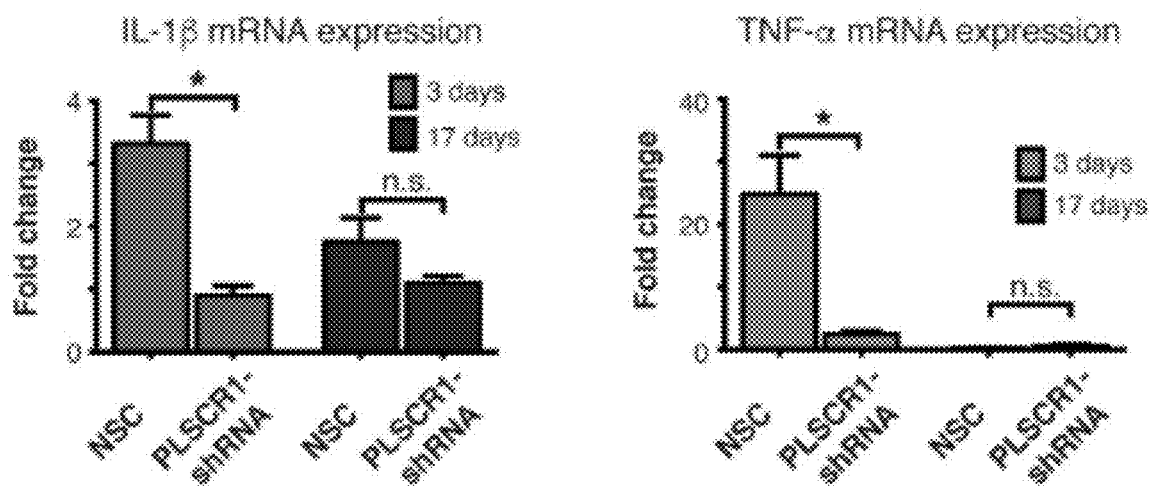

PLSCR is a conserved family of four genes (PLSCR1-4) of which PLSCR1, PLSCR3 and PLSCR4 are expressed in the cortex (Zhang et al., *J Neurosci* 34, 11929-11947, 2014). PLSCR1/3/4 possess a conserved calcium ion binding domain and a putative transmembrane region. In addition, PLSCR1 contains a nuclear localization signal and a DNA binding domain, and is upregulated in response to inflammatory stimuli (Kodigepalli et al., *FEBS Lett* 589, 3-14, 2015). Because PLSCR1 had previously been implicated in calcium-dependent PtdSer externalization (Zhao et al., *J Biol Chem* 273, 6603-6606, 1998), regulating inositol 1,4, 5-triphosphate receptor (IP3R) expression (Zhou et al., *J Biol Chem* 280, 35062-35068, 2005), and antiviral responses in vitro (Dong et al., *J Virol* 78, 8983-8993, 2004; Yang et al., *Antiviral Res* 94, 9-17, 2012), experiments were conducted to inhibit its activity in vivo. First, a small hairpin-forming interference RNA (shRNA) was identified that provided specific and efficient knock down of mouse phospholipid scramblase 1 (PLSCR1) in vitro (FIG. 11A). Next, two Ad5 vectors driving tdTomato expression under control of the CMV promoter were constructed, one containing the miR30-based PLSCR1-shRNA (SEQ ID NO: 2) and the other incorporating a non-silencing control (NSC) shRNA (SEQ ID NO: 1) (FIGS. 4A-4D). Remarkably, Ad5-mediated expression of PLSCR1-shRNA led to a nearly complete abrogation of microglia-mediated cell clearance in vivo (FIGS. 4A-4C; FIGS. 11B-11H). Additionally, it significantly reduced Iba-1, GFAP and CD68 expression levels (FIGS. 4D-4F; FIG. 11I; FIGS. 12A and 12B). Likewise, pSIVA and microglial TAM receptor levels were significantly reduced (FIGS. 4G and 4H; FIGS. 12C-12F). Tissue cytokine levels were also reduced (FIG. 4I).

Additional studies were conducted to determine whether a similar effect could be achieved by expression of calcium-insensitive PLSCR1$_{D284A}$, thought to act as a dominant-negative mutant (Ory et al., *J Neurosci* 33, 3545-3556, 2013). It was found that this protein again abrogated cell clearance but had little effect on Iba-1 or GFAP expression levels (FIGS. 13A-13D).

PLSCR1 Modulation Promotes Normal Calcium Signaling and Long-Term Protection from Microglia-Mediated Cell Clearance Given the broadly protective effects of PLSCR1-shRNA on innate immune responses, the viability and function of Ad5 vector-transduced cells were investigated more closely.

To assess functional aspects, two-photon calcium imaging was performed in behaving mice (Mukamel et al., *Neuron* 63, 747-760, 2009; Nimmerjahn et al., *Neuron* 62, 400-412, 2009). Because most transduced and cleared cells were astrocytes (FIGS. 11B-11F), mice expressing the genetically encoded calcium indicator GCaMP5G under control of the GFAP promoter were generated (Garcia et al., *Nat Neurosci* 7, 1233-1241, 2004; Gee et al., *Neuron* 83, 1058-1072, 2014). 17 days after Ad5-CMV-tdTomato-NSC-shRNA vector delivery, calcium imaging in the cortex of awake, head-restrained mice on an exercise ball revealed pronounced reduction of evoked calcium transients in NSC virus-transduced compared to non-transduced GCaMP5G-expressing cells from the same animal (FIGS. 5A-5C). In contrast, mice injected with either Ad5-CMV-tdTomato-PLSCR1-shRNA or Ad5-CMV-tdTomato-PLSCR1$_{D284A}$ showed evoked calcium transients similar to those in non-transduced cells from the same animal (FIGS. 5D-5F; FIGS. 14A-14C). Closer analysis of this data revealed that calcium transient amplitude and cellular responsiveness to running onset was impaired throughout the NSC-shRNA transduced region, particularly near cell clearance regions (FIGS. 5G and 5H). In contrast, PLSCR1-shRNA or PLSCR1$_{D284A}$ expressing cells showed significantly less impaired or normal calcium transients in all transduced areas (FIGS. 5G and 5H; FIGS. 14D and 14E). Additionally, it was found that NSC-shRNA expressing cells had an increased calcium baseline (FIG. 5I). In contrast, in PLSCR1-shRNA or PLSCR1$_{D284A}$ expressing cells' calcium baseline was significantly less increased (FIG. 5I; FIG. 14F). The observed changes in intracellular calcium signaling appeared independent of tdTomato expression levels (FIG. 5J; FIG. 14G) and were unlikely due to regional differences in calcium signaling (FIGS. 14H-14J).

Figure 6A:
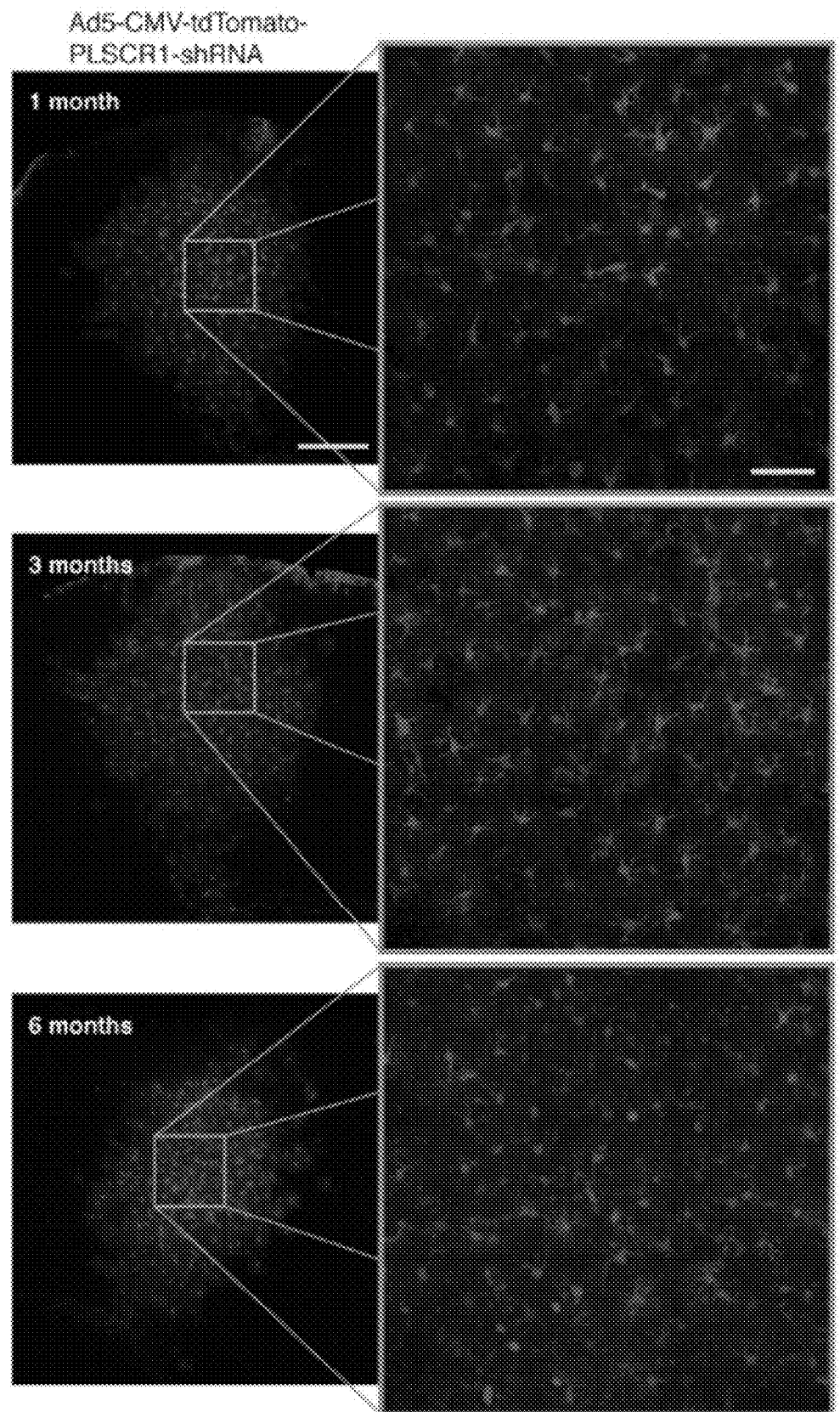
FIGS. 6A-6B: PLSCR1 Inhibition Provides Long-term Protection from Microglia-mediated Cell Clearance.
Figure 6B:
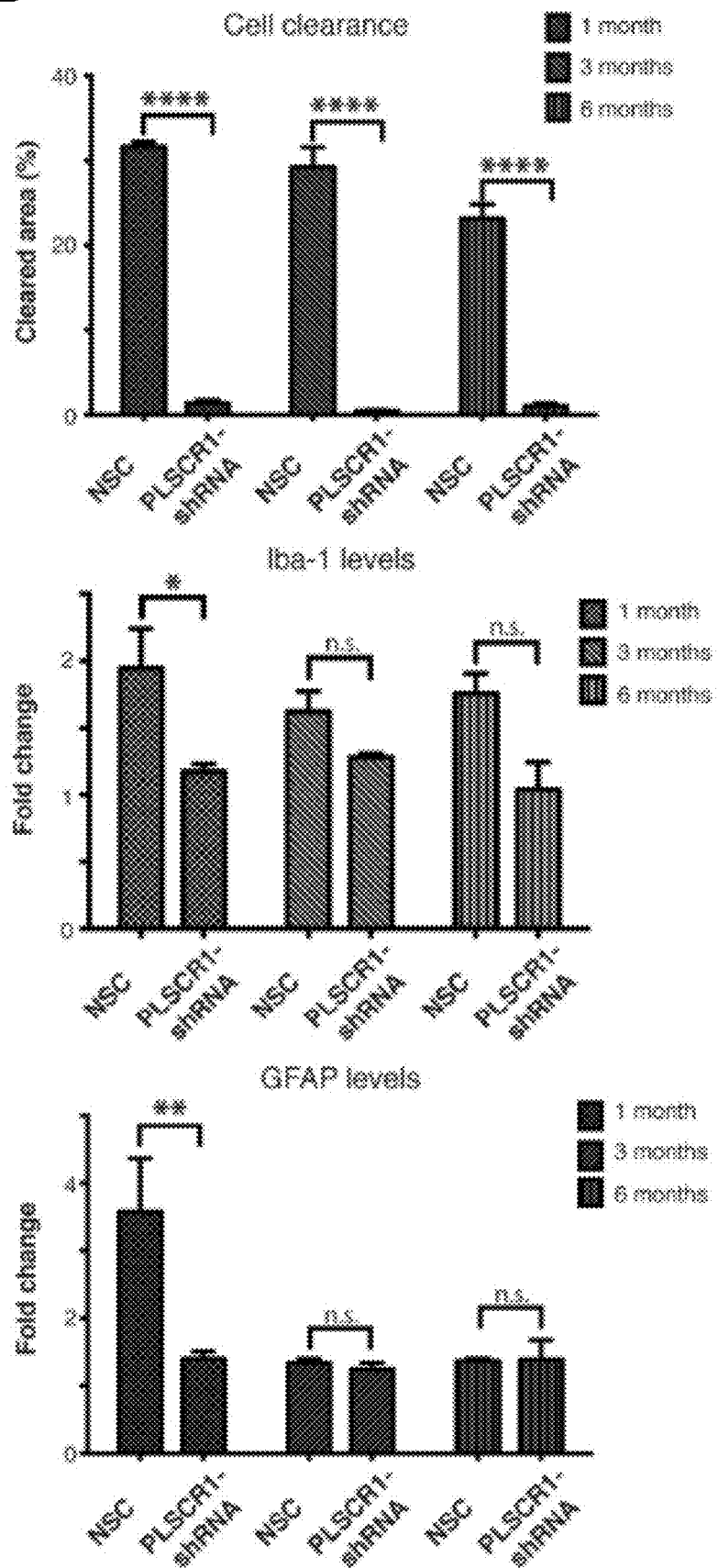

To assess long-time viability of Ad5 transduced cells, transgene expression was evaluated over several months in mice injected with either Ad5-CMV-tdTomato-NSC-shRNA or Ad5-CMV-tdTomato-PLSCR1-shRNA. It was found that cell clearance, Iba-1 and GFAP levels remained low for at least six months after Ad5 injection when PLSCR1 activity was inhibited (FIGS. 6A and 6B). The vast majority of Ad5 vector-transduced, tdTomato-expressing cells, most of which were astrocytes (FIG. 6A; FIGS. 11B and 11E), showed no overt signs of reactive morphological changes, such as thickening, blebbing or polarization of their processes (FIG. 6A).

Another study was performed using eGFP-Claudin5 mice to evaluate tight junction protein expression in Ad5 transduced mice. eGFP-Claudin5 mice were injected with either Ad5-CMV-tdTomato-NSC or Ad5-CMV-tdTomato-PLSCR1-shRNA. As shown in FIGS. 15A-15B, tight junction protein expression was reduced in eGFP-Claudin5 mice injected with Ad5-CMV-tdTomato-NSC, but this effect was rescued in mice expressing PLSCR1 shRNA.

To test the effect of different vector doses, adult mice were administered 5.35×10$^5$ PFU or 4.93×10$^6$ PFU of Ad5-CMV-tdTomato-PLSCR1-shRNA vector by intracortical delivery. Seventeen days after administration, serial coronal brain sections were obtained and prepared for imaging. As shown in FIGS. 16A-16B, PLSCR1 inhibition protected animals from cell loss at both vector doses.

Together, these data indicate that Ad5-transduced cells with inhibited PLSCR1 activity are protected from engulfment by microglia, and persist as viable, functional transformants for weeks to months.

DISCUSSION

Figure 7:
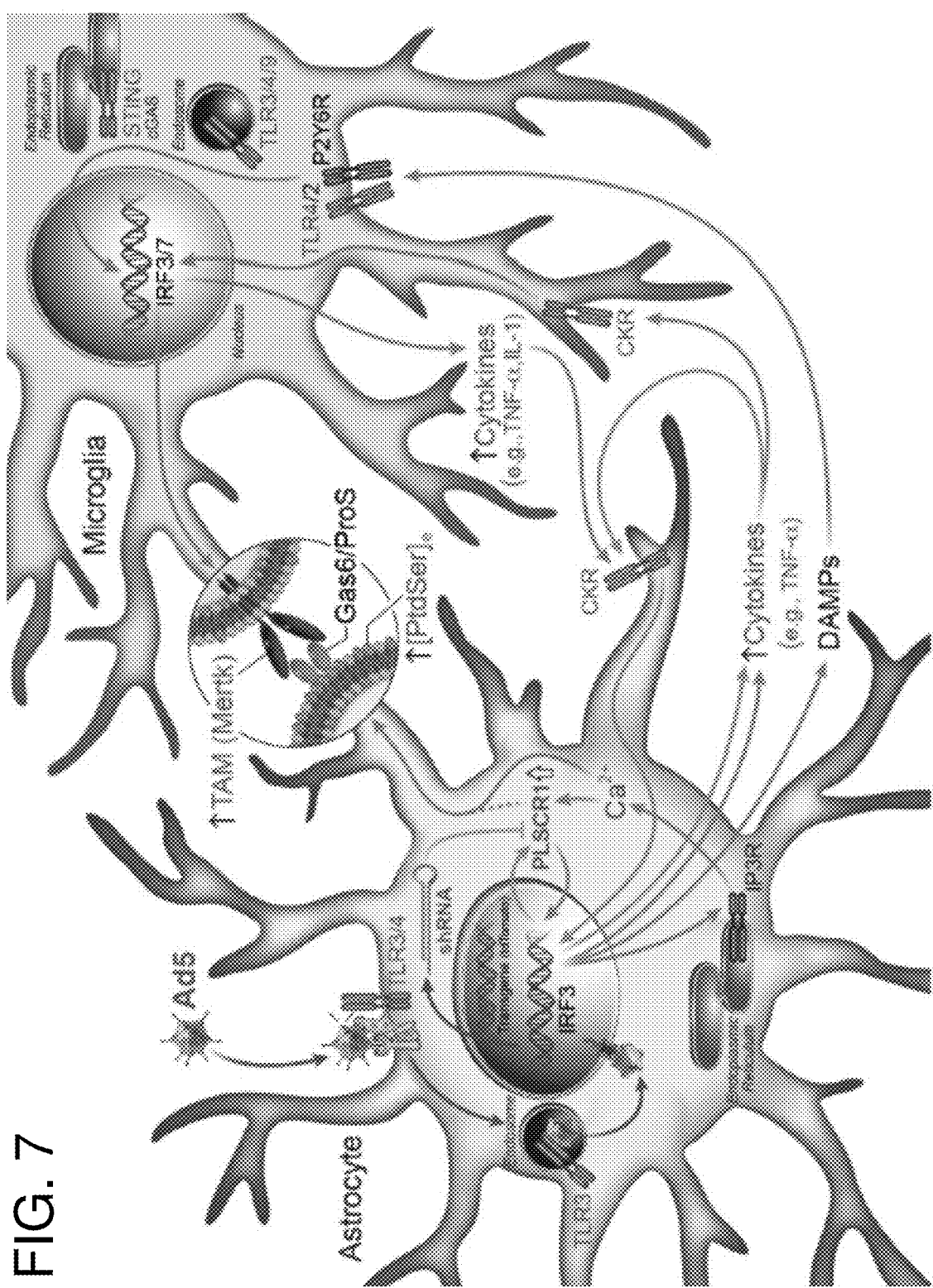
FIG. 7: Model of Signaling Pathways Involved in Microglia Phagocytosis of Adenoviral Vector-transduced Cells. Ad5 enters cells with appropriate surface receptors, particularly astrocytes. During entry or intracellular trafficking Ad5 is sensed, a process that likely involves Toll-like receptor (TLR) signaling (FIG. 9). This results in an initial burst of pro-inflammatory cytokines and phospholipid scramblase 1 (PLSCR1) activity modulation. PLSCR1 in turn induces changes in intracellular calcium ($Ca^{2+}$) signaling, including blunted $Ca^{2+}$ transients and increased calcium baseline (FIG. 5). Dysregulation of intracellular $Ca^{2+}$ homeostasis promotes phosphatidylserine (PtdSer) externalization, either directly or indirectly. Additionally, it may lead to the release of damage-associated molecular patterns (DAMPs). Chemotactic gradients established by DAMPs or cytokines attract microglia to central transduced regions. TAM receptor-mediated recognition of PtdSer-tagged cells triggers microglia phagocytosis. Engulfment of transduced cells facilitates detection of cellular DNA by microglial TLRs or STING, stimulating the production of secondary cytokines, thereby promoting cell death and bystander damage. shRNA-mediated knock down of PLSCR1 reduces dysregulation of intracellular $Ca^{2+}$ homeostasis, PtdSer externalization and DAMP release. This in turn lowers TAM receptor-mediated detection of stressed cells, their phagocytosis and secondary cytokine production. A similarly protective effect can be achieved by expression of calcium-insensitive, mutant $PLSCR1_{D284A}$ (FIG. 13). PLSCR1 modulation can therefore act as a potent inhibitor of innate immune responses to Ad5-based vectors, enabling long-term expression of desired transgene(s). Arrows indicate likely events upstream of PLSCR1 activation and pathways affected by PLSCR1 modulation. Abbreviations: CKR, cytokine receptor; cGAS, cyclic GMP-AMP synthase; Gas6, growth arrest-specific 6; IP3R, inositol 1,4,5-triphosphate receptor; IRF3/7, interferon regulatory factor 3/7, ProS, protein S; P2Y6R, P2Y purinoreceptor 6; STING, stimulator of interferon genes.

We demonstrate that inhibiting PtdSer externalization and PLSCR1 activity can potently inhibit microglial responses to Ad5 vector transduction, without overt adverse consequences on the morphology, calcium excitability, or long-term viability of transduced cells (FIGS. 4-6; FIGS. 13-14). These data are consistent with a model (FIG. 7) in which transduced cells sense viral particles during entry or intracellular trafficking, a process that likely involves TLR signaling (FIGS. 9A and 9B). Viral particle sensing results in an initial burst of pro-inflammatory cytokines and modulates PLSCR1 activity. The latter may be induced downstream of interferon regulatory factor 3 (IRF3), activated by calcium release and/or through an independent mechanism triggered upon viral uptake (Anand and Tikoo, *Adv Virol* 2013, 738794, 2013; Dong et al., *J Virol* 78, 8983-8993, 2004; Kodigepalli and Nanjundan, *PLoS One* 10, e0117464, 2015; Lu et al., *Biochim Biophys Acta* 1771, 1177-1185, 2007). Activated PLSCR1 can translocate into the nucleus, for example, to enhance inositol 1,4,5-triphosphate receptor (IP3R) expression, thereby influencing intracellular calcium homeostasis (Ben-Efraim et al., *Biochemistry* 43, 3518-3526, 2004; Zhou et al., *J Biol Chem* 280, 35062-35068, 2005). Dysregulated calcium signaling, mediated by IP3Rs or membrane channels (Chami et al., *Biochim Biophys Acta* 1763, 1344-1362, 2006; Khakh and McCarthy, *Cold Spring Harb Perspect Biol* 7, a020404, 2015), activates plasma membrane scramblase(s). This in turn increases PtdSer exposure on the external surface of the plasma membrane (FIGS. 2A and 2B) (Frey and Gaipl, *Semin Immunopathol* 33, 497-516, 2011; Segawa and Nagata, *Trends Cell Biol* 25, 639-650, 2015). It is unlikely that PLSCR1 promotes phospholipid scrambling at the plasma membrane directly, as phospholipid scramblase activity is unaffected in PLSCR1-deficient cells or in *Drosophila* in which all PLSCR homologs are deleted (Kodigepalli et al., *FEBS Lett* 589, 3-14, 2015; Segawa and Nagata, *Trends Cell Biol* 25, 639-650, 2015). PtdSer exposure then allows microglia to recognize stressed Ad5 vector-transduced cells, initiate changes in TAM receptor expression and activity (FIGS. 2C and 2D; FIG. 4H), and finally to engulf the transduced but still living cells (FIG. 3). Additionally, stressed cells may release damage associated molecular patterns (DAMPs), such as ATP or high mobility group box-1 (HMGB1), which can be recognized by microglia. Engulfment of transduced cells allows microglia to detect cellular DNA, for example, through cyclic guanine adenine synthase (cGAS)/STING or TLR9, resulting in the release of additional cytokines (FIGS. 9 and 10). Notably, type I IFN signaling, which is responsible for nearly all innate immune activity after lymphocytic choriomeningitis virus (LCMV) infection (Nayak et al., *PLoS Pathog* 9, e1003395, 2013), plays only a minor role in Ad5 transduction (FIG. 10). Microglia engulfment of stressed cells commences near central regions of Ad5 transduction, where multiply transduced and highly stressed cells reside and cytokine or DAMP gradients are likely highest. These gradients may serve to attract microglia or stimulate their proliferation (Neniskyte et al., *FEBS Lett* 588, 2952-2956, 2014), providing a potential explanation for the increased microglia density near central regions (FIG. 1B; FIG. 11I).

Microglial engulfment of transduced cells can be prevented by loss of TAM receptors (FIGS. 3A and 3B) or by inhibiting PLSCR1 activity (FIGS. 4A-4D; FIGS. 13A and 13B). Inhibiting PLSCR1 activity, through knock down or expression of dominant-negative calcium-insensitive PLSCR1, reduces dysregulation of intracellular calcium homeostasis (FIG. 5; FIG. 14) and PtdSer exposure (FIG. 4G; FIG. 13D) and, as a result, contact-mediated TAM receptor signaling (FIG. 4H). Additionally, inhibited PLSCR1 activity results in reduced TNF-α and IL-1β expression (FIG. 4I), and reduced cytokine or DAMP levels may limit attraction of microglia to central regions (FIG. 4B; FIG. 11I). Reduced PtdSer exposure and TAM receptor signaling promote long-term survival of transduced cells (FIGS. 4G and 4H; FIG. 6).

PLSCR1 activity modulation in Ad5 vector-transduced cells was broadly protective to both transgene-expressing and surrounding cells (FIGS. 4-6; FIGS. 11, 13-14), suggesting that this perturbation exerts protective effects beyond intracellular calcium and PtdSer regulation. Diminished reactive changes in and loss of transduced astrocytes, an important regulatory cell type in the CNS, likely contribute to maintained tissue homeostasis, reduced secondary cell damage/loss (FIGS. 11E and 11F) or blood-brain barrier integrity (Obermeier et al., *Nat Med* 19, 1584-1596, 2013). Also observed was a reduction in tdTomato levels in PLSCR1-shRNA- and PLSCR1$_{D284A}$- compared to NSC-vector-transduced cells (FIG. 5J; FIG. 14G). While this effect may contribute to reduced cell stress, microglia activation was comparable in Ad5-CMV-Null-transduced mice (FIGS. 8A and 8B).

The experiments described herein show that by reducing the levels of chemotactic cues and externalized PtdSer, vector-transduced cells can escape microglia detection and phagocytosis. This approach therefore can be used for constructing Ad-based vectors with reduced inflammatory responses and cell loss, allowing for prolonged expression of therapeutic genes in preclinical and clinical gene therapy trials (Castro et al., *Expert Opin Biol Ther* 14, 1241-1257, 2014; Soria et al., *Nature* 466, 1076-1081, 2010; Tobias et al., *J Neurol Neurosurg Psychiatry* 84, 213-222, 2013; Wold and Toth, *Curr Gene Ther* 13, 421-433, 2013). In vitro studies indicate that PLSCR1 may also play important roles in the antiviral response to other viruses, including herpes simplex virus (Talukder et al., *Cell Res* 22, 1129-1139, 2012), vesicular stomatitis virus (Dong et al., *J Virol* 78, 8983-8993, 2004), and hepatitis B and C viruses (Metz et al., *Hepatology* 56, 2082-2093, 2012; Yuan et al., *J Proteome Res* 14, 154-163, 2015). Beyond virus infection, PLSCR1 may be of importance in bacterial infection (Goth and Stephens, *Infect Immun* 69, 1109-1119, 2001; Lu et al., *Biochim Biophys Acta* 1771, 1177-1185, 2007), autoimmune disease (Amengual et al., *Mod Rheumatol* 23, 81-88, 2013; Bernales et al., *Genes Immun* 9, 38-46, 2008; Suzuki et al., *Rheumatol* 37, 1639-1645, 2010), or cancer development (Fan et al., *J Transl Med* 10, 254, 2012; Kodigepalli et al., *Mol Cancer* 12, 32, 2013; Kuo et al., *Mol Med* 17, 41-47, 2011).

Example 3: PLSCR1 Inhibition Reduces Inflammatory Responses after HSV-1 Vector Transduction This example describes the finding that PLSCR1 inhibition is also capable of reducing inflammatory responses induced by herpes simplex virus (HSV) vectors.

The vectors pDE1/DE3-CMV-tdTomato-mPLSCR1-shRNA and pDE1/DE3-CMV-tdTomato-NSC-shRNA were digested with NdeI to remove tdTomato, which was replaced by a 713 bp NdeI fragment containing mCherry in both plamids. The 1040 bp mCherry-mPLSCR1 or mCherry-NSC shRNA cassettes were PCR amplified using the following primers: TOPO/mCherry-FWD, CACCATGGT-GAGCAAGGGCGAGGAGGATAAC (SEQ ID NO: 20), and TOPO/shRNA-REV, AGTGATTTAATTTATAC-CATTTTAATTCAGCTTTGTAAAAATGTATCAAAGA-GATAGC (SEQ ID NO: 21). Both cassettes were then subcloned into the vector pENTR/D-TOPO using the reagents and protocol of the pENTR Directional TOPO Cloning Kit (Life Technologies) to create the vectors pENTR/mCherry-mPLSCR1-shRNA and pENTR/mCherry-NSC-shRNA. The mCherry-shRNA cassettes of both vectors were Gateway cloned into the mCMV-GW-pA vector, under the control of the murine cytomegalovirus immediate-early promoter. The "short-term" HSV vectors were derived from HSV-1. Both replication-deficient viruses were then packaged via the amplicon system and purified on a sucrose gradient. The titer of both viruses was approximately $1.5 \times 10^9$ I.U./ml.

Figure 17A:
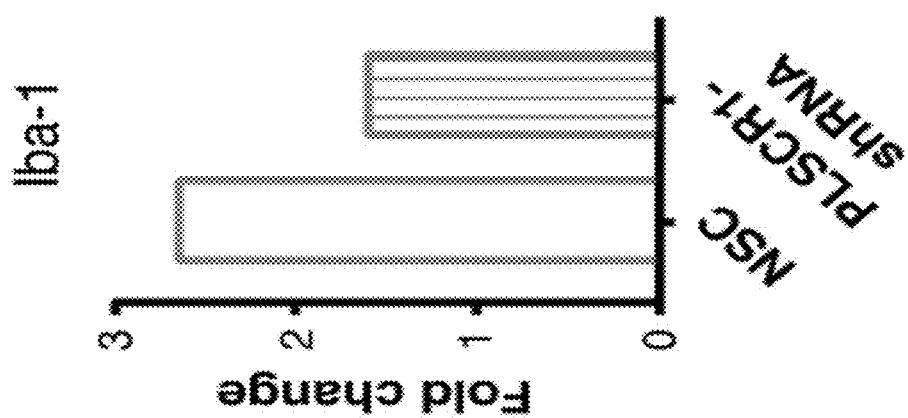
FIGS. 17A-17C PLSCR1 Inhibition Reduces Inflammatory Responses after HSV-1 Vector Transduction. Brain sections showing HSV1-mCMV-mCherry-NSC-shRNA- (FIG. 17A) or HSV1-mCMV-mCherry-PLSCR1-shRNA- (FIG. 17 B) transduced cells in the cortex of wild-type mice 4 days after intracortical vector delivery. Iba-1 immunoreactivity is also shown.
Figure 17B:
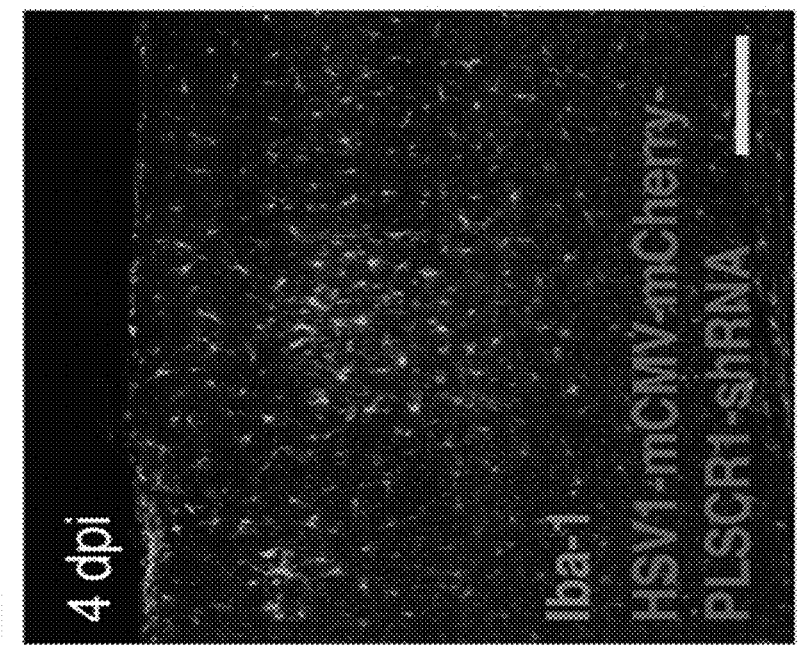
Figure 17C:
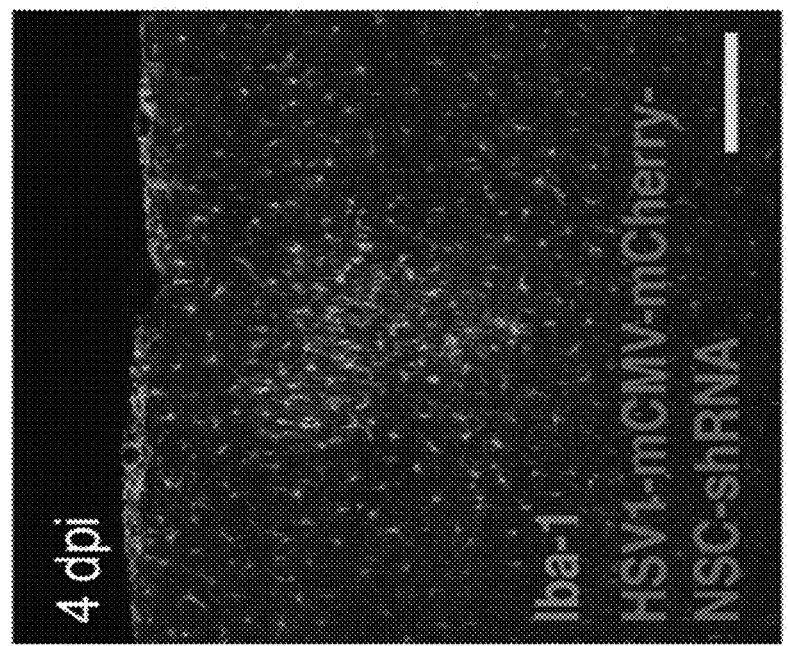

To assess the effect of PLSCR1 inhibition in mice transduced with an HSV vector, wild-type mice were administered either HSV1-mCMV-mCherry-NSC-shRNA or HSV1-mCMV-mCherry-PLSCR1-shRNA. Brain sections were obtained and prepared for imaging four days after intracortical vector delivery. Expression of mCherry and Iba-1 in mice injected with HSV1-mCMV-mCherry-NSC-shRNA and HSV1-mCMV-mCherry-PLSCR1-shRNA is shown in FIG. 17A and FIG. 17B, respectively. Quantitation of Iba-1 immunoreactivity is shown in FIG. 17C. The results show that PLSCR1 inhibition reduces HSV-1 vector-mediated inflammatory responses.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

---

The invention claimed is:

1. A method of inhibiting a virus vector-induced inflammatory response in tissue of a subject, comprising administering to the subject the virus vector and an inhibitor of phospholipid scramblase 1 (PLSCR1), thereby inhibiting the virus vector-induced inflammatory response in the tissue.

2. The method of claim 1, wherein the tissue is central nervous system (CNS) tissue.

3. The method of claim 1, wherein the inhibitor of PLSCR1 is encoded by the virus vector.

4. The method of claim 1, wherein the inhibitor of PLSCR1 is administered as a separate composition from the virus vector.

5. The method of claim 4, wherein the inhibitor of PLSCR1 is administered 24-72 hours prior to administration of the virus vector.

6. The method of claim 5, wherein multiple doses of the PLSCR1 inhibitor is administered 24-72 hours prior to administration of the virus vector.

7. The method of claim 1, wherein the virus vector is an adenovirus (Ad), canine adenovirus (CAV), herpes simplex virus (HSV), hepatitis B virus (HBV), hepatitis C virus (HCV), or vesicular stomatitis virus (VSV) vector.

8. The method of claim 1, wherein the virus vector is an Ad vector.

9. The method of claim 8, wherein the Ad vector is an Ad5 vector, a replication-incompetent virus vector, or both.

10. The method of claim 1, wherein the virus vector comprises a transgene.

11. The method of claim 10, wherein the transgene is a reporter gene.

12. The method of claim 10, wherein the transgene encodes a therapeutic protein or nucleic acid.

13. The method of claim 1, wherein the inhibitor of PLSCR1 comprises:
a short hairpin RNA (shRNA) that targets PLSCR1 mRNA,
a small interfering RNA (siRNA),
an antisense oligonucleotide that targets PLSCR1 mRNA, or
dominant-negative mutant PLSCR1.

14. The method of claim 13, wherein
the shRNA that targets PLSCR1 mRNA comprises a nucleotide sequence that is at least 85% identical to SEQ ID NO: 7, or
wherein the dominant-negative mutant PLSCR1 is $PLSCR1_{D284A}$.

15. A recombinant adenovirus vector comprising a nucleotide sequence at least 85% identical to SEQ ID NO: 2, SEQ ID NO: 3, SEQ ID NO: 22 or SEQ ID NO: 23.

16. A recombinant cell comprising the recombinant adenovirus vector of claim 15.

17. A method of modulating an inflammatory response in tissue of a subject suffering from a viral infection, a bacterial infection, or an autoimmune disease, comprising administering to the subject an inhibitor of phospholipid scramblase 1 (PLSCR1), thereby modulating the inflammatory response in the tissue of the subject.

18. The method of claim 17, wherein the tissue is central nervous system (CNS) tissue.

19. The method of claim 17, wherein the viral infection is caused by an adenovirus (Ad), a herpes simplex virus (HSV), a hepatitis B virus (HBV), a hepatitis C virus (HCV), a vesicular stomatitis virus (VSV), a human immunodeficiency virus (HIV), an influenza virus, a varicella zoster virus (VZV), a human papillomavirus (HPV), an Epstein-Barr virus (EBV), a cytomegalovirus (CMV), an enterovirus, a togavirus or a flavivirus;

the bacterial infection is caused by *Chlamydia trachomatis, Streptococcus agalactiae, Streptococcus pneumoniae, Escherichia coli, Listeria monocytogenes, Neisseria meningitides, Haemophilus influenza, Mycobacterium tuberculosis,* or *Borrelia burgdorferi*; or the autoimmune disease is antiphospholipid syndrome, multiple sclerosis, rheumatoid arthritis, systemic lupus erythematosus, inflammatory bowel disease, type 1 diabetes, Guillain-Barrsyndrome, myasthenia gravis or Sjögren's syndrome.

20. The method of claim 17, wherein the inhibitor of PLSCR1 is a short hairpin RNA (shRNA), a small interfering RNA (siRNA), an antisense oligonucleotide that targets PLSCR1 mRNA, a dominant-negative mutant PLSCR1, or a small molecule inhibitor.

21. A method of modulating an inflammatory response in tissue of a subject suffering from a viral infection, a bacterial infection, an autoimmune disease, or cancer, comprising administering to the subject an inhibitor of phospholipid scramblase 1 (PLSCR1), wherein the inhibitor of PLSCR1 is a short hairpin RNA (shRNA) that is at least 85% identical to SEQ ID NO: 7 and targets PLSCR1 mRNA, thereby modulating the inflammatory response in the tissue of the subject.

22. The method of claim 21, wherein the shRNA is at least 90% identical to SEQ ID NO: 7.

23. The method of claim 22, wherein the subject is suffering from an adenovirus infection or a herpes simplex virus infection and the shRNA is at least 95% identical to SEQ ID NO: 7.

24. A method of inhibiting an adenovirus vector-induced inflammatory response in central nervous system (CNS) tissue of a subject, comprising administering to the subject the adenovirus vector and an inhibitor of phospholipid scramblase 1 (PLSCR1), wherein:

the inhibitor of PLSCR1 is a short hairpin RNA (shRNA) that targets PLSCR1 mRNA and comprises a nucleotide sequence that is at least 95% identical to SEQ ID NO: 7, thereby inhibiting the adenovirus vector-induced inflammatory response in the CNS tissue.

* * * * *